United States Patent
Wu et al.

(10) Patent No.: US 9,856,256 B2
(45) Date of Patent: Jan. 2, 2018

(54) PYRIDINO[1,2-A]PYRIMIDONE ANALOGUE USED AS P13K INHIBITOR

(71) Applicant: CHIA TAI TIANQING PHARMACEUTICAL GROUP CO., LTD., Lianyungang (CN)

(72) Inventors: Chengde Wu, Shanghai (CN); Tao Yu, Shanghai (CN); Shuhui Chen, Shanghai (CN)

(73) Assignee: CHIA TAI TIANQING PHARMACEUTICAL GROUP CO., LTD., Lianyungang, Jiangsu (CN)

( * ) Notice: Subject to any disclaimer, the term of this patent is extended or adjusted under 35 U.S.C. 154(b) by 0 days.

(21) Appl. No.: 15/319,726

(22) PCT Filed: Jun. 16, 2015

(86) PCT No.: PCT/CN2015/081518
§ 371 (c)(1),
(2) Date: Dec. 16, 2016

(87) PCT Pub. No.: WO2015/192760
PCT Pub. Date: Dec. 23, 2015

(65) Prior Publication Data
US 2017/0137420 A1 May 18, 2017

(30) Foreign Application Priority Data

Jun. 17, 2014 (CN) .......................... 2014 1 0271282
Jun. 12, 2015 (CN) .......................... 2015 1 0324348

(51) Int. Cl.
| *C07D 471/04* | (2006.01) |
| *C07D 487/04* | (2006.01) |
| *C07D 491/147* | (2006.01) |
| *C07D 519/00* | (2006.01) |

(52) U.S. Cl.
CPC ......... *C07D 471/04* (2013.01); *C07D 519/00* (2013.01)

(58) Field of Classification Search
CPC . C07D 471/04; C07D 487/04; C07D 491/147
See application file for complete search history.

(56) References Cited

U.S. PATENT DOCUMENTS

2015/0166539 A1  6/2015  Wu et al.

FOREIGN PATENT DOCUMENTS

| CN | 103539777 A | 1/2014 |
| WO | 2013/071698 A1 | 5/2013 |
| WO | 2014/022128 A1 | 2/2014 |

OTHER PUBLICATIONS

English Translation Written Opinion and International Search Report corresponding to PCT/CN2015/081518 dated Sep. 16, 2015; 5 pages.
Office Action issued in Eurasian Patent Application No. 201790016, dated Sep. 25, 2017.

*Primary Examiner* — Kahsay Habte
(74) *Attorney, Agent, or Firm* — Mintz Levin Cohn Ferris Glovsky and Popeo, P.C.

(57) ABSTRACT

The present invention relates to novel pyridino[1,2-α]pyrimidone compounds represented by formula (I) or pharmaceutically acceptable salts thereof; and a method of use thereof for treating tumors, such as colon cancer and gastric cancer.

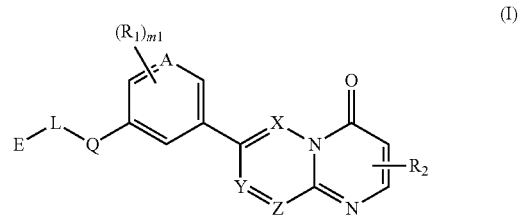

(I)

16 Claims, 3 Drawing Sheets

PYRIDINO[1,2-A]PYRIMIDONE ANALOGUE USED AS PI3K INHIBITOR

TECHNICAL FIELD

The present invention relates to a class of pyrido[1,2-a]pyrimidone analogues as PI3K inhibitors, and more specifically, relates to a compound represented by Formula (I) or a pharmaceutically acceptable salt thereof.

BACKGROUND

PI3K pathway is the most common place where human cancer cells mutate which may lead to cell proliferation, activation and signal amplification.

PI3K kinases (phosphatidylinositol 3-kinases, PI3Ks) belong to the lipid kinase family and are capable of phosphorylating the 3'-OH end of the inositol ring of phosphatidylinositols. Phosphatidylinositol 3-kinase (PI3K) is a lipid kinase composed of a regulatory subunit p85 or p101 and a catalytic subunit p110. It catalyzes the phosphorylation of phosphatidylinositol 4,5-bisphosphate (PIP2) to form phosphatidylinositol 3,4,5-trisphosphate (PIP3), thereby activating downstream Akt, etc., so as to play a key role in proliferation, survival, metabolism and the like of cells. Therefore, the inhibition of phosphatidylinositol 3-kinases can influence the PI3K pathway, thereby inhibiting the proliferation and activation of cancer cells.

The tumor suppressor gene PTEN (phosphatase and tension homolog deleted on chromosome ten) dephosphorylates PIP3 to generate PIP2, thereby achieving the negative regulation of PI3K/Akt signal pathway, inhibiting cell proliferation and promoting cell apoptosis. The frequent occurrences of PI3K gene mutation and amplification in cancers, the absence of PTEN in cancers and the like indicate that PI3K is closely associated with the occurrence of tumors.

SUMMARY OF THE INVENTION

An objective of the present invention is to provide a compound represented by Formula (I) or a pharmaceutically acceptable salt thereof.

wherein (I)

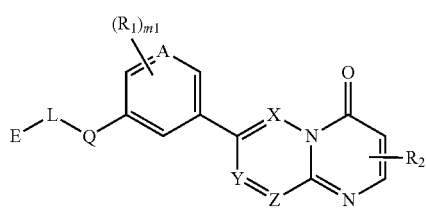

the structure unit

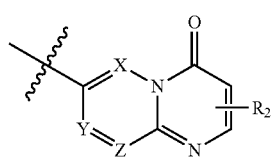

may be replaced with

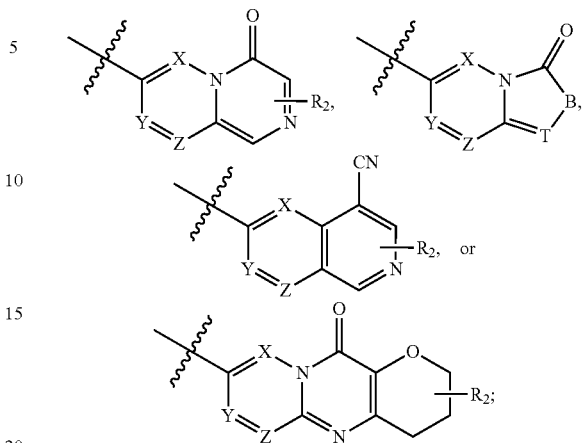

E is selected from the group consisting of $C_{1-6}$ alkyl, and 3- to 10-membered cyclohydrocarbyl or heterocyclohydrocarbyl, wherein said $C_{1-6}$ alkyl and 3- to 10-membered cyclohydrocarbyl or heterocyclohydrocarbyl are optionally substituted with 1, 2 or 3 $R_3$;

one of L and Q is selected from the group consisting of $—C(R_{d1})(R_{d2})—$, $—C(=O)N(R_{d3})—$, $—N(R_{d4})—$, $—C(=NR_{d5})—$, $—S(=O)_2N(R_{d6})—$, $—S(=O)N(R_{d7})—$, $—O—$, $—S—$, $—C(=O)O—$, $—C(=O)—$, $—C(=S)—$, $—S(=O)—$, $—S(=O)_2—$ and $—N(R_{d8})C(=O)N(R_{d9})—$, and the other one is selected from the group consisting of a single bond and $—C(R_{d1})(R_{d2})—$;

A and T are each independently selected from the group consisting of N and $C(R_t)$;

none or one of X, Y and Z is N, and the others are $C(R_t)$;

B is selected from the group consisting of $—C(R_{d1})(R_{d2})—$, $—C(=O)N(R_{d3})—$, $—N(R_{d4})—$, $—C(=NR_{d5})—$, $—S(=O)_2N(R_{d6})—$, $—S(=O)N(R_{d7})—$, $—O—$, $—S—$, $—C(=O)O—$, $—C(=O)—$, $—C(=S)—$, $—S(=O)—$, $—S(=O)_2—$, and $—N(R_{d8})C(=O)N(R_{d9})—$;

the heteroatom or heteroatom group is each independently selected from the group consisting of $—C(=O)N(R_{d3})—$, $—N(R_{d4})—$, $—C(=NR_{d5})—$, $—S(=O)_2N(R_{d6})—$, $—S(=O)N(R_{d7})—$, $—O—$, $—S—$, $—C(=O)O—$, $—C(=O)—$, $—C(=S)—$, $—S(=O)—$, $—S(=O)_2—$ and $—N(R_{d8})C(=O)N(R_{d9})—$;

$m_1$ is independently 0, 1, 2 or 3;

one of $R_{1-3}$ is

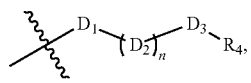

and the others are selected from the group consisting of H, F, Cl, Br, I, CN, OH, SH, $NH_2$, CHO, COOH, $C_{1-10}$ alkyl or heteroalkyl, 3- to 10-membered cyclohydrocarbyl or heterocyclohydrocarbyl, $C_{1-10}$ alkyl or heteroalkyl substituted with 3- to 10-membered cyclohydrocarbyl or heterocyclohydrocarbyl, 3- to 10-membered cyclohydrocarbyl-O— or heterocyclohydrocarbyl-O—, and 3- to 10-membered cyclohydrocarbyl-amino- or heterocyclohydrocarbyl-amino-, wherein said $C_{1-10}$ alkyl or heteroalkyl, 3- to 10-membered cyclohydrocarbyl or heterocyclohydrocarbyl, $C_{1-10}$ alkyl or heteroalkyl substituted with 3- to 10-membered cyclohydrocarbyl or heterocyclohydrocarbyl, 3- to 10-membered cyclohydrocarbyl-O— or heterocyclohydrocarbyl-O—, and 3- to 10-membered cyclohydrocarbyl-amino- or heterocyclohydrocarbyl-amino- are optionally substituted with $R_{01}$;

$D_1$ is selected from the group consisting of a single bond, $-C(R_{d1})(R_{d2})-$, $-C(=O)N(R_{d3})-$, $-N(R_{d4})-$, $-C(=NR_{d5})-$, $-S(=O)_2N(R_{d6})-$, $-S(=O)N(R_{d7})-$, $-O-$, $-S-$, $-C(=O)O-$, $-C(=O)-$, $-C(=S)-$, $-S(=O)-$, $-S(=O)_2-$ and $-N(R_{d8})C(=O)N(R_{d9})-$;

$D_2$ is $-C(R_{d1})(R_{d2})-$;

$D_3$ is selected from the group consisting of $-N(R_{d4})-$, $-C(=O)N(R_{d4})-$, $-N(R_{d4})C(=O)-$, $-N(R_{d4})C(=O)O-$, $-N(R_{d4})OC(=O)-$, $-N(R_{d4})C(=O)N(R_{d4})-$, $-S(=O)-$, $-S(=O)_2-$, $-S(=O)_2N(R_{d6})-$ and $-S(=O)N(R_{d7})-$.

$R_4$ is selected from the group consisting of H, $C_{1-10}$ alkyl or heteroalkyl, 3- to 10-membered cyclohydrocarbyl or heterocyclohydrocarbyl, and $C_{1-10}$ alkyl or heteroalkyl substituted with 3- to 10-membered cyclohydrocarbyl or heterocyclohydrocarbyl, wherein said $C_{1-10}$ alkyl or heteroalkyl, 3- to 10-membered cyclohydrocarbyl or heterocyclohydrocarbyl, and $C_{1-10}$ alkyl or heteroalkyl substituted with 3- to 10-membered cyclohydrocarbyl or heterocyclohydrocarbyl are optionally substituted with $R_{01}$;

n is 1, 2, 3, 4, 5 or 6;

optionally, any two $R_1$, $R_{d1}$ and $R_{d2}$ in the same $D_2$, two $D_2$, $R_4$ and one $D_2$, or $R_4$ and $D_3$ are attached together to the same carbon atom or heteroatom to form one or two 3-, 4-, 5- or 6-membered carbocyclic ring or heterocyclic ring;

$R_t$, $R_{d1}$ and $R_{d2}$ are each independently selected from the group consisting of H, F, Cl, Br, I, CN, OH, SH, $NH_2$, CHO, COOH, $C(=O)NH_2$, $S(=O)NH_2$, $S(=O)_2NH_2$, $C_{1-10}$ alkyl or heteroalkyl, 3- to 10-membered cyclohydrocarbyl or heterocyclohydrocarbyl, and $C_{1-10}$ alkyl or heteroalkyl substituted with 3- to 10-membered cyclohydrocarbyl or heterocyclohydrocarbyl, wherein said $C_{1-10}$ alkyl or heteroalkyl, 3- to 10-membered cyclohydrocarbyl or heterocyclohydrocarbyl, and $C_{1-10}$ alkyl or heteroalkyl substituted with 3- to 10-membered cyclohydrocarbyl or heterocyclohydrocarbyl are optionally substituted with $R_{01}$;

$R_{01}$ is selected from the group consisting of F, Cl, Br, I, CN, OH, SH, $NH_2$, CHO, COOH, and $R_{02}$;

$R_{02}$ is selected from the group consisting of $C_{1-10}$ alkyl, $C_{1-10}$ alkylamino, N,N-di($C_{1-10}$ alkyl)amino, $C_{1-10}$ alkoxy, $C_{1-10}$ alkanoyl, $C_{1-10}$ alkoxycarbonyl, $C_{1-10}$ alkylsulfonyl, $C_{1-10}$ alkylsulfinyl, $C_{3-10}$ cycloalkyl, $C_{3-10}$ cycloalkylamino, $C_{3-10}$ heterocycloalkylamino, $C_{3-10}$ cycloalkoxy, $C_{3-10}$ cycloalkylacyl, $C_{3-10}$ cycloalkoxycarbonyl, $C_{3-10}$ cycloalkylsulfonyl, $C_{3-10}$ cycloalkylsulfinyl, 5- to 6-membered unsaturated heterocyclyl, and 6- to 12-membered aryl or heteroaryl;

the heteroatom or heteroatom group is each independently selected from the group consisting of $-C(=O)N(R_{d3})-$, $-N(R_{d4})-$, $-C(=NR_{d5})-$, $-S(=O)_2N(R_{d6})-$, $-S(=O)N(R_{d7})-$, $-O-$, $-S-$, $=O$, $=S$, $-C(=O)O-$, $-C(=O)-$, $-C(=S)-$, $-S(=O)-$, $-S(=O)_2-$ and $-N(R_{d8})C(=O)N(R_{d9})-$;

$R_{d3-d9}$ are each independently selected from the group consisting of H, OH, $NH_2$, and $R_{02}$;

$R_{02}$ is optionally substituted with $R_{001}$;

$R_{001}$ is selected from the group consisting of F, Cl, Br, I, CN, OH, $N(CH_3)_2$, $NH(CH_3)$, $NH_2$, CHO, COOH, trifluoromethyl, aminomethyl, hydroxymethyl, methyl, methoxy, formyl, methoxycarbonyl, methylsulfonyl, and methylsulfinyl;

in any of the foregoing cases, the number of $R_{01}$ or $R_{001}$ is each independently 0, 1, 2 or 3, and the number of the heteroatom or heteroatom group is each independently 1, 2 or 3.

In one embodiment of the present invention, the above-mentioned E is selected from the group consisting of $C_{1-6}$ alkyl and $C_{3-6}$ cycloalkyl wherein said $C_{1-6}$ alkyl and $C_{3-6}$ cycloalkyl are substituted with $R_3$, and the number of $R_3$ is 0, 1, 2 or 3, or E is selected from the group consisting of

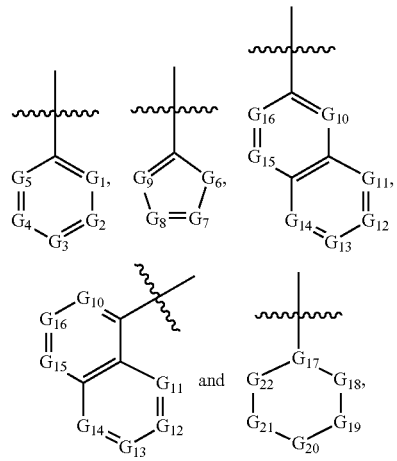

wherein, none or one or two or three of $G_{1-5}$ are N, and the others are $C(R_3)$;

$G_6$ is selected from the group consisting of $-C(R_3)(R_3)-$, $-C(=O)N(R_{3a})-$, $-N(R_{3a})-$, $-C(=NR_{3a})-$, $-S(=O)_2N(R_{3a})-$, $-S(=O)N(R_{3a})-$, $-O-$, $-S-$, $-C(=O)O-$, $-C(=O)-$, $-C(=S)-$, $-S(=O)-$, $-S(=O)_2-$ and $-N(R_{3a})C(=O)N(R_{3a})-$, none or one or two of $G_{7-9}$ are N, and the others are $C(R_3)$;

none or one or two or three or four of $G_{10-16}$ are N, and the others are $C(R_3)$;

$G_{17}$ is selected from the group consisting of N and $C(R_3)$;

none or one or two or three of $G_{18-22}$ are selected from the group consisting of $-C(=O)N(R_{3a})-$, $-N(R_{3a})-$, $-C(=NR_{3a})-$, $-S(=O)_2N(R_{3a})-$, $-S(=O)N(R_{3a})-$, $-O-$, $-S-$, $-C(=O)O-$, $-C(=O)-$, $-C(=S)-$, $-S(=O)-$, $-S(=O)_2-$ and $-N(R_{3a})_3C(=O)N(R_{3a})-$, and the others are $-C(R_3)(R_3)-$;

$R_{3a}$ is selected from the group consisting of $C_{1-10}$ alkyl, $C_{1-10}$ alkylacyl, $C_{1-10}$ alkoxycarbonyl, $C_{1-10}$ alkylsulfonyl, $C_{1-10}$ alkylsulfinyl, $C_{3-10}$ cycloalkyl, $C_{3-10}$ cycloalkylacyl, $C_{3-10}$ cycloalkoxycarbonyl, $C_{3-10}$ cycloalkylsulfonyl, $C_{3-10}$ cycloalkylsulfinyl, 5- to 6-membered unsaturated heterocyclyl, and 6- to 10-membered aryl or heteroaryl.

In one embodiment of the present invention, the above-mentioned E is selected from the group consisting of methyl, ethyl, propyl,

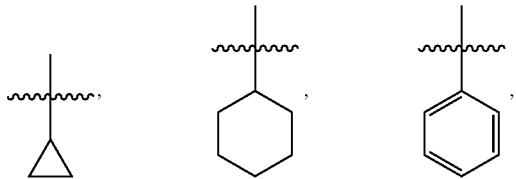

all of which are optionally substituted with 1, 2 or 3 $R_3$.

In one embodiment of the present invention, the above-mentioned E is selected from the group consisting of and $C_{1-3}$ alkyl, all of which are optionally substituted with 1, 2, or 3 halogens, OH, $OC_{1-3}$alkyl, CN, $NH_2$, $NH(C_{1-3}$alkyl), $N(C_{1-3}$alkyl$)_2$, $C_{1-3}$alkyl, trifluoromethyl, trifluoroethyl, $C(=O)NH_2$, $C_{1-3}$alkylC(=O), $C_{1-3}$alkylC(=O)NH, $C_{1-3}$alkylS(=O), $C_{1-3}$ alkylS(=O)NH, $C_{1-3}$alkylS(=O)$_2$ or $C_{1-3}$alkylS(=O)$_2$NH.

In one embodiment of the present invention, the above-mentioned E is selected from the group consisting of

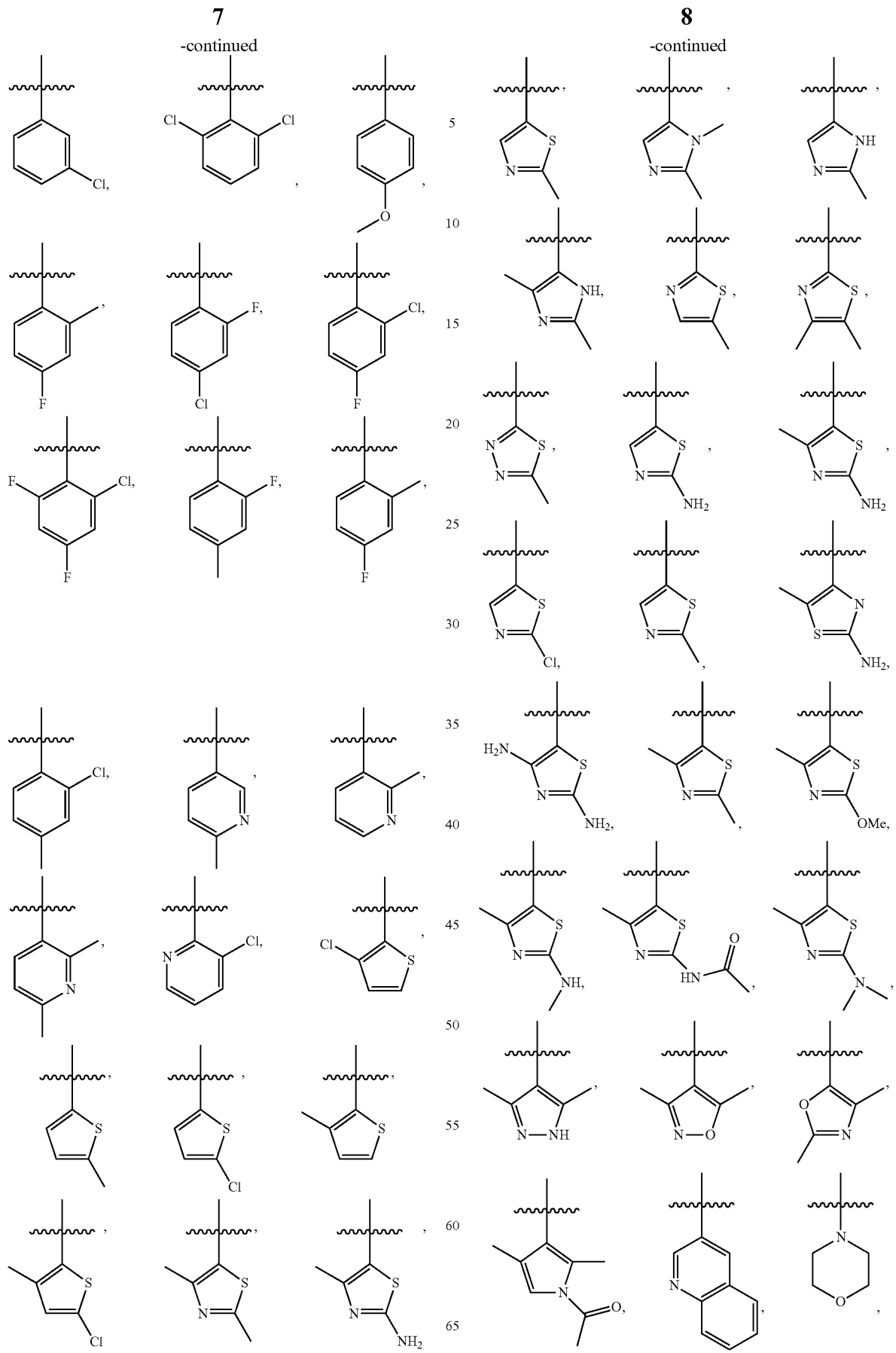

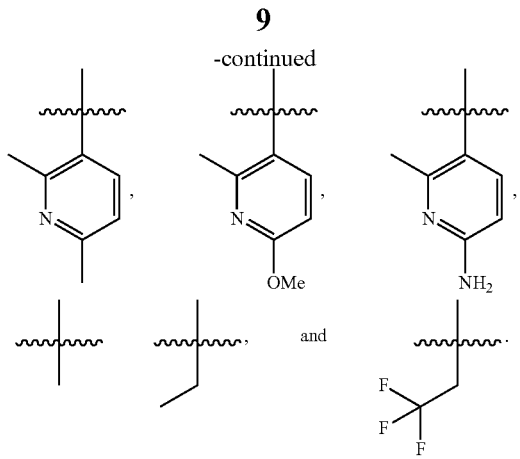

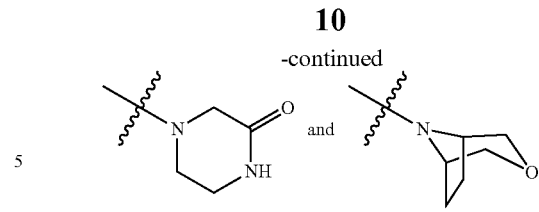

In one embodiment of the present invention, one of the above-mentioned L and Q is selected from the group consisting of —S(=O)$_2$NH—, —S(=O)$_2$—, —NH—, and —NHC(=O)NH—, and the other one is selected from the group consisting of a single bond and —CH$_2$—.

In one embodiment of the present invention, none or one of the above-mentioned X, Y and Z is N, and the others are selected from the group consisting of CH, C(CH$_3$), C(CF$_3$), CCl, and CF.

In one embodiment of the present invention, the above-mentioned A and T are each independently selected from the group consisting of N, CH, C(CH$_3$), C(CF$_3$), CCl, and CF; alternatively, B is selected from the group consisting of NH, N(CH$_3$) and N(CF$_3$).

In one embodiment of the present invention, the above-mentioned ring formed between any two R$_1$, R$_{d1}$ and R$_{d2}$ in the same D$_2$, two D$_2$, R$_4$ and one D$_2$, or R$_4$ and D$_3$, is selected from the group consisting of

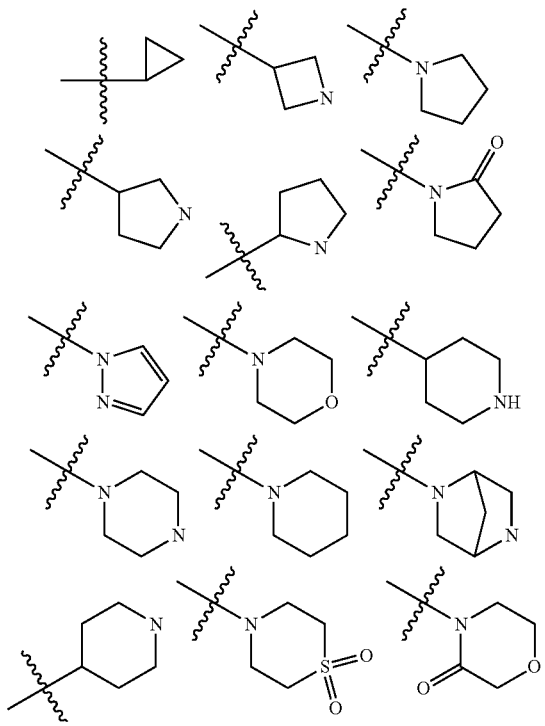

all of which are optionally substituted with 1, 2, or 3 halogens, OH, OC$_{1-3}$alkyl, CN, NH$_2$, NH(C$_{1-3}$alkyl), N(C$_{1-3}$alkyl)$_2$, C$_{1-3}$alkyl, trifluoromethyl, trifluoroethyl, C(=O)NH$_2$, C$_{1-3}$alkylC(=O), C$_{1-3}$alkylC(=O)NH, C$_{1-3}$alkylS(=O), C$_{1-3}$alkylS(=O)NH, C$_{1-3}$alkylS(=O)$_2$ or C$_{1-3}$alkylS(=O)$_2$NH.

In one embodiment of the present invention, the above-mentioned ring formed between any two R$_1$, R$_{d1}$ and R$_{d2}$ in the same D$_2$, two D$_2$, R$_4$ and one D$_2$, or R$_4$ and D$_3$, is selected from the group consisting of

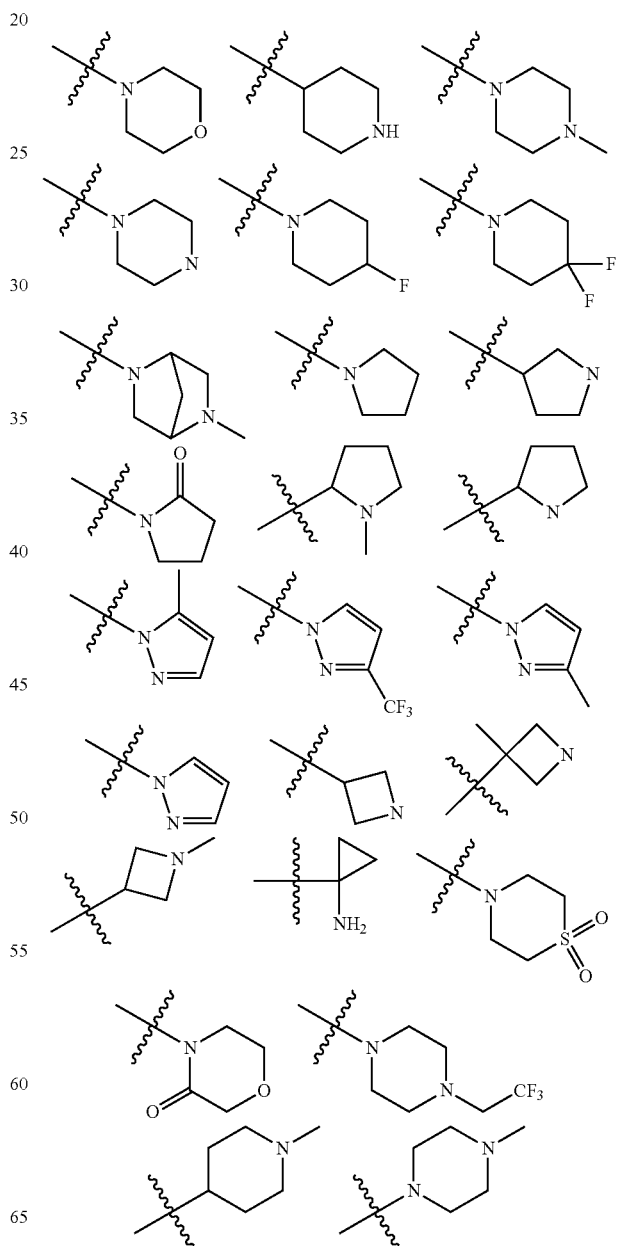

-continued

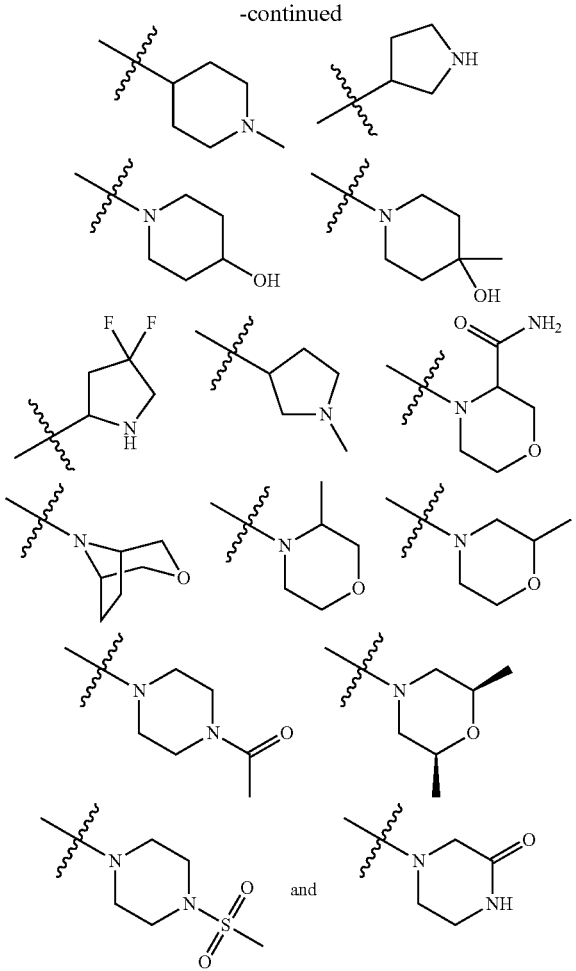

In one embodiment of the present invention, one of the above-mentioned $R_{1-3}$ is

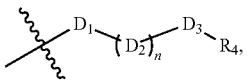

and the others are selected from the group consisting of H, F, Cl, Br, I, CN, OH, SH, $NH_2$, CHO, COOH, $OR_a$, $N(R_b)(R_c)$, $C_{1-3}$ alkyl and cyclopropyl, wherein said $C_{1-3}$ alkyl and cyclopropyl are optionally substituted with $R_d$;

$D_1$ is selected from the group consisting of a single bond, $-C(R_e)(R_e)-$, $-C(=O)N(R_a)-$, $-N(R_a)-$, $-C(=NR_a)-$, $-S(=O)_2N(R_a)-$, $-S(=O)N(R_a)-$, $-O-$, $-S-$, $-C(=O)O-$, $-C(=O)-$, $-C(=S)-$, $-S(=O)-$, $-S(=O)_2-$ and $-N(R_a)C(=O)N(R_a)-$;

$D_2$ is $-C(R_a)(R_a)-$;

n is 1, 2, 3, 4, 5 or 6;

$R_a$, $R_b$ and R are each independently selected from the group consisting of H, $C_{1-6}$ alkyl and $C_{3-6}$ cycloalkyl, wherein said $C_{1-6}$ alkyl and $C_{3-6}$ cycloalkyl are optionally substituted with $R_d$;

$R_e$ is selected from the group consisting of H, $C_{1-6}$ alkyl or alkoxy, and $C_{3-6}$ cycloalkyl or cycloalkoxy, wherein said $C_{1-6}$ alkyl or alkoxy and said $C_{3-6}$ cycloalkyl or cycloalkoxy are optionally substituted with $R_d$;

$R_d$ is selected from the group consisting of F, Cl, Br, I, CN, OH, CHO, COOH, $CH_3$, $CF_3$, $CH_3O$, and $CH_3CH_2O$, and the number of $R_d$ is 0, 1, 2 or 3;

Optionally, any two $R_1$, $R_a$ and $R_a$ in the same $D_2$, two $D_2$, or $R_a$ and one $D_2$ are attached together to the same carbon atom or oxygen atom to form one or two 3-, 4-, 5- or 6-membered carbocyclic ring or oxacyclic ring, wherein the number of oxygen atoms is 1 or 2.

In one embodiment of the present invention, the above-mentioned ring formed between any two $R_1$, $R_a$ and $R_a$ in the same $D_2$, two $D_2$, or $R_a$ and one $D_2$, is selected from the group consisting of cyclopropyl, cyclobutyl, cyclopentyl, cyclohexyl, oxetanyl, and 1,3-dioxolanyl.

In one embodiment of the present invention, one of the above-mentioned $R_{1-3}$ is selected from the group consisting of

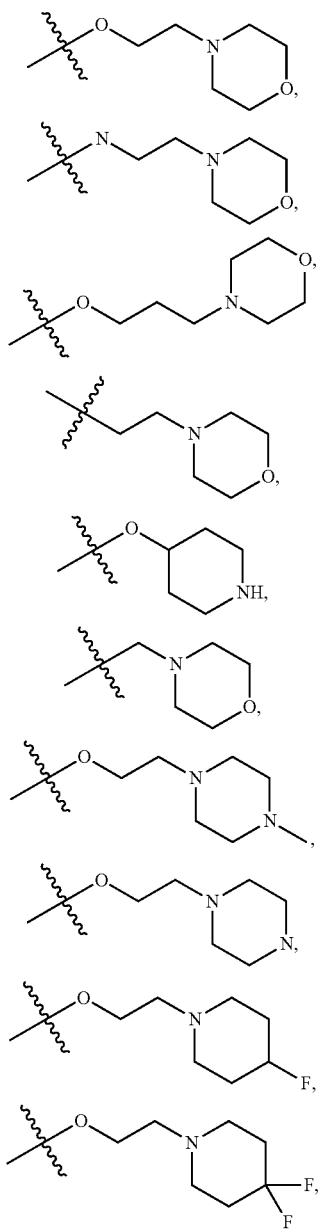

13
-continued
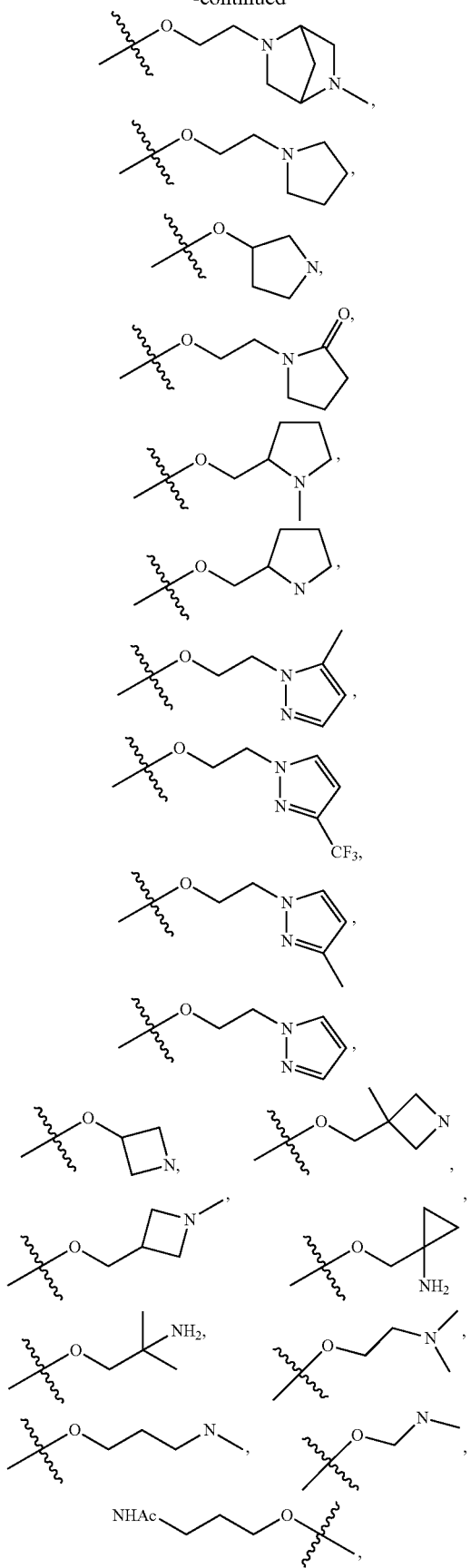
14
-continued
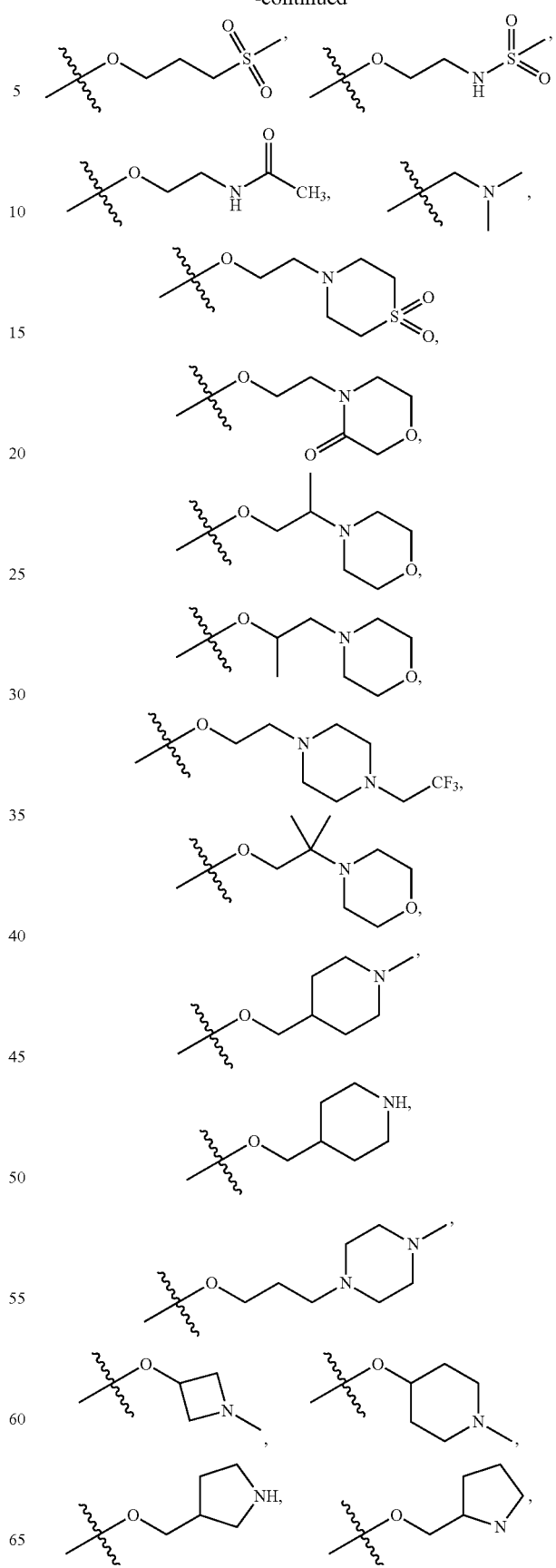

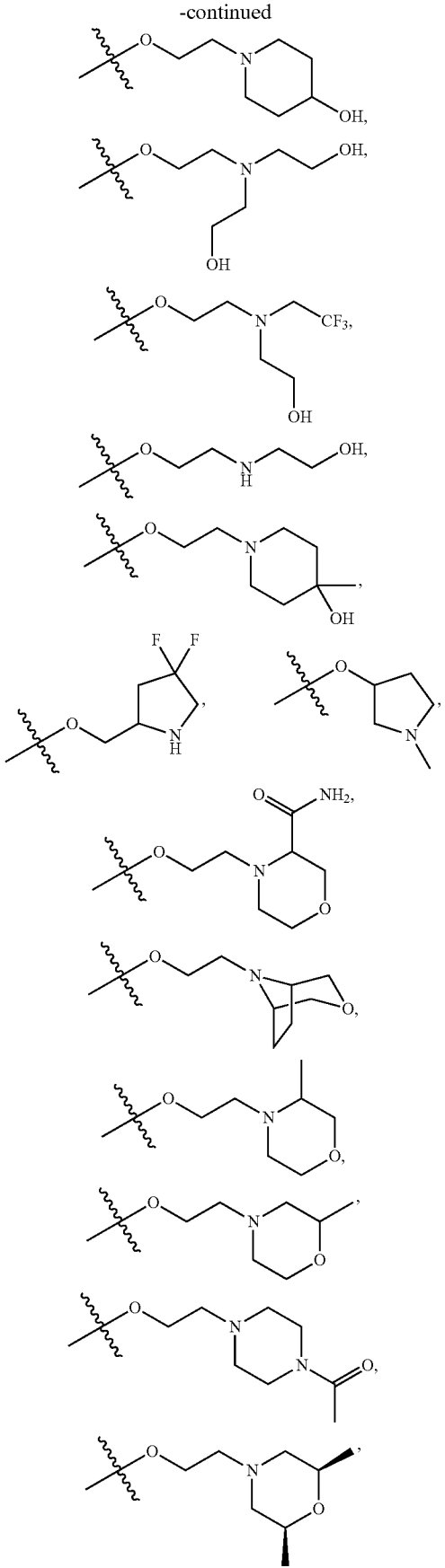
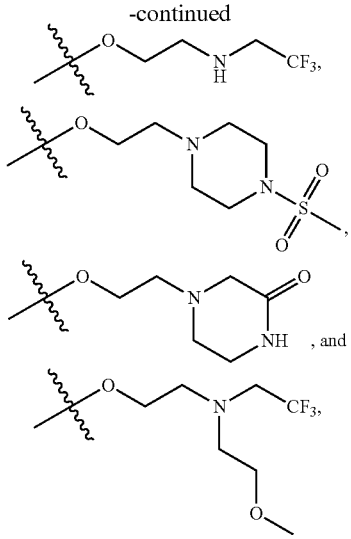

and the others are selected from the group consisting of H, F, Cl, Br, I, CN, OH, $NH_2$, methyl, ethyl, propyl, methoxy, ethoxy, propoxymethylamino, dimethylamino, halomethyl, haloethyl, halopropyl, aminomethyl, aminoethyl, aminopropyl and cyclopropyl.

In one embodiment of the present invention, the above-mentioned compound or a pharmaceutically acceptable salt thereof is selected from the group consisting of Compounds 1 to 25 and Compounds 27 to 99.

Relevant Definitions

Unless otherwise indicated, the following terms and phrases as used herein are intended to have the following meanings. A particular term or phrase without a particular definition should not be regarded as being indefinite or unclear, but should be understood in its ordinary sense. When a tradename is used herein, it is intended to refer to the corresponding commodity or its active ingredient.

$C_{1-10}$ is selected from the group consisting of $C_1$, $C_2$, $C_3$, $C_4$, $C_5$, $C_6$, $C_7$, $C_8$, $C_9$ and $C_{10}$; $C_{3-10}$ is selected from the group consisting of $C_3$, $C_4$, $C_5$, $C_6$, $C_7$, $C_8$, $C_9$ and $C_{10}$.

$C_{1-10}$ alkyl or heteroalkyl, $C_{3-10}$ cyclohydrocarbyl or heterocyclohydrocarbyl, and $C_{1-10}$ alkyl or heteroalkyl wherein said $C_{1-10}$ alkyl or heteroalkyl is substituted with $C_{3-10}$ cyclohydrocarbyl or heterocyclohydrocarbyl, include, but not limited to:

$C_{1-10}$ alkyl. $C_{1-10}$ alkylamino, N,N-di($C_{1-10}$ alkyl)amino, $C_{1-10}$ alkoxy, $C_{1-10}$ alkanoyl, $C_{1-10}$ alkoxycarbonyl, $C_{1-10}$ alkylsulfonyl, $C_{1-10}$ alkylsulfinyl, $C_{3-10}$ cycloalkyl, $C_{3-10}$ cycloalkylamino, $C_{3-10}$ heterocycloalkylamino, $C_{3-10}$ cycloalkoxy. $C_{3-10}$ cycloalkylacyl, $C_{3-10}$ cycloalkyloxycarbonyl, $C_{3-10}$ cycloalkylsulfonyl, and $C_{3-10}$ cycloalkylsulfinyl;

methyl, ethyl, n-propyl, isopropyl, —$CH_2C(CH_3)(CH_3)$(OH) cyclopropyl, cyclobutyl, propylmethylene, cyclopropionyl, benzyloxy, trifluoromethyl, aminomethyl, hydroxymethyl, methoxy, formyl, methoxycarbonyl, methylsulfonyl, methylsulfinyl, ethoxy, acetyl, ethylsulfonyl, ethoxycarbonyl, dimethylamino, diethylamino, dimethylaminocarbonyl, and diethylaminocarbonyl;

$N(CH_3)_2$, $NH(CH_3)$, —$CH_2CF_3$, —$CH_2CH_2CF_3$, —$CH_2CH_2F$, —$CH_2CH_2S(=O)_2CH_3$, —$CH_2CH_2CN$,

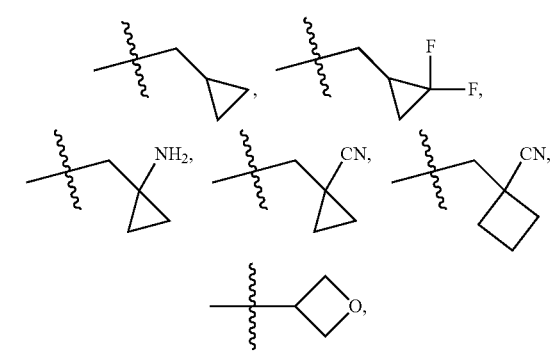
—CH₂CH(OH)(CH₃)₂, —CH₂CH(F)(CH₃)₂, —CH₂CH₂F, —CH₂CF₃, —CH₂CH₂CF₃, —CH₂CH₂NH₂, —CH₂CH₂OH, —CH₂CH₂OCH₃, —CH₂CH₂CH₂OCH₃, —CH₂CH₂N(CH₃)₂, —S(=O)₂CH₃, —CH₂CH₂S(=O)₂CH₃,
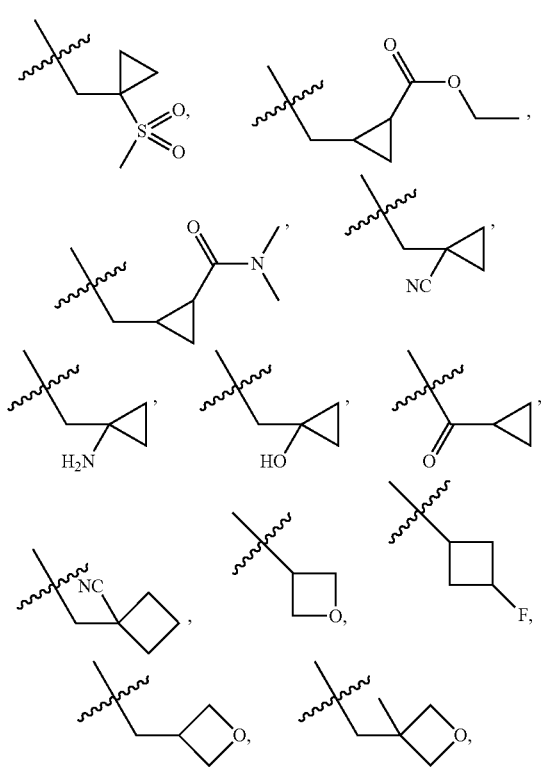
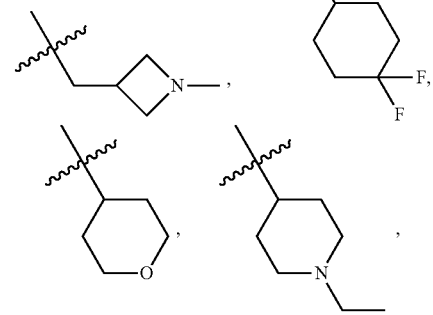
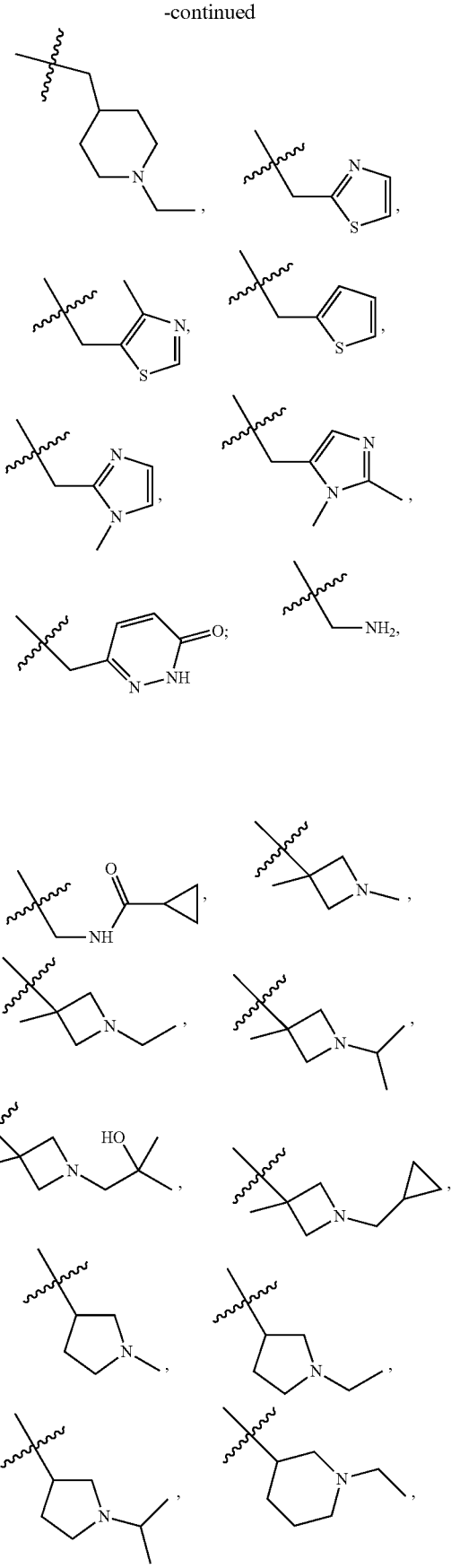

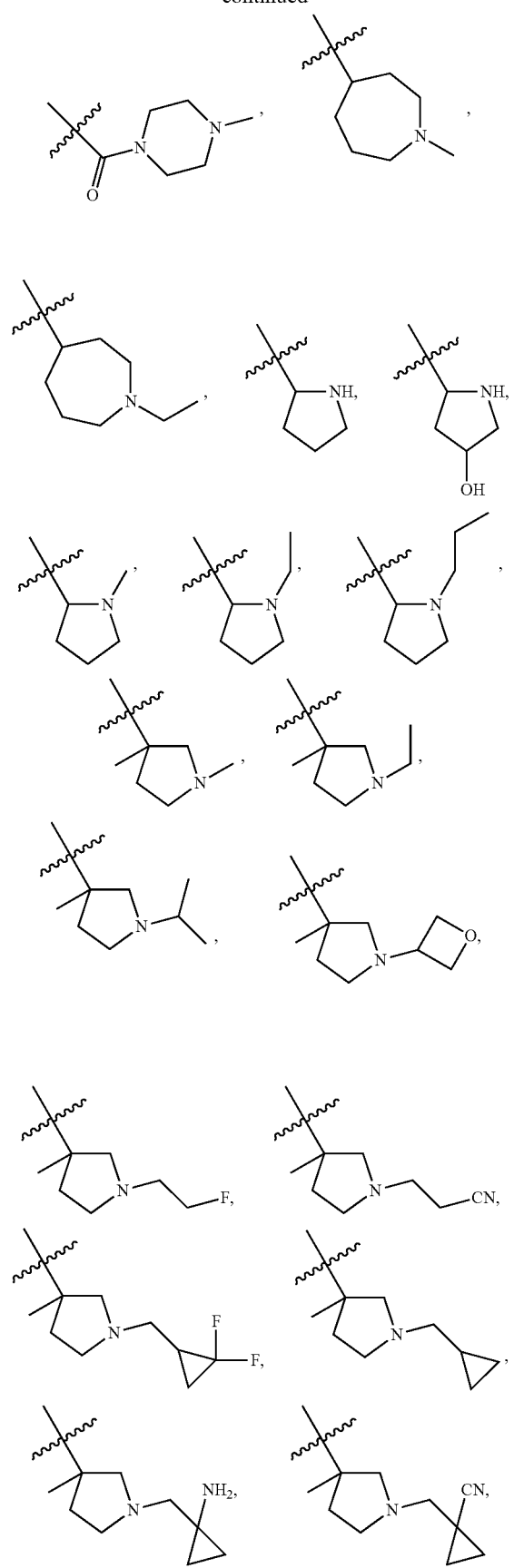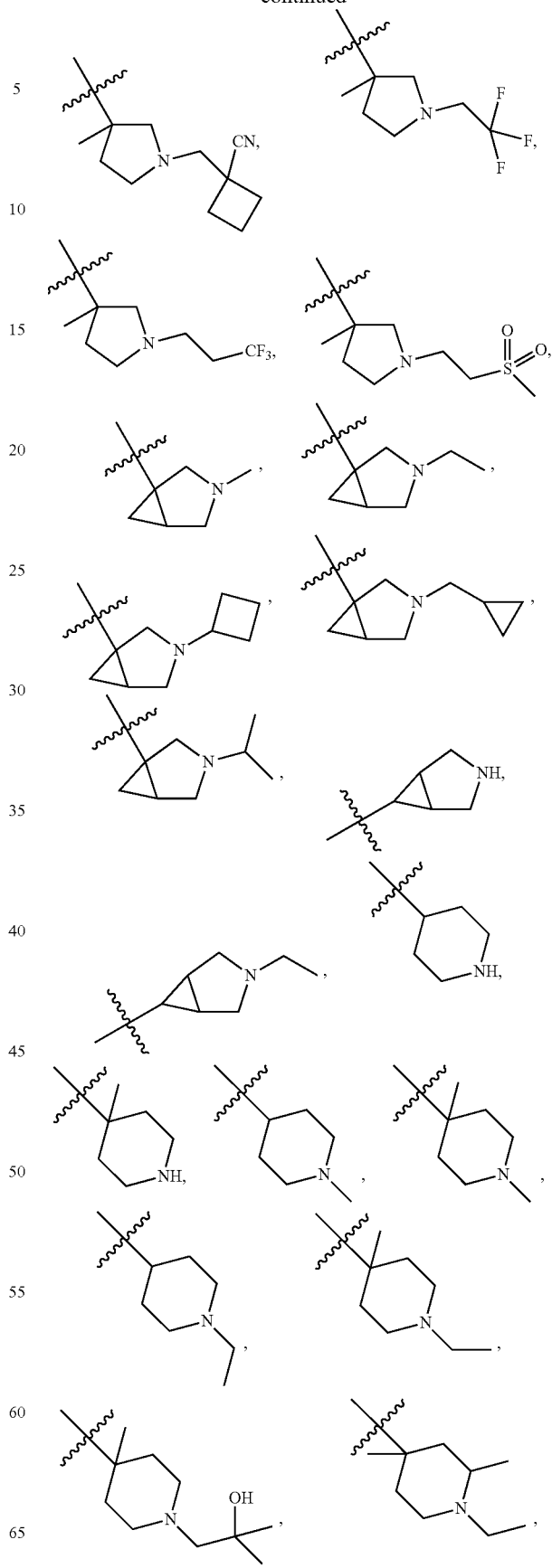

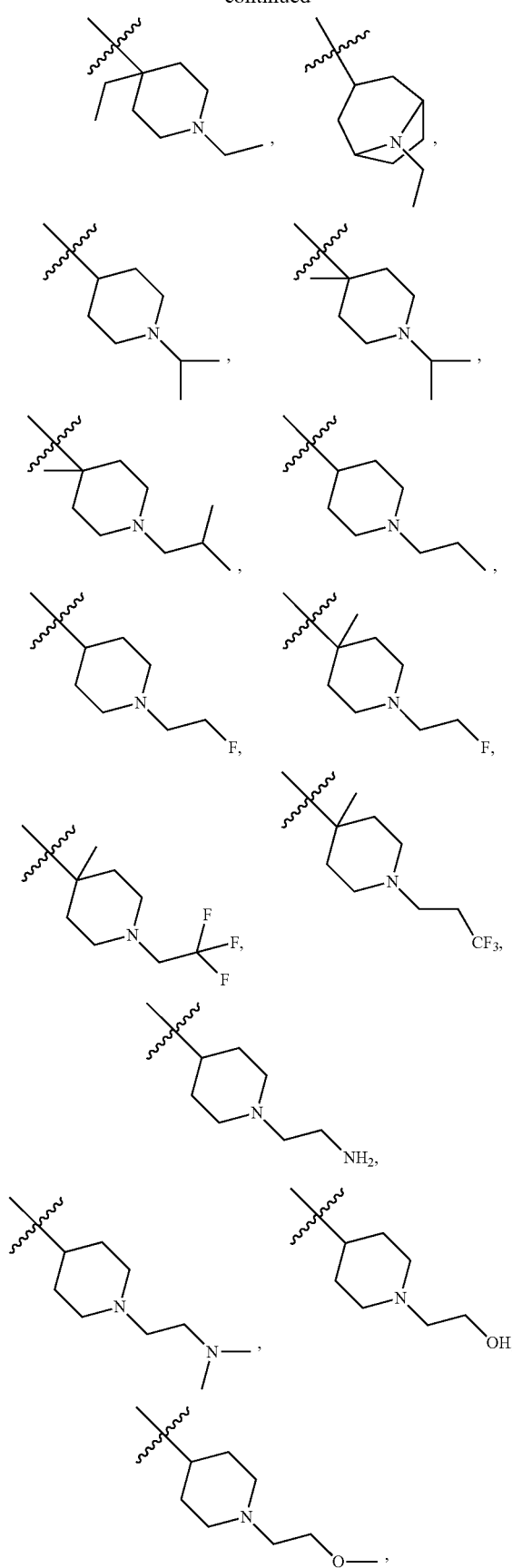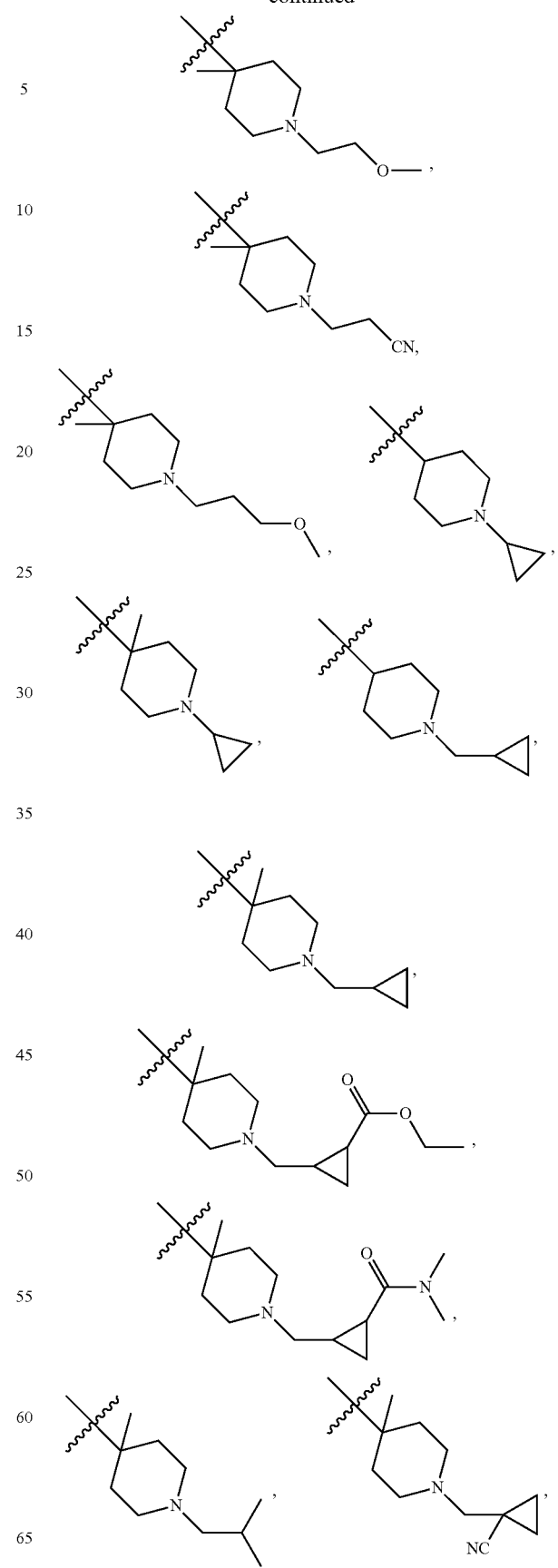

-continued
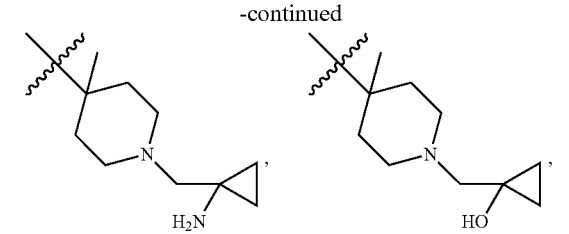
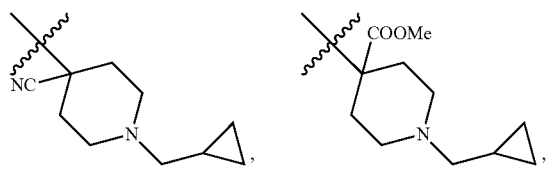
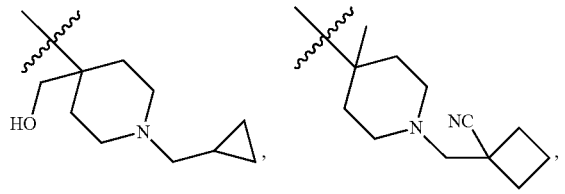
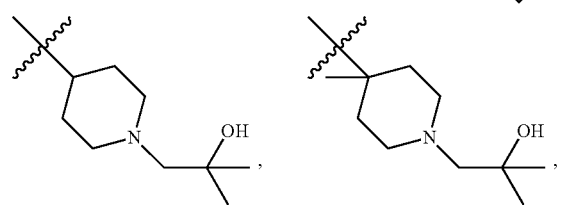
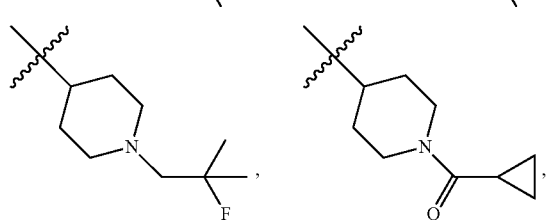
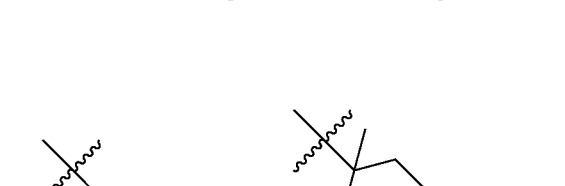
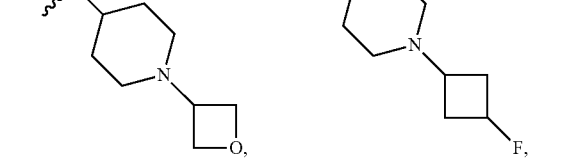
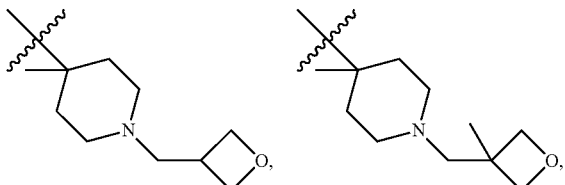
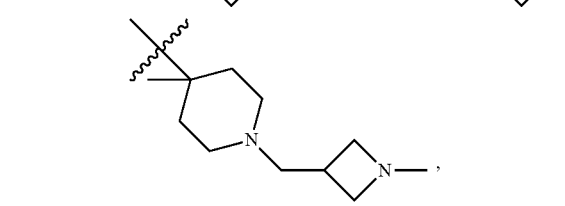
-continued
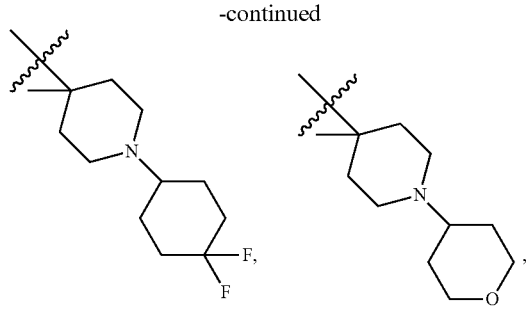
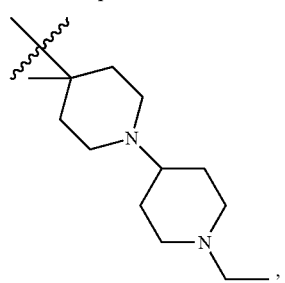
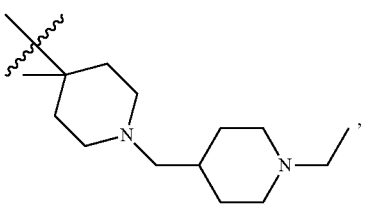
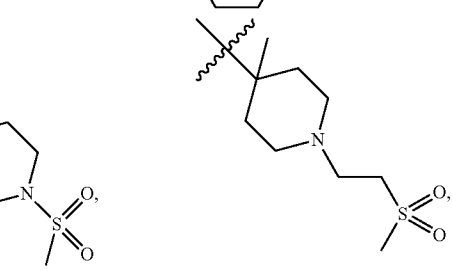
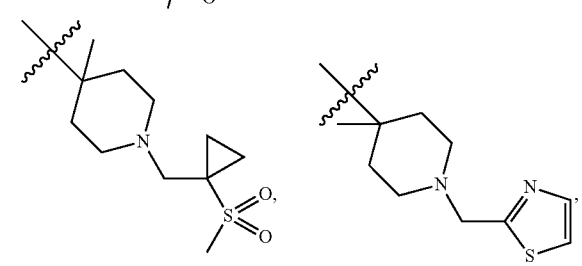
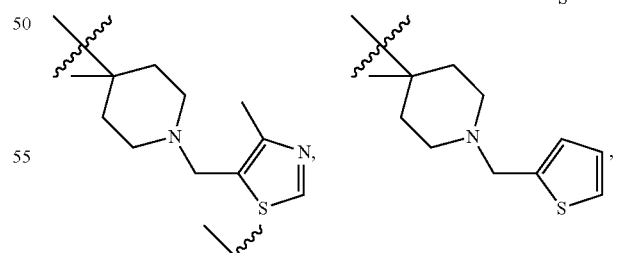
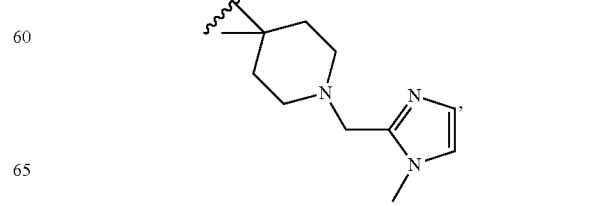

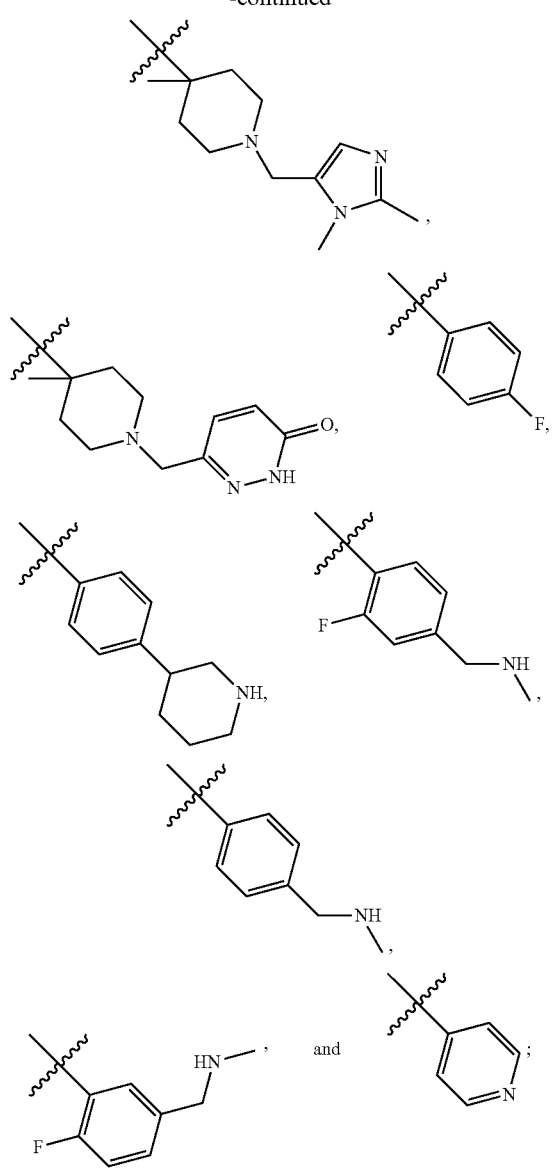
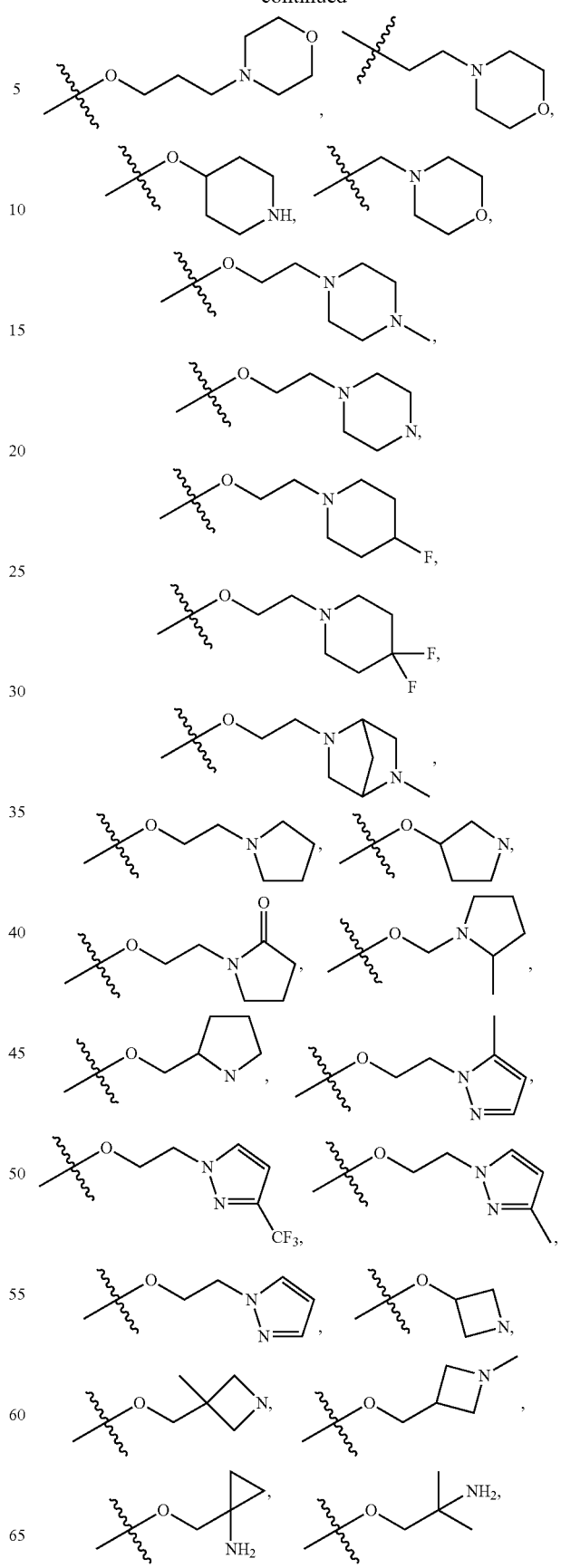

phenyl, thiazolyi, biphenyl, naphthyl, cyclopentyl, furyl, 3-pyrrolinyl, pyrrolidinyl, 1,3-dioxolanyl, pyrazolyl, 2-pyrazolinyl, pyrazolidinyl, imidazolyl, oxazolyl, thiazolyl, 1,2,3-azolyl, 1,2,3-triazolyl, 1,2,4-triazolyl, 1,3,4-thiadiazolyl, 4H-pyranyl, pyridyl, piperidyl, 1,4-dioxanyl, morpholinyl, pyridazinyl, pyrimidinyl, pyrazinyl, piperazinyl, 1,3,5-trithianyl, 1,3,5-triazinyl, benzofuranyl, benzothiophenyl, indolyl, benzimidazolyl, benzothiazolyl, purinyl, quinolyl, isoquinolyl, cinnolinyl and quinoxalinyl;

methyl, ethyl, propyl, methoxy, ethoxy, methylamino, dimethylamino, halomethyl, haloethyl, halopropyl, aminomethyl, aminoethyl, aminopropyl, cyclopropyl; and -continued

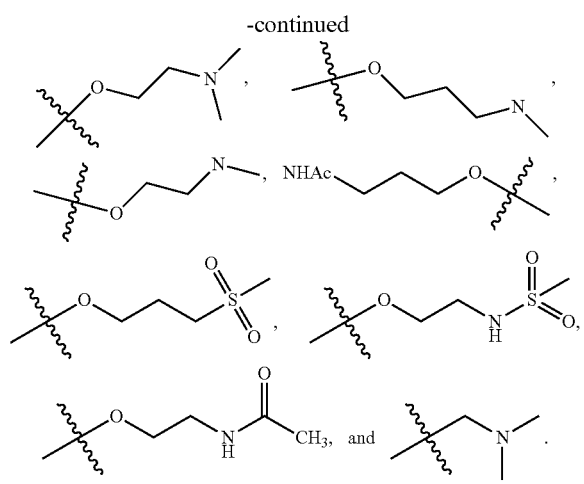

The term "pharmaceutically acceptable" as used herein means those compounds, materials, compositions and/or dosage forms, within the scope of reliable medical judgment, are suitable for use in contact with the tissues of humans and animals without excessive toxicity, irritation, allergic reactions or other problems or complications, while being commensurate with a reasonable benefit/risk ratio.

The term "pharmaceutically acceptable salt" refers to the salt of the compound of the present invention, which is prepared by the compound with specific substituents discovered by the present invention and a relatively non-toxic acid or base. When the compound of the present invention contains a relatively acidic functional group, a base addition salt can be obtained by contacting the compound in a neutral form with a sufficient amount of a base in a pure solution or suitable inert solvent. The pharmaceutically acceptable base addition salt includes the salts of sodium, potassium, calcium, ammonium, organic ammonia or magnesium or the like. When the compound of the present invention contains a relatively alkaline functional group, an acid addition salt can be obtained by contacting the compound in a neutral form with a sufficient amount of an acid in a pure solution or suitable inert solvent. Examples of the pharmaceutically acceptable acid addition salt include an inorganic acid salt, wherein the inorganic acid includes such as hydrochloric acid, hydrobromic acid, nitric acid, carbonic acid, bicarbonate, phosphoric acid, hydrogen phosphate, dihydrogen phosphate, sulfuric acid, hydrogen sulfate, hydriodic acid, phosphorous acid, etc.; and an organic acid salt, wherein the organic acid includes such as acetic acid, propionic acid, isobutyric acid, maleic acid, malonic acid, benzoic acid, succinic acid, suberic acid, fumaric acid, lactic acid, mandelic acid, phthalic acid, phenylsulfonic acid, p-toluene sulfonic acid, citric acid, tartaric acid, methylsulfonic acid and the like; and also includes a salt of an amino acid (e.g. arginine), and a salt of an organic acid such as glucuronic acid and the like (see Berge et al., "Pharmaceutical Salts", Journal of Pharmaceutical Science 66: 1-19 (1977)). Some specific compounds of the present invention contain alkaline and acidic functional groups so as to be able to be converted to any base addition salts or acid addition salts.

Preferably, the neutral form of a compound is regenerated by contacting a salt with a base or an acid in a conventional manner and then separating the parent compound. The difference between a parent form of a compound and the various salt forms thereof lies in some physical properties (such as the solubilities in a polar solvent are different).

The "pharmaceutically acceptable salt" as used herein belongs to the derivatives of the compound of the present invention, wherein the parent compound is modified by being salified with an acid or base. Examples of the pharmaceutically acceptable salt include but not limited to: an inorganic or organic acid salt of a base (such as amine), an alkali metal or organic salt of an acid (such as carboxylic acid), and so on. The pharmaceutically acceptable salt includes common non-toxic salts or quaternary ammonium salts of the parent compound, such as a salt formed by a non-toxic inorganic or organic acid. The common non-toxic salts include but not limited to those salts derived from inorganic acids and organic acids, wherein the inorganic acids or organic acids are selected from 2-acetoxybenzoic acid, 2-isethionic acid acetic acid, ascorbic acid, benzenesulfonic acid, benzoic acid, bicarbonate, carbonic acid, citric acid, edetic acid, ethanedisulfonic acid, ethanesulfonic acid, fumaric acid glucoheptose, gluconic acid, glutamic acid, glycolic acid, hydrobromic acid, hydrochloric acid, hydriodate, hydroxyl, hydroxylnaphthalene, isethionic acid, lactic acid, lactose, dodecanesulfonic acid, maleic acid, malic acid, mandelic acid, methanesulfonic acid, nitric acid, oxalic acid, pamoic acid, pantothenic acid, phenylacetic acid, phosphoric acid, polygalacturonan, propionic acid, salicylic acid, stearic acid, subacetic acid, succinic acid, aminosulfonic acid, sulfanilic acid, sulphuric acid, tannic acid, tartaric acid and p-toluene sulfonic acid.

The pharmaceutically acceptable salt of the present invention can be synthesized with a parent compound containing an acidic or alkaline group by a conventional chemical method. Generally, the preparation method of the salt comprises: reacting these compounds in the forms of free acids or bases with a stoichiometric amount of proper bases or acids in water or an organic solvent or the mixture of water and an organic solvent. In general, a non-aqueous media such as ether, ethyl acetate, ethanol, isopropanol or acetonitrile is preferable.

Except for a salt form, there is a prodrug form for the compound of the present invention. The prodrug of the compound described in the present invention is easily converted to the compound of the present invention via chemical changes under physiological conditions. Besides, the prodrug can be converted to the compound of the present invention via a chemical or biochemical method in vivo environment.

Some compounds of the present invention may exist in non-solvate or solvate forms, including hydrate forms. In general, the solvate form is similar to the non-solvate form, both of which are included within the scope of the present invention. Some compounds of the present invention may exist in polycrystalline or amorphous forms.

Some compounds of the present invention may contain asymmetric carbon atoms (optical center) or double bonds. Racemic isomers, diastereomers, geometric isomers and single isomers are included within the scope of the present invention.

The diagrammatic representation of the racemic, ambiscalemic and scalemic or enantiomerically pure compound of the present invention is from Maehr, J. Chem. Ed. 1985, 62: 114-120. Unless otherwise indicated, the absolute configuration of a stereocenter is represented by wedge and dashed bonds. When the compound of the present invention contains a vinyl double bond or other geometric asymmetric centers, unless otherwise specified, E and Z geometric isomers are included. Similarly, all tautomeric forms are included within the scope of the present invention.

The compound of the present invention may exist as specific geometric or stereoisomeric isomers. The present invention envisages all of these compounds, including cis- and trans-isomers, (−)- and (+)-enantiomers. (R)- and (S)-enantiomers, diastereomers, (D)-isomers, (L)-isomers, as well as racemic mixtures and other mixtures, such as enantiomer- or diastereoisomer-enriched mixtures, all of these mixtures are included within the scope of the present invention. Other asymmetric carbon atoms may exist in substituents such as alkyl. All of these isomers and their mixtures are included within the scope of the present invention.

Optically active (R)- and (S)-isomers and (D)- and (L)-isomers can be prepared by asymmetric synthesis or chiral reagents or other conventional techniques. If an enantiomer of a compound of the present invention is wanted, it can be prepared by asymmetric synthesis or the derivatization action with chiral auxiliaries, in which the resulting diastereomer mixtures are isolated, and the auxiliary groups are cleaved to provide the desired pure enantiomer. Alternatively, when a molecule contains an alkaline functional group (such as amino) or an acidic functional group (such as carboxyl), the molecule is reacted with an appropriate optical active acid or base to form a diastereomer salt, the diastereomer is resoluted by fractional crystallization or chromatography method which are known in the art, and then pure enantiomers can be recycled. In addition, the separation of enantiomers and diastereomers is usually realized by chromatographic method, and the chromatography method employs a chiral stationary phase, and optionally is combined with the chemical derivatization method (e.g. a carbamate is generated from an amine).

The compound of the present invention may comprise unnatural proportion of atomic isotopes at one or more atoms that constitute the compound. For example, the compound can be labeled by a radioactive isotope, such as tritium ($^3H$), iodine-125($^{125}I$) or C-14($^{14}C$). All the variants composed by isotopes of the compound disclosed in the present invention, whether radioactive or not, are included within the scope of the present invention.

The term "a pharmaceutically acceptable carrier" refers to any formulation or carrier medium which is capable of delivering an effective amount of the active substance disclosed in the present invention, does not interfere with the biological activity of the active substance, and has no toxic side-effects on a host or patient. Representative carriers include water, oil, vegetables and minerals, cream base, lotion matrix, ointment matrix, etc. These matrixes include suspensions, viscosity increasers, transdermal enhancers, etc. Their formulations are well known to the artisan in the cosmetic or topical drug field. Other information about the carrier can refer to Remington: The Science and Practice of Pharmacy, 21st Ed., Lippincott, Williams & Wilkins (2005), the content of which is incorporated herein by reference.

The term "excipient" usually refers to a carrier, diluent and/or medium required for the preparation of an effective pharmaceutical composition.

For a drug or pharmacological active agent, the term "effective amount" or "therapeutically effective amount" refers to a sufficient amount of a drug or formulation that can achieve desired effects but is non-toxic. For the oral dosage form of the present invention, "an effective amount" of an active substance in a composition refers to an amount required to achieve desired effects when the active substance is combined with another active substance in the composition. The determination of an effective amount varies from person to person, depending on the age and the general condition of a subject, and also depending on the specific active substance. An appropriate effective amount in individual cases can be determined by the person skilled in the art according to conventional tests.

The term "active ingredient", "therapeutic agent", "active substance" or "active agent" refers to a chemical entity, which can effectively treat a target disorder, disease or condition.

The term "substituted" refers to one or more hydrogen atoms in a specific atom are substituted by a substituent, including deuterium and variants of hydrogen, as long as the valence state of the specific atom is normal and the compound obtained after substitution is stable. When the substituent is a ketone group (i.e. ═O), it means that two hydrogen atoms are substituted. The substitution of a ketone group does not occur in an aryl. The term "optionally substituted" means that it may be substituted or not be substituted, and unless otherwise specified, the type and number of substituents can be arbitrary under the premise that it can be achieved in chemistry.

When one of the variables is a single bond, it means that the two groups to which the varfiable is connected are directly connected to each other. For example, when L in A-L-Z represents a single bond, A-L-Z actually means that the structure is A-Z.

When any variable (e.g. R) occurs more than one time in the composition or structure of a compound, the definition in each occurrence is independent. Therefore, for example, if a group is substituted by 0-2 of R, the group may optionally be substituted by at most two R, and R in each case has an independent option. In addition, the combination of substituents and/or their variants is allowed only if such a combination will lead to a stable compound. For example, the structure unit

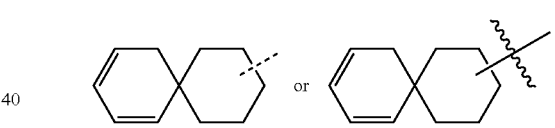

represents that the substitution may occur at any position in the cyclohexyl or cyclohexadienyl.

When the bonds of a substituent may be crossly connected to two atoms of a ring, the substituent may be bonded to any atoms in the ring. When the listed substituent does not specify through which atom it is connected to the chemical structure formula including the compound that is not specifically mentioned, the substituent can be bonded through any of its atoms. The combination of substituents and/or their variants is allowed only if such a combination will lead to a stable compound.

The substituent for an alkyl and heteroalkyl group (including those groups commonly referred to as alkylene, alkenyl, heteroalkylene, heteroalkenyl, alkynyl, cycloalkyl, heterocycloalkyl, cycloalkenyl and heterocycloalkenyl) is generally called as "alkyl substituent", which may be selected from but not limited to one or more of the following groups: —R', —OR', ═O, ═NR', ═N—OR', —NR'R", —SR', halogen, —SiR'R"R'", OC(O)R', —C(O)R', —CO$_2$R', —CONR'R", —OC(O)NR'R", —NR"C(O)R', NR'C(O)NR"R'", —NR"C(O)$_2$R', —NR''''—C(NR'R"R''') ═NR'''', NR''''C(NR'R")═NR''', —S(O)R', —S(O)$_2$R', —S(O)$_2$NR'R", NR"SO$_2$R', —CN, —NO$_2$, —N$_3$, —CH(Ph)$_2$ and fluoro(C$_1$-C$_4$)alkyl, and the number of the substituent is 0 to (2 m'+1), wherein m' is the total number of the carbon atoms in the group. R', R", R'", R"" and R""" are each independently preferably H, substituted or unsubstituted heteroalkyl, substituted or unsubstituted aryl (e.g. aryl substituted by 1~3 of halogen), and substituted or unsubstituted alkyl, alkoxy, thioalkoxy or aralkyl. When the compound of the present invention includes more than one R group, for example, each of the R groups is independently selected, as each of R', R", R'", R"" and R""" groups when more than one of those groups is included. When R' and R" are attached to the same nitrogen atom, they together with the nitrogen atom may form a 5-, 6-, or 7-membered ring. For example, —NR'R" is intended to include but not limited to 1-pyrrolidinyl and 4-morpholinyl. According to the above discussion on substituents, a person skilled in the art can understand, the term "alkyl" is intended to include a group formed by bonding a carbon atom to a non-hydrogen group, such as a haloalkyl (e.g. —CF$_3$, —CH$_2$CF$_3$) and an acyl (e.g. —C(O)CH$_3$, —C(O)CF$_3$, —C(O)CH$_2$OCH$_3$, etc.).

Similar to the substituent for an alkyl group, the substituent for aryl and heteroaryl groups is generally collectively called as "aryl substituent", which may be selected from such as —R', —OR', —NR'R", —SR', -halogen, —SiR'R"R'", OC(O)R', —C(O)R', —CO$_2$R', —CONR'R", —OC(O)NR'R", —NR"C(O)R', NR'C(O)NR"R'", —NR"C(O)$_2$R', —NR""—C(NR'R"R'")=NR"", NR""C(NR'R")=NR'", —S(O)R', —S(O)$_2$R', —S(O)$_2$NR'R", NR"SO$_2$R', —CN, —NO$_2$, —N$_3$, —CH(Ph)$_2$, fluoro(C$_1$-C$_4$) alkoxy and fluoro(C$_1$-C$_4$)alkyl, the number of the substituent ranges from zero to the total number of the open valences on the aromatic ring system; wherein R', R", R'", R"" and R""" are independently and preferably selected from H, substituted or unsubstituted alkyl, substituted or unsubstituted heteroalkyl, substituted or unsubstituted aryl and substituted or unsubstituted heteroaryl.

When the compound of the present invention includes more than one R group, for example, each of the R groups is independently selected, as each of R', R", R'", R"" and R""" groups when more than one of those groups is included.

Two substituents attached to adjacent atoms in an aryl or heteroaryl ring may optionally be substituted by a substituent with the general formula -T-C(O)—(CRR')q-U—, wherein the T and U are independently selected from the group consisting of —NR—, —O—, CRR'— and a single bond, and q is an integer from 0 to 3. As an alternative, two substituents attached to adjacent atoms in an aryl or heteroaryl ring may optionally be substituted by a substituent with the general formula -A(CH$_2$)rB—, wherein the A and B are independently selected from the group consisting of —CRR'—, —O—, —NR—, —S—, —S(O)—, S(O)$_2$—, —S(O)$_2$NR'— and a single bond, and r is an integer from 1 to 4. Optionally, a single bond in the new ring thereby formed may be replaced by a double bond. As an alternative, two substituents attached to adjacent atoms in an aryl or heteroaryl ring may optionally be substituted by a substituent with the general formula -A(CH$_2$)rB—, wherein the s and d are each independently selected from an integer from 0 to 3, and X is —O—, —NR', —S—, —S(O)—, —S(O)$_2$— or —S(O)$_2$NR'—. The substituents R, R', R'" and R'" are each independently preferably selected from the group consisting of hydrogen and substituted or unsubstituted (C$_1$-C$_6$) alkyl.

Unless otherwise specified, the term "halo" or "halogen" itself or as a part of another substituent refers to fluorine, chlorine, bromine or iodine atom. In addition, the term "haloalkyl" is intended to include monohaloalkyl and polyhaloalkyl. For example, the term "halo(C$_1$-C$_4$) alkyl" is intended to include but not limited to trifluoromethyl, 2,2,2-trifluoroethyl, 4-chlorobutyl and 3-bromopropyl, etc.

Examples of haloalkyl include but not limited to trifluoromethyl, trichloromethyl, pentafluoroethyl, and pentachloroethyl. The "alkoxy" represents that the above-mentioned alkyl group with a specific number of carbon atoms is connected to an oxygen bridge. C$_{1-6}$ alkoxy includes C$_1$, C$_2$, C$_3$, C$_4$, C$_5$ and C$_6$ alkoxy. Examples of alkoxy include but not limited to methoxy, ethoxy, n-propoxy, iso-propoxy, n-butoxy, sec-butoxy, tert-butoxy, n-pentyloxy and S-pentyloxy. The "cycloalkyl" includes saturated cycloalkyls, such as cyclopropyl, cyclobutyl and cyclopentyl. The 3- to 7-membered cycloalkyl includes C$_3$, C$_4$, C$_5$, C$_6$ and C$_7$ cycloalkyl. The "alkenyl" includes linear or branched hydrocarbon chains, wherein there are one or more C—C double bonds on any stable sites on the chain, such as vinyl and propenyl.

The term "halo" or "halogen" refers to fluorine, chlorine, bromine and iodine.

Unless otherwise specified, the term "hetero" represents a heteroatom or a heteroatom group (i.e. a group containing a heteroatom), including atoms except for carbon (C) and hydrogen (H) and groups containing these heteroatoms, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)N(H)— or —S(=O)N(H)—.

Unless otherwise specified, the "ring" represents substituted or unsubstituted cycloalkyl, heterocycloalkyl, cycloalkenyl, heterocycloalkenyl, cycloalkynyl, heterocycloalkynyl, aryl or heteroaryl. The ring includes a single ring, a linked ring, a spiro ring, a fused ring or a bridged ring. The number of the atoms in the ring is usually defined as the member of the ring, for example, "5- to 7-membered ring" is a ring looped with 5 to 7 atoms. Unless otherwise specified, the ring optionally contains 1-3 of heteroatoms. Therefore, "5- to 7-membered ring" includes, for example, phenyl, pyridinyl and piperidinyl; on the other hand, the term "5- to 7-membered heterocycloalkyl" includes pyridyl and piperidinyl, but does not include phenyl. The term "ring" also includes a ring system containing at least one ring, wherein each "ring" independently meets the above definition.

Unless otherwise specified, the term "heterocycle" or "heterocyclyl" refers to a stable monocyclic, bicyclic or tricyclic ring containing a heteroatom or a heteroatom group, they may be saturated, partially unsaturated or unsaturated (aromatic), and they contain carbon atoms and 1, 2, 3 or 4 heteroatoms in the ring which are independently selected from the group consisting of N, O and S, wherein any of the above-mentioned heterocycle may be fused to a benzene ring to form a bicyclic ring. Nitrogen and sulfur heteroatoms may be optionally oxidized (i.e., NO and S(O) p). The nitrogen atom may be substituted or unsubstituted (i.e. N or NR, wherein R is H or other substituents that have been defined herein). The heterocycle may be attached to the side group of any heteroatoms or carbon atoms to form a stable structure. If the formed compound is stable, the heterocycle described herein may be substituted on its carbon or nitrogen atom. The nitrogen atom in the heterocycle is optionally quaternized. A preferred embodiment is, when the total number of S and O atoms in the heterocycle is more than 1, these heteroatoms are not adjacent to each other. Another preferred embodiment is the total number of S and O atoms in the heterocycle is not more than 1. As used herein, the term "aromatic heterocyclic group" or "heteroaryl" refers to a stable 5-, 6-, 7-membered monocyclic or bicyclic or 7-, 8-, 9- or 10-membered bicyclic heteroaromatic ring, which contains carbon atoms and 1, 2, 3 or 4 heteroatoms in the ring which are independently selected from the group consisting of N, O and S. The nitrogen atom may be substituted or unsubstituted (i.e. N or NR, wherein R is H or other substituents that have been defined herein). Nitrogen and sulfur atoms may be optionally oxidized (i.e., NO and S(O)p). It is worth noting that, the total number of S and O atoms in the heteroaromatic ring is not more than 1. Bridged rings are also included in the definition of the heterocycle. When one or more atoms (i.e. C, O, N, or S) are connected to two nonadjacent carbon atoms or nitrogen atoms, a bridged ring is formed. The preferred bridged ring includes but not limited to one carbon atom, two carbon atoms, one nitrogen atom, two nitrogen atoms and one carbon-nitrogen group. It is worth noting that, a bridge always converts a monocyclic ring into a tricyclic ring. In the bridged ring, the substituent in the ring may also locate on the bridge.

Examples of heterocyclyl include but not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indoalkenyl, indolinyl, indolizinyl, indolyl, 3H-indolyl, isatino group, isobenzofuranyl, isoindolyl, isoindolinyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidyl, phenanthridinyl, phenanthrolinyl, phenazine, phenothiazine, benzoxanthinyl, phenoxazinyl, phthalazinyl, piperazinyl, piperidyl, piperidonyl, 4-piperidonyl, piperonyl, pteridyl, purinyl, pyranyl, pyrazinyl, pyrazolidinyl, pyrazolinyl, pyrazolyl, pyridazinyl, pyridooxazole, pyridoimidazole, pyridothiazole, pyridyl, pyrrolidinyl, pyrrolinyl, 2H-pyrrolyl, pyrrolyl, quinazolinyl, quinolyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazyl, isothiazolylthienyl, thienoxazolyl, thienothiazolyl, thienoimidazolyl, thienyl, triazinyl, 1,2,3-triazolyl, 1,2,4-triazolyl, 1,2,5-triazolyl, 1,3,4-triazolyl and xanthenyl. Fused-ring and spiro-ring compounds are also included.

Unless otherwise specified, the term "hydrocarbyl" or its specific terms (such as alkyl, alkenyl, alknyl and phenyl) themself or as a part of another substituent represent a linear, branched or cyclic hydrocarbon group or a combination thereof, which may be completely saturated, or mono- or poly-unsaturated, may be monosubstituted, disubstituted or multisubstituted, may include bivalent or multivalent atomic groups, and have a specified number of carbon atoms (for example, $C_1$-$C_{10}$ represents 1 to 10 carbon atoms). The term "hydrocarbyl" includes but not limited to aliphatic hydrocarbyl and aromatic hydrocarbyl. The aliphatic hydrocarbyl includes linear and cyclic aliphatic hydrocarbyl, and specifically includes but not limited to alkyl, alkenyl and alkynyl. The aromatic hydrocarbyl includes but not limited to 6- to 12-membered aromatic hydrocarbyl, such as phenyl, naphthyl and the like. In some embodiments, the term "alkyl" represents a linear or branched atomic group or a combination thereof, which may be completely saturated, or mono- or poly-unsaturated, and may include divalent and polyvalent groups. Examples of saturated hydrocarbon groups include but not limited to homologues or isomers of methyl, ethyl, n-propyl, iso-propyl, n-butyl, tert-butyl, iso-butyl, sec-butyl, iso-butyl, cyclohexyl, (cyclohexyl)methyl, cyclopropyl methyl, and n-amyl, n-hexyl, n-heptyl, n-octyl and the like. Unsaturated alkyl has one or more double bonds or triple bonds, and its examples include but not limited to vinyl, 2-propenyl, butenyl, crotyl, 2-isopentenyl, 2-butadienyl, 2,4-pentadienyl, 3-(1,4-pentadienyl), acetenyl, 1- and 3-propinyl, 3-butynyl, and more advanced homologues and isomers.

Unless otherwise specified, the term "heterohydrocarbyl" or its specific terms (such as heteroalkyl, heteroalkenyl, heteroalkynyl and heteroaryl) themself or combining with another term represents a stable linear, branched or cyclic hydrocarbon group or a combination thereof, which consists of a certain number of carbon atoms and at least one heteroatom. In some embodiments, the term "heteroalkyl" itself or combining with another term represents to a stable linear, or branched hydrocarbon group or a combination thereof, which consists of a certain number of carbon atoms and at least one heteroatom. In a typical embodiment, the heteroatom is selected from the group consisting of B, O, N and S, in which the nitrogen and sulfur atoms are optionally oxidized, and the nitrogen atom is optionally quaternized. Heteroatoms B, O, N and S may be located in any internal positions of the heterohydrocarbyl (including the position where the hydrocarbyl is attached to the rest part of the molecule). Examples include but not limited to —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$ and —CH=CH—N(CH$_3$)—CH$_3$. At most two heteroatoms may be adjacent, such as —CH$_2$—NH—OCH$_3$.

The terms "alkoxy", "alkylamino" and "alkylthio" (or thioalkoxy) are the idiomatic expressions, which refer to the alkyl groups which are attached to the rest of a molecule through an oxygen atom, an amino, or a sulfur atom, respectively.

Unless otherwise specified, the terms "cyclohydrocarbyl", "heterocyclohydrocarbyl" or specific terms thereof (such as aryl, heteroaryl, cycloalkyl, heterocycloalkyl, cycloalkenyl, heterocycloalkenyl, cycloalkynyl and heterocycloalkynyl) themself or combining with other terms respectively represent a cyclic "hydrocarbyl" or "heterohydrocarbyl". In addition, in terms of heterohydrocarbyl or heterocyclohydrocarbyl (such as heteroalkyl and heterocycloalkyl), heteroatoms may occupy the position where the heterocyclic ring is attached to the rest part of the molecule. Examples of cycloalkyl include but not limited to cyclopentyl, cyclohexyl, 1-cyclohexenyl, 3-cyclohexenyl, cycloheptyl, etc. Non-limited examples of heterocyclyl include 1-(1,2,5,6-tetrahydropyridinyl), 1-piperidyl, 2-piperidyl, 3-piperidyl, 4-morpholinyl, 3-morpholinyl, tetrahydrofuran-2-yl, tetrahydrofuranylindol-3-yl, tetrahydrothiophen-2-yl, tetrahydrothiophen-3-yl, 1-piperazinyl and 2-piperazinyl.

Unless otherwise specified, the term "aryl" represents a polyunsaturated aromatic hydrocarbon substituent, which may be monosubstituted, disubstituted or multisubstituted. It may be monocyclic or polycyclic (preferably 1-3 rings). They are fused together or connected covalently. The term "heteroaryl" refers to an aryl (or ring) containing 1 to 4 heteroatoms. In an exemplary embodiment, the heteroatom is selected from the group consisting of B, N, O, and S, in which the nitrogen and sulfur atoms are optionally oxidized, and the nitrogen atom is optionally quaternized. The heteroaryl may be connected to the rest part of the molecule via a heteroatom. Non-limited examples of aryl or heteroaryl include phenyl, 1-naphthyl, 2-naphthyl, 4-biphenyl, I-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzoimidazolyl, 5-indolyl, 1-isoquinolyl, 5-isoquinolyl, 2-quinoxalyl, 5-quinoxalyl, 3-quinolyl and 6-quinolyl. The substituents of any one of the above-mentioned aryl and heteroaryl ring system are selected from the acceptable substituents described below.

For the sake of briefness, when used in combination with other terms (e.g. aryloxy, arylthio, aralkyl), the aryl includes the aryl and heteroaryl ring as defined above. Therefore, the term "aralkyl" is intended to include those groups in which aryl is attached to alkyl (e.g. benzyl, phenethyl, pyridyl methyl), including those alkyls wherein carbon atoms (such as methylene) have been replaced by, for example, oxygen atoms, such as phenoxy methyl, 2-pyridyloxymethyl 3-(1-naphthoxy)propyl.

The term "leaving group" refers to a functional group or atom which can be replaced by another functional group or atom through a substitution reaction (e.g., nucleophilic substitution reaction). For example, representative leaving groups include triflate; chlorine, bromine, iodine; sulfonate groups, such as mesylate, tosylate, p-bromobenzene sulfonate, p-tosylate; acyloxy, such as acetoxy, trifluoroacetoxy and so on.

The term "protecting group" includes but not limited to "amino protecting groups", "hydroxyl protecting groups", and "mercapto protecting groups". The term "amino protecting groups" refers to a protecting group that is suitable for preventing side reactions from occurring at the nitrogen atom of an amino group. A representative amino protecting group includes but not limited to: formyl; acyl, such as alkanoyl (such as acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenylmethyl (Tr), 1,1-bis-(4'-methoxyphenyl)methyl; silyl, such as trimethylsilyl (TMS) and tert-butyldimethylsilyl (TBS). The term "hydroxyl protecting groups" refers to a protecting group that is suitable for preventing side reactions of a hydroxyl group. A representative hydroxyl protecting group includes but not limited to: alkyl, such as methyl, ethyl, and tert-butyl; acyl, such as alkanoyl (such as acetyl); arylmethyl, such as benzyl (Bn), p-methoxybenzyl (PMB), 9-fluorenylmethyl (Fm) and diphenylmethyl (DPM); silyl, such as trimethylsilyl (TMS) and tert-butyldimethylsilyl (TBS).

The compound of the present invention can be prepared through many synthetic methods which are well-known to the person skilled in the art, including the specific embodiments listed below, embodiments obtained by combining the specific embodiments with other chemical synthetic methods and the equivalent alternative methods which are well-known to the person skilled in the art. The preferred embodiments include but not limited to the examples of the present invention.

All solvents used in the present invention are commercially available and can be used without a further purification. The reactions are generally carried out under an inert nitrogen atmosphere in an anhydrous solvent. Proton nuclear magnetic resonance data were recorded on a Bruker Avance III 400 (400 MHz) spectrometer with chemical shifts expressed in ppm downfield from tetramethylsilane. Mass spectra were measured on an Agilent 1200 Series Plus 6110 (&1956A). LC/MS or Shimadzu MS contains a DAD: SPD-M20A (LC) and Shimadzu Micromass 2020 detector. The mass spectrometer is equipped with an electrospray ionization (ESI) source operated in a positive or negative mode.

The present invention adopts the following abbreviations: aq represents water; HATU represents O-(7-azabenzotriazol-1-yl)-N,N,N',N'-tetramethyluronium hexafluorophosphate; EDC represents N-(3-dimethylaminopropyl)-N'-ethyl carbodiimide hydrochloride; m-CPBA represents 3-chloroperbenzoic acid; eq represents equivalent, equal-quantitative; CDI represents carbonyl diimidazole; DCM represents dichloromethane; PE represents petroleum ether; DIAD represents diisopropyl azodicarboxylate; DMF represents N,N-dimethylformamide; DMSO represents dimethylsulfoxide; EtOAc represents ethyl acetate; EtOH represents ethanol; MeOH represents methanol; CBz represents benzyloxycarbonyl, which is an amino protecting group; Boc represents tert-butoxycarbonyl, which is an amine protecting group; HOAc represents acetic acid; $NaCNBH_3$ represents sodium cyanoborohydride; r.t. represents room temperature; O/N represents overnight; THF represents tetrahydrofuran; $Boc_2O$ represents di-tert-butyl dicarbonate; TFA represents trifluoroacetic acid; DIPEA represents diisopropylethylamine; $SOCl_2$ represents thionyl chloride; $CS_2$ represents carbon disulfide; TsOH represents p-toluenesulfonic acid; NFSI represents N-fluoro-N-(phenylsulfonyl)benzenesulfonamide; NCS represents 1-chloropyrrolidine-2,5-dione; n-$Bu_4$NF represents tetrabutylammonium fluoride; iPrOH represents 2-propanol; mp represents melting point.

The compounds are named artificially or named by ChemDraw® software, and vendor directory names are used for the commercially available compounds.

BRIEF DESCRIPTION OF THE DRAWINGS

FIG. 1-2a shows the results of a pharmacodynamic study II in vivo of a tested drug in a human-derived colon cancer CO-04-0032 subcutaneous xenograft tumor model, wherein:
1) the number of mice in each group was 6;
2) dosing volume: 10 μl/g according to the body weight of mice. If the body weight loss was more than 15%, the dosing regimen should be adjusted accordingly;
3) the solvent of BKM120: 10% NMP+90% PEG300, PO, QD×4 Weeks;
4) the solvent of Compound 11: water, PO, QD×4 Weeks;
5) the solvent of Compounds 25, 27, and 32: 5% DMSO+60% PEG400+35% water.

FIG. 1-2b shows the results of a pharmacodynamic study II in vivo of a tested drug in a human-derived colon cancer CO-04-0032 subcutaneous xenograft tumor model, wherein:
1) the number of mice in each group was 6;
2) dosing volume: 10 μl/g according to the body weight of mice. If the body weight loss was more than 15%, the dosing regimen should be adjusted accordingly;
3) the solvent of BKM120: 10% NMP+90% PEG300, PO, QD×4 Weeks;
4) the solvent of Compound 11: water, PO, QD×4 Weeks;
5) the solvent of Compounds 25, 27, and 32: 5% DMSO+60% PEG400+35% water.

FIG. 2-1 shows the results of a pharmacodynamic study I in vivo of a tested drug in a human gastric cancer ST-02-0013 subcutaneous xenograft mouse model, wherein:
1) the number of mice in each group was 5;
2) dosing volume: 10 l/g according to the body weight of mice. If the body weight loss was more than 15%, the dosing regimen should be adjusted accordingly;
3) the solvent of BKM120: 10%6 NMP+90% PEG300, PO, QD×18 days;
4) the solvent of Compound 11: water, PO, QD×18 days;
5) the solvent of Compound 15: 1% MC, PO, QD×18 days.

FIG. 2-2 shows the results of a pharmacodynamic study II in vivo of a tested drug in a human gastric cancer ST-02-0013 subcutaneous xenograft mouse model, wherein:
1) the number of mice in each group was 8;
2) dosing volume: 10 l/g according to the body weight of mice. If the body weight loss was more than 15%, the dosing regimen should be adjusted accordingly;
3) the solvent of Compounds 25, 27, and 32: 5%0/ DMSO+60% PEG400+35% water.

SPECIFIC EMBODIMENTS

Figure 1:
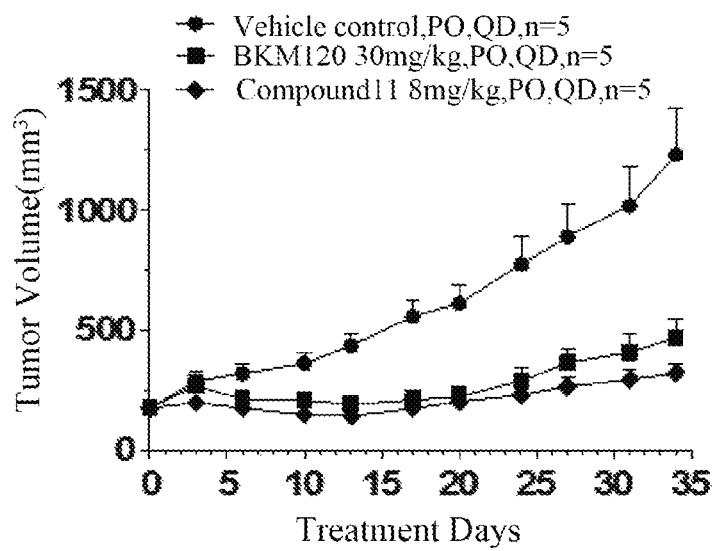
FIG. 1-1 shows the results of a pharmacodynamic study I in vivo of a tested drug in a human-derived colon cancer CO-04-0032 subcutaneous xenograft tumor model, wherein:
1) the number of mice in each group was 5;
2) dosing volume: 10 μl/g according to the body weight of mice. If the body weight loss was more than 15%, the dosing regimen should be adjusted accordingly;
3) the solvent of BKM120: 10% NMP+90% PEG300, PO, QD×5 Weeks;
4) the solvent of Compound 11: water, PO, QD×5 Weeks.

The following examples are given to illustrate the present invention in more detail, but the scope of the present invention is not limited thereto.

Scheme 1:

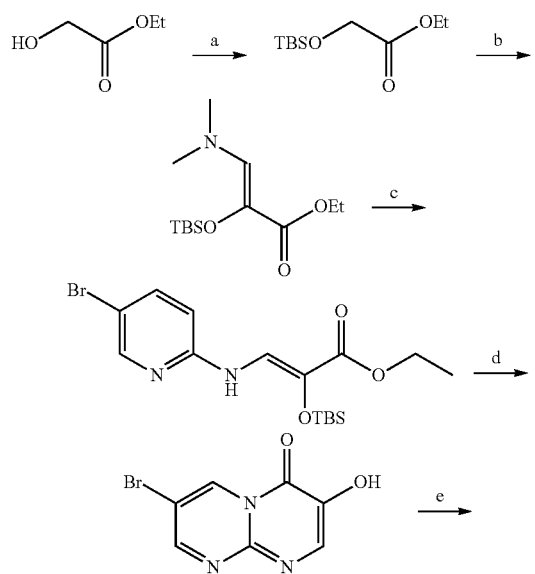

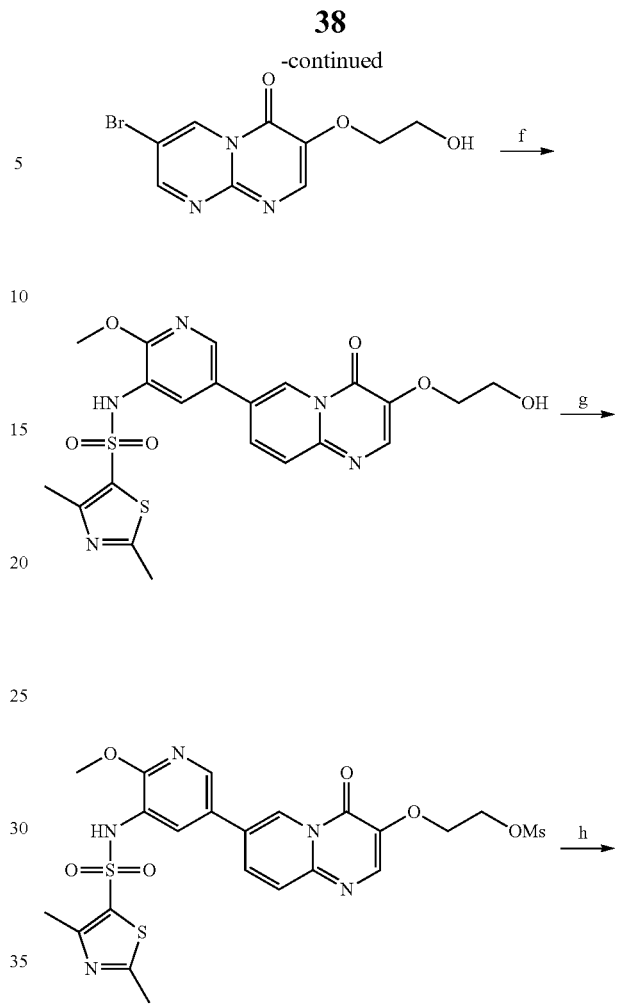

Reaction conditions: a) tert-butyldimethylsilyl chloride, 1H-imidazole; b) 1-tert-butoxy-N,N,N',N'-tetramethyl-diaminomethane, heating; c) 2-amino-5-bromopyridine, acetic acid, heating; d) acetic acid, microwave; e) potassium carbonate. DMF, heating; f) R borate (boric acid), 1,1'-bis(diphenylphosphino)ferrocene palladium chloride, potassium carbonate, dioxane, water, heating; g) methanesulfonyl chloride, triethylamine, dichloromethane, 0° C.; h) 4,4-difluoropiperidine, diisopropylethylamine, acetonitrile, heating.

Example 1

N-(5-(3-(2-(4,4-difluoro-1-piperidinyl)ethoxy)-4-oxo-pyrido[1,2-a]pyrimidin-7-yl]-2-methoxypyridin-3-yl]-2,4-dimethylthiazole-5-sulfonamide

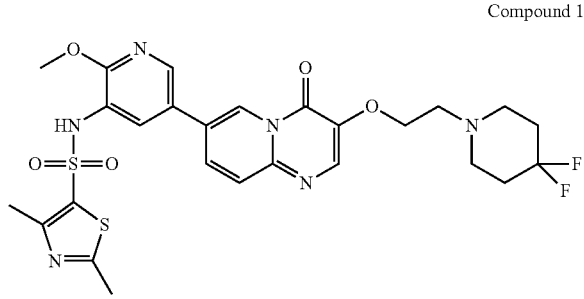 [SMILES: COc1ncc(-c2ccc3ncc(OCCN4CCC(F)(F)CC4)c(=O)n3c2)cc1NS(=O)(=O)c1sc(C)nc1C]

Compound 1 a) Ethyl 2-((tert-butyldimethylsilyl)oxy)acetate

Ethyl glycolate (100 g, 961 mmol) and 1H-imidazole (130 g, 1.9 mol) were dissolved in dichloromethane (1 L) and placed in a three-necked round-bottomed flask, and tert-butyldimethylsilyl chloride (158 g, 1 mol) was added at 0° C. The mixture was stirred at room temperature for 8 hours, washed with water (1 L*3) and dried over sodium sulfate and concentrated to give the title compound (195 g, 93%) as a yellow oil.

1H NMR (400 MHz, CDCl$_3$) ppm δ 4.14-4.09 (m, 4H), 1.20-1.16 (t, 3H), 0.83 (s, 9H), 0.01 (s, 6H).

b) (Z)-Ethyl 2-((tert-butyldimethylsilyl)oxy)-3-(dimethylamino)acrylate

Ethyl 2-((tert-butyldimethylsilyl)oxy)acetate (96 g, 0.44 mol) and 1-tert-butoxy-N,N,N',N'-tetramethyldiaminomethane (91.9 g, 0.53 mol) were stirred under reflux for 24 hours. The mixture was concentrated and the residual liquid was purified by silica gel column chromatography to give the title compound (80 g, 66.6%) as a yellow oil, 1H NMR (400 MHz, CDCl$_3$) ppm δ 6.68 (s, 1H), 4.13-4.11 (q, 2H), 2.96 (s, 6H), 1.28-1.24 (t, 3H), 0.95 (s, 9H), 0.14 (s, 6H).

c) (Z)-Ethyl 3-((5-bromopyridin-2-yl)amino)-2-((tert-butyldimethylsilyl)oxy)acrylate (Z)-Ethyl 3-((5-bromopyridin-2-yl)amino)-2-((tert-butyldimethylsilyl)oxy)acrylate (80 g, 293 mmol) and 2-amino-5-bromopyridine (50.6 g, 293 mmol) were dissolved in acetic acid (800 mL), and stirred at 80° C. for 2 hours. The mixture was concentrated, and the residue was dissolved in ethyl acetate (500 mL), washed with a sodium carbonate solution (500 mL) and saturated brine (500 mL), dried over sodium sulfate and concentrated. The resulting residue was purified by silica gel column chromatography to give the title compound (74 g, 63.0%) as a yellow oil.

1H NMR (400 MHz, CDCl$_3$) ppm δ 8.24 (s, 1H), 7.75-7.72 (d, 1H), 7.63-7.60 (d, 1H), 6.75-6.72 (d, 1H), 6.57-6.54 (d, 1H), 4.25-4.20 (q, 2H), 1.34-1.30 (t, 3H), 1.02 (s, 9H), 0.22 (s, 6H).

d) 7-Bromo-3-hydroxy-4H-pyrido[1,2-a]pyrimidin-4-one (Z)-Ethyl 3-((5-bromopyridin-2-yl)amino)-2-((tert-butyldimethylsilyl)oxy)acrylate (2 g*34, 169 mmol) was dissolved in acetic acid (13 mL*34) and stirred under microwave at 140° C. for 4 hours. The mixture was concentrated, and the residue was dissolved in ethanol (50 mL*34) and filtered to give the title compound (20.4 g, 50%).

1H NMR (400 MHz, CDCl$_3$) ppm δ 8.98 (s, 1H), 8.14 (s, 1H), 8.00-7.98 (d, 1H), 7.79-7.77 (d, 1H).

e) 7-Bromo-3-(2-hydroxyethyl)-4H-pyrido[1,2-a]pyrimidin-4-one

2-Bromoethanol (933 mg, 7.47 mmol), 7-bromo-3-hydroxy-4H-pyrido[1,2-a]pyrimidin-4-one (600 mg, 2.49 mmol) and potassium carbonate (1.03 g, 7.47 mmol) were dissolved in N,N-dimethylformamide (10 mL), and the mixture was stirred at 110° C. for 1 hour under nitrogen protection. LCMS showed that the reaction was completed. The reaction solution was concentrated to give a crude product. The crude product was used directly in the next step.

f) N-(5-(3-(2-hydroxyethyl)-4-oxo-4H-pyrido[1,2-a]pyrimidin-7-yl)-2-methoxypyridin-3-yl)-2,4-dimethylthiazole-5-sulfonamide 7-Bromo-3-(2-hydroxyethyl)-4H-pyrido[1,2-a]pyrimidin-4-one (704 mg, 2.49 mmol) was dissolved in dioxane (10 mL) and water (2 mL), and N-(2-methoxy-5-(4,4,5,5-tetramethyl-1,3,2-dioxaborolan-2-yl)pyridin-3-yl)-2,4-dimethylthiazole-5-sulfonamide (1.06 g, 2.49 mmol), potassium carbonate (687 mg, 4.97 mmol) and 1,1'-bis(diphenylphosphino)ferrocene palladium chloride (50 mg) were added. The reaction solution was stirred to react at 100° C. for 3 hours. LCMS showed that the reaction was completed. The reaction solution was filtered and concentrated to give a crude product, and the crude product was purified by preparative high performance liquid chromatography to give the title product (500 mg, 40%0) as a white solid.

1H NMR (400 MHz, CDCl$_3$) ppm δ 9.09 (s, 1H), 8.24 (s, 1H), 8.18 (d, 1H), 8.01 (d, 1H), 7.80-7.67 (m, 1H), 4.28-4.22 (m, 2H), 4.01-3.92 (m, 5H), 2.65 (s, 3H). 2.56 (s, 3H).

g) 2-((7-(5-(2,4-Dimethylthiazole 2,4-dimethylthiazole-5-sulfonamido)-6-methoxypyridin-3-yl)-4-oxo-4H-pyrido[1,2-a]pyrimidin-3-yl)oxy)ethyl methanesulfonate N-(5-(3-(2-Hydroxyethoxy)-4-oxo-4H-pyrido[1,2-a]pyrimidin-7-yl)pyridin-3-yl)-2,4-dimethylthiazole-5-sulfonamide (50.00 mg, 99.30 μmol) and triethylamine (20.10 mg, 198.60 μmol) were dissolved in dichloromethane, and methanesulfonyl chloride (13.65 mg, 119.16 μmol) was added thereto at 0° C. The mixture was stirred to react at 0° C. for 1 hour. TLC showed that the reaction was completed, and then dichloromethane (10 mL) and water (8 mL) were added to the reaction solution. The organic phase was washed with saturated brine (10 mL), dried over anhydrous sodium sulfate, filtered and concentrated to give a crude product. The crude product was purified by silica gel column chromatography to give the title compound (55 mg, 95.2%) as a pale yellow solid.

$^1$H NMR (400 MHz, CDCl$_3$) ppm 9.08 (d, J=1.10 Hz, 1H), 8.54 (d, J=2.43 Hz, 1H), 8.21 (s, 1H), 7.67-7.79 (m, 3H), 4.58-4.66 (m, 2H), 4.43-4.50 (m, 2H), 4.01 (s, 3H), 3.17 (s, 3H), 2.74 (s, 3H), 2.46 (s, 3H).

h) N-(5-(3-(2-(4,4-Difluoro-1-piperidinyl)ethoxy)-4-oxo-pyrido[1,2-a]pyrimidin-7-yl]-2-methoxypyridin-3-yl]-2,4-dimethylthiazole-5-sulfonamide 2-((7-(5-(2,4-Dimethylthiazole 2,4-dimethylthiazole-5-sulfonamido)-6-methoxypyridin-3-yl)-4-oxo-4H-pyrido[1,2-a]pyrimidin-3-yl)oxy)ethyl methanesulfonate (50.00 mg, 85.96 μmol) and 4,4-difluoropiperidine (12.50 mg, 103.16 μmol) were dissolved in acetonitrile (2 mL), and diisopropylethylamine (22.22 mg, 171.93 Ξmol) was added thereto. The mixture was stirred to react at 50° C. for 12 hours. Liquid Chromatography Mass Spectrometry showed that the reaction was completed. The reaction solution was filtered and concentrated to give a crude product. The crude product was purified by preparative high performance liquid chromatography to give the title product (15.00 mg, 28.77%) as a pale yellow solid.

$^1$H NMR (400 MHz, CD$_3$OD) ppm 9.11 (d, J=1.51 Hz, 1H), 8.30 (d, J=2.26 Hz, 1H), 8.27 (s, 1H), 8.01-8.11 (m, 2H), 7.74 (d, J=9.29 Hz, 1H), 4.35 (t, J=5.40 Hz, 2H), 3.89 (s, 3H), 2.94-2.97 (m, 2H), 2.78 (d, J=5.02 Hz, 4H), 2.64 (s, 3H), 2.49 (s, 3H), 1.98-2.05 (m, 4H).

The following 5 compounds were also synthesized with reference to the process for preparing Compound 1:

| Compound | Structure | MS(ES) [M + H]$^+$ |
|---|---|---|
| 2 | 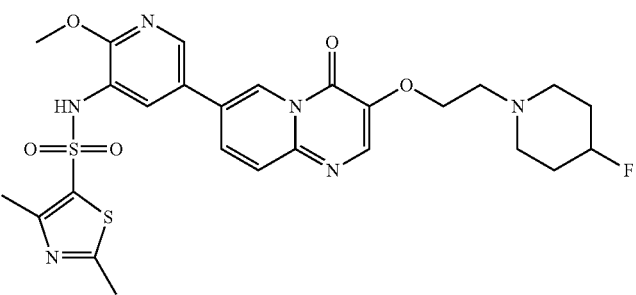 [SMILES: COc1ncc(-c2ccc3ncc(OCCN4CCC(F)CC4)c(=O)n3c2)cc1NS(=O)(=O)c1sc(C)nc1C] | 589 |
| 3 | 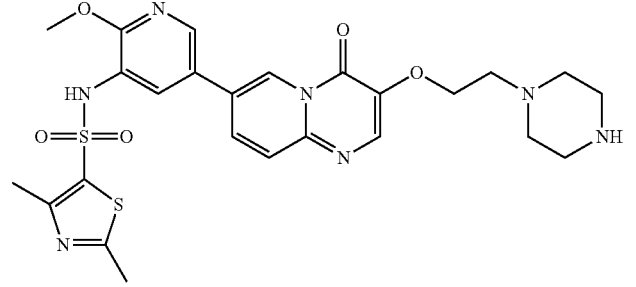 [SMILES: COc1ncc(-c2ccc3ncc(OCCN4CCNCC4)c(=O)n3c2)cc1NS(=O)(=O)c1sc(C)nc1C] | 572 |
| 4 | 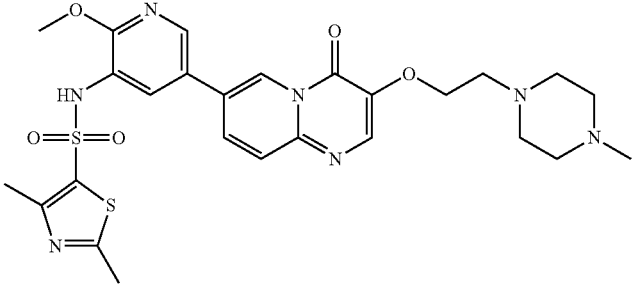 | 586 |
| 5 | 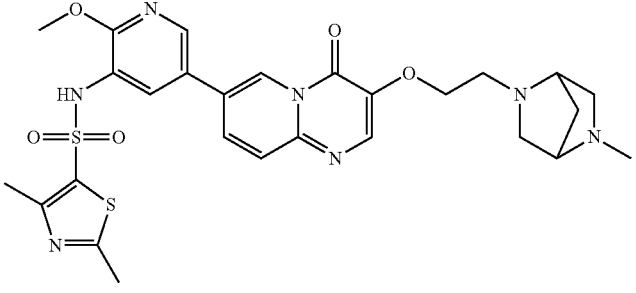 | 598 |

| Compound | Structure | MS(ES) [M + H]+ |
|---|---|---|
| 6 | 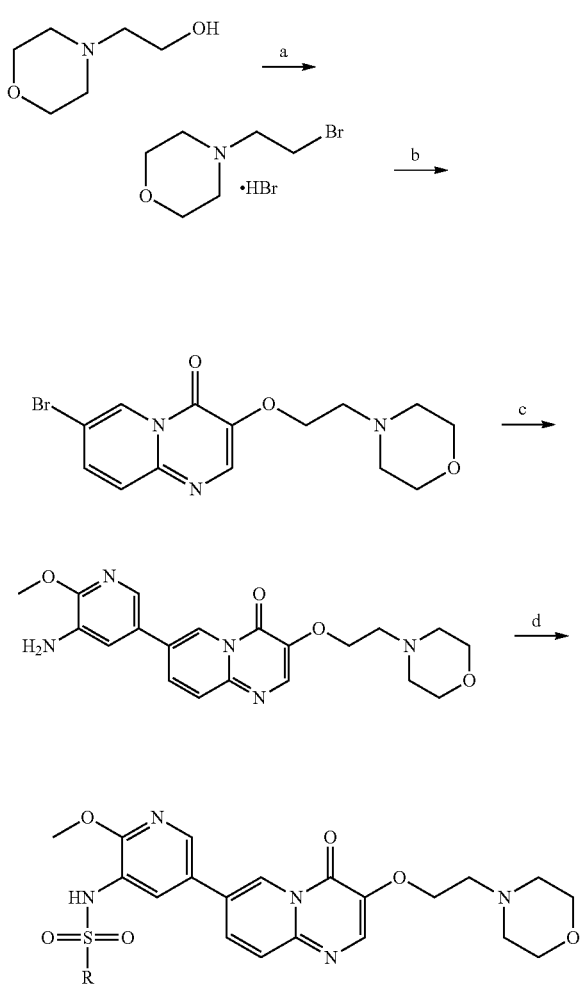 | 517 |

Scheme 2:

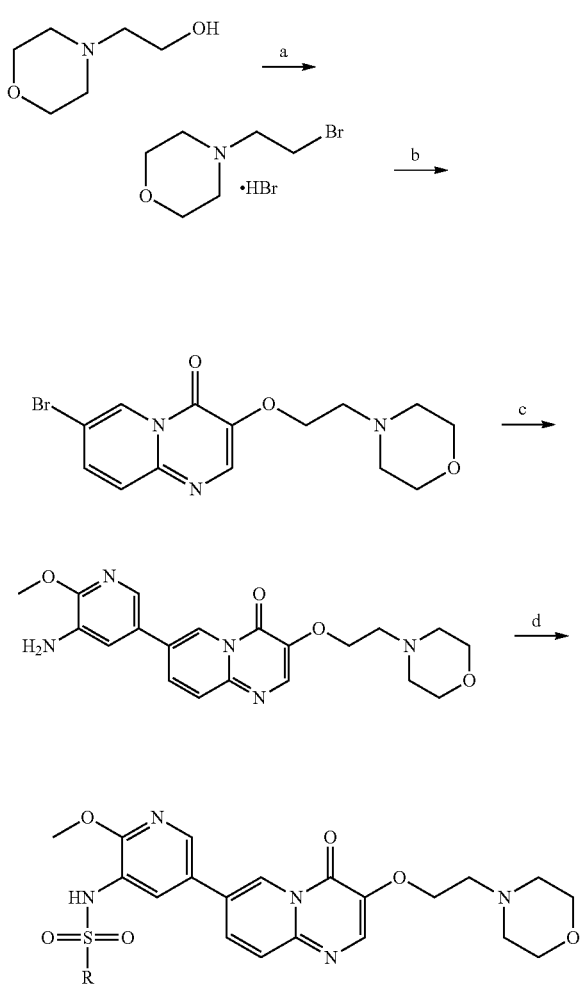

Reaction conditions: a) 2-morpholinoethanol, dibromotriphenylphosphine, dichloromethane; b) 7-bromo-3-hydroxy-4H-pyrido[1,2-a]pyrimidin-4-one, potassium carbonate, N,N-dimethylformamide; c) 2-methoxy-5-(4,4,5,5-tetramethyl-1,3,2-dioxaborolan-2-yl)pyridin)-3-amine, 1,1'-bis(diphenylphosphino)ferrocene palladium chloride, potassium carbonate, dioxane, water, heating; d) R-sulfonyl chloride, pyridine.

Example 7

2,4-Dimethyl-N-(2-methoxy-5-(3-(2-morpholinoethoxy)-4-oxo-4H-pyrido[1,2-a]pyrimidin-4-one-7-yl)pyridin-3-yl)benzenesulfonamide Compound 7

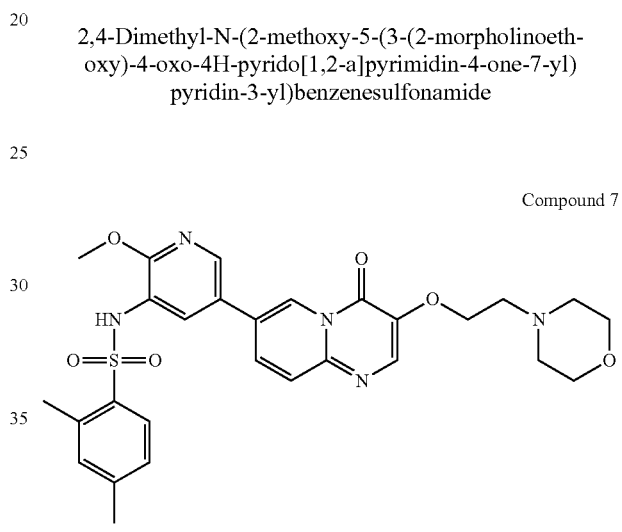

a) 4-(2-Bromoethyl)morpholine hydrobromide

To a solution of 2-morpholinoethanol (4 g, 30.49 mmol) in dichloromethane (80 mL), was added in batches dibromotriphenylphosphine (15.45 g, 36.59 mmol) at 0° C. under nitrogen protection. The mixture solution was stirred at 15° C. for 18 hours. After the completion of the reaction, the reaction solution was filtered and the filter cake was washed with dichloromethane and dried under reduced pressure to give a nearly white solid (5.1 g, 60.8%).

1H NMR (400 MHz, CDCl$_3$) ppm δ 4.06 (d, J=12.2 Hz, 2H), 3.89-3.75 (m, 4H), 3.71-3.63 (m, 2H), 3.56 (d, J=12.5 Hz, 2H), 3.28-3.18 (m, 2H).

b) 7-Bromo-3-(2-morpholinoethoxy)-4H-pyrido[1,2-a]pyrimidin-4-one

Under nitrogen protection, 7-bromo-3-hydroxy-4H-pyrido[1,2-a]pyrimidin-4-one (1 g, 4.15 mmol), 4-(2-bromoethyl)morpholine hydrobromide (1.14 g, 4.15 mmol) and potassium carbonate (1.72 g, 12.45 mmol) were added to N,N-dimethylformamide (80 mL) and the mixture was stirred at 120° C. for 2 hours. After the completion of the reaction, the reaction solution was concentrated to remove N,N-dimethylformamide. Dichloromethane was added to the concentrated solution and the resulting mixture was filtered. The filtrate was concentrated to give a brown solid product (1.3 g, 88.4%).

¹H NMR (400 MHz CDCl₃) ppm δ 9.03 (d, J=1.7 Hz, 1H), 8.07 (s, 1H), 7.51 (dd, J=2.2, 9.5 Hz, 1H), 7.45-7.29 (m, 1H), 4.24 (t, J=5.7 Hz, 2H), 3.75-3.56 (m, 4H), 2.78 (t, J=5.6 Hz, 2H), 2.62-2.47 (m, 4H).

c) 7-(5-Amino-6-methoxypyridin-3-yl)-3-(2-morpholinoethoxy)-4H-pyrido[1,2-a]pyrimidin-4-one Under nitrogen protection, to a mixture solution of 7-bromo-3-(2-morpholinoethoxy)-4H-pyrido[1,2-a]pyrimidin-4-one (100 mg, 0.28 mmol), 2-methoxy-5-(4,4,5,5-tetramethyl-1,3,2-dioxaborolan-2-yl)pyridine)-3-amine (46 mg, 0.31 mmol), and potassium carbonate (117 mg, 0.85 mmol) in dioxane (5 mL), were added 1,1'-bis(diphenylphosphino)ferrocene palladium chloride (8 mg, 0.008 mmol) and water (1 mL). The mixture solution was stirred at 90° C. for 18 hours under nitrogen protection. After the completion of the reaction, the reaction solution was extracted with dichloromethane. The organic phase was dried over anhydrous sodium sulfate and then concentrated. The resulting crude product was purified by preparative thin layer chromatography and preparative liquid chromatography to give a nearly white solid (23.82 mg, 22.06%).

1H NMR (400 MHz, CDCl₃) ppm δ 9.13 (d, J=1.5 Hz, 1H), 8.46 (d, J=2.5 Hz, 1H), 8.19 (s, 1H), 7.86 (dd, J=2.5, 8.5 Hz, 1H), 7.79 (dd, J=2.0, 9.0 Hz, 1H), 7.72-7.64 (m, 1H), 6.89 (d, J=8.5 Hz, 1H), 4.33 (t, J=5.5 Hz, 2H), 4.01 (s, 3H), 3.82-3.66 (m, 4H), 2.87 (t, J=5.8 Hz, 2H), 2.62 (br. s., 4H).

d) 2,4-Dimethyl-N-(2-methoxy-5-(3-(2-morpholinoethoxy)-4-oxo-4H-pyrido[1,2-a]pyrimidin-4-one-7-yl) pyridin-3-yl)benzenesulfonamide To a solution of 7-(5-amino-6-methoxypyridin-3-yl)-3-(2-morpholinoethoxy)-4H-pyrido[1,2-a]pyrimidin-4-one (100.00 mg, 251.62 μmol) in pyridine (3 mL), was added dropwise 2-methyl-4-fluorobenzenesulfonyl chloride (61.8 mg, 301.94 μmol). The reaction solution was stirred at 18° C. for 18 hours. After the completion of the reaction, the pyridine was distilled off under reduced pressure. The residue was dissolved in dichloromethane and washed with water and saturated brine. The organic phase was dried over anhydrous sodium sulfate and then concentrated to give a crude product. The crude product was purified by preparative liquid chromatography to give a yellow solid product (23.16 mg, 16.11%).

1H NMR (400 MHz, CDCl₃) ppm δ 8.97 (s, 1H), 8.16 (s, 1H), 8.03 (d, J=2.2 Hz, 1H), 7.91 (d, J=8.1 Hz, 1H), 7.82 (d, J=2.0 Hz, 1H), 7.65 (d, J=1.0 Hz, 2H), 7.16 (d, J=8.1 Hz, 1H), 7.10 (s, 1H), 4.31 (t, J=5.6 Hz, 2H), 3.99 (s, 3H), 3.82-3.66 (m, 4H), 2.86 (t, J=5.6 Hz, 2H), 2.64 (s, 3H), 2.61 (d, J=4.2 Hz, 4H), 2.33 (s, 3H).

The following 13 compounds were also synthesized with reference to the process for preparing Compound 7:

| Compound | Structure | MS(ES) [M + H]⁺ |
|---|---|---|
| 8 | 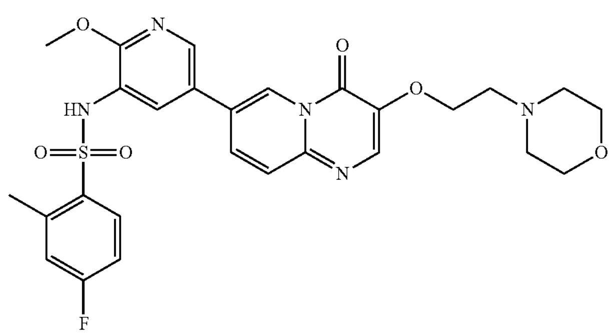 [SMILES: COc1ncc(-c2ccc3ncc(OCCN4CCOCC4)c(=O)n3c2)cc1NS(=O)(=O)c1ccc(F)cc1C] | 570 |
| 9 | 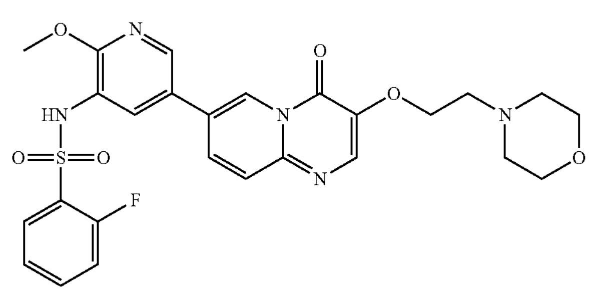 | 556 |

-continued

| Compound | Structure | MS(ES) [M + H]+ |
|---|---|---|
| 10 | 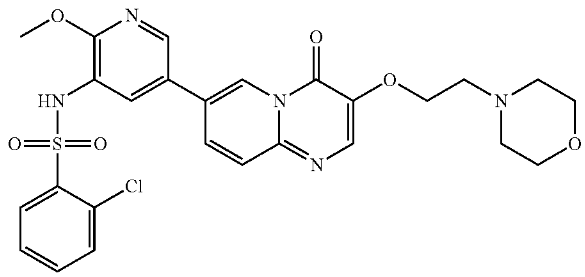 [SMILES: COc1ncc(-c2ccc3ncc(OCCN4CCOCC4)c(=O)n3c2)cc1NS(=O)(=O)c1ccccc1F] | 572 |
| 11 | 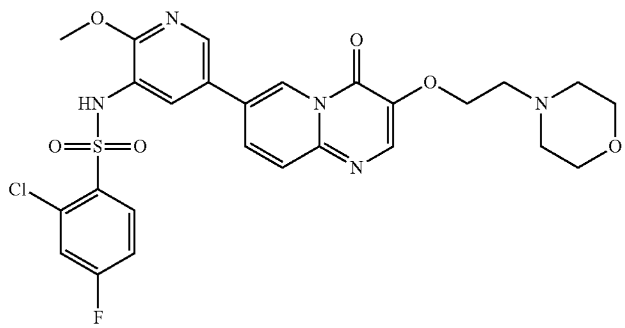 [SMILES: COc1ncc(-c2ccc3ncc(OCCN4CCOCC4)c(=O)n3c2)cc1NS(=O)(=O)c1ccc(F)cc1Cl] | 590 |
| 12 | 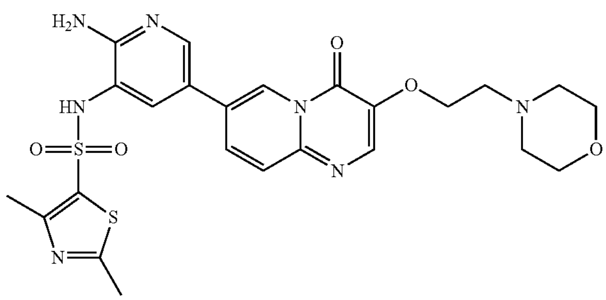 [SMILES: Cc1nc(C)c(S(=O)(=O)Nc2cc(-c3ccc4ncc(OCCN5CCOCC5)c(=O)n4c3)cnc2N)s1] | 558 |
| 13 | 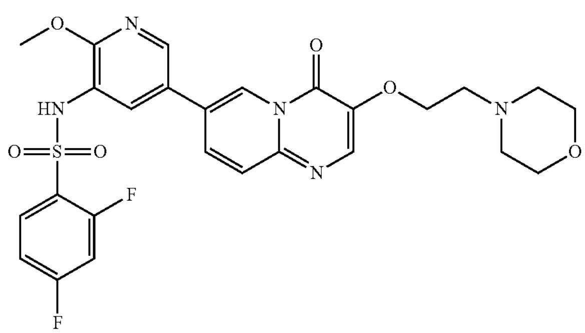 [SMILES: COc1ncc(-c2ccc3ncc(OCCN4CCOCC4)c(=O)n3c2)cc1NS(=O)(=O)c1ccc(F)cc1F] | 574 |
| 14 | 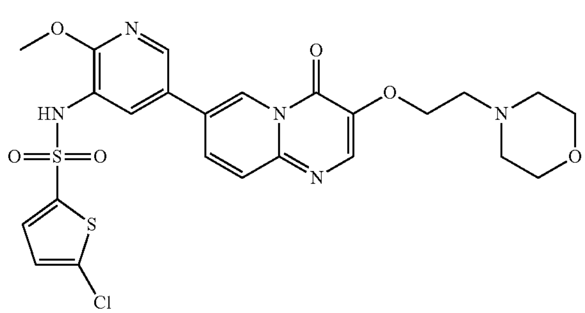 [SMILES: COc1ncc(-c2ccc3ncc(OCCN4CCOCC4)c(=O)n3c2)cc1NS(=O)(=O)c1ccc(Cl)s1] | 578 |

-continued

| Compound | Structure | MS(ES) [M + H]+ |
|---|---|---|
| 15 | 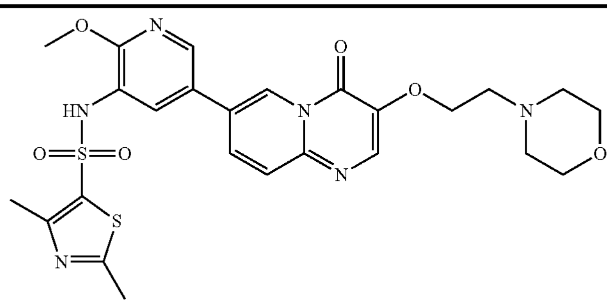 | 573 |
| 16 | 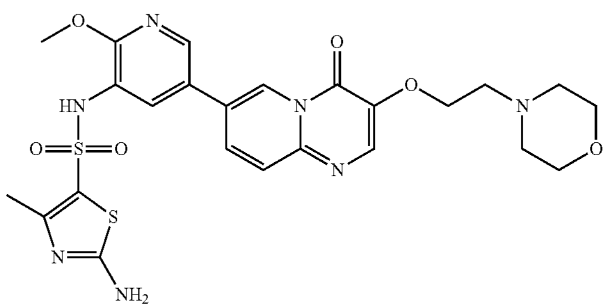 [SMILES: COc1ncc(-c2ccc3ncc(OCCN4CCOCC4)c(=O)n3c2)cc1NS(=O)(=O)c1sc(N)nc1C] | 574 |
| 17 | 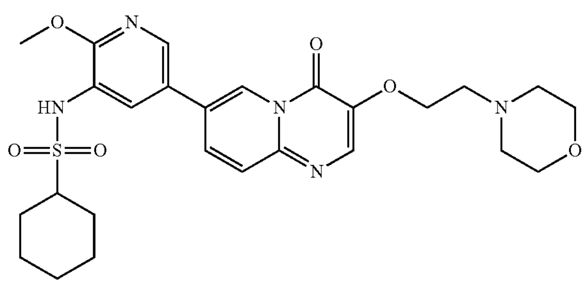 [SMILES: COc1ncc(-c2ccc3ncc(OCCN4CCOCC4)c(=O)n3c2)cc1NS(=O)(=O)C1CCCCC1] | 544 |
| 18 | 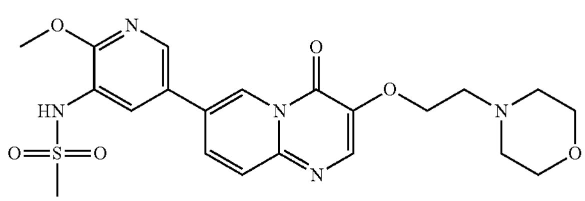 [SMILES: COc1ncc(-c2ccc3ncc(OCCN4CCOCC4)c(=O)n3c2)cc1NS(C)(=O)=O] | 476 |
| 19 | 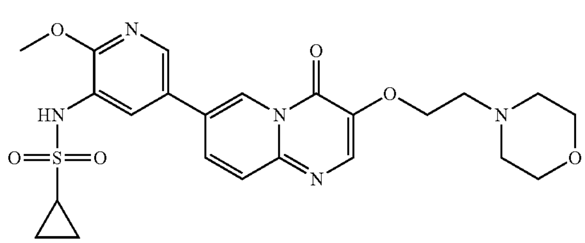 [SMILES: COc1ncc(-c2ccc3ncc(OCCN4CCOCC4)c(=O)n3c2)cc1NS(=O)(=O)C1CC1] | 502 |
| 20 | 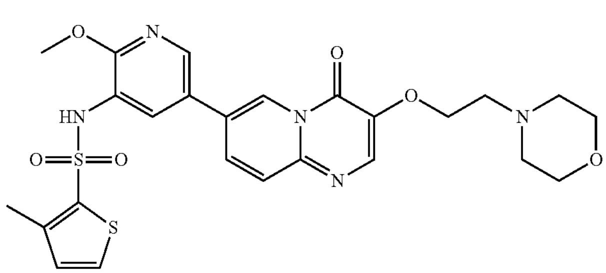 [SMILES: COc1ncc(-c2ccc3ncc(OCCN4CCOCC4)c(=O)n3c2)cc1NS(=O)(=O)c1sccc1C] | 588 |

Scheme 3:

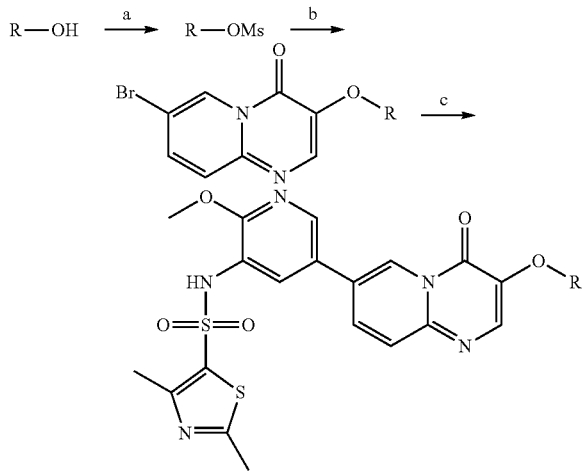

Reaction conditions: a) methanesulfonyl chloride, triethylamine, dichloromethane; b) potassium carbonate, N,N-dimethylformamide; c) N-(2-methoxy-5-(4,4,5,5-tetramethyl-1,3,2-dioxaborolan-2-yl)pyridin-3-yl)-2,4-dimethylthiazole-5-sulfonamide, palladium, potassium carbonate, dioxane, water, heating.

Example 21

N-(2-Methoxy-5-(4-oxo-3-(2-(2-oxopyrrolidin-1-yl)ethoxy)-4H-pyrido[1,2-a]pyrimidin-7-yl)pyridin-3-yl)-2,4-dimethylthiazole-5-sulfonamide Compound 21

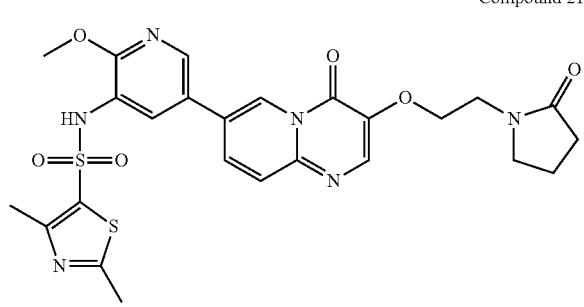

a) 2-(2-Oxopyrrolidin-1-yl)ethyl methanesulfonate

To a solution of 1-(2-hydroxyethyl)pyrrolidin-2-one (500.00 mg, 3.87 mmol) and triethylamine (1.17 g, 11.61 mmol) in dichloromethane (5 mL), was added methanesulfonyl chloride (531.97 mg, 4.64 mmol) at 0° C. The reaction solution was stirred at 0° C. for 1 hour. After the completion of the reaction, the reaction solution was washed with water and brine. The organic phase was dried over anhydrous sodium sulfate and then concentrated to give a crude product (470.00 mg, 58.60%) as a yellow oil.

1H NMR (400 MHz, CDCl$_3$) δ 4.35 (t, J=5.1 Hz, 2H), 3.62 (t, J=5.1 Hz, 2H), 3.51 (t, J=7.1 Hz, 2H), 3.03 (s, 3H), 2.40 (t, J=8.1 Hz, 2H), 2.06 (quin, J=7.6 Hz, 2H).

b) 7-Bromo-3-(2-(2-oxopyrrolidin-1-yl)ethoxy)-4H-pyrido[1,2-a]pyrimidin-4-one A mixture solution of 7-bromo-3-hydroxy-4H-pyrido[1,2-a]pyrimidin-4-one (100.00 mg, 414.87 µmol), 2-(2-oxopyrrolidin-1-yl)ethylmethanesulfonate (257.94 mg, 1.24 mmol) and potassium carbonate (229.36 mg, 1.66 mmol) in N,N-dimethylformamide (10 mL) was stirred at 120° C. for 18 hours under nitrogen protection. After the completion of the reaction, the reaction solution was concentrated. The concentrate was purified by silica gel chromatography column to give the product (210.00 mg, 79.05%, purity: 55%) as a yellow oil.

1H NMR (400 MHz, CDCl$_3$) δ 9.02 (d, J=1.7 Hz, 1H), 8.03 (s, 1H), 7.51 (dd, J=2.1, 9.4 Hz, 1H), 7.44-7.37 (m, 1H), 4.23 (t, J=5.1 Hz, 2H), 3.67 (s, 2H), 3.62 (t, J=7.0 Hz, 2H), 2.34 (t, J=8.0 Hz, 2H), 2.10-1.86 (m, 2H).

c) N-(2-Methoxy-5-(4-oxo-3-(2-(2-oxopyrrolidin-1-yl)ethoxy)-4H-pyrido[1,2-a]pyrimidin-7-yl)pyridin-3-yl)-2,4-dimethylthiazole-5-sulfonamide Under nitrogen protection, to a mixture solution of 7-bromo-3-(2-(2-oxopyrrolidin-1-yl)ethoxy)-4H-pyrido[1,2-a]pyrimidin-4-one (210.00 mg, 327.96 µmol), N-(2-methoxy-5-(4,4,5,5-tetramethyl-1,3,2-dioxaborolan-2-yl)pyridin-3-yl)-2,4-dimethylthiazole-5-sulfonamide (145.19 mg, 327.96 µmol), and potassium carbonate (135.98 mg, 983.87 µmol) in dioxane (5 mL), were added 1,1'-bis(diphenylphosphino)ferrocene palladium chloride (2.40 mg, 3.28 µmol) and water (1 mL). The mixture solution was stirred at 90° C. for 18 hours under nitrogen protection. After the completion of the reaction, the reaction solution was concentrated. The concentrated residue was purified by preparative thin layer chromatography to give the title compound (60.07 mg, 30.41%) as a yellow solid.

1H NMR (400 MHz, CDCl$_3$) δ 8.98 (s, 1H), 8.20-8.06 (m, 3H), 7.92 (d, J=2.2 Hz, 1H), 7.68 (d, J=1.1 Hz, 2H), 7.58 (s, 1H), 7.28 (d, J=2.4 Hz, 1H), 7.20-7.09 (m, 1H), 4.32 (t, J=5.1 Hz, 2H), 4.00 (s, 3H), 3.84-3.65 (m, 4H), 2.42 (t, J=8.0 Hz, 2H), 2.08 (quin, J=7.6 Hz, 2H).

The following 15 compounds were also synthesized with reference to the process for preparing Compound 21:

| Compound | Structure | MS(ES) [M + H]+ |
|---|---|---|
| 22 | 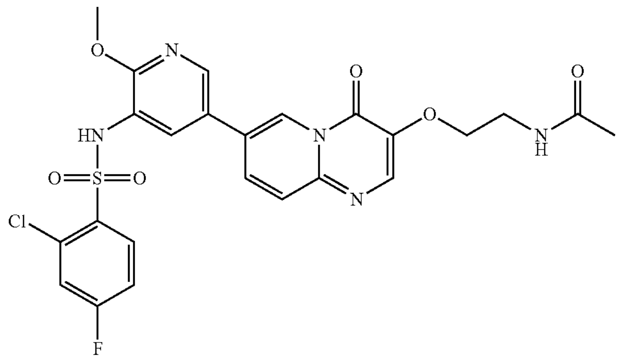 [SMILES: COc1ncc(-c2ccc3ncc(OCCNC(C)=O)c(=O)n3c2)cc1NS(=O)(=O)c1ccc(F)cc1Cl] | 562 |
| 23 | 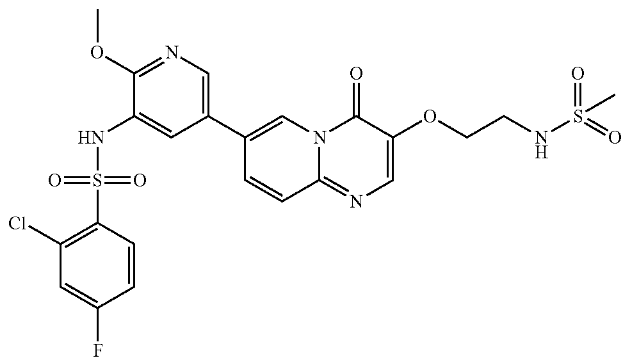 [SMILES: COc1ncc(-c2ccc3ncc(OCCNS(C)(=O)=O)c(=O)n3c2)cc1NS(=O)(=O)c1ccc(F)cc1Cl] | 598 |
| 24 | 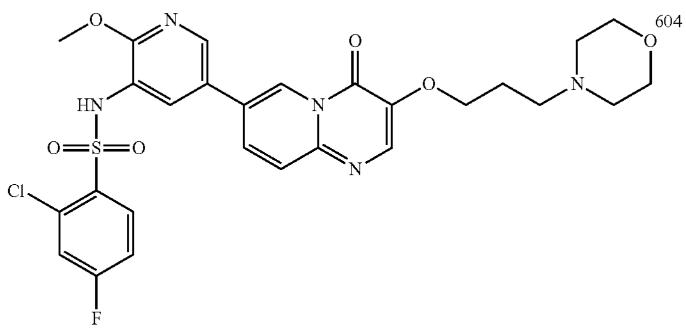 | 604 |
| 25 | 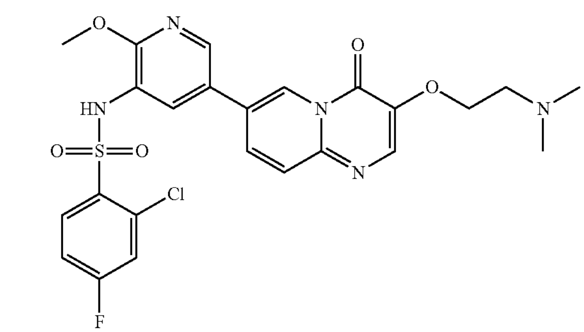 [SMILES: COc1ncc(-c2ccc3ncc(OCCN(C)C)c(=O)n3c2)cc1NS(=O)(=O)c1ccc(F)cc1Cl] | 548 |

-continued

| Compound | Structure | MS(ES) [M + H]+ |
|---|---|---|
| 27 | 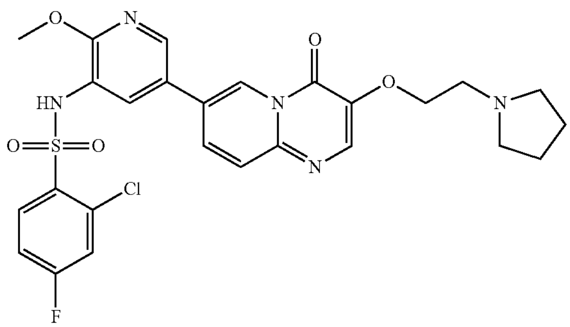 | 574 |
| 28 | 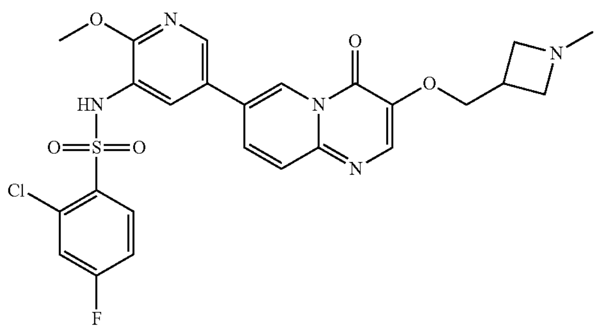 [SMILES: COc1ncc(-c2ccc3ncc(OCC4CN(C)C4)c(=O)n3c2)cc1NS(=O)(=O)c1ccc(F)cc1Cl] | 560 |
| 29 | 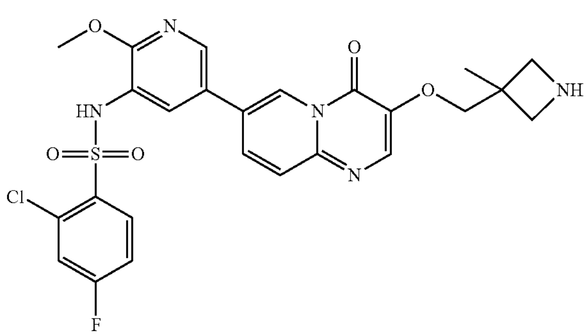 [SMILES: COc1ncc(-c2ccc3ncc(OCC4(C)CNC4)c(=O)n3c2)cc1NS(=O)(=O)c1ccc(F)cc1Cl] | 560 |
| 30 | 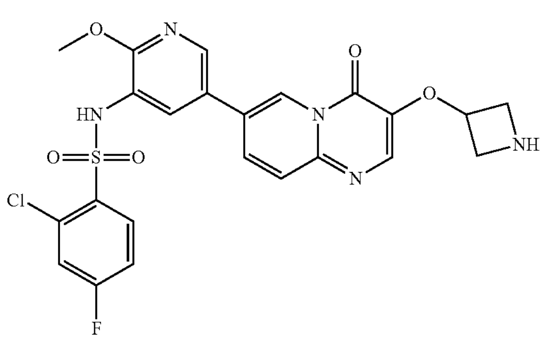 [SMILES: COc1ncc(-c2ccc3ncc(OC4CNC4)c(=O)n3c2)cc1NS(=O)(=O)c1ccc(F)cc1Cl] | 532 |

-continued

| Compound | Structure | MS(ES) [M + H]+ |
|---|---|---|
| 31 | 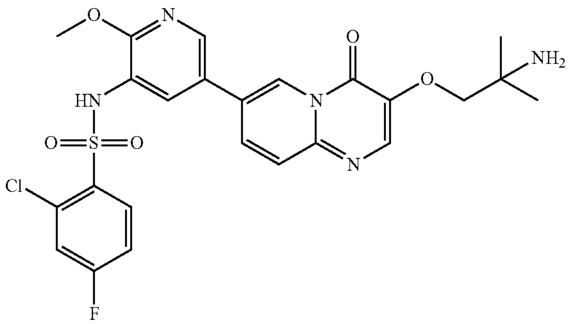 [SMILES: COc1ncc(-c2ccc3ncc(OCC(C)(C)N)c(=O)n3c2)cc1NS(=O)(=O)c1ccc(F)cc1Cl] | 548 |
| 32 | 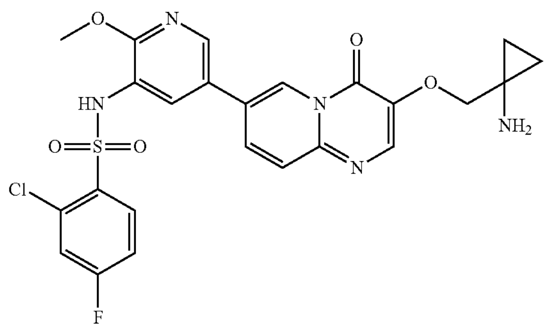 [SMILES: COc1ncc(-c2ccc3ncc(OCC4(N)CC4)c(=O)n3c2)cc1NS(=O)(=O)c1ccc(F)cc1Cl] | 546 |
| 33 | 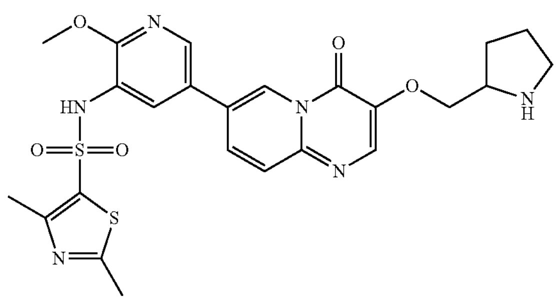 [SMILES: COc1ncc(-c2ccc3ncc(OCC4CCCN4)c(=O)n3c2)cc1NS(=O)(=O)c1sc(C)nc1C] | 543 |
| 34 | 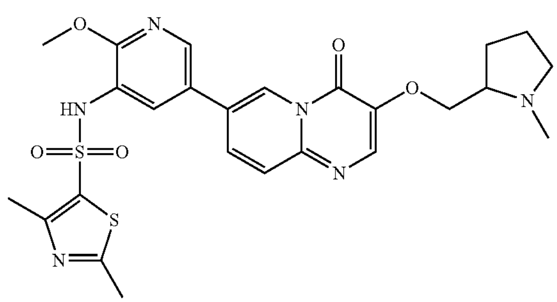 [SMILES: COc1ncc(-c2ccc3ncc(OCC4CCCN4C)c(=O)n3c2)cc1NS(=O)(=O)c1sc(C)nc1C] | 557 |
| 35 | 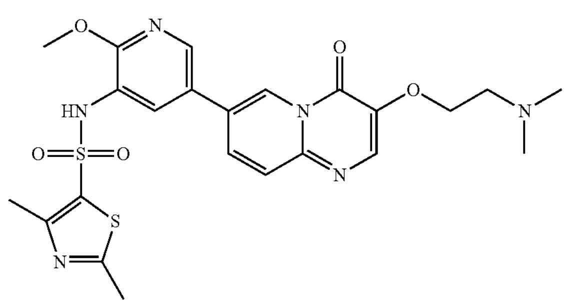 | 531 |

| Compound | Structure | MS(ES) [M + H]+ |
|---|---|---|
| 36 | 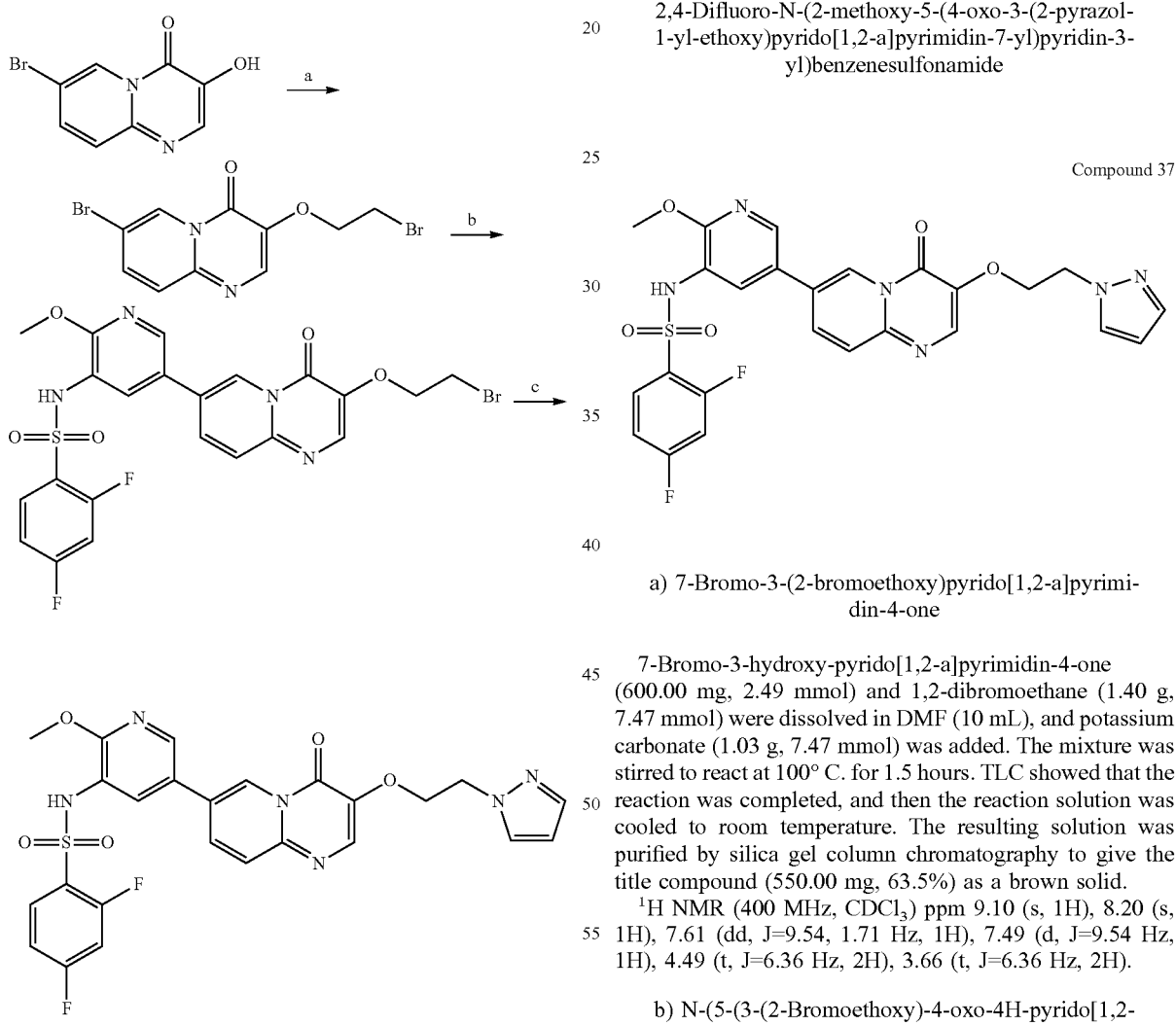 | 516 |

Scheme 4:

Example 37

2,4-Difluoro-N-(2-methoxy-5-(4-oxo-3-(2-pyrazol-1-yl-ethoxy)pyrido[1,2-a]pyrimidin-7-yl)pyridin-3-yl)benzenesulfonamide Compound 37

Reaction conditions: a) 1,2-dibromoethane, potassium carbonate, DMF, heating; b) 2,4-difluoro-N-(2-methoxy-5-(4,4,5,5-tetramethyl-1,3,2-dioxaborolan-2-yl)pyridin-3-yl)benzenesulfonamide, 1,1'-bis(diphenylphosphino)ferrocene palladium chloride, potassium carbonate, dioxane, water, heating; c) 1H-pyrazole, cesium carbonate, acetonitrile, heating.

a) 7-Bromo-3-(2-bromoethoxy)pyrido[1,2-a]pyrimidin-4-one

7-Bromo-3-hydroxy-pyrido[1,2-a]pyrimidin-4-one (600.00 mg, 2.49 mmol) and 1,2-dibromoethane (1.40 g, 7.47 mmol) were dissolved in DMF (10 mL), and potassium carbonate (1.03 g, 7.47 mmol) was added. The mixture was stirred to react at 100° C. for 1.5 hours. TLC showed that the reaction was completed, and then the reaction solution was cooled to room temperature. The resulting solution was purified by silica gel column chromatography to give the title compound (550.00 mg, 63.5%) as a brown solid.

$^1$H NMR (400 MHz, CDCl$_3$) ppm 9.10 (s, 1H), 8.20 (s, 1H), 7.61 (dd, J=9.54, 1.71 Hz, 1H), 7.49 (d, J=9.54 Hz, 1H), 4.49 (t, J=6.36 Hz, 2H), 3.66 (t, J=6.36 Hz, 2H).

b) N-(5-(3-(2-Bromoethoxy)-4-oxo-4H-pyrido[1,2-a]pyrimidin-7-yl)-2-methoxypyridin-3-yl)-2,4-difluorobenzenesulfonamide 7-Bromo-3-(2-bromoethoxy)pyrido[1,2-a]pyrimidin-4-one (550.00 mg, 1.58 mmol) was dissolved in dioxane (15 mL) and water (2 mL), and then 2,4-difluoro-N-(2-methoxy-5-(4,4,5,5-tetramethyl-1,3,2-dioxaborolan-2-yl)pyridin-3-yl)benzenesulfonamide (673.67 mg, 1.58 mmol), potassium carbonate (436.74 mg, 3.16 mmol) and 1,1'-bis(diphenylphosphino)ferrocene palladium chloride (117.20 mg, 158.00 µmol) were added under nitrogen protection. The mixture was stirred to react at 90° C. for 1.5 hours.

Liquid Chromatography Mass Spectrometry showed that the reaction was completed. The reaction solution was filtered and concentrated to give a crude product. The crude product was purified by silica gel column chromatography to give the title product (250.00 mg, 27.89%) as a pale yellow solid.

$^1$H NMR (400 MHz, CDCl$_3$) ppm 9.03 (s, 1H), 8.24 (s, 1H), 8.12 (d, J=2.20 Hz, 1H), 7.89-7.98 (m, 2H), 7.68-7.76 (m, 2H), 7.32 (br. s., 1H), 6.99-7.06 (m, 1H), 6.90-6.98 (m, 1H), 4.52 (t, J=6.24 Hz, 2H), 3.98 (s, 3H), 3.69 (t, J=6.36 Hz, 2H).

c) 2,4-Difluoro-N-(2-methoxy-5-(4-oxo-3-(2-pyrazol-1-yl-ethoxy)pyrido[1,2-a]pyrimidin-7-yl)pyridin-3-yl)benzenesulfonamide N-(5-(3-(2-Bromoethoxy)-4-oxo-4H-pyrido[1,2-a]pyrimidin-7-yl)-2-methoxypyridin-3-yl)-2,4-difluorobenzenesulfonamide (50.00 mg, 88.13 µmol), and 1H-pyrazole (9.00 mg, 132.20 µmol) were dissolved in acetonitrile (0.5 mL), and then cesium carbonate (57.43 mg, 176.26 mol) was added. The mixture was stirred to react at 70° C. for 2 hours. Liquid Chromatography Mass Spectrometry showed that the reaction was completed. The reaction solution was filtered and concentrated to give a crude product. The crude product was purified by preparative high performance liquid chromatography to give the title product (15.00 mg, 30.69%) as a yellow solid.

$^1$H NMR (400 MHz, CDCl$_3$) ppm 9.00 (d, J=0.98 Hz, 1H), 8.11 (d, J=2.20 Hz, 1H), 7.87-7.99 (m, 3H), 7.61-7.73 (m, 3H), 7.49-7.57 (m, 1H), 7.34 (br. s., 1H), 6.98-7.06 (m, 1H), 6.90-6.98 (m, 1H), 6.26 (t, J=1.96 Hz, 1H), 4.57 (dd, J=10.88, 4.28 Hz, 4H), 3.97 (s, 3H).

The following 3 compounds were also synthesized with reference to the process for preparing Compound 37:

| Compound | Structure | MS(ES) [M + H]$^+$ |
|---|---|---|
| 38 | 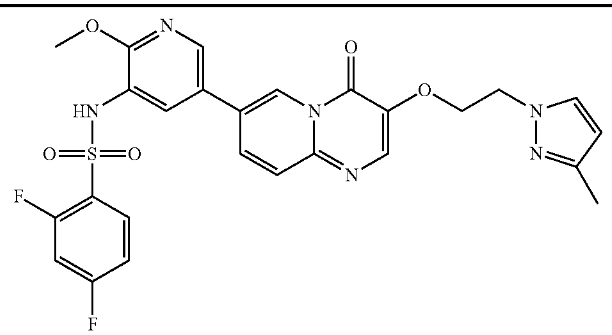 | 569 |
| 39 | 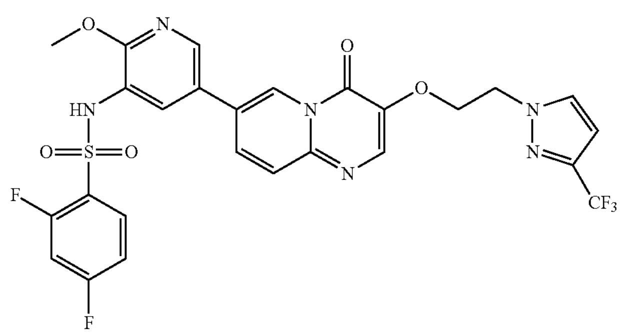 [SMILES: COc1ncc(-c2ccc3ncc(OCCn4ccc(C(F)(F)F)n4)c(=O)n3c2)cc1NS(=O)(=O)c1ccc(F)cc1F] | 623 |
| 40 | 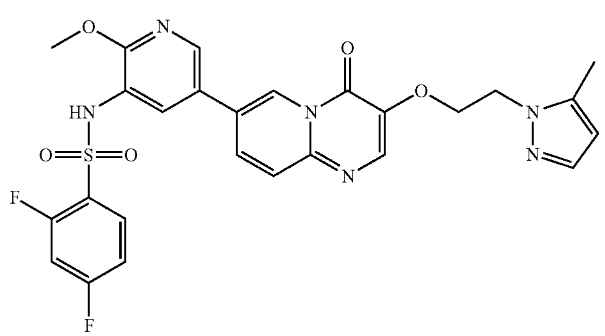 [SMILES: COc1ncc(-c2ccc3ncc(OCCn4nccc4C)c(=O)n3c2)cc1NS(=O)(=O)c1ccc(F)cc1F] | 569 |

Scheme 5:

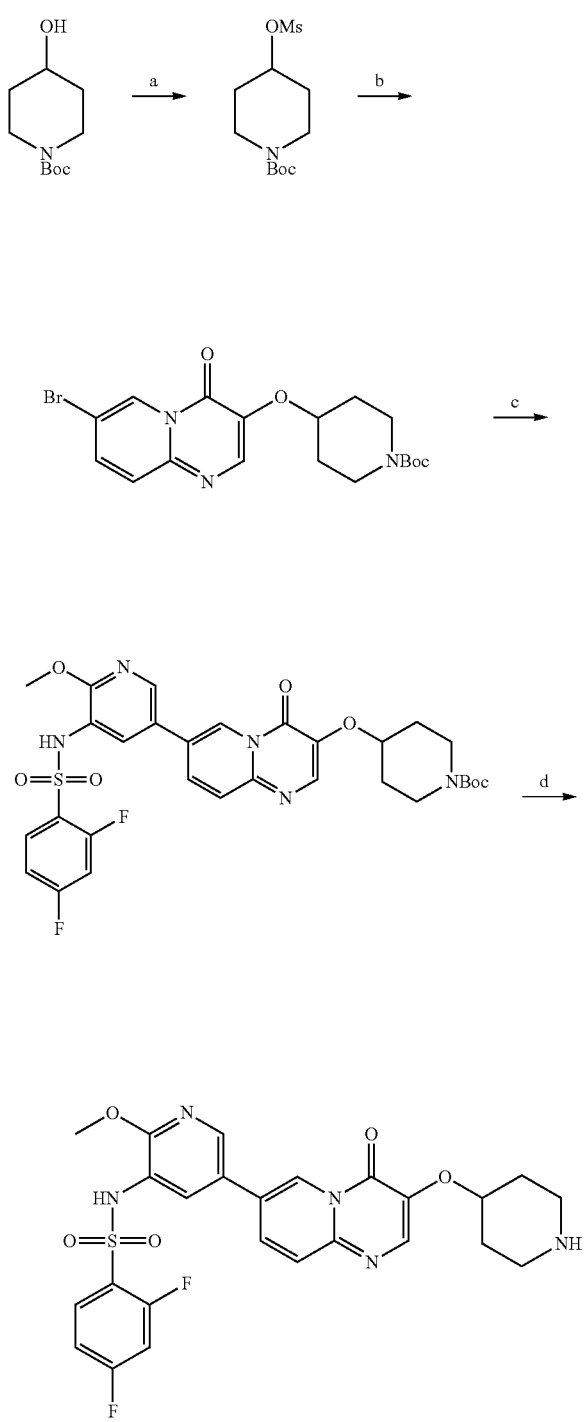

Reaction conditions: a) methanesulfonyl chloride, triethylamine, dichloromethane, 0° C. to room temperature; b) potassium carbonate. DMF, heating; c) R borate (boric acid), 1,1'-bis(diphenylphosphino)ferrocene palladium chloride, potassium carbonate, dioxane, water, heating; d) hydrochloric acid-ethyl acetate, ethyl acetate, room temperature.

Example 41

2,4-Difluoro-N-(2-methoxy-5-(4-oxo-3-(piperidin-4-yloxy)-4H-pyrido[1,2-a]pyrimidin-7-yl)pyridin-3-yl)benzenesulfonamide

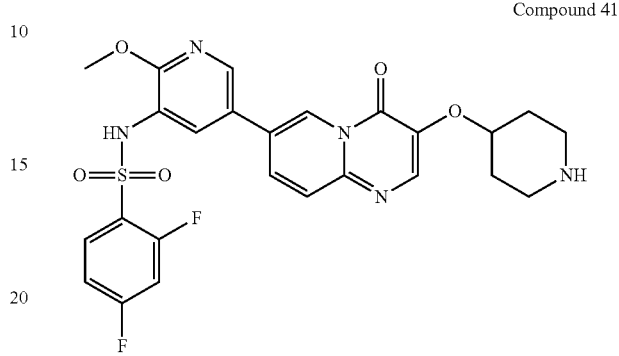

Compound 41 a) tert-Butyl 4-((methylsulfonyl)oxy)piperidine-1-carboxylate tert-Butyl 4-hydroxypiperidine-1-carboxylate (1 g, 4.97 mmol) and triethylamine (1 g, 9.95 mmol) were dissolved in dichloromethane (4 mL), and then methanesulfonyl chloride (1 g, 8.72 mmol) was added dropwise at 0° C. After the completion of the dropwise addition, the reaction solution was warmed to room temperature and was stirred to react for 2 hours. The reaction solution was poured into ice water to quench the reaction, and the resulting mixture was extracted with dichloromethane. The organic phase was washed with saturated brine, dried over anhydrous sodium sulfate and filtered. The filtrate was concentrated to give the title compound (1.6 g, a crude product) as a red solid.

b) tert-Butyl 4-((7-bromo-4-oxo-4H-pyrido[1,2-a]pyrimidin-3-yl)oxy)piperidine-1-carboxylate tert-Butyl 4-((methylsulfonyl)oxy)piperidine-1-carboxylate (200 mg, 0.72 mmol), 7-bromo-3-hydroxy-4H-pyrido[1,2-a]pyrimidin-4-one (115 mg, 0.48 mmol) and potassium carbonate (198 mg, 1.43 mmol) were dissolved in N,N-dimethylformamide (2 mL). The mixture was stirred to react at 120° C. for 2 hours under nitrogen protection. Water was added to the reaction solution, and the mixture was extracted with ethyl acetate. The organic phase was washed with saturated brine, dried over anhydrous sodium sulfate and filtered, and the filtrate was concentrated to obtain a crude product. The crude product was purified by silica gel column chromatography to give the title compound (170 mg, 84%) as a red solid.

1H NMR (400 MHz, CDCl$_3$) ppm 9.14-9.10 (m, 1H), 8.17 (s, 1H), 7.65-7.59 (m, 1H), 7.53-7.47 (m, 1H), 4.90-4.88 (m, 1H), 3.85 (m, 2H), 3.71-3.70 (m, 2H), 1.95 (s, 3H), 1.47 (s, 9H).

c) tert-Butyl 4-((7-(5-(2,4-difluorobenzenesulfonamido)-6-methoxypyridin-3-yl)-4-oxo-4H-pyrido[1,2-a]pyrimidin-3-yl)oxy)piperidine-1-carboxylate tert-Butyl 4-((7-bromo-4-oxo-4H-pyrido[1,2-a]pyrimidin-3-yl)oxy)piperidine-1-carboxylate (130 mg, 0.3 mmol), 2,4-difluoro-N-(2-methoxy-5-(4,4,5,5-tetramethyl-1,3,2-dioxaborolan-2-yl)pyridin-3-yl)benzenesulfonamide (130 mg, 0.3 mmol), potassium carbonate (85 mg, 0.61 μmol) and 1,1'-bis(diphenylphosphino)ferrocene palladium chloride (22 mg, 0.03 mmol) were dissolved in dioxane (2 mL) and water (0.4 mL). The reaction solution was stirred at 100° C. for 2 hours under nitrogen protection and microwave condition. The crude product was purified by silica gel column chromatography to give the title compound (80 mg, 30%) as a red oil.

d) 2,4-Difluoro-N-(2-methoxy-5-(4-oxo-3-(piperidin-4-yloxy)-4H-pyrido[1,2-a]pyrimidin-7-yl)pyridin-3-yl)benzenesulfonamide hydrochloride tert-Butyl 4-((7-(5-(2,4-difluorobenzenesulfonamido)-6-methoxypyridin-3-yl)-4-oxo-4H-pyrido[1,2-a]pyrimidin-3-yl)oxy)piperidine-1-carboxylate (28 mg, 0.043 mmol) was dissolved in ethyl acetate (2 mL), and hydrochloric acid/ethyl acetate (15 mL) was added. The reaction solution was stirred at room temperature for 1 hour. The reaction solution was filtered and the solid was rotary evaporated to dryness to give the title product (7.4 mg, 29%) as a brown solid.

1H NMR (400 MHz, CD$_3$OD) ppm 9.24 (s, 1H), 8.47-8.46 (m, 2H), 8.37 (s, 1H), 8.13 (s, 1H), 7.97-7.86 (m, 2H), 7.26-7.21 (m, 1H), 7.12-7.08 (m, 1H), 4.85-4.84 (m, 1H), 3.86 (s, 1H), 3.55-3.50 (m, 2H), 3.31-3.25 (m, 2H), 2.19 (s, 4H).

The following 3 compounds were also synthesized with reference to the process for preparing Compound 41:

| Compound | Structure | MS(ES) [M + H]+ |
|---|---|---|
| 42 | 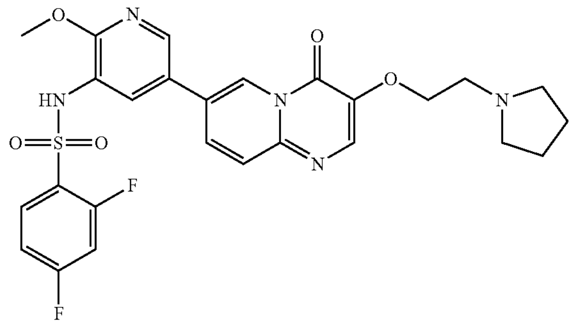 [SMILES: COc1ncc(-c2ccc3ncc(OCCN4CCCC4)c(=O)n3c2)cc1NS(=O)(=O)c1ccc(F)cc1F] | 558 |
| 43 | 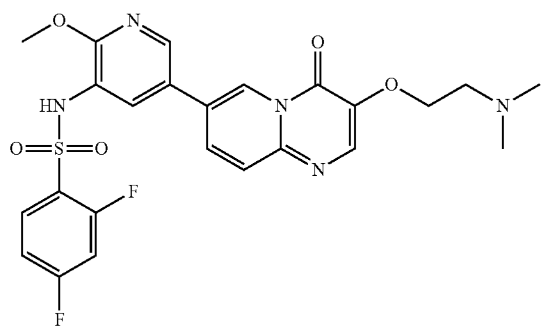 [SMILES: COc1ncc(-c2ccc3ncc(OCCN(C)C)c(=O)n3c2)cc1NS(=O)(=O)c1ccc(F)cc1F] | 532 |
| 44 | 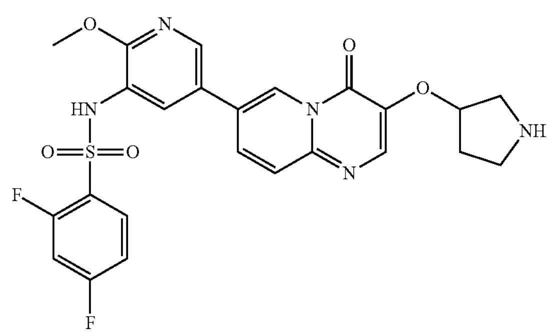 [SMILES: COc1ncc(-c2ccc3ncc(OC4CCNC4)c(=O)n3c2)cc1NS(=O)(=O)c1ccc(F)cc1F] | 530 |

Scheme 6:

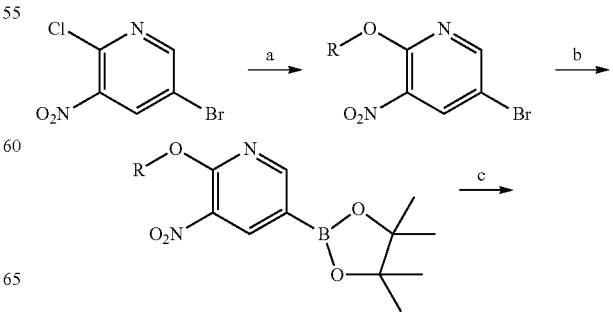

-continued

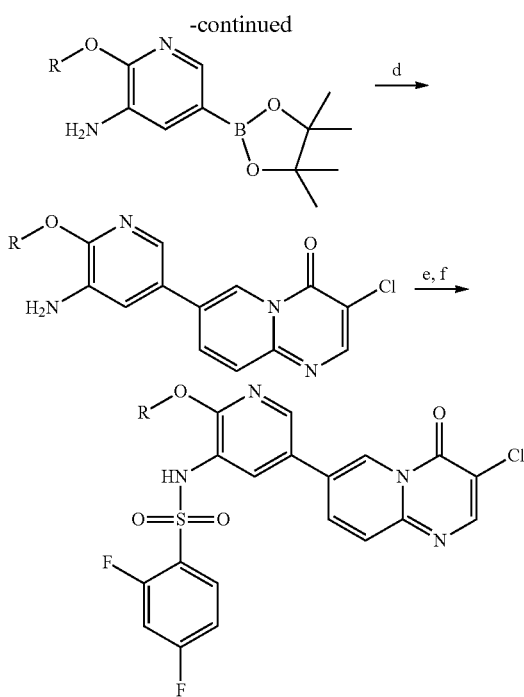

Reaction conditions: a) 5-bromo-2-chloro-3-nitropyridine, R alcohol, potassium hydroxide, potassium carbonate, 2-(2-methoxyethoxy)-N,N-di[2-(2-methoxyethoxy)ethyl]ethanamine, toluene; b) 4,4,5,5-tetramethyl-2-(4,4,5,5-tetramethyl-1,3,2-dioxaborolan-2-yl)-1,3,2-dioxaborolane, 1,1'-bis(diphenylphosphino)ferrocene palladium chloride, potassium acetate, dioxane, heating; c) Pd/C, methanol; d) 7-bromo-3-chloro-pyrido[1,2-a]pyrimidin-4-one, 1,1'-bis(diphenylphosphino)ferrocene palladium chloride, potassium carbonate, dioxane, water, heating; e) 2,4-difluorobenzenesulfonyl chloride, pyridine; f) hydrochloric acid/dioxane, dioxane.

Example 45

N-[5-(3-Chloro-4-oxo-4H-pyrido[1,2-a]pyrimidin-7-yl)-2-(3-(methylamino)propoxy) pyridin-3-yl]-2,4-difluoro-benzenesulfonamide Compound 45

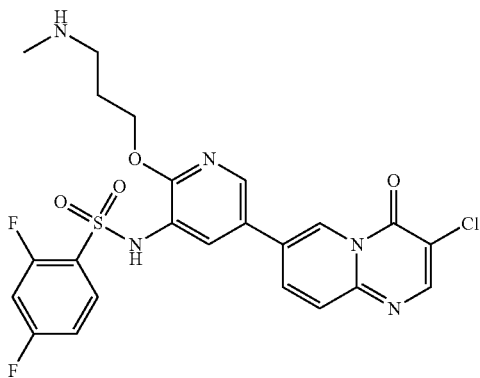

a) tert-Butyl (3-((5-bromo-3-nitropyridin-2-yl)oxy) propyl)(methyl)carbamate

To a mixture solution of potassium hydroxide (723 mg, 12.89 mmol) and potassium carbonate (1.78 g, 12.89 mmol) in toluene (30 mL), were added 5-bromo-2-chloro-3-nitropyridine (1.8 g, 7.58 mmol), tert-butyl (3-hydroxypropyl)(methyl)carbamate (1.72 g, 9.1 mmol) and 2-(2-methoxyethoxy)-N,N-di[2-(2-methoxyethoxy)ethyl]ethanamine (245 mg, 0.758 mmol). The mixture solution was stirred at 15° C. for 18 hours under nitrogen protection. After the completion of the reaction, the reaction solution was filtered, and the filtrate was concentrated and then purified by silica gel chromatography column (PE:EA=20:1-4:1) to give the title compound (1.5 g, 50%) as a yellow oil.

1H NMR (400 MHz, CDCl$_3$) ppm δ 8.40 (d, J=2.0 Hz, 1H), 8.36 (d, J=2.2 Hz, 1H), 4.47 (t, J=6.1 Hz, 2H), 3.40 (t, J=6.8 Hz, 2H), 2.87 (s, 3H), 2.03 (s, 2H), 1.41 (s, 9H).

b) tert-Butyl methyl(3-((3-nitro-5-(4,4,5,5-tetramethyl-1,3,2-dioxaborolan-2-yl)pyridin-2-yl)oxy)propyl)carbamate Under nitrogen protection, to a mixture solution of tert-butyl (3-((5-bromo-3-nitropyridin-2-yl)oxy)propyl)(methyl)carbamate (1.5 g, 3.84 mmol), 4,4,5,5-tetramethyl-2-(4,4,5,5-tetramethyl-1,3,2-dioxaborolan-2-yl)-1,3,2-dioxaborolane (1.17 g, 4.61 mmol) and potassium acetate (1.13 g, 11.53 mmol) in dioxane (30 mL), was added 1,1'-bis(diphenylphosphino)ferrocene palladium chloride (97 mg, 0.11 mmol). The mixture solution was stirred at 80° C. for 18 hours under nitrogen protection. After the completion of the reaction by detection, the reaction solution was filtered and the filtrate was concentrated and then purified by silica gel chromatography to give a crude product (0.9 g, 53%) as a yellow oil.

1H NMR (400 MHz, CDCl$_3$) ppm 8.65 (d, J=1.5 Hz, 1H), 8.55 (d, J=1.5 Hz, 1H), 4.52 (t, J=5.7 Hz, 2H), 3.41 (t, J=6.8 Hz, 2H), 2.87 (s, 3H), 2.04 (br. s., 2H), 1.41 (s, 9H), 1.33 (s, 12H).

c) tert-Butyl (3-((3-amino-5-(4,4,5,5-tetramethyl-1,3,2-dioxaborolan-2-yl)pyridin-2-yl) oxy)propyl) (methyl)carbamate Pd/C (90.00 mg) was added to a solution of tert-butyl methyl(3-((3-nitro-5-(4,4,5,5-tetramethyl-1,3,2-dioxaborolan-2-yl)pyridin-2-yl)oxy)propyl)carbamate (900 mg, 2.06 mmol) in methanol (10 mL). The mixture solution was stirred at 15° C. for 4 hours under hydrogen atmosphere. After the completion of the reaction by detection, the reaction solution was filtered and the filtrate was concentrated to give a crude product (870 mg, 95%) as a yellow oil.

1H NMR (400 MHz, CDCl$_3$) ppm δ 7.93 (s, 1H), 7.21 (s, 1H), 4.41 (t, J=6.0 Hz, 2H), 3.39 (br. s., 2H), 2.85 (br. s., 3H), 2.00 (br. s., 2H), 1.41 (br. s., 9H), 1.31 (s, 12H).

d) tert-Butyl (3-((3-amino-5-(3-chloro-4-oxo-4H-pyrido[1,2-a]pyrimidin-7-yl)pyridin-2-yl) oxy)propyl)(methyl)carbamate Under nitrogen protection, to a mixture solution of 7-bromo-3-chloro-pyrido[1,2-a]pyrimidin-4-one (503 mg, 1.94 mmol), tert-butyl (3-((3-amino-5-(4,4,5,5-tetramethyl-1,3,2-dioxaborolan-2-yl)pyridin-2-yl)oxy)propyl)(methyl)carbamate (790 mg, 1.94 mmol), and sodium carbonate (1M, 4.85 mL, 4.85 mmol) in dioxane (10 mL), was added 1,1'-bis(diphenylphosphino)ferrocene palladium chloride (17 mg, 0.019 mmol) at room temperature. The mixture solution was stirred at 80° C. for 18 hours under nitrogen protection. After the completion of the reaction by detection, the reaction solution was filtered, and the filtrate was dried over anhydrous sodium sulfate and then concentrated under reduced pressure. The residue was purified by silica gel chromatography column to give the title compound (600 mg, 67%) as a yellow solid.

1H NMR (400 MHz, CDCl$_3$) δ 9.18 (d, J=1.7 Hz, 1H), 8.48 (s, 1H), 7.97 (dd, J=2.1, 9.2 Hz, 1H), 7.84-7.66 (m, 2H), 7.13 (d, J=1.7 Hz, 1H), 4.45 (br. s., 2H), 3.43 (br. s., 2H), 2.88 (br. s., 3H), 2.05 (t, J=6.5 Hz, 2H), 1.43 (s, 9H).

e) tert-Butyl (3-((5-(3-chloro-4-oxo-4H-pyrido[1,2-a]pyrimidin-7-yl)-3-(2,4-difluorobenzenesulfonamido)pyridin-2-yl)oxy)propyl)(methyl)carbamate 2,4-Difluorobenzenesulfonyl chloride (333 mg, 1.57 mmol) was added to a mixture solution of tert-butyl (3-((3-amino-5-(3-chloro-4-oxo-4H-pyrido[1,2-a]pyrimidin-7-yl)pyridin-2-yl)oxy)propyl)(methyl)carbamate (600 mg, 1.3 mmol) in pyridine (5 mL). The mixture solution was allowed to react at 15° C. for 18 hours. After the completion of the reaction, the reaction solution was concentrated. The residue was dissolved in dichloromethane and washed with water and brine. The organic phase was dried over anhydrous sodium sulfate and then concentrated. The resulting product was purified by silica gel chromatography to give the title compound (404 mg, 48%) as a yellow solid.

f) N-[5-(3-Chloro-4-oxo-4H-pyrido[1,2-a]pyrimidin-7-yl)-2-(3-(methylamino)propoxy) pyridin-3-yl]-2,4-difluoro-benzenesulfonamide To a solution of tert-butyl (3-((5-(3-chloro-4-oxo-4H-pyrido[1,2-a]pyrimidin-7-yl)-3-(2,4-difluorobenzenesulfonamido)pyridin-2-yl)oxy)propyl)(methyl)carbamate (450 mg, 0.43 mmol) in dioxane (30 mL), was added a hydrochloric acid/dioxane solution (4 mL). The mixture solution was stirred at 15° C. for 3 hours. After the completion of the reaction, the reaction solution was concentrated. To the concentrated residue was added an aqueous solution of sodium bicarbonate. The precipitate was filtered off and pumped to dryness, and washed with dichloromethane to give the title product as a pale yellow solid (175.56 mg, 75.9%).

1H NMR (400 MHz. DMSO-d$_6$) δ 8.81 (d, J=1.5 Hz, 1H), 8.56 (s, 1H), 8.13 (dd, J=2.0, 9.3 Hz, 1H), 8.02-7.89 (m, 1H), 7.85-7.73 (m, 2H), 7.47 (d, J=2.2 Hz, 1H), 7.33-7.21 (m, 1H), 7.19-7.09 (m, 1H), 4.29 (t, J=5.4 Hz, 2H), 3.20-3.08 (m, 2H), 2.72 (s, 3H), 2.08 (m, 2H).

The following 5 compounds were also synthesized with reference to the process for preparing Compound 45:

| Compound | Structure | MS(ES) [M + H]⁺ |
|---|---|---|
| 46 | 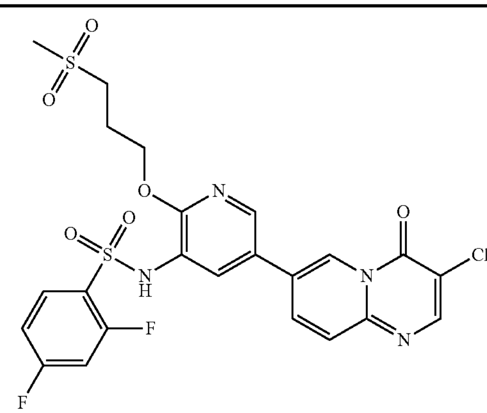 | 585 |
| 47 | 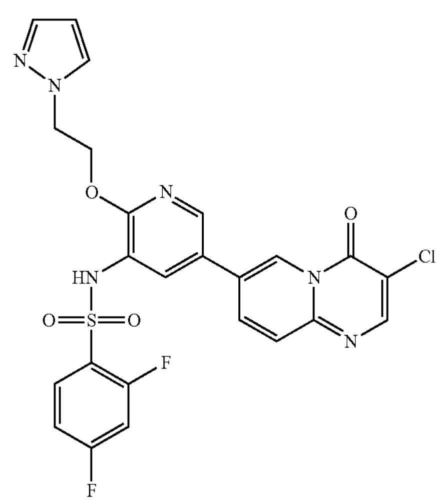 [SMILES: O=c1c(Cl)cnc2ccc(-c3cnc(OCCn4cccn4)c(NS(=O)(=O)c4ccc(F)cc4F)c3)cn12] | 559 |

-continued
| Compound | Structure | MS(ES) [M + H]+ |
|---|---|---|
| 48 | 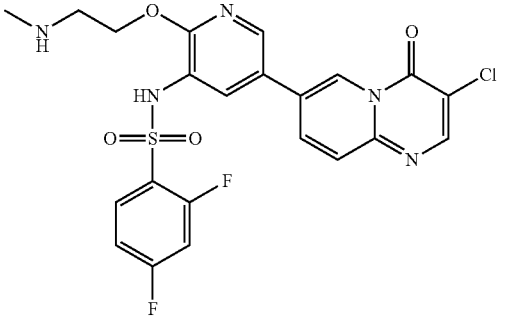 [SMILES: CNCCOc1ncc(-c2ccc3ncc(Cl)c(=O)n3c2)cc1NS(=O)(=O)c1ccc(F)cc1F] | 522 |
| 49 | 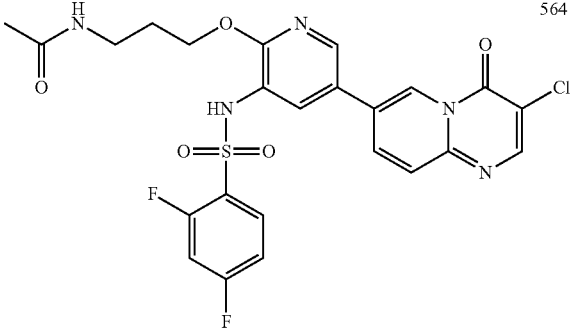 [SMILES: CC(=O)NCCCOc1ncc(-c2ccc3ncc(Cl)c(=O)n3c2)cc1NS(=O)(=O)c1ccc(F)cc1F] | 564 |
| 50 | 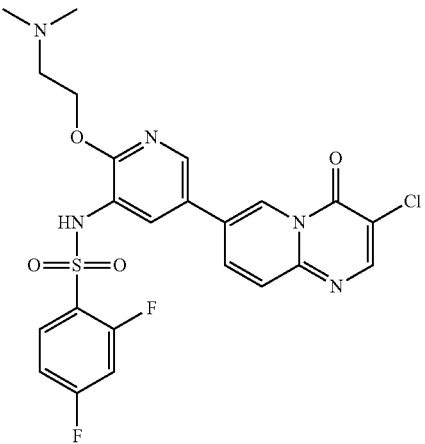 [SMILES: CN(C)CCOc1ncc(-c2ccc3ncc(Cl)c(=O)n3c2)cc1NS(=O)(=O)c1ccc(F)cc1F] | 536 |

Scheme 7:

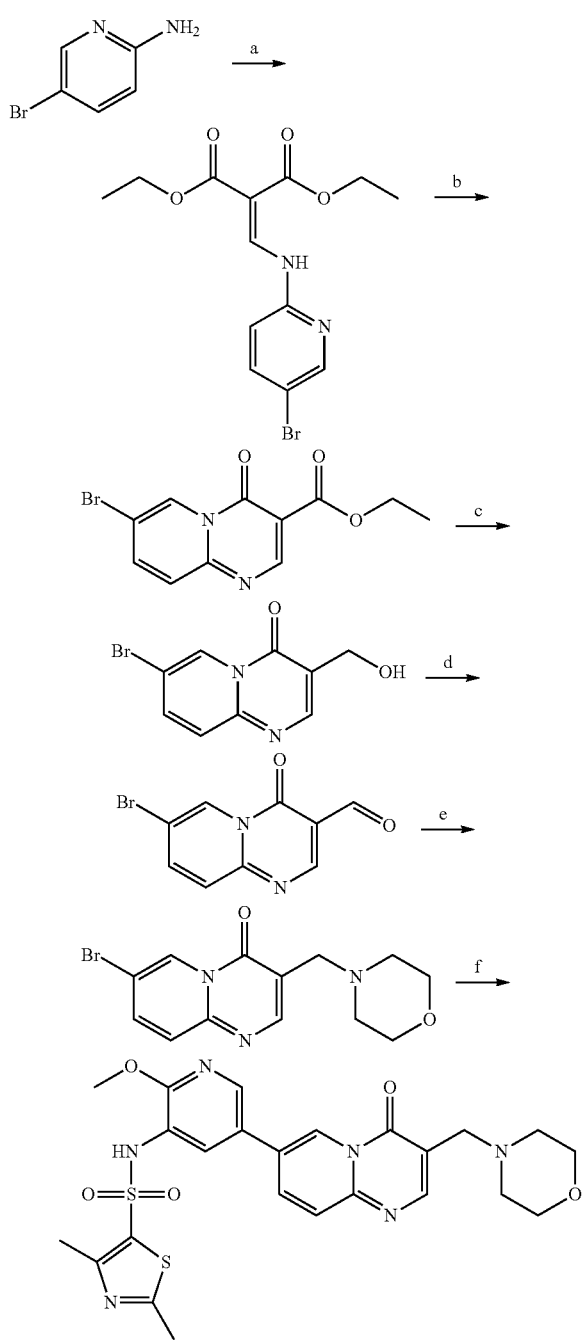

Reaction Conditions:

a) diethyl ethoxymethylenemalonate, ethanol, heating; b) phosphorusoxybromide, heating; c) DIBAL-H, tetrahydrofuran, −5° C.-0° C.; d) manganese dioxide, dioxane, heating; (e) morpholine, sodium triacetoborohydride, acetic acid, methanol, heating; f) N-[2-methoxy-5-(4,4,5,5-tetramethyl-1,3,2-dioxaborolan-2-yl)pyridin-3-yl]-2,4-dimethyl-5-sulfonamide, 1,1′-bis(diphenylphosphino)ferrocene palladium chloride, potassium carbonate, dioxane, water, heating.

Example 51

N-(2-Methoxy-5-(3-(morpholinomethyl)-4-oxo-4H-pyrido[1,2-a]pyrimidin-7-yl)pyridin-3-yl)-2,4-dimethylthiazole-5-sulfonamide

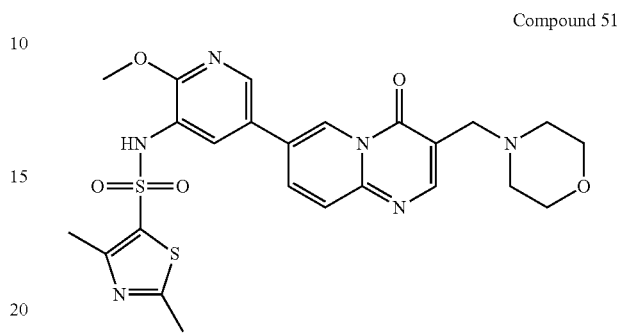

Compound 51 a) Diethyl 2-(((5-bromopyridin-2-yl)amino)methylene)malonate

2-Amino-5-bromopyridine (1.72 g, 9.94 mmol) and diethyl ethoxymethylenemalonate (4.51 g, 20.87 mmol) were placed in a round-bottomed flask and the mixture was stirred to react at 130° C. for 2 hours. TLC showed that the reaction was completed, and then the mixture was cooled to 25° C. and filtered. The filter cake was rinsed with petroleum ether (20 mL*3) to give the title compound (3.14 g, 92%) as a white solid.

$^1$H NMR (400 MHz, CDCl$_3$) ppm 11.10 (d, J=12.47 Hz, 1H), 9.06 (d, J=12.72 Hz, 1H), 8.38 (d, J=2.20 Hz, 1H), 7.74 (dd, J=8.56, 2.45 Hz, 1H), 6.76 (d, J=8.56 Hz, 1H), 4.21-4.34 (m, 4H), 1.35 (dt, J=16.02, 7.15 Hz, 6H).

b) Ethyl 7-bromo-4-oxo-4H-pyrido[1,2-a]pyrimidine-3-carboxylate

Diethyl 2-(((5-bromopyridin-2-yl)amino)methylene)malonate (21.76 g, 63.41 mmol) and phosphorusoxybromide (54.54 g, 190.23 mmol) were placed in a round-bottomed flask, and the mixture was stirred to react at 80° C. for 4 hours. TLC showed that the reaction was completed. The mixture was cooled to 25° C. and then was slowly added to ice water. To the mixture was added an aqueous solution of sodium carbonate, and the pH was adjusted to about 8. The resulting mixture was extracted with dichloromethane (300 mL*3), and the organic phase was washed with saturated brine (200 mL*2), dried over anhydrous sodium sulfate, filtered and concentrated to give the title compound (18.8 g, 99.8%) as a white solid.

$^1$H NMR (400 MHz, CDCl$_3$) ppm 9.36 (d, J=1.98 Hz, 1H), 9.03 (s, 1H), 7.97 (dd, J=9.26, 1.98 Hz, 1H), 7.67 (d, J=9.26 Hz, 1H), 4.42 (q, J=7.06 Hz, 2H), 1.41 (t, J=7.06 Hz, 3H).

c) 7-Bromo-3-(hydroxymethyl)-4H-pyrido[1,2-a]pyrimidin-4-one

Ethyl 7-bromo-4-oxo-4H-pyrido[1,2-a]pyrimidine-3-carboxylate (5.00 g, 16.83 mmol) dissolved in tetrahydrofuran (150 mL) was placed in a three-necked, round-bottomed flask. A solution of DIBAL-H (50.49 mmol) in toluene (50 mL) was added dropwise to the above mixture at −5° C. The reaction solution was stirred at 0° C. for 2 hours. TLC showed that the reaction was completed. A saturated aqueous solution of ammonium chloride was slowly added to the reaction solution, and the resulting mixture was extracted with ethyl acetate (200 mL*3), washed with saturated brine (200 mL*2), dried over anhydrous sodium sulfate, filtered and concentrated to give a crude product. The crude product was purified by silica gel column chromatography to give the title compound (1.1 g, 25.6%) as a brick red solid.

$^1$H NMR (400 MHz, CDCl$_3$) ppm 9.15 (d, J=1.96 Hz, 1H), 8.39 (s, 1H), 7.98 (dd, J=9.54, 2.20 Hz, 1H), 7.59 (d, J=9.29 Hz, 1H), 4.64 (s, 2H).

d) 7-Bromo-4-oxo-4H-pyrido[1,2-a]pyrimidine-3-carbaldehyde

7-Bromo-3-(hydroxymethyl)-4H-pyrido[1,2-a]pyrimidin-4-one (0.7 g, 2.74 mmol) dissolved in dioxane (15 mL) was placed in a 50 mL round-bottomed flask, and manganese dioxide (2.39 g, 27.44 mmol) was added thereto. The mixture was stirred to react at 80° C. for 3 hours. TLC showed that the reaction was completed, and the reaction solution was cooled to room temperature. The reaction solution was diluted with dichloromethane (50 mL) and filtered. The filtrate was concentrated to give the title compound (0.6 g, 86.5%) as a yellow solid.

$^1$H NMR (400 MHz, CDCl$_3$) ppm 10.38 (s, 1H), 9.39 (d, J=2.21 Hz, 1H), 8.90 (s, 1H), 8.06 (dd, J=9.26, 2.21 Hz, 1H), 7.73 (d, J=9.26 Hz, 1H).

e) 7-Bromo-3-(morpholinomethyl)-4H-pyrido[1,2-a]pyrimidin-4-one

7-Bromo-4-oxo-4H-pyrido[1,2-a]pyrimidine-3-carbaldehyde (88.00 mg, 347.75 μmol) dissolved in methanol (4 mL) was placed in a 10 mL thumb vial, and morpholine (45.44 mg, 521.63 μmol) and AcOH (41.77 mg, 695.51 μmol) were added thereto. The mixture was stirred at 50° C. for 2 hours. Sodium triacetoborohydride (294.81 mg, 1.39 mmol) was added to the above-mentioned reaction solution, and the stirring was continued at 50° C. for 12 hours. TLC showed that the reaction was completed, and then the reaction solution was cooled to room temperature, and purified by silica gel column chromatography to give the title compound (45 mg, 40%) as a yellow solid.

$^1$H NMR (400 MHz, CDCl$_3$) ppm 9.13 (d, J=1.71 Hz, 1H), 8.38 (s, 1H), 7.70 (dd, J=9.41, 2.08 Hz, 1H), 7.49 (d, J=9.29 Hz, 1H), 3.68-3.73 (m, 4H), 3.62 (s, 2H), 2.57 (br. s., 4H).

f) N-(2-Methoxy-5-(3-(morpholinomethyl)-4-oxo-4H-pyrido[1,2-a]pyrimidin-7-yl)pyridin-3-yl)-2,4-dimethylthiazole-5-sulfonamide 7-Bromo-3-(morpholinomethyl)-4H-pyrido[1,2-a]pyrimidin-4-one (60.00 mg, 185.09 μmol) was dissolved in dioxane (3 mL) and water (0.5 mL), and N-[2-methoxy-5-(4,4,5,5-tetramethyl-1,3,2-dioxaborolan-2-yl)pyridin-3-yl]-2,4-dimethylthiazole-5-sulfonamide (86.60 mg, 203.60 μmol), potassium carbonate (51.16 mg, 370.18 μmol), and 1,1'-bis(diphenylphosphino)ferrocene palladium chloride (13.54 mg, 18.51 μmol) were added under nitrogen protection. The mixture was stirred to react at 80° C. for 2 hours. Liquid Chromatography Mass Spectrometry showed that the reaction was completed. The reaction solution was filtered and concentrated to give a crude product. The crude product was purified by preparative high performance liquid chromatography to give the title product (50.00 mg, 50%) as a yellow solid.

$^1$H NMR (400 MHz, CDCl$_3$) ppm 9.23 (s, 1H), 8.42 (s, 1H), 8.20 (d, J=1.76 Hz, 1H), 8.06 (s, 1H), 7.90 (dd, J=9.04, 1.76 Hz, 1H), 7.77 (d, J=9.04 Hz, 1H), 4.00 (s, 3H), 3.76 (t, J=4.41 Hz, 4H), 3.65 (s, 2H), 2.66 (s, 3H), 2.59 (s, 7H).

The following 1 compound was also synthesized with reference to the process for preparing Compound 51:

| Compound | Structure | MS(ES) [M + H]$^+$ |
|---|---|---|
| 52 | 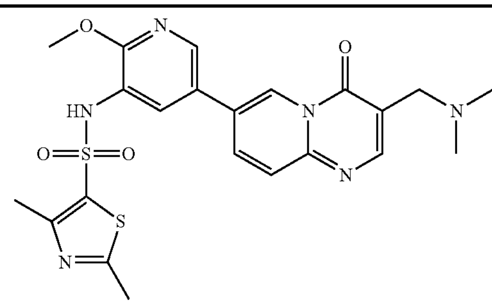 | 501 |

Scheme 8:

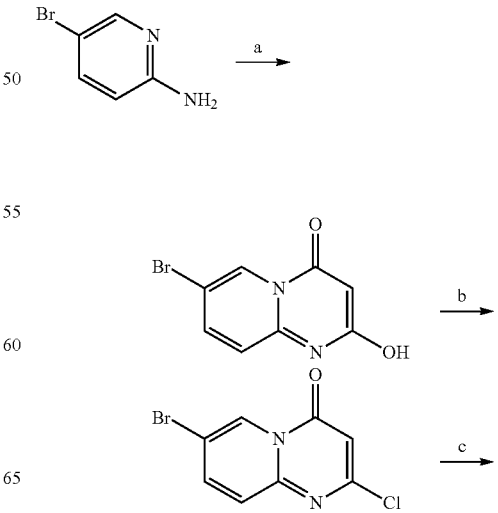

-continued

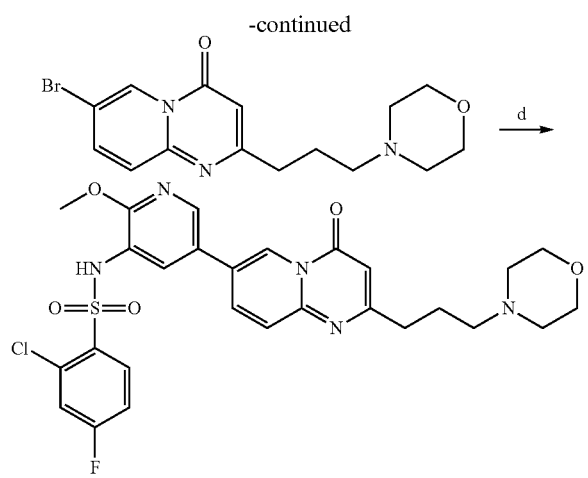

Conditions: a) malonyl chloride, dichloromethane, room temperature; b) phosphorous oxychloride, refluxing; c) N-(2-hydroxypropyl)morpholine, sodium hydride, tetrahydrofuran, 0° C. to room temperature; d) R borate (boric acid), 1,1'-bis(diphenylphosphino)ferrocene palladium chloride, potassium carbonate, dioxane, water, heating.

Example 53

2-Chloro-4-fluoro-N-(2-methoxy-5-(2-(2-morpholinoethoxy)-4-oxo-4H-pyrido[1,2-a]pyrimidin-7-yl)pyridin-3-yl benzenesulfonamide Compound 53

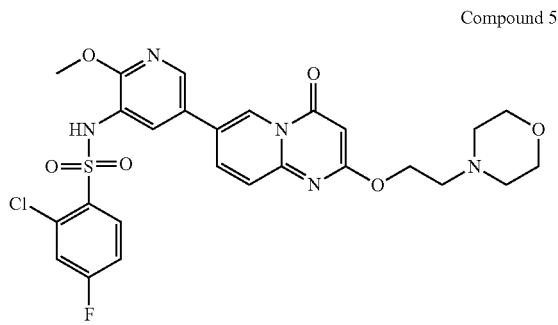

a)
7-Bromo-2-hydroxy-4H-pyrido[1,2-a]pyrimidin-4-one

2-Amino-5-bromopyridine (1.0 g, 5.7 mmol) dissolved in dichloromethane (10 mL) was placed in a 50 mL round-bottomed flask. Malonyl chloride (977 mg, 6.9 mmol) was added dropwise at 0° C. After the completion of the dropwise addition, the reaction solution was warmed to 15° C. and was stirred to react at 15° C. for 48 hours. LCMS showed that the reaction was completed. The reaction solution was filtered and the filter cake was rinsed with dichloromethane (20 mL) to give the title compound (1.4 g, 100%) as a yellow solid.

b)
7-Bromo-2-chloro-4H-pyrido[1,2-a]pyrimidin-4-one

7-Bromo-2-hydroxy-4H-pyrido[1,2-a]pyrimidin-4-one (900 mg, 3.73 mmol) dissolved in phosphorous oxychloride (8 mL) was placed in a 50 mL round-bottomed flask, and the mixture was stirred to react at 110° C. for 18 hours. LCMS showed that the reaction was completed. The reaction solution was cooled to room temperature, and slowly poured into ordinary temperature water (50 mL) to quench the reaction, and the resulting mixture was extracted with ethyl acetate (20 mL*3). The organic phase was dried over anhydrous sodium sulfate and filtered, and the filtrate was concentrated to give a crude product. The crude product was purified by silica gel column chromatography to give the title compound (300 mg, 31%6) as a yellow solid.

1H NMR (400 MHz, DMSO-$d_6$) ppm 8.99 (d, 1H), 8.21 (dd, 1H), 7.65 (d, 1H), 6.56 (s, 1H).

c) 7-Bromo-2-(2-morpholinoethoxy)-4H-pyrido[1,2-a]pyrimidin-4-one

N-(2-Hydroxypropyl)morpholine (404 mg, 3.08 mmol) dissolved in tetrahydrofuran (5 mL) was placed in a 50 mL round-bottomed flask, sodium hydride (308 mg, 7.71 mmol, 60% purity) was added at 0° C., and the reaction was stirred at 0° C. for 30 minutes. Then, 7-bromo-2-(2-morpholinoethoxy)-4H-pyrido[1,2-a]pyrimidin-4-one (200 mg, 770 μmol) was added dropwise. The reaction solution was warmed to 15° C. and the mixture was stirred to react for 3 hours. TLC showed that the reaction was completed. The reaction solution was poured slowly into ice water (50 mL) to quench the reaction, and the resulting mixture was extracted with ethyl acetate (20 mL*3). The organic phase was dried over anhydrous sodium sulfate and filtered, and the filtrate was concentrated to give a crude product. The crude product was purified by preparative thin layer chromatography to give the title compound (40 mg, 14%).

d) 2-Chloro-4-fluoro-N-(2-methoxy-5-(2-(2-morpholinoethoxy)-4-oxo-4H-pyrido[1,2-a]pyrimidin-7-yl)pyridin-3-yl)benzenesulfonamide 7-Bromo-2-(2-morpholinoethoxy)-4H-pyrido[1,2-a]pyrimidin-4-one (70 mg, 197 μmol) was dissolved in dioxane (5 mL) and water (1 mL), and 2-chloro-4-fluoro-N-(2-methoxy-5-(4,4,5,5-tetramethyl-1,3,2-dioxaborolan-2-yl)pyridin-3-yl)benzenesulfonamide (87 mg, 197 μmol), potassium carbonate (54 mg, 395 μmol) and 1,1'-bis(diphenylphosphino)ferrocene palladium chloride (7 mg) were added. The reaction solution was stirred at 100° C. for 3 hours under nitrogen protection. LCMS showed that the reaction was completed. The reaction solution was concentrated to give a crude product. The crude product was purified by preparative high performance liquid chromatography to give the title product (50 mg, 42%) as a white solid.

1H NMR (400 MHz, CDCl$_3$) ppm 9.08 (d, 1H), 8.14 (dd, 1H), 8.09 (d, 1H), 7.90 (d, 1H), 7.87 (dd, 1H), 7.58 (d, 2H), 7.28 (d, 1H), 7.19-7.12 (m, 1H), 5.86 (s, 1H), 4.58-4.48 (m, 2H), 3.99 (s, 3H), 3.76 (br. s., 4H), 2.85 (br. s., 2H), 2.62 (br. s., 3H).

Scheme 9:

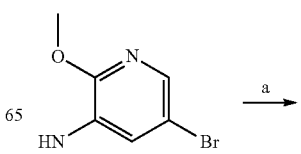

-continued

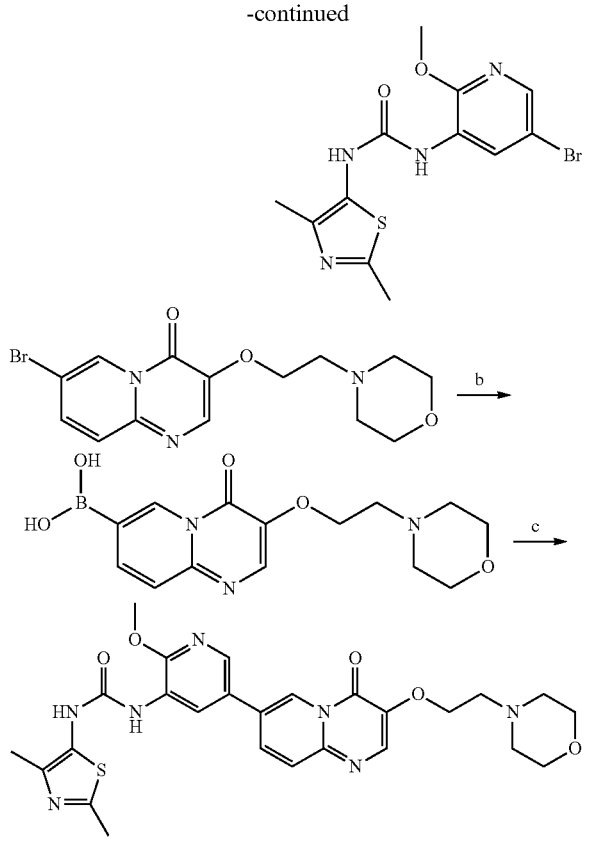

Reaction conditions: a) triphosgene, triethylamine, 2,4-dimethyl-5-aminothiazole, 0° C.; anhydrous dichloromethane, room temperature; b) 1,1'-bis(diphenylphosphino)ferrocene palladium chloride, potassium acetate, bis(pinacolato)diboron, anhydrous dioxane, heating; c) 1-(2-methoxy-5-bromopyridin-3-yl)-3-(2,4-dimethylthiazol-5-yl)urea, 1,1'-bis(di-tert-butylphosphino)ferrocene palladium dichloride, potassium phosphate trihydrate, tetrahydrofuran, water, and heating.

Example 54

1-(2,4-Dimethylthiazol-5-yl)-3-(2-methoxy-5-(3-(2-morpholinoethyl)-4-oxo-4H-pyrido[1,2-a]pyrimidin-7-yl)pyridin-3-yl)urea Compound 54

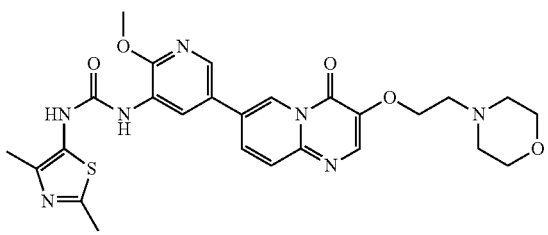

a) 1-(2-Methoxy-5-bromopyridin-3-yl)-3-(2,4-dimethylthiazol-5-yl)urea

2-Methoxy-3-amino-5-bromopyridine (100.00 mg, 492.52 μmol), triethylamine (498.38 mg, 4.93 mmol) and anhydrous dichloromethane (5 mL) were placed in a 10 mL three-necked, round-bottomed flask, a solution of triphosgene (438.47 mg, 1.48 mmol) in dichloromethane (1 mL) was slowly added dropwise at 0° C. under nitrogen protection, and the mixture was stirred to react at room temperature for 2 hours, 2,4-Dimethyl-5-aminothiazole (162.20 mg, 985.04 μmol) was added at 0° C. under nitrogen protection, and the reaction was stirred at room temperature overnight. Liquid Chromatography Mass Spectrometry showed that the reaction was completed, and then water (50 mL) was added to the mixture and the resulting mixture was extracted with dichloromethane (50 mL*3). The organic phases were combined, washed with saturated brine (50 mL*2), dried over anhydrous sodium sulfate, filtered and concentrated, and the title compound (85.00 mg, 48%) was obtained by silica gel chromatography.

$^1$H NMR (400 MHz. CD$_3$OD) ppm δ 8.57 (d, 1H), 7.82 (d, 1H), 4.02 (s, 3H), 2.56 (s, 3H), 2.26 (s, 3H).

b) (3-(2-Morpholinoethyl)-4-oxo-4H-pyrido[1,2-a]pyrimidin-7-yl)boronic acid

7-Bromo-3-(2-morpholinoethyl)-4H-pyrido[1,2-a]pyrimidin-4-one (200.00 mg, 564.65 μmol) was placed in a 10 mL long-necked, round-bottomed flask and was dissolved in dioxane (3 mL) at room temperature. Then, bis(pinacolato)diboron (430.16 mg, 1.69 mmol), potassium acetate (221.57 mg, 2.26 mmol), and 1,1'-bis(diphenylphosphino)ferrocene palladium dichloride (41.32 mg, 56.47 μmol) were added under nitrogen protection. The mixture was allowed to react at 100° C. for 2 hours. Liquid Chromatography Mass Spectrometry showed that the reaction was completed. The reaction solution was diluted with ethyl acetate (20 mL) and extracted with water (20 mL*3). The aqueous phases were combined and concentrated to give the title compound (120.00 mg, a crude product). The crude product was used directly in the next reaction without purification.

c) 1-(2,4-Dimethylthiazol-5-yl)-3-(2-methoxy-5-(3-(2-morpholinoethyl)-4-oxo-4H-pyrido[1,2-a]pyrimidin-7-yl)pyridin-3-yl)urea To a solution of (3-(2-morpholinoethyl)-4-oxo-4H-pyrido[1,2-a]pyrimidin-7-yl)boronic acid (120.00 mg, a crude product) in tetrahydrofuran (4 mL) and water (1 mL), were added 1-(2-methoxy-5-bromopyridin-3-yl)-3-(2,4-dimethylthiazol-5-yl)urea (30.00 mg, 83.98 μmol), potassium phosphate trihydrate (38.68 mg, 167.96 μmol) and 1,1'-bis(di-tert-butylphosphino)ferrocene palladium dichloride (5.47 mg, 8.40 μmol). The mixture was allowed to react at 80° C. for 5 hours. Liquid Chromatography Mass Spectrometry showed that the reaction was completed. The reaction solution was filtered and concentrated to give a crude product. The crude product was purified by preparative high performance liquid chromatography to give the title product (24.00 mg, 52%).

$^1$H NMR (400 MHz. DMSO-d$_6$) ppm δ 8.92 (d, 1H), 8.73 (d, 1H), 8.18 (s, 1H), 8.13 (d, 1H), 8.01-8.03 (m, 1H), 7.66 (d, 1H), 4.19-4.22 (m, 2H), 4.01 (s, 3H), 3.54-3.56 (m, 4H), 2.67-2.70 (m, 2H), 2.45-2.49 (m, 7H), 2.23 (s, 3H).

The following 1 compound was also synthesized with reference to the process for preparing Compound 54:

| Compound | Structure | MS(ES) [M + H]+ |
|---|---|---|
| 55 | 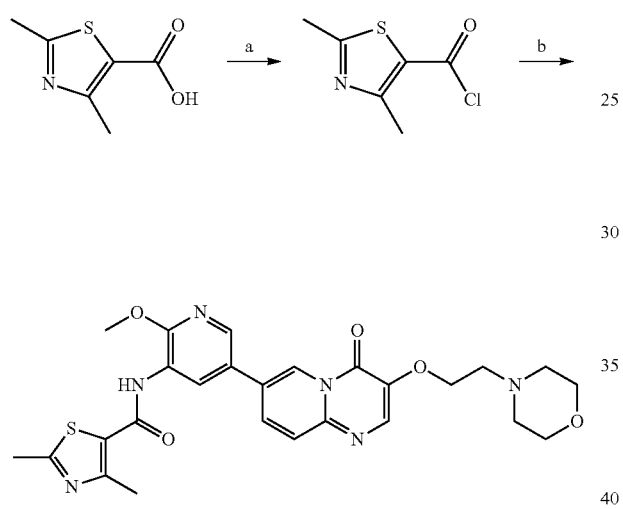 | 569 |

Scheme 10:

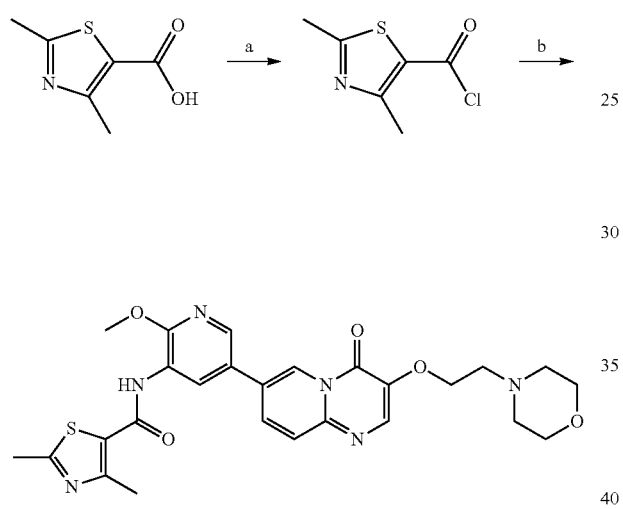

Reaction Conditions:
a) sulfoxide chloride, dichloromethane, room temperature; b) 7-(5-amino-6-methoxypyridin-3-yl)-3-(2-morpholinoethoxy)-4H-pyrido[1,2-a]pyrimidin-4-one, DMF, heating.

Example 56

N-(2-Methoxy-5-(3-(2-morpholinoethoxy)-4-oxo-4H-pyrido[1,2-a]pyrimidin-7-yl)pyridin-3-yl)-2,4-dimethylthiazole-5-carboxamide Compound 56

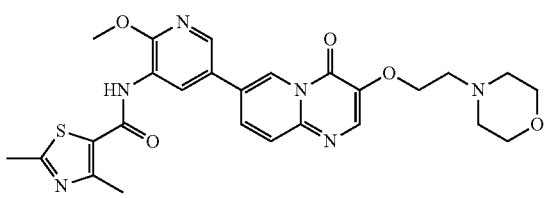

a) 2,4-Dimethylthiazole-5-carbonyl chloride 2,4-Dimethylthiazole-5-carboxylic acid (50.0 mg, 0.318 mmol) and dichloromethane (2 mL) were placed in a 10 mL round-bottomed flask, sulfoxide chloride (378.43 mg, 3.18 mmol) was added at 0° C., and the mixture was stirred to react at room temperature for 1 hour. TLC showed that the reaction was completed. The mixture was concentrated to give the title compound as a black solid which was directly used in the next reaction without purification.

b) N-(2-Methoxy-5-(3-(2-morpholinoethoxy)-4-oxo-4H-pyrido[1,2-a]pyrimidin-7-yl) pyridin-3-yl)-2,4-dimethylthiazole-5-carboxamide 2,4-Dimethylthiazole-5-carbonyl chloride (50.0 mg, 0.284 mmol), 7-(5-amino-6-methoxypyridin-3-yl)-3-(2-morpholinoethoxy)-4H-pyrido[1,2-a]pyrimidin-4-one (113.1 mg, 0.284 mmol) and DMF (0.5 mL) were placed in a 10 mL round-bottomed flask and the reaction was stirred at 60° C. for 0.5 hour. TLC showed that the reaction was completed, and then the reaction solution was cooled to room temperature and purified by preparative thin layer chromatoplate to give the title compound (10 g, 80%).

1H NMR (400 MHz, CD$_3$OD) ppm δ 9.19 (s, 1H), 8.82 (d, 1H), 8.35-8.37 (m, 1H), 8.16-8.19 (m, 1H), 7.81 (d, 1H), 4.50-4.52 (m, 2H), 4.13 (s, 3H), 3.97 (s, 4H), 3.59 (s, 1H), 3.49 (s, 1H), 2.73 (d, 1H).

The following 1 compound was also synthesized with reference to the process for preparing Compound 56:

| Compound | Structure | MS(ES) [M + H]+ |
|---|---|---|
| 57 | 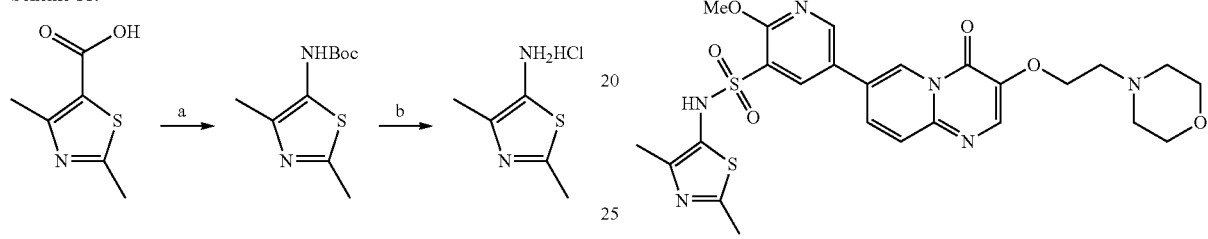 | 554 |

Scheme 11:

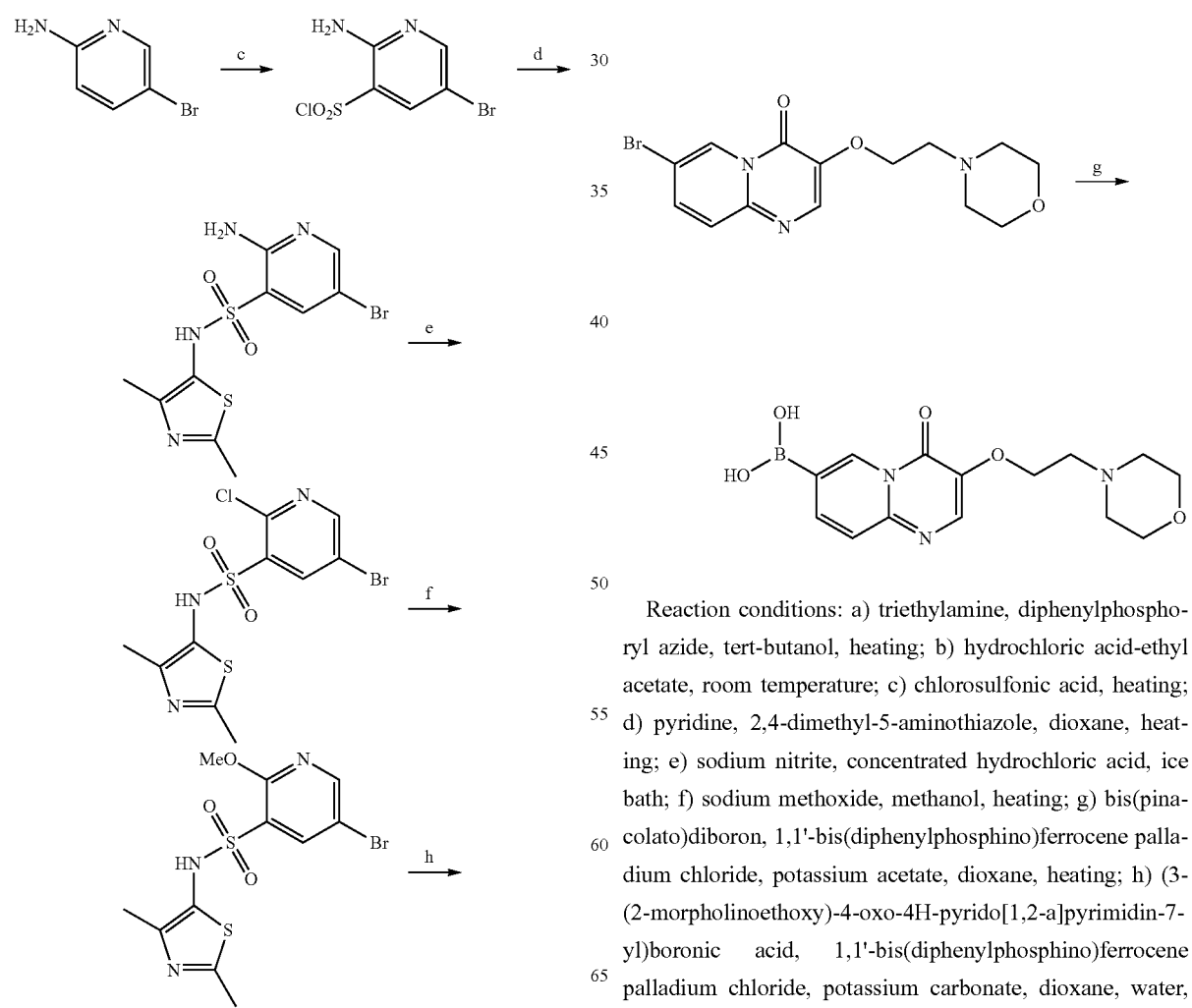

Reaction conditions: a) triethylamine, diphenylphosphoryl azide, tert-butanol, heating; b) hydrochloric acid-ethyl acetate, room temperature; c) chlorosulfonic acid, heating; d) pyridine, 2,4-dimethyl-5-aminothiazole, dioxane, heating; e) sodium nitrite, concentrated hydrochloric acid, ice bath; f) sodium methoxide, methanol, heating; g) bis(pinacolato)diboron, 1,1'-bis(diphenylphosphino)ferrocene palladium chloride, potassium acetate, dioxane, heating; h) (3-(2-morpholinoethoxy)-4-oxo-4H-pyrido[1,2-a]pyrimidin-7-yl)boronic acid, 1,1'-bis(diphenylphosphino)ferrocene palladium chloride, potassium carbonate, dioxane, water, heating.

Example 58

N-(2,4-dimethylthiazol-5-yl)-2-methoxy-5-(3-(2-morpholinoethoxy)-4-oxo-4H-4H-pyrido[1,2-a]pyrimidin-7-yl)pyridine-3-sulfonamide Coumpound 58

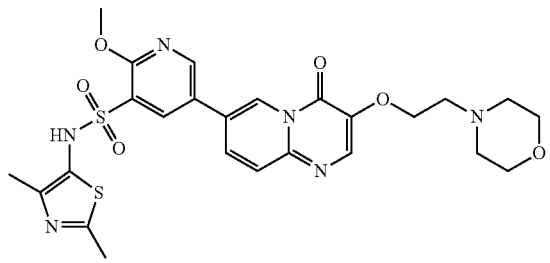

a) tert-Butyl (2,4-dimethylthiazol-5-yl)carbamate 2,4-Dimethylthiazole-5-carboxylic acid (700.00 mg, 4.45 mmol), diphenylphosphoryl azide (1.65 g, 6.00 mmol), triethylamine (1.13 g, 11.13 mmol) and tert-butanol (35 mL) were placed in a 100 mL round-bottomed, single-necked flask and the mixture was stirred to react at 85° C. for 4 hours. TLC showed that the reaction was completed. The reaction solution was cooled to room temperature. $H_2O$ (20 mL) was added thereto and the resulting mixture was extracted with ethyl acetate three times. The organic phases were combined, dried over anhydrous sodium sulfate and filtered, and the filtrate was rotary evaporated to dryness. The resulting crude product was purified by silica gel column chromatography to give the title compound (900.00 mg, 88.54%).

$^1$H NMR (400 MHz, DMSO-$d_6$) δ 9.46 (br. s., 1H), 2.46 (s, 3H), 2.14 (s, 3H), 1.43 (s, 9H).

b) 2,4-Dimethyl-5-aminothiazole hydrochloride tert-Butyl (2,4-dimethylthiazol-5-yl)carbamate was dissolved in hydrochloric acid-ethyl acetate (10 mL). The solution was stirred at room temperature for 1 hour and then rotary evaporated to dryness. The resulting crude product was slurried with ethyl acetate to give the title compound (700 mg).

$^1$H NMR (400 MHz, DMSO-d) δ 2.66 (s, 3H), 2.19 (s, 3H).

c) 2-Amino-5-bromopyridine-3-sulfonyl chloride

Chlorosulfonic acid (136.18 g, 57.80 mmol) was placed in a 250 mL round-bottomed three-necked flask and cooled to −15° C. and then 2-amino-5-bromopyridine (10.00 g, 57.80 mmol) was added dropwise thereto under nitrogen protection. After the completion of the dropwise addition, the resulting mixture was gradually heated to 160° C. in an oil bath and was stirred for 5 hours under heating. After the completion of the reaction, the reaction mixture was cooled to room temperature and slowly poured into ice. After the ice melted, the precipitated solid was filtered and washed with ice water to give the title compound (10.00 g, 63.72%).

$^1$H NMR (400 MHz, DMSO-$d_6$) δ 8.27 (d, J=2.3 Hz, 1H), 8.08 (d, J=2.0 Hz, 1H).

d) 2-Amino-5-bromo-N-(2,4-dimethylthiazol-5-yl)pyridine-3-sulfonamide

A solution of 2-amino-5-bromopyridine-3-sulfonyl chloride (164.90 mg, 607.33 mmol) in dioxane (3 mL) was placed in a 50 mL round-bottomed three-necked flask and cooled to 0° C., and pyridine (196.00 mg, 2.48 mmol) and 2,4-dimethyl-5-aminothiazole hydrochloride (100.00 mg, 607.33 mmol) were added thereto. The reaction solution was gradually warmed to room temperature and stirred for 2 hours, and then was heated to 50° C. and allowed to react for 1 hour. After the completion of the reaction, the mixture was cooled to room temperature and dissolved in a mixture solution of dichloromethane and methanol (dichloromethane:methanol=20:1). After stirred for 30 minutes, the mixture was filtered, the resulting filtrate was rotary evaporated to dryness, and the resulting crude product was purified by silica gel column chromatography to give the title compound (60.00 mg, 27.20%).

$^1$H NMR (400 MHz, CD$_3$OD) δ 8.27 (d, J=2.5 Hz, 1H), 7.81 (d, J=2.5 Hz, 1H), 2.56 (s, 3H), 2.06 (s, 3H).

e) 2-Chloro-5-bromo-N-(2,4-dimethylthiazol-5-yl)pyridine-3-sulfonamide

2-Amino-5-bromo-N-(2,4-dimethylthiazol-5-yl)pyridine-3-sulfonamide (100.00 mg, 275.29 µmol) was placed in a 25 mL round-bottomed flask and cooled to 0° C., and concentrated hydrochloric acid (7 mL) was added thereto. Then, an aqueous solution of sodium nitrite (855.00 mg, 12.39 mmol, 1.5 mL) was added dropwise thereto at 0° C. After the completion of the dropwise addition, the mixture was warmed to room temperature, stirred for 1 hour and filtered, and the filtrate was adjusted to pH 8 with a saturated sodium bicarbonate solution. The resulting solution was rotary evaporated to dryness and then dissolved in a mixture solution of dichloromethane and methanol (dichloromethane:methanol=10:1). After stirred for 30 minutes, the resulting mixture was filtered, and the filtrate was rotary evaporated to dryness and the resulting crude product was purified by thin layer chromatography to give the title compound (30.00 mg, 28.48%).

$^1$H NMR (400 MHz, CD$_3$OD) δ 8.76 (d, J=2.3 Hz, 1H), 8.40 (d, J=2.5 Hz, 1H), 2.55 (s, 3H), 2.17 (s, 3H).

f) 2-Methoxy-5-bromo-N-(2,4-dimethylthiazol-5-yl)pyridine-3-sulfonamide

A solution of 2-chloro-5-bromo-N-(2,4-dimethylthiazol-5-yl)pyridine-3-sulfonamide (30.00 mg, 78.39 µmol) and sodium methoxide (10.00 mg, 185.19 µmol) in methanol was placed in a sealed microwave tube, and heated to 110° C. and stirred for 3 hours. After the completion of the reaction, the reaction mixture was cooled to room temperature, and saturated sodium bicarbonate (5 mL) was added thereto. The resulting mixture was extracted with dichloromethane three times. The organic phases were combined, dried over anhydrous sodium sulfate, filtered and rotary evaporated to dryness to give the title compound (20.00 mg, 67.45%).

$^1$H NMR (400 MHz, CD$_3$OD) δ 8.24 (d, J=2.5 Hz, 1H), 8.10 (d, J=2.5 Hz, 1H), 3.97 (s, 3H), 2.44 (s, 3H), 2.06 (s, 3H).

g) (3-(2-Morpholinoethoxy)-4-oxo-4H-pyrido[1,2-a]pyrimidin-7-yl)boronic acid A solution of 7-bromo-3-(2-morpholinoethoxy)-4H-4-oxo-pyrido[1,2-a]pyrimidine (80.00 mg, 225.86 µmol), bis (pinacolato)diboron (172.06 mg, 677.58 μmol), 1,1'-bis(diphenylphosphino)ferrocene palladium chloride (49.58 mg, 67.76 μmol) and potassium acetate (66.50 mg, 677.58 μmol) in dioxane (3 mL) was placed in a 50 mL round-bottomed single-necked flask, and heated to 80° C. and stirred for 1 hour under nitrogen protection. After the completion of the reaction, water (5 mL) was added thereto, and the mixture was extracted with ethyl acetate three times. The aqueous phase was rotary evaporated to dryness, and the resulting crude product was slurried with a mixture solution of dichloromethane and methanol (dichloromethane:methanol=20:1) and filtered to give the title compound (60.00 mg, 83.24%).

$^1$H NMR (400 MHz, CD$_3$OD) δ 9.00 (br. s., 1H), 8.23 (s, 1H), 8.00 (d, J=7.8 Hz, 1H), 7.53 (d, J=8.3 Hz, 1H), 4.31 (br. s., 2H), 3.73 (br. s., 4H), 2.87 (br. s., 2H), 2.65 (br. s., 4H), 1.22 (s, 4H).

h) N-(2,4-Dimethylthiazol-5-yl)-2-methoxy-5-(3-(2-morpholinoethoxy)-4-oxo-4H-4H-pyrido[1,2-a]pyrimidin-7-yl)pyridine-3-sulfonamide 2-Methoxy-5-bromo-N-(2,4-dimethylthiazol-5-yl)pyridine-3-sulfonamide (20.00 mg, 52.87 μmol), (3-(2-morpholinoethoxy)-4-oxo-4H-pyrido[1,2-a]pyrimidin-7-yl)boronic acid (60.00 mg, 188.02 μmol), 1,1'-bis(diphenylphosphino)ferrocene palladium chloride (3.87 mg, 5.29 μmol), and potassium carbonate (21.92 mg, 158.61 μmol) were dissolved in dioxane (3 mL) and water (0.3 mL). The reaction solution was heated to 80° C. and stirred for 1 hour under nitrogen protection. After the completion of the reaction, the solution was rotary evaporated to dryness, and the resulting crude product was purified by preparative high performance liquid chromatography to give the title compound (5.00 mg, 16.51%).

$^1$H NMR (400 MHz, CD$_3$OD) δ 9.14 (s, 1H), 8.64 (s, 1H), 8.39 (d, J=2.5 Hz, 1H), 8.26 (s, 1H), 8.03 (d, J=11.3 Hz, 1H), 7.74 (d, J=9.3 Hz, 1H), 4.35 (t, J=5.4 Hz, 2H), 4.10 (s, 3H), 3.76-3.69 (m, 4H), 2.88 (t, J=5.5 Hz, 2H), 2.66 (br. s., 4H), 2.44 (s, 3H), 2.11 (s, 3H); MS (ESI) m/z: 573 (M+H$^+$).

Scheme 12:

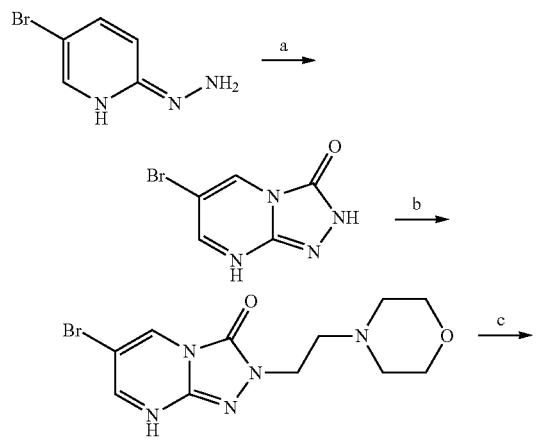

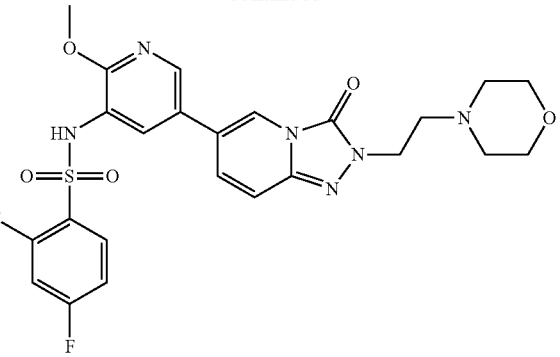

Reaction conditions: a) carbonyldiimidazole, acetonitrile, heating; b) 4-(2-chloroethyl)morpholine, cesium carbonate, dimethyl sulfoxide, heating; c) 2,4-difluoro-N-(2-methoxy-5-(4,4,5,5-tetramethyl-1,3,2-dioxaborolan-2-yl)pyridin-3-yl) benzenesulfonamide. [1,1'-bis(diphenylphosphino)ferrocene]palladium chloride, potassium carbonate, dioxane, water, heating.

Example 59

2,4-Difluoro-N-(2-methoxy-5-(2-(2-morpholinoethyl)-3-oxo-2,3-dihydro-[1,2,4]triazolo[4,3-a]pyridin-6-yl)pyrimidin-3-yl)benzenesulfonamide Compound 59

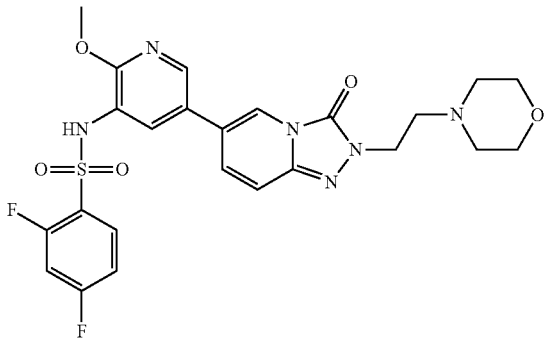

a) 6-Bromo-[1,2,4]triazolo[4,3-a]pyridine-3(2H)-one

5-Bromo-2-hydrazono-1,2-dihydropyridine (5.00 g, 26.59 mmol) and acetonitrile (100 mL) were placed in a 250 mL round-bottomed single-necked flask, and then carbonyldiimidazole (4.75 g, 29.29 mmol) was added under nitrogen protection. The reaction solution was allowed to react at 80° C. for 2 hours, and filtered to precipitate a solid. Then, acetonitrile (20 mL) was added for slurry purification. After filtration, the title compound was given (3.90 g, 68.53%).

$^1$H NMR (400 MHz, DMSO-d$_6$) δ 12.63 (br. s., 1H), 8.07 (s, 1H), 7.28-7.19 (m, 2H).

b) 6-Bromo-2-(2-morpholinoethyl)-[1,2,4]triazolo[4,3-a]pyridine-3(2H)-one

6-Bromo-[1,2,4]triazolo[4,3-a]pyridine-3(2H)-one (1.00 g, 4.67 mmol) was dissolved in dimethyl sulfoxide (10 mL), and cesium carbonate (3.80 g, 11.68 mmol) and 4-(2-chloroethyl)morpholine (1.40 g, 9.34 mmol) were added. The resulting solution was stirred at room temperature for 16 hours. After the completion of the reaction, the reaction mixture was filtered. Water (10 mL) was added to the filtrate and then the resulting mixture was extracted with ethyl acetate three times. The organic phases were combined, dried over anhydrous sodium sulfate, filtered and rotary evaporated to dryness, and the crude product was separated and purified by column chromatography to give the title compound (500.00 mg, 32.72%).

$^1$H NMR (400 MHz, DMSO-d$_6$) δ 8.14 (s, 1H), 7.38-7.19 (m, 2H), 4.02 (t, J=6.5 Hz, 2H), 3.53-3.49 (m, 4H), 2.68 (t, J=6.3 Hz, 2H), 2.41 (br. s., 4H).

c) 2,4-Difluoro-N-(2-methoxy-5-(2-(2-morpholinoethyl)-3-oxo-2,3-dihydro-[1,2,4]triazolo[4,3-a]pyridin-6-yl)pyrimidin-3-yl)benzenesulfonamide 6-Bromo-2-(2-morpholinoethyl)-[1,2,4]triazolo[4,3-a]pyridine-3(2H)-one (100.00 mg, 305.64 μmol), 2,4-difluoro-N-[2-methoxy-5-(4,4,5,5-tetramethyl-1,3,2-dioxaborolan-2-yl)-3-pyridyl]benzenesulfonamide (130.28 mg, 305.64 μmol), potassium carbonate (42.24 mg, 305.64 μmol) and 1,1'-bis(diphenylphosphino)ferrocene palladium chloride (223.64 mg, 305.64 μmol) were dissolved in dioxane (1.5 mL) and water (0.3 mL). The reaction solution was allowed to react at 80° C. for 2 hours under nitrogen protection. After the completion of the reaction, the resulting solution was rotary evaporated to dryness to give a crude product. The crude product was purified by preparative high performance liquid chromatography to give the title compound (50.00 mg, 29.93%).

$^1$H NMR (400 MHz, CD$_3$OD) δ 7.99-7.92 (m, 1H), 7.84 (s, 1H), 7.75 (d, J=2.0 Hz, 1H), 7.60 (d, J=2.0 Hz, 1H), 7.50-7.43 (m, 1H), 7.27 (d, J=9.5 Hz, 1H), 7.08-6.95 (m, 2H), 4.18 (t, J=6.3 Hz, 2H), 3.88 (s, 3H), 3.71-3.64 (m, 4H), 2.88-2.83 (m, 2H), 2.58 (br. s., 4H).

Scheme 13:

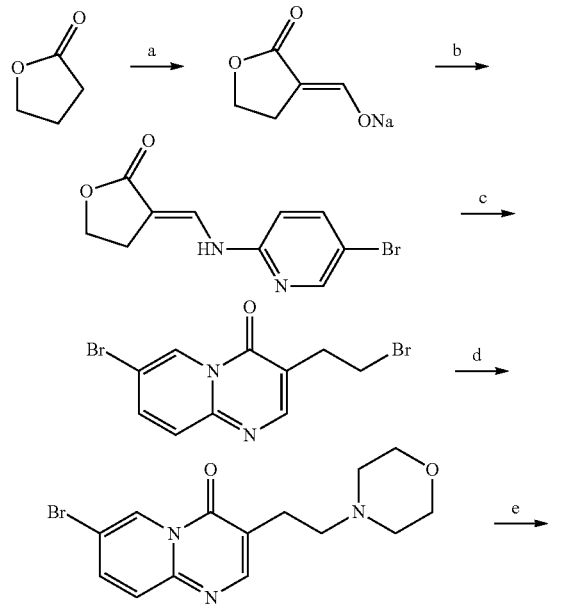

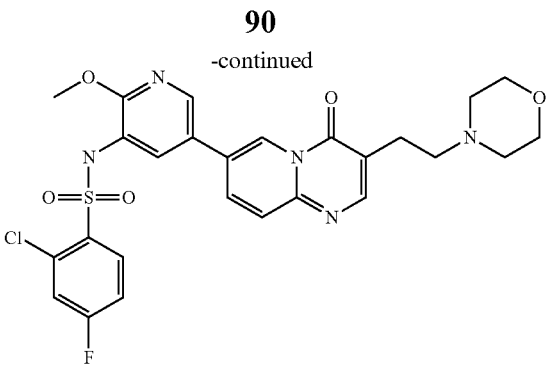

Reaction conditions: a) ethyl formate, sodium hydride, dimethoxyethane, heating; b) 5-bromopyridine-2-amine, ammonium acetate, heating; c) phosphorusoxybromide, heating; d) cesium carbonate, acetonitrile, heating; e) R boric acid (borate), 1,1'-bis(diphenylphosphino)ferrocene palladium chloride, potassium carbonate, dioxane, water, heating.

Example 60

2-Chloro-4-fluoro-N-(2-methoxy-5-(3-(2-ethylmorpholinyl)-4-oxo-4H-pyrido[1,2-a]pyrimidin-7-yl)pyridin-3-yl)benzenesulfonamide Coumpound 60

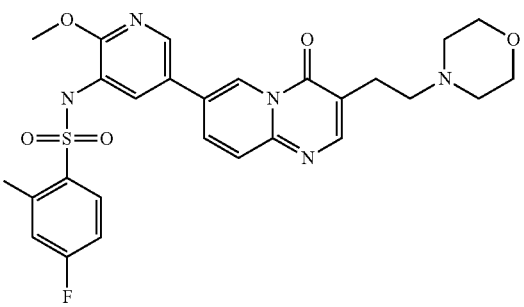

a) Sodium (E)-(2-oxo-dihydrofuran-3(2H)-ylidene)methoxide

Sodium hydride (0.93 g, 23.23 mmol) was slowly added in batches to a 500 mL round-bottomed flask containing dimethoxyethane (96 mL). To the mixture was added dropwise a solution of dihydrofuran-2(3H)-one (2 g, 23.23 mmol) and ethyl formate (1.72 g, 23.23 mmol) in dimethoxyethane (12 mL) under stirring, and then ethanol (0.15 mL) was added. The reaction solution was stirred to react at 60° C. for 16 hours. The mixture was cooled to 25° C. and filtered, and the filter cake was rinsed with ethyl acetate (20 mL*3) to give the title compound (2.1 g, 66%) as a yellow-green solid.

1H NMR (400 MHz. D$_2$O) ppm δ 8.45-8.31 (m, 1H), 4.27 (t, 2H), 2.71 (t, 2H).

b) (E)-3-(((5-Bromopyridin-2-yl)amino)methyl-idene)dihydrofuran-2(3H)-one

Sodium (E)-(2-oxo-dihydrofuran-3(2H)-ylidene)methoxide (1.42 g, 10.4 mmol), 5-bromopyridine-2-amine (1.2 g, 6.94 mmol) and ammonium acetate (2.67 g, 34.68 mmol) were placed in a 50 mL round-bottomed flask, and stirred to react at 120° C. for 1 hour. Liquid Chromatography Mass Spectrometry showed that the reaction was completed, and then the reaction solution was cooled to room temperature and slowly poured into ice water. A solid was precipitated and filtered. The filter cake was rinsed with water (20 mL*3) to give the title compound as a crude solid. The crude solid was then slurried with petroleum ether (30 mL) to give the title compound (1.4 g, 75%) as a gray solid, 1H NMR (400 MHz, CDCl$_3$) ppm δ 8.29 (d, 1H), 8.02 (d, 1H), 7.74 (dd, 1H), 6.79 (d, 1H), 4.44 (t, 2H), 2.90 (dt, 2H).

c) 7-Bromo-3-(2-bromoethyl)-4H-pyrido[1,2-a]py-rimidin-4-one (E)-3-(((5-bromopyridin-2-yl)amino)methylidene)dihydrofuran-2(3H)-one (1.4 g, 5.2 mmol) and phosphorusoxybromide (6.98 g, 24.35 mmol) were placed in a 50 mL round-bottomed flask, and stirred to react at 80° C. for 1.5 hours. Liquid Chromatography Mass Spectrometry showed that the reaction was completed, and then the reaction solution was cooled to room temperature and slowly poured into ice water. The resulting mixture was adjusted to pH 8 and extracted with dichloromethane (20 mL*3). The organic phase was washed with saturated brine, dried over anhydrous sodium sulfate and concentrated to give the title compound (1.2 g, 69%) as a yellow solid.
1H NMR (400 MHz, CDCl$_3$) ppm δ 9.17 (d, 1H), 8.27 (s, 1H), 7.74 (dd, 1H), 7.54 (d, 1H), 3.73 (t, 2H), 3.21 (t, 2H).

d) 7-Bromo-3-(2-ethylmorpholinyl)-4H-pyrido[1,2-a]pyrimidin-4-one

7-Bromo-3-(2-bromoethyl)-4H-pyrido[1,2-a]pyrimidin-4-one (0.2 g, 0.6 mmol), morpholine (78.73 mg, 0.9 mmol) and cesium carbonate (0.59 g, 1.81 mmol) were placed in a 50 mL round-bottomed flask, and stirred to react at 70° C. for 12 hours. Liquid Chromatography Mass Spectrometry showed that the reaction was completed, and then the reaction solution was cooled to room temperature, water was added, and the resulting mixture was extracted with dichloromethane (20 mL*3). The organic phase was washed with saturated brine, dried over anhydrous sodium sulfate and concentrated to give the crude title compound as an oil, which was used directly in the next reaction.

e) 2-Chloro-4-fluoro-N-(2-methoxy-5-(3-(2-ethyl-morpholinyl)-4-oxo-4H-pyrido[1,2-a]pyrimidin-7-yl)pyridin-3-yl)benzenesulfonamide 7-Bromo-3-(2-ethylmorpholinyl)-4H-pyrido[1,2-a]pyrimidin-4-one (0.59 mmol) was dissolved in dioxane (2 mL) and water (0.4 mL), and 2-chloro-4-fluoro-N-(2-methoxy-5-(4,4,5,5-tetramethyl-1,3,2-dioxaborolan-2-yl)pyridin-3-yl)benzenesulfonamide (0.59 mmol), potassium carbonate (1.18 mmol) and 1,1'-bis(diphenylphosphino)ferrocene palladium chloride (22 mg) were added under nitrogen protection. The mixture was allowed to react at 100° C. for 1 hour under a microwave reaction condition. Liquid Chromatography Mass Spectrometry showed that the reaction was completed. The reaction solution was filtered and concentrated to give a crude product. The crude product was purified by silica gel column chromatography and preparative high performance liquid chromatography to give the title product.

1H NMR (400 MHz. CDCl$_3$) ppm δ 9.08 (s, 1H), 8.29 (s, 1H), 8.17-8.09 (m, 2H), 7.94 (d, 1H), 7.85-7.77 (m, 1H), 7.75-7.68 (m, 1H), 7.28 (d, 1H), 7.18-7.12 (m, 1H), 4.00 (s, 3H), 3.79 (br. s., 3H), 2.93 (br. s., 1H).

The following 1 compound was also synthesized with reference to the process for preparing Compound 1.

| Compound | Structure | MS(ES) [M + H]⁺ |
|---|---|---|
| 61 | 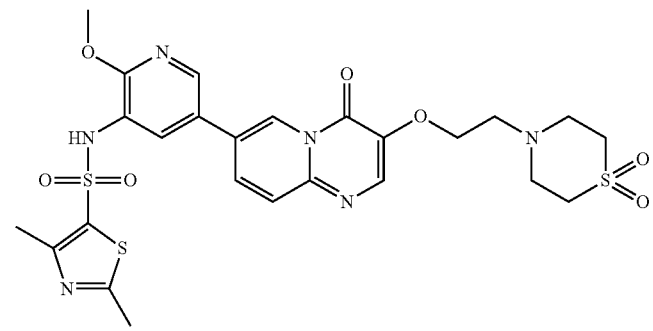 [SMILES: COc1ncc(-c2ccc3ncc(OCCN4CCS(=O)(=O)CC4)c(=O)n3c2)cc1NS(=O)(=O)c1sc(C)nc1C] | 621.7 |

The following 3 compounds were also synthesized with reference to the process for preparing Compound 7.

| Compound | Structure | MS(ES) [M + H]+ |
|---|---|---|
| 62 | 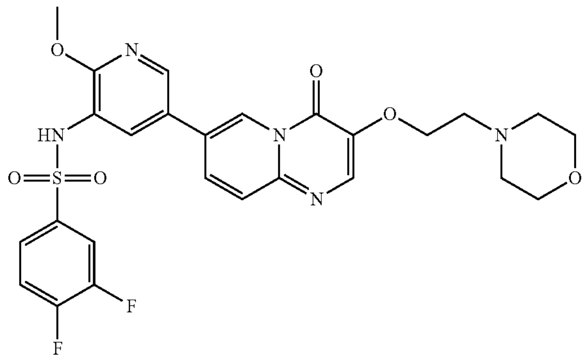 [SMILES: COc1ncc(-c2ccc3ncc(OCCN4CCOCC4)c(=O)n3c2)cc1NS(=O)(=O)c1ccc(F)c(F)c1] | 574.5 |
| 63 | 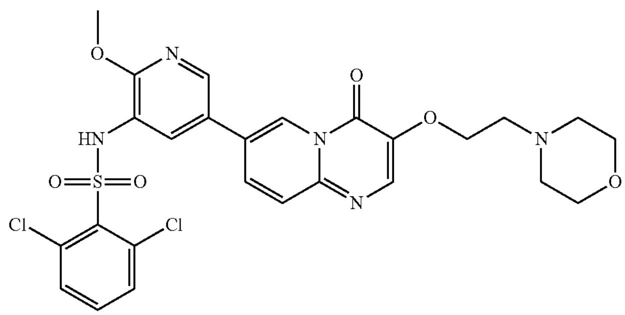 [SMILES: COc1ncc(-c2ccc3ncc(OCCN4CCOCC4)c(=O)n3c2)cc1NS(=O)(=O)c1c(Cl)cccc1Cl] | 607.5 |
| 64 | 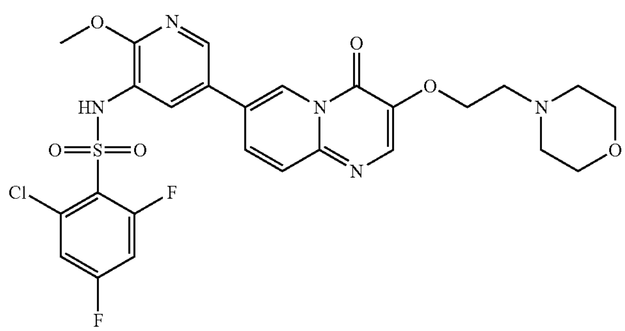 [SMILES: COc1ncc(-c2ccc3ncc(OCCN4CCOCC4)c(=O)n3c2)cc1NS(=O)(=O)c1c(F)cc(F)cc1Cl] | 609 |

The following 31 compounds were also synthesized with reference to the process for preparing Compound 21.

| Compound | Structure | MS(ES) [M + H]+ |
|---|---|---|
| 65 | 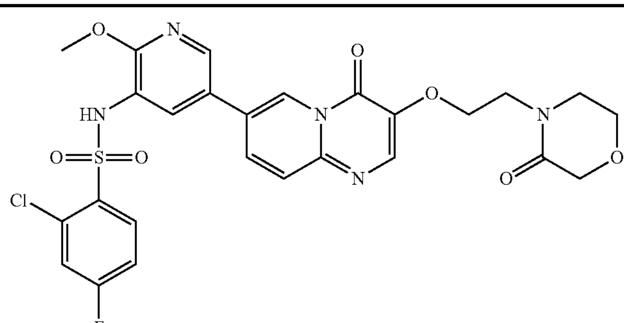 | 604 |

| Compound | Structure | MS(ES) [M + H]+ |
|---|---|---|
| 66 | 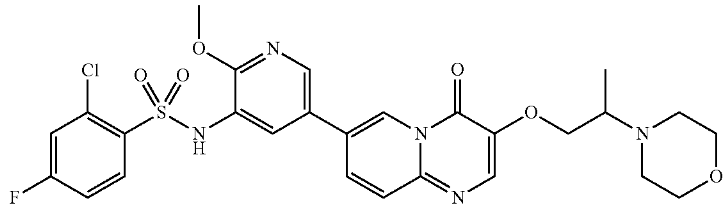 [SMILES: COc1ncc(-c2ccc3ncc(OCC(C)N4CCOCC4)c(=O)n3c2)cc1NS(=O)(=O)c1ccc(F)cc1Cl] | 606 |
| 67 | 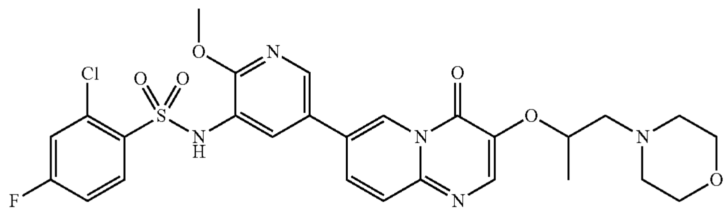 [SMILES: COc1ncc(-c2ccc3ncc(OC(C)CN4CCOCC4)c(=O)n3c2)cc1NS(=O)(=O)c1ccc(F)cc1Cl] | 604 |
| 68 | 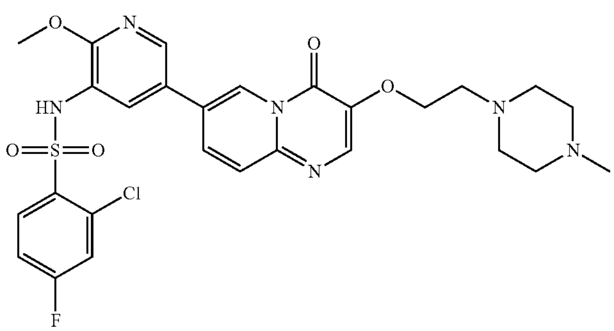 [SMILES: COc1ncc(-c2ccc3ncc(OCCN4CCN(C)CC4)c(=O)n3c2)cc1NS(=O)(=O)c1ccc(F)cc1Cl] | 604 |
| 69 | 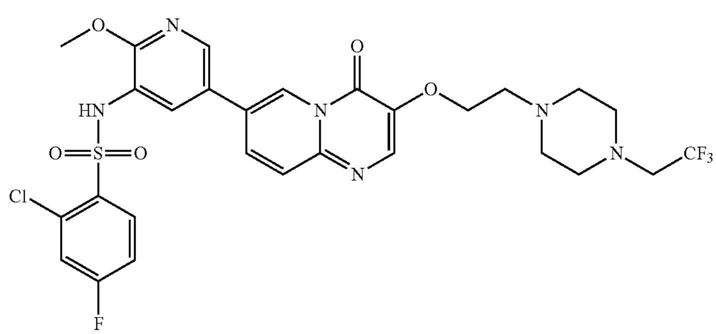 [SMILES: COc1ncc(-c2ccc3ncc(OCCN4CCN(CC(F)(F)F)CC4)c(=O)n3c2)cc1NS(=O)(=O)c1ccc(F)cc1Cl] | 672 |
| 70 | 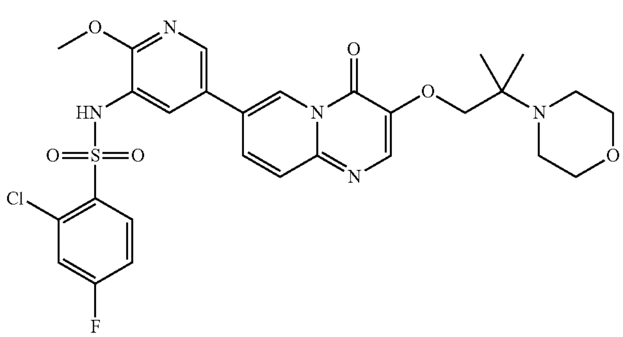 [SMILES: COc1ncc(-c2ccc3ncc(OCC(C)(C)N4CCOCC4)c(=O)n3c2)cc1NS(=O)(=O)c1ccc(F)cc1Cl] | 619 |

| Compound | Structure | MS(ES) [M + H]+ |
|---|---|---|
| 71 | 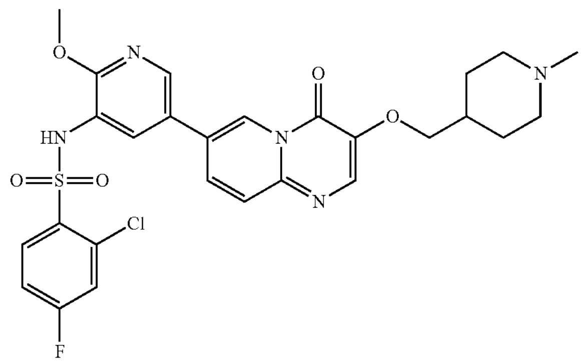 [SMILES: COc1ncc(-c2ccc3ncc(OCC4CCN(C)CC4)c(=O)n3c2)cc1NS(=O)(=O)c1ccc(F)cc1Cl] | 589 |
| 72 | 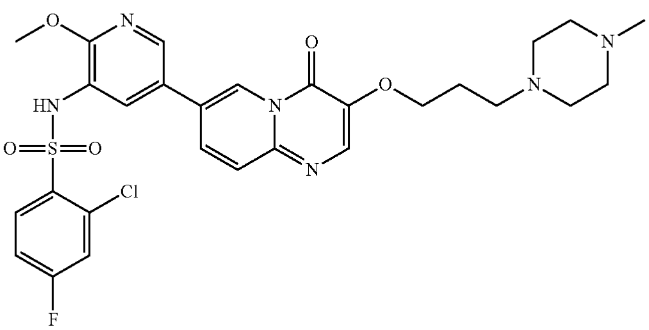 [SMILES: COc1ncc(-c2ccc3ncc(OCCCN4CCN(C)CC4)c(=O)n3c2)cc1NS(=O)(=O)c1ccc(F)cc1Cl] | 618 |
| 73 | 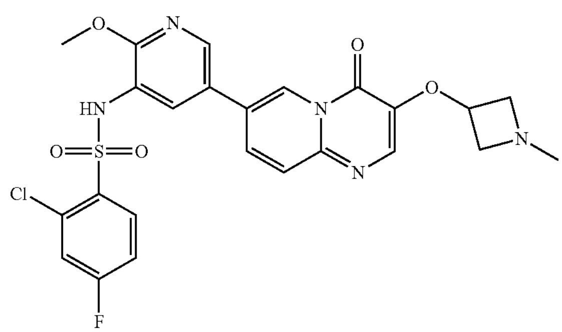 [SMILES: COc1ncc(-c2ccc3ncc(OC4CN(C)C4)c(=O)n3c2)cc1NS(=O)(=O)c1ccc(F)cc1Cl] | 547 |
| 74 | 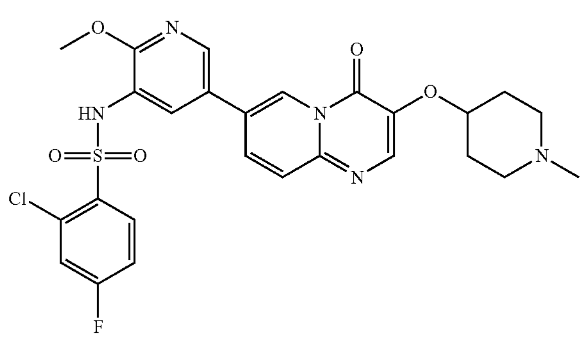 [SMILES: COc1ncc(-c2ccc3ncc(OC4CCN(C)CC4)c(=O)n3c2)cc1NS(=O)(=O)c1ccc(F)cc1Cl] | 575 |

-continued

| Compound | Structure | MS(ES) [M + H]+ |
|---|---|---|
| 75 | 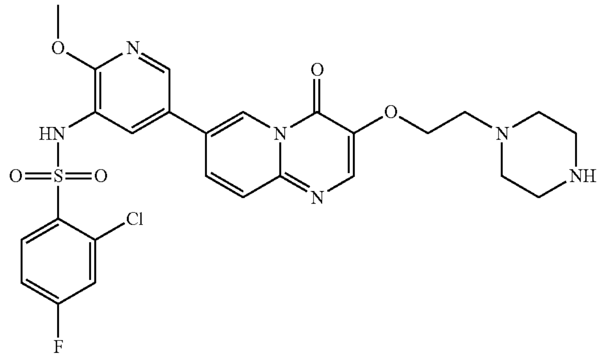 [SMILES: COc1ncc(-c2ccc3ncc(OCCN4CCNCC4)c(=O)n3c2)cc1NS(=O)(=O)c1ccc(F)cc1Cl] | 590 |
| 76 | 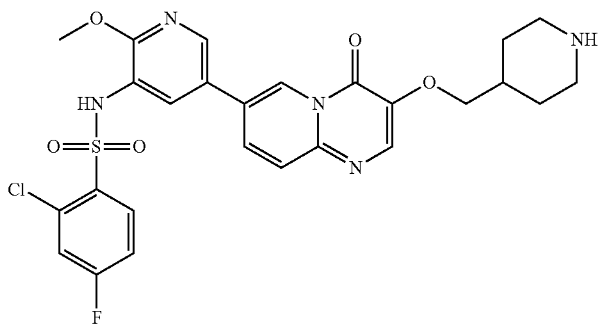 [SMILES: COc1ncc(-c2ccc3ncc(OCC4CCNCC4)c(=O)n3c2)cc1NS(=O)(=O)c1ccc(F)cc1Cl] | 575 |
| 77 | 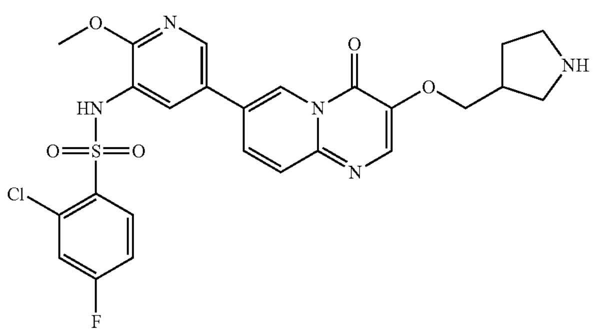 [SMILES: COc1ncc(-c2ccc3ncc(OCC4CCNC4)c(=O)n3c2)cc1NS(=O)(=O)c1ccc(F)cc1Cl] | 561 |
| 78 | 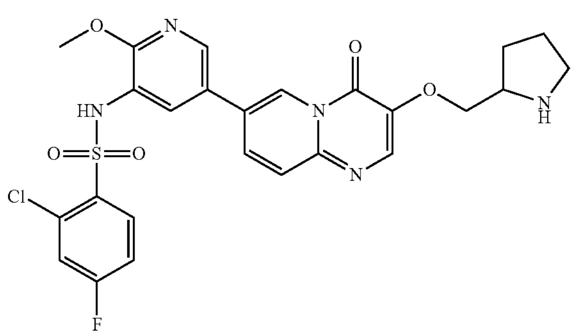 [SMILES: COc1ncc(-c2ccc3ncc(OCC4CCCN4)c(=O)n3c2)cc1NS(=O)(=O)c1ccc(F)cc1Cl] | 561 |

| Compound | Structure | MS(ES) [M + H]+ |
|---|---|---|
| 79 | 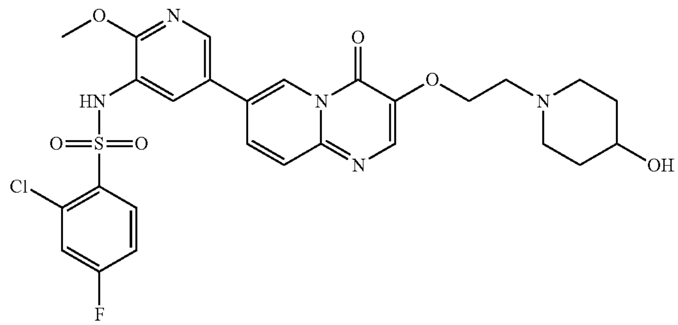 [SMILES: COc1ncc(-c2ccc3ncc(OCCN4CCC(O)CC4)c(=O)n3c2)cc1NS(=O)(=O)c1ccc(F)cc1Cl] | 605 |
| 80 | 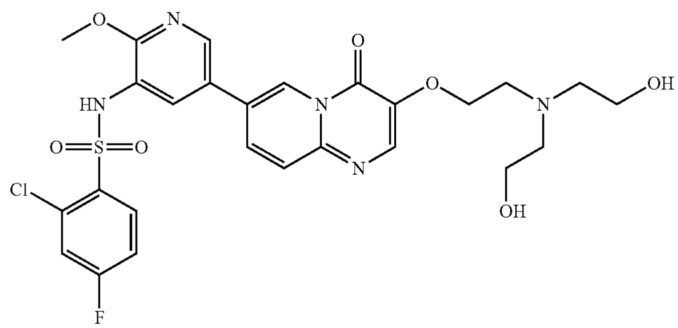 [SMILES: COc1ncc(-c2ccc3ncc(OCCN(CCO)CCO)c(=O)n3c2)cc1NS(=O)(=O)c1ccc(F)cc1Cl] | 609 |
| 81 | 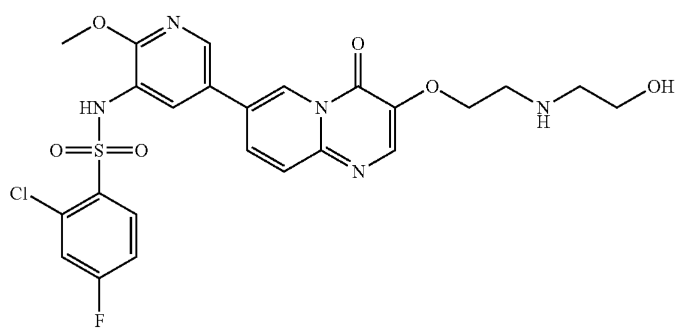 [SMILES: COc1ncc(-c2ccc3ncc(OCCNCCO)c(=O)n3c2)cc1NS(=O)(=O)c1ccc(F)cc1Cl] | 565 |
| 82 | 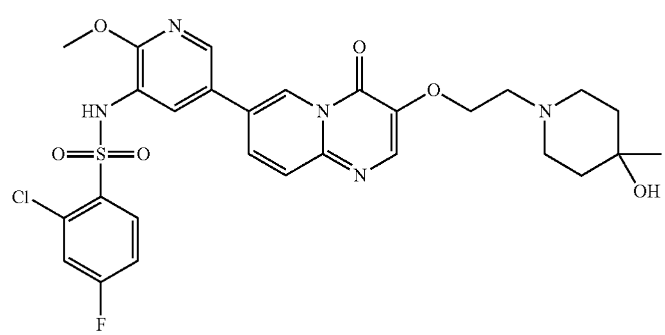 [SMILES: COc1ncc(-c2ccc3ncc(OCCN4CCC(C)(O)CC4)c(=O)n3c2)cc1NS(=O)(=O)c1ccc(F)cc1Cl] | 619 |
| 83 | 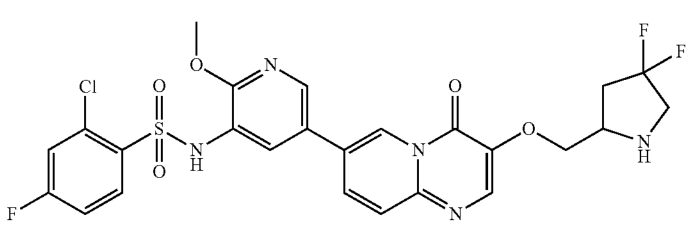 [SMILES: COc1ncc(-c2ccc3ncc(OCC4CC(F)(F)CN4)c(=O)n3c2)cc1NS(=O)(=O)c1ccc(F)cc1Cl] | 595 |

| Compound | Structure | MS(ES) [M + H]+ |
|---|---|---|
| 84 | 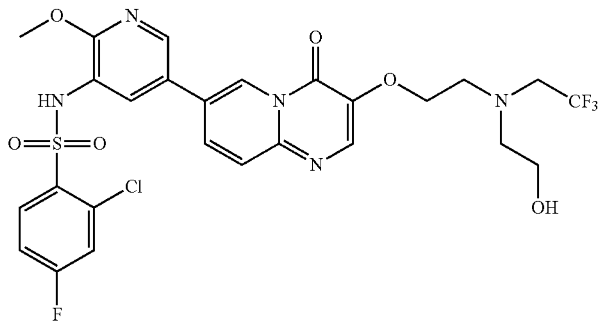 [SMILES: COc1ncc(-c2ccc3ncc(OCCN(CCO)CC(F)(F)F)c(=O)n3c2)cc1NS(=O)(=O)c1ccc(F)cc1Cl] | 647 |
| 85 | 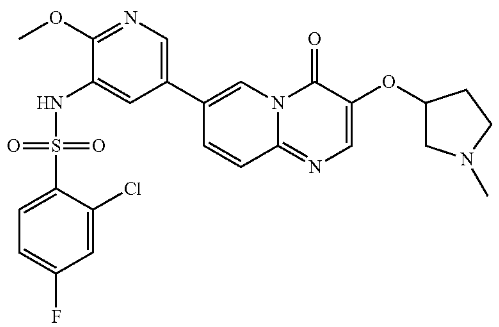 [SMILES: COc1ncc(-c2ccc3ncc(OC4CCN(C)C4)c(=O)n3c2)cc1NS(=O)(=O)c1ccc(F)cc1Cl] | 561 |
| 86 | 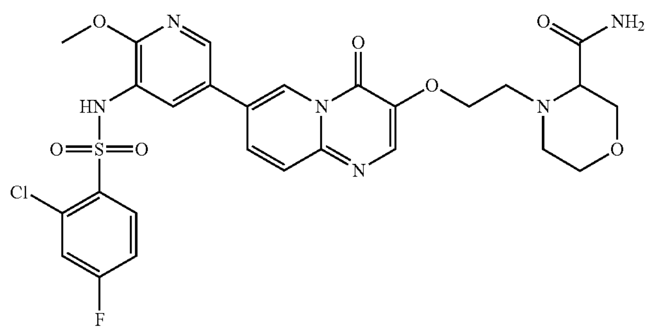 [SMILES: COc1ncc(-c2ccc3ncc(OCCN4CCOCC4C(N)=O)c(=O)n3c2)cc1NS(=O)(=O)c1ccc(F)cc1Cl] | 634 |
| 87 | 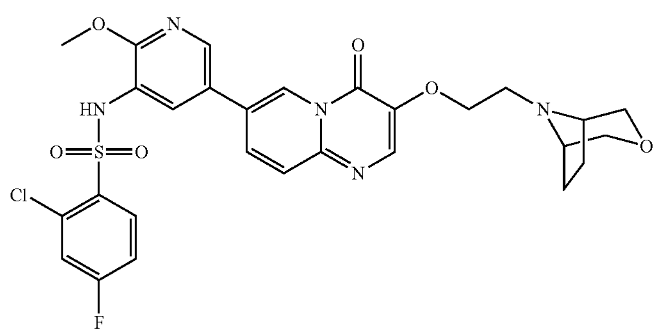 [SMILES: COc1ncc(-c2ccc3ncc(OCCN4C5CCC4COC5)c(=O)n3c2)cc1NS(=O)(=O)c1ccc(F)cc1Cl] | 616 |
| 88 | 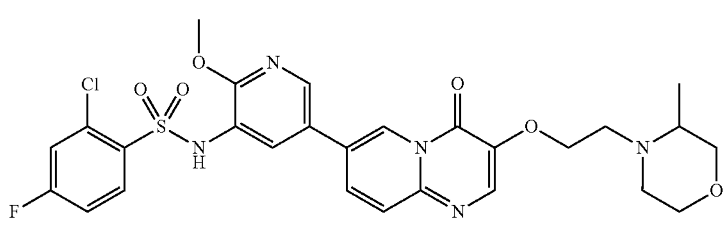 [SMILES: COc1ncc(-c2ccc3ncc(OCCN4CCOCC4C)c(=O)n3c2)cc1NS(=O)(=O)c1ccc(F)cc1Cl] | 606 |

-continued

| Compound | Structure | MS(ES) [M + H]+ |
|---|---|---|
| 89 | 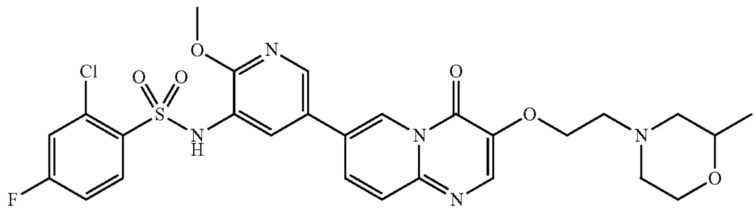 [SMILES: COc1ncc(-c2ccc3ncc(OCCN4CCOC(C)C4)c(=O)n3c2)cc1NS(=O)(=O)c1ccc(F)cc1Cl] | 606 |
| 90 | 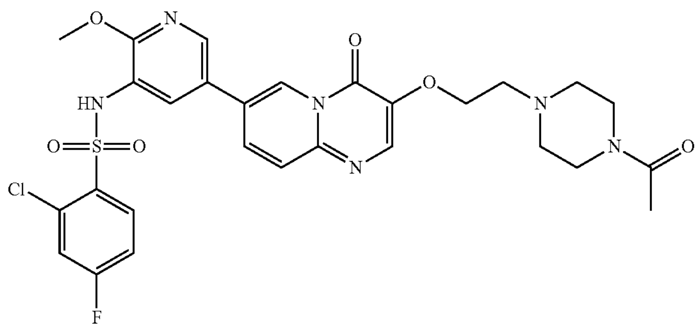 [SMILES: COc1ncc(-c2ccc3ncc(OCCN4CCN(C(C)=O)CC4)c(=O)n3c2)cc1NS(=O)(=O)c1ccc(F)cc1Cl] | 632 |
| 91 | 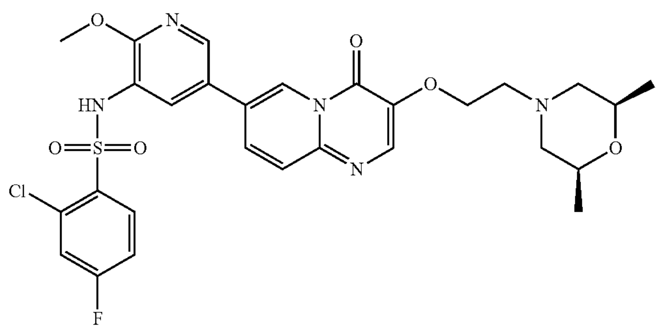 [SMILES: COc1ncc(-c2ccc3ncc(OCCN4C[C@@H](C)O[C@@H](C)C4)c(=O)n3c2)cc1NS(=O)(=O)c1ccc(F)cc1Cl] | 619 |
| 92 | 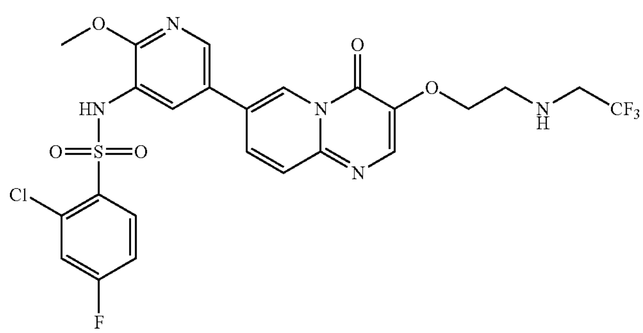 [SMILES: COc1ncc(-c2ccc3ncc(OCCNCC(F)(F)F)c(=O)n3c2)cc1NS(=O)(=O)c1ccc(F)cc1Cl] | 603 |
| 93 | 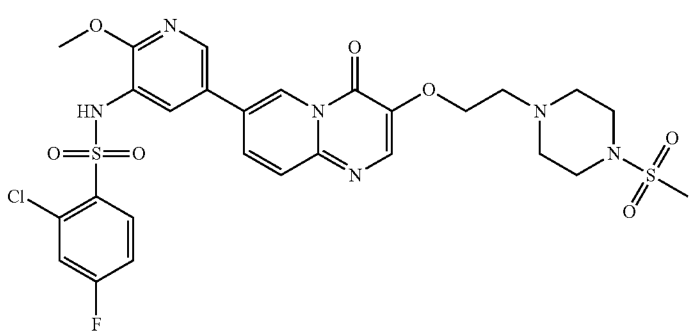 [SMILES: COc1ncc(-c2ccc3ncc(OCCN4CCN(S(C)(=O)=O)CC4)c(=O)n3c2)cc1NS(=O)(=O)c1ccc(F)cc1Cl] | 668 |

-continued

| Compound | Structure | MS(ES) [M + H]+ |
|---|---|---|
| 94 | 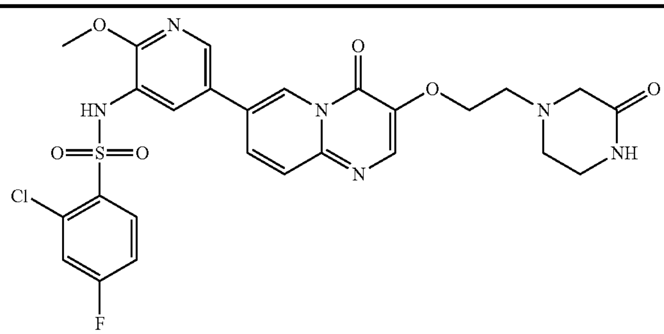 | 604 |
| 95 | 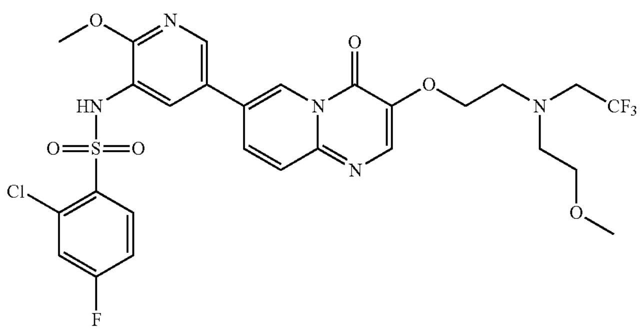 [SMILES: COCCN(CCOc1cnc2ccc(-c3cnc(OC)c(NS(=O)(=O)c4ccc(F)cc4Cl)c3)cn2c1=O)CC(F)(F)F] | 661 |

The following 2 compounds were also synthesized with reference to the process for preparing Compound 45.

| Compound | Structure | MS(ES) [M + H]+ |
|---|---|---|
| 96 | 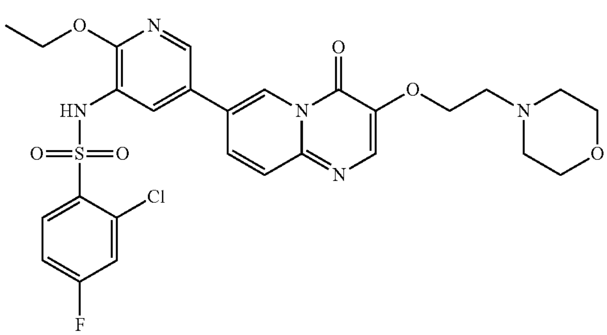 [SMILES: CCOc1ncc(-c2ccc3ncc(OCCN4CCOCC4)c(=O)n3c2)cc1NS(=O)(=O)c1ccc(F)cc1Cl] | 606 |
| 97 | 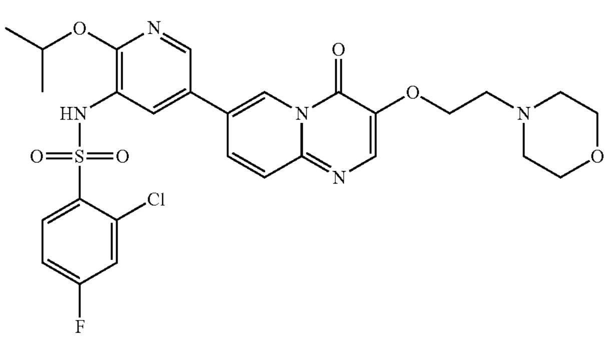 [SMILES: CC(C)Oc1ncc(-c2ccc3ncc(OCCN4CCOCC4)c(=O)n3c2)cc1NS(=O)(=O)c1ccc(F)cc1Cl] | 619 |

Scheme 14:

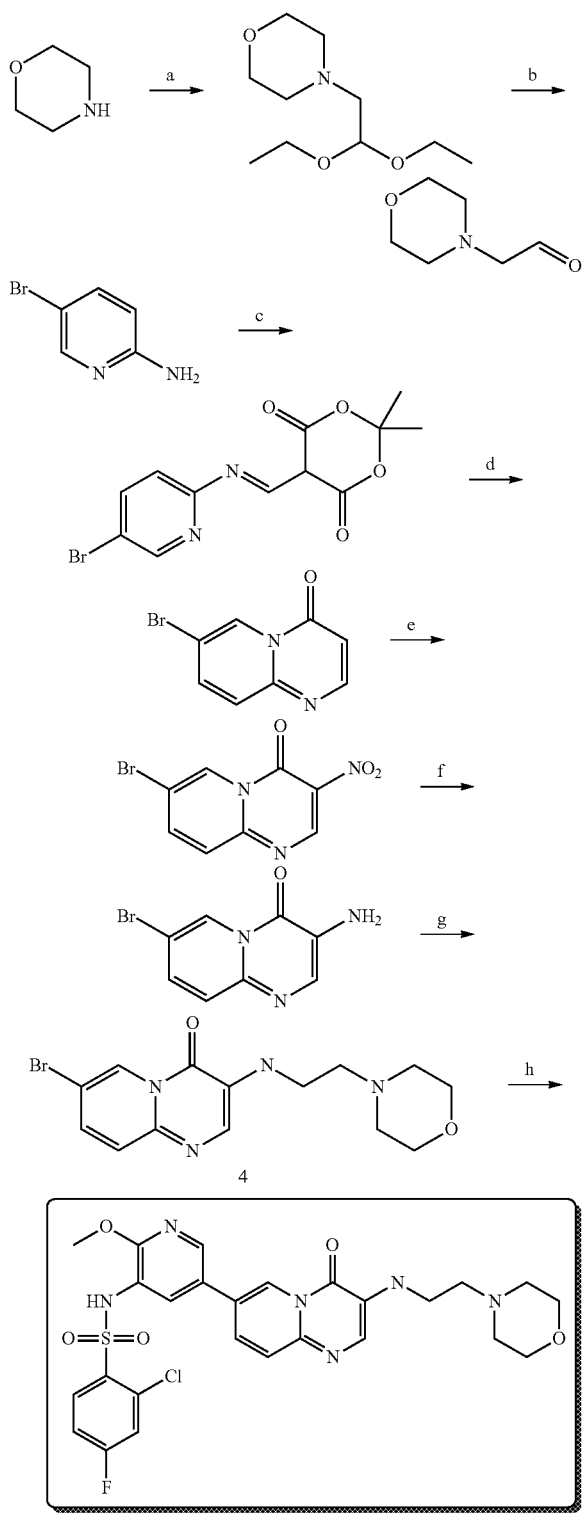

Reaction conditions: a) 2-bromo-1,1-diethoxy-ethane, potassium carbonate, heating; b) concentrated hydrochloric acid, heating; c) triethylorthoformate, 2,2-dimethyl-1,3-dioxane-4,6-dione, heating; EtOH, heating; d) diphenyl ether, refluxing; e) concentrated sulfuric acid, nitric acid; f) Fe powder, ammonium chloride, ethanol, water, heating; g) 3-amino-7-bromo-4H-pyrido[1,2-a]pyrimidin-4-one, dichloromethane, 4 A powder molecular sieve, acetic acid, sodium triacetoxyborohydride; h) 2-chloro-4-fluoro-N-(2-methoxy-5-(4,4,5,5-tetramethyl-1,3,2-dioxaborolan-2-yl)pyridin-3-yl)benzenesulfonamide, dioxane, [1,1'-bis(diphenylphosphino)ferrocene]palladium chloride, potassium carbonate, water, heating.

Example 98

2-Chloro-4-fluoro-N-(2-methoxy-5-(3-((2-morpholinoethyl)amino)-4-oxo-4H-pyrido[1,2-a]pyrimidin-7-yl)pyridin-3-yl)benzenesulfonamide Coumpound 98

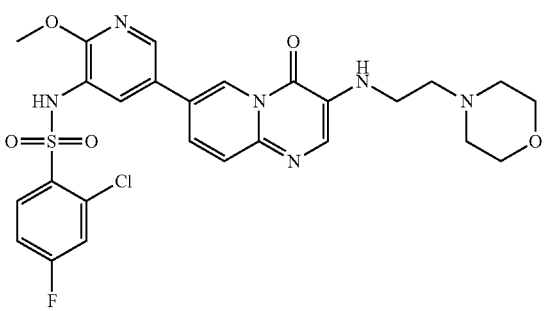

a) 4-(2,2-Diethoxyethyl)morpholine

Morpholine (2.21 g, 25.37 mmol, 1.00 Eq) and 2-bromo-1,1-diethoxy-ethane (5.00 g, 25.37 mmol, 1.00 Eq) were placed in a three-necked round-bottomed flask, potassium carbonate (7.01 g, 50.73 mmol, 2.00 Eq) was added and the mixture was stirred at 80° C. for 2 hours. The reaction mixture was cooled to room temperature, and 20 mL of water was added. The mixture was extracted with dichloromethane (20 mL×2), dried over anhydrous sodium sulfate and concentrated to give the title compound (3.50 g, 67.87%) as a yellow oil. The crude product was directly used in the next reaction.

1H NMR (400 MHz. CDCl$_3$) δ 4.62-4.65 (m, 1H), 4.61 (s, 1H), 3.66 (t, J=4.6 Hz, 4H), 3.45-3.59 (m, 3H), 3.33 (d, J=5.6 Hz, 2H), 2.49 (d, J=5.1 Hz, 4H), 1.19-1.22 (m, 5H), 1.18 (s, 2H).

b) 2-Morpholinoacetaldehyde 4-(2,2-Diethoxyethyl)morpholine (800.00 mg, 3.94 mmol, 1.00 Eq) dissolved in concentrated hydrochloric acid (4 mL) was placed in a three-necked round-bottomed flask. The mixture was stirred at 80° C. for 3 hours. The mixture was cooled to room temperature, adjusted to pH 10 with a saturated aqueous solution of sodium bicarbonate, and extracted with dichloromethane DCM (50 mL×3), dried over anhydrous sodium sulfate and concentrated to give the title compound (350.00 mg, 67.87%) as a colorless oil. The crude product was directly used in the next reaction.

$^1$H NMR (400 MHz, CDCl$_3$) δ 9.69 (s, 1H), 3.62-3.67 (m, 4H), 3.18 (s, 2H), 2.54-2.60 (m, 4H).

c) (E)-5-(((5-bromopyridin-2-yl)imino)methyl)-2,2-dimethyl-1,3-dioxane-4,6-dione Triethylorthoformate (25.8 g, 0.174 mol) and 2,2-dimethyl-1,3-dioxane-4,6-dione (25.1 g, 0.174 mol) were placed in a three-necked round-bottomed flask and stirred to react at 60° C. for 2 hours. To the above mixture was added dropwise a solution of 2-amino-5-bromopyridine (30 g, 0.174 mol) in ethanol (150 mL). The reaction solution was stirred to react at 60° C. for 2 hours. The resulting mixture was cooled to 25° C. and filtered and the filter cake was rinsed with ethanol (200 mL*3) to give the title compound (40 g, 70%) as a white solid.

1H NMR (400 MHz, CDCl$_3$) δ 1.77 (s, 6H), 6.93-7.04 (m, 1H), 8.44-8.53 (m, 1H), 7.85-7.91 (m, 1H), 9.31-9.42 (m, 1H), 11.28-11.40 (m, 1H).

d) 7-Bromo-4H-pyrido[1,2-a]pyrimidin-4-one (E)-5-(((5-bromopyridin-2-yl)imino)methyl)-2,2-dimethyl-1,3-dioxane-4,6-dione (18 g, 0.056 mmol) and diphenyl ether (180 mL) were placed in a 250 mL round-bottomed flask, and stirred to react at 220° C. for 1 hour. TLC showed that the reaction was completed, and then the reaction solution was cooled to room temperature and purified by silica gel column chromatography to give the title compound (10 g, 80%).

1H NMR (400 MHz, CDCl$_3$) δ 6.46 (d, 1H), 7.53 (d, 1H), 7.75 (dd, 1H), 8.27 (d, 1H), 9.19 (d, 1H).

e) 7-Bromo-3-nitro-4H-pyrido[1,2-a]pyrimidin-4-one

7-Bromo-4H-pyrido[1,2-a]pyrimidin-4-one (5 g, 22.2 mmol) was placed in a 100 mL three-necked round-bottomed flask, concentrated sulfuric acid (11.2 mL) was added, and nitric acid (5.2 mL) was added dropwise at 5-10° C. The mixture reacted at 20° C. for 3 hours. The reaction solution was slowly poured into ice water, adjusted to pH=8 with 1N sodium hydroxide and filtered. The filter cake was collected and rotary evaporated to dryness under reduced pressure to give the yellow title product (4.0 g, 66.7%).

1H NMR (400 MHz, CDCl$_3$) δ 9.47 (d, 1H), 9.35 (s, 1H), 8.14 (dd, 1H), 7.81 (d, 1H).

f) 3-Amino-7-bromo-4H-pyrido[1,2-a]pyrimidin-4-one

7-Bromo-3-nitro-4H-pyrido[1,2-a]pyrimidin-4-one (4.0 g, 14.7 mmol, 1.0 eq) and ammonium chloride (11.8 g, 220.54 mmol, 15.0 eq) were placed in a 250 mL round-bottomed flask, and ethanol (50 mL) and water (10 mL) were added. Iron powder (1.32 g, 220.54 mmol, 15.0 eq) was added in batches at room temperature. The mixture was placed in an oil bath at 70° C. and stirred to react for 12 hours. The reaction solution was cooled to room temperature and filtered. The filter cake was rinsed with dichloromethane (50 mL). The organic phases were combined and washed with water (30 mL*2) and saturated brine (30 mL*2). The organic phase was dried over anhydrous sodium sulfate and filtered, and the filtrate was concentrated under reduced pressure to give a crude product (3.29 g, 93%) as a yellow solid.

$^1$H NMR (400 MHz, CDCl$_3$) δ 4.13 (br. s, 2H) 7.39 (d, J=0.98 Hz, 2H) 7.96 (s, 1H) 9.00 (s, 1H).

g) 7-Bromo-3-((2-morpholinoethyl)amino)-4H-pyrido[1,2-a]pyrimidin-4-one

2-Morpholinoacetaldehyde (80.70 mg, 624.84 μmol, 3.00 Eq) and 3-amino-7-bromo-4H-pyrido[1,2-a]pyrimidin-4-one (50.00 mg, 208.28 μmol, 1.00 Eq) dissolved in dichloromethane (5 mL) were placed in a three-necked round-bottomed flask, 4 A powder molecular sieve was added and the reaction mixture was stirred at 25° C. for 1 hour. Acetic acid (15.01 mg, 249.94 μmol, 1.20 Eq) and sodium triacetoxyborohydride (52.97 mg, 249.94 μmol, 1.20 Eq) were added and the resulting mixture was stirred at 25° C. for 1 hour. The color of the reaction solution was changed from yellow to red. The reaction was quenched with 0.5 mL of methanol and the reaction mixture was filtered. The filter cake was washed with 10 mL of dichloromethane and the filtrate was concentrated and purified by preparative silica gel chromatoplate to give the title compound (32.00 mg, 43.50%) as a brown solid.

h) 2-Chloro-4-fluoro-N-(2-methoxy-5-(3-((2-morpholinoethyl)amino)-4-oxo-4H-pyrido[1,2-a]pyrimidin-7-yl)pyridin-3-yl)benzenesulfonamide 7-Bromo-3-((2-morpholinoethyl)amino)-4H-pyrido[1,2-a]pyrimidin-4-one (40.00 mg, 90.60 μmol, 1.00 Eq) and 2-chloro-4-fluoro-N-(2-methoxy-5-(4,4,5,5-tetramethyl-1,3,2-dioxaborolan-2-yl)pyridin-3-yl)benzenesulfonamide (48.13 mg, 108.72 μmol, 1.20 Eq) dissolved in dioxane (3 mL) were placed in a three-necked round-bottomed flask. [1,1'-Bis(diphenylphosphino)ferrocene]palladium chloride (3.31 mg, 4.53 μmol, 0.05 Eq), potassium carbonate (37.56 mg, 271.79 μmol, 3.00 Eq) and water (1 mL) were added. The mixture was stirred at 80° C. for 2 hours under nitrogen protection. Liquid Chromatography Mass Spectrometry showed that the reaction was completed. The reaction solution was filtered and concentrated to give a crude product. The crude product was separated by preparative liquid chromatography to give the title compound (5.70 mg, 10.25%) as a white solid.

$^1$H NMR (400 MHz, CDCl$_3$) δ 8.83 (s, 1H), 8.06-8.15 (m, 2H), 7.90 (d, J=2.2 Hz, 1H), 7.71 (s, 1H), 7.54 (d, J=9.3 Hz, 1H), 7.38 (dd, J=9.4, 1.8 Hz, 1H), 7.26 (d, J=2.4 Hz, 1H), 7.09-7.17 (m, 1H), 5.17 (br. s., 1H), 3.97 (s, 3H), 3.74 (t, J=4.4 Hz, 4H), 3.29 (d, J=5.4 Hz, 2H), 2.72 (t, J=5.9 Hz, 2H), 2.51 (br. s., 4H).

Scheme 15:

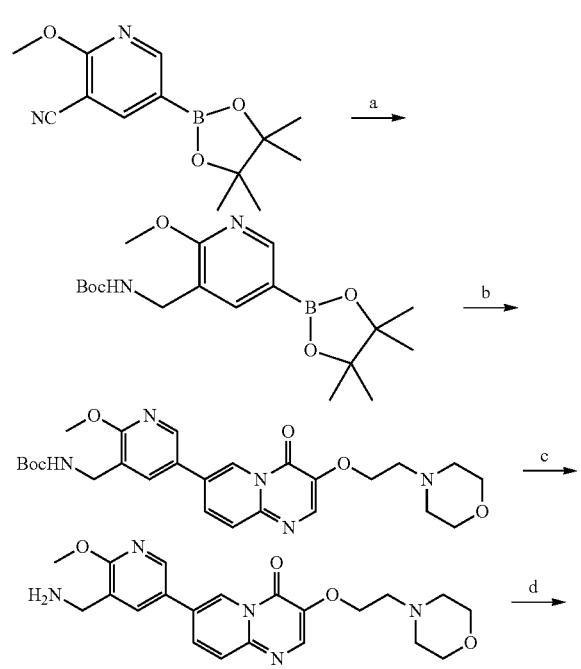

-continued

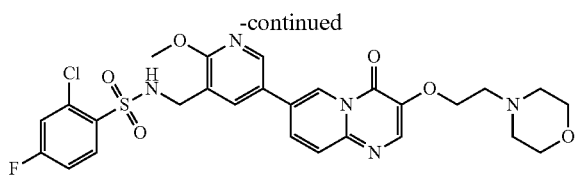

Reaction conditions: a) Raney nickel, tetrahydrofuran, tert-butoxyformic anhydride, hydrogen, heating; b) 7-bromo-3-(2-morpholinoethoxy)pyrido[1,2-a]pyrimidin-4-one, dioxane, potassium carbonate, water, [1,1'-bis(diphenylphosphino)ferrocene]palladium chloride, heating; c) dichloromethane, a dioxane solution of hydrogen chloride; d) 2-chloro-4-fluoro-benzenesulfonyl chloride, pyridine.

Example 99

2-Chloro-4-fluoro-N-((2-methoxy-5-(3-(2-morpholinoethoxy)-4-oxo-4H-pyrido[1,2-a]pyrimidin-7-yl)pyridin-3-yl)methyl)benzenesulfonamide Coumpound 99

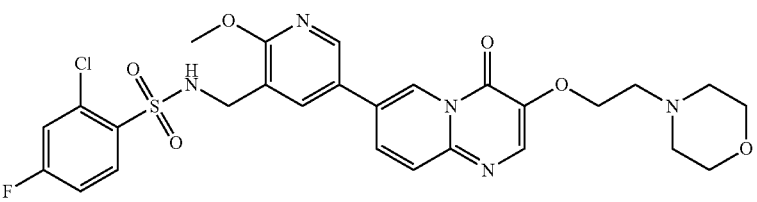

a) tert-Butyl ((2-methoxy-5-(4,4,5,5-tetramethyl-1,3,2-dioxaborolan-2-yl)pyridin-3-yl) methyl)carboxamide Raney nickel (9.88 mg, 115.34 μmol) was added to a single-necked round-bottomed flask filled with nitrogen. Tetrahydrofuran (10.00 mL) was added and 2-methoxy-5-(4,4,5,5-tetramethyl-1,3,2-dioxaborolan-2-yl)pyridine-3-cyano (150.00 mg, 576.70 μmol) and tert-butoxyformic anhydride (151.04 mg, 692.04 μmol) were added. The mixture was stirred at 80° C. for 2 hours under 40 psi hydrogen. LCMS showed that the reaction was completed. The reaction mixture was filtered through celite, and the filtrate was rotary evaporated to dryness to give the yellow title compound (200.00 mg, 69.50%), which was directly used in the next reaction.

b) tert-Butyl ((2-methoxy-5-(3-(2-morpholinoethoxy)-4-oxo-4H-pyrido[1,2-a]pyrimidin-7-yl)pyridin-3-yl)methyl)carboxamide tert-Butyl ((2-methoxy-5-(4,4,5,5-tetramethyl-1,3,2-dioxaborolan-2-yl) pyridin-3-yl)methyl)carboxamide (200.00 mg, 400.83 μmol) and 7-bromo-3-(2-morpholinoethoxy)pyrido[1,2-a]pyrimidin-4-one (141.98 mg, 400.83 μmol) were dissolved in dioxane (10.00 mL), and a solution of potassium carbonate (110.80 mg, 801.67 μmol) in water (3.00 mL) was added. [1,1'-Bis(diphenylphosphino)ferrocene]palladium chloride (14.66 mg, 20.04 μmol) was added. The mixture was stirred at 80° C. for 2 hours under nitrogen protection. LCMS showed that the reaction was completed. The reaction solution was concentrated, washed with 5 mL of water and purified via p-TLC (dichloromethane:methanol=20:1) to give the yellow title compound (100.00 mg, 46.33%).

$^1$H NMR (400 MHz, CDCl$_3$) δ 9.11 (s, 1H), 8.35 (d, J=2.0 Hz, 1H), 8.17 (s, 1H), 7.74-7.83 (m, 2H), 7.64-7.71 (m, 1H), 4.32 (t, J=5.5 Hz, 4H), 4.04 (s, 3H), 3.73-3.76 (m, 4H), 2.85-2.89 (m, 2H), 2.62 (br. s., 4H), 1.45 (s, 9H).

c) 7-(5-(Aminomethyl)-6-methoxypyridin-3-yl)-3-(2-morpholinoethoxy)-4-oxo-4H-pyrido[1,2-a]pyrimidin-4-one tert-Butyl ((2-methoxy-5-(3-(2-morpholinoethoxy)-4-oxo-4H-pyrido[1,2-a]pyrimidin-7-yl)pyridin-3-yl)methyl) carboxamide (80.00 mg, 148.56 μmol) was dissolved in dichloromethane (10.00 mL), and a dioxane solution of hydrogen chloride (4M, 2.00 mL) was added dropwise at 0° C. The mixture was warmed to room temperature (25° C.) and stirred for 1 hour. LCMS showed that the reaction was completed. Potassium carbonate (1.12 g) was added and the resulting mixture was stirred for 30 minutes and filtered, and the filter cake was washed with dichloromethane (10 mL) and the filtrate was rotary evaporated to dryness to give the title compound (70.00 mg) as a yellow crude product, which was directly used in the next reaction.

d) 2-Chloro-4-fluoro-N-((2-methoxy-5-(3-(2-morpholinoethoxy)-4-oxo-4H-pyrido[1,2-a]pyrimidin-7-yl)pyridin-3-yl)methyl)benzenesulfonamide 7-(5-(Aminomethyl)-6-methoxypyridin-3-yl)-3-(2-morpholinoethoxy)-4-oxo-4H-pyrido[1,2-a]pyrimidin-4-one (70.00 mg, 119.09 μmol) was dissolved in pyridine (3.00 mL), and 2-chloro-4-fluoro-benzenesulfonyl chloride (30.01 mg, 131.00 μmol) was added dropwise. The mixture was stirred at 25° C. for 1 hour. LCMS showed that the reaction was completed. The reaction solution was concentrated and purified via p-TLC (dichloromethane:methanol=10:1) and recrystallized with methanol (3 mL) to give the title compound (26.00 mg, 36.14%) as a white solid.

$^1$H NMR (400 MHz. CDCl$_3$) δ 8.95 (s, 1H), 8.26 (d, J=2.5 Hz, 1H), 8.19 (s, 1H), 8.02 (dd, J=8.3, 5.8 Hz, 1H), 7.62-7.72 (m 2H), 7.46 (d, J=2.0 Hz, 1H), 7.01-7.11 (m, 2H), 5.87 (t, J=6.5 Hz, 1H), 4.34 (t, J=5.5 Hz, 2H), 4.25 (d, J=6.5 Hz, 2H), 4.02 (s, 3H), 3.75 (t, J=4.5 Hz, 4H), 2.89 (t, J=5.5 Hz, 2H), 2.63 (br. s., 4H).

Experimental Example 1: In Vitro Enzyme Activity Assay

PI3K (p110α) kinase activities of the compounds in all the examples of the present invention were tested via the following two methods, respectively.

Method I:
Reaction buffer: HEPES 50 mM (pH7.0), NaN3 0.02%, BSA 0.01%. Orthovanadate 0.1 mM, and 1% DMSO.
Detection buffer: HEPES 10 mM (pH7.0), BSA 0.02%, KF 0.16 M, and EDTA 4 mM.
Enzymes for reaction: recombinant full-length human PI3K p110α subunit (molecular weight=128.4 kDa) with a His-tag at the N-terminus and unlabeled p85α subunit (molecular weight=83.6 kDa), which were expressed in insect cells.
Substrate for reaction: 10 M PIP2 substrate (PI(4,5)P2).
Reaction conditions: 10 μM PI(4,5)P2 and 10 μM ATP.
Reaction Steps Comprise:
1. preparing the substrate in the freshly prepared reaction buffer;
2. adding the kinase into the substrate reaction solution, and mixing gently;
3. transferring the compound dissolved in 100% DMSO into the kinase reaction solution by using Acoustic technique (Echo550; nanoliter rang), and incubating at room temperature for 10 minutes;
4. adding an appropriate concentration of ATP into the reaction system,
5. incubating at 30° C. for half an hour;
6. terminating the reaction by adding a stop solution;
7. adding the detection buffer and incubating overnight; and
8. detecting by using homogeneous time-resolved fluorescence (HTRF) method (excitation wavelength of 320 nm, measuring the ratio of the emission wavelength readings at 615 nm and 665 nm).

Method II:
ADP-Glo Assay Method
Dilution of the Compound:
The compound to be tested was diluted with a 3-fold concentration gradient, and 10 concentrations (from 10000 nM to 0.5 nM) were obtained in total.
Assay Method:
50 nL of the compound was transferred to a reaction plate (PerkinElmer #6007299) and 3 μL of enzyme/substrate mixture (0.33 nM PI3Kalpha, Millipore #14-602-K/166.5 μM PIP2) was added. After 20 min incubation, 2 uL of ATP solution (100 uM) was added to initiate the reaction. After reacting for 2 hours at room temperature, 5 μL of ADP-Glo reagent was added to terminate the kinase reaction. Then the mixture was incubated at room temperature for 60 min to completely digest the remaining unreacted ATP, 10 uL of kinase detection reagent was added, and after 40 min incubation at room temperature, fluorescence was read on an Envision. PIP2, ATP, ADP-Glo and the kinase detection reagent were all from ADP-Glo kinase assay kit (Promega #V1792).
Data Analysis:
IC50 was calculated using standard 4-parameter fit method (Model205, XL-fit, iDBS).
mTOR kinase activities of the compounds in all the examples of the present invention were tested via the following method.
Reaction buffer: 20 mM Hepes (pH 7.5), 10 mM $MgCl_2$, 2 mM $MnCl_2$, 1 mM EGTA, 0.02% Brij35, 0.02 mg/mL BSA, 0.1 mM $Na_3VO_4$, 2 mM DTT, and 2% DMSO.
Enzyme for reaction: recombinant human mTOR fragment (amino acid 1360-2549, molecular weight=163.9 kDa) with a GST-tag at the N-terminus, which was expressed in insect cells.

Substrate for reaction: recombinant full-length human 4EBPI (molecular weight=13.6 kDa) with a His-tag at the N-terminus, which was expressed in bacteria.
Reaction conditions: 3 CpM 4EBPI and 10 μM ATP.
Reaction Steps Comprise:
1. adding the reaction substrate and other reaction factors into the freshly prepared reaction buffer;
2. adding the kinase into the substrate reaction solution, and mixing gently;
3. transferring the compound dissolved in 100% DMSO into the kinase reaction solution by using Acoustic technique (Echo550; nanoliter rang), and incubating at room temperature for 20 minutes;
4. adding an appropriate concentration of $^{32}$P-ATP into the reaction system;
5. incubating at room temperature for 2 hours;
6. detecting the kinase activity by using P81 filter-binding method.
The assay results were shown in Table 3 as follows.

TABLE 3 in vitro enzyme activity assay results

| Compound | PI3K (p110α) enzyme activity_IC50 | mTOR enzyme activity_IC50 | PI3K assay method |
|---|---|---|---|
| 1 | A | C | Method I |
| 2 | A | C | Method I |
| 3 | A | D | Method I |
| 4 | A | NT | Method II |
| 5 | A | NT | Method II |
| 6 | A | D | Method I |
| 7 | A | D | Method I |
| 8 | A | D | Method I |
| 9 | A | D | Method I |
| 10 | A | D | Method I |
| 11 | A | D | Method I |
| 12 | A | C | Method I |
| 13 | A | D | Method I |
| 14 | A | D | Method I |
| 15 | A | C | Method I |
| 16 | A | C | Method I |
| 20 | A | C | Method I |
| 21 | A | NT | Method II |
| 22 | A | NT | Method II |
| 23 | A | NT | Method II |
| 25 | A | D | Method II |
| 27 | A | C | Method II |
| 32 | A | C | Method II |
| 33 | A | NT | Method II |
| 34 | A | NT | Method II |
| 35 | A | C | Method I |
| 36 | A | D | Method I |
| 37 | A | C | Method I |
| 38 | B | NT | Method II |
| 39 | B | NT | Method II |
| 40 | B | NT | Method II |
| 41 | B | D | Method I |
| 42 | A | D | Method I |
| 43 | A | D | Method I |
| 44 | A | D | Method I |
| 51 | B | NT | Method II |
| 52 | B | NT | Method II |
| 54 | D | NT | Method II |
| 56 | D | NT | Method II |
| 58 | D | NT | Method II |
| 61 | A | NT | Method II |
| 62 | A | NT | Method II |
| 63 | A | NT | Method II |
| 64 | A | NT | Method II |
| 65 | A | NT | Method II |
| 66 | B | NT | Method II |
| 67 | B | NT | Method II |
| 68 | A | NT | Method II |
| 70 | B | NT | Method II |
| 71 | B | NT | Method II |

TABLE 3-continued in vitro enzyme activity assay results

| Compound | PI3K (p110α) enzyme activity_IC50 | mTOR enzyme activity_IC50 | PI3K assay method |
|---|---|---|---|
| 73 | B | NT | Method II |
| 74 | B | NT | Method II |
| 75 | A | NT | Method II |
| 77 | B | NT | Method II |
| 78 | B | NT | Method II |
| 79 | A | NT | Method II |
| 80 | A | NT | Method II |
| 81 | A | NT | Method II |
| 82 | A | NT | Method II |
| 83 | B | NT | Method II |
| 84 | B | NT | Method II |
| 85 | B | NT | Method II |
| 86 | A | NT | Method II |
| 87 | A | NT | Method II |
| 88 | A | NT | Method II |
| 89 | A | NT | Method II |
| 90 | A | NT | Method II |
| 92 | A | NT | Method II |
| 93 | A | NT | Method II |
| 95 | B | NT | Method II |

Note:
A ≤1 nM;
1 nM < B ≤ 50 nM;
50 nM < C ≤ 200 nM;
200 nM <D; and
NT means not measured.

Experimental Example 2: In Vitro Cell Activity Assay

Experimental Steps and Method Comprise:

1. MCF-7 cells were seeded at 2,5000 cells per well in a 96 well tissue culture plate in a complete media containing 10%/FBS.

2. On the second day, the media was removed from the wells, and the cells were treated with compounds at a specific concentration (for primary screening) or serial dilutions (for IC50 test) in serum-free media for 2 hours.

3. The cells were treated with 10 μg/ml insulin in serum-free media for 30 min.

4. During waiting period, lysis solution was prepared as below:
   a) Enhancer Solution needs to be taken out from the refrigerator to be thawed.
   b) Concentrated lysis solution was prepared by diluting Enhancer Solution 10-fold in 5× Lysis Buffer.
   c) Lysis solution was prepared by diluting concentrated lysis solution 5-fold with ddH$_2$O.

5. Any media were removed from wells and the wells were rinsed with PBS once quickly.

6. 50 μL of freshly prepared lysis solution were added into each well, with shaking at room temperature for 10 min.

7. After confirming that all cells get detached from wells, the lysis solution together with the cell debris was transferred to 1.5 ml tubes.

8. The tubes were vortexed several times to thoroughly mix the lysis solution and cells, and then, and then the mixture was centrifuged at 12,000 g for 10 min at 4° C.;

9. The desired number of ELISA-One microplate strips was determined. Unused strips were removed from frame and returned to storage pouch and seal. Wells for use in the assay were rinsed with 200 μL ddH$_2$O to remove preservatives prior to use.

10. 50 μL of antibody mixture solution was added into each well. (Antibody mixture solution was prepared by mixing capture antibody reagent and detection antibody reagent equally, avoid vortexing)

11. 25 μL of lysate was added into each well of the ELISA-One microplate. The microplate was covered with adhesive seal and incubated for 1 hour at room temperature on a microplate shaker.

12. Each well was washed with 150 μL 1× wash buffer 3 times. After final wash, any remaining wash buffer was removed from wells. If necessary, leave microplate in 1× Wash Buffer for up to 30 min, until substrate mixture solution has been prepared.

13. The substrate mixture solution should be prepared when used, 100 μL of substrate mixture solution was added into each well, and then the microplate was sealed with tin foil and incubated at room temperature for 10 minutes on a microplate shaker.

14. 10 μL of stop solution was added into each well, and then mixed slightly (5-10 seconds) on a microplate shaker.

15. Corresponding ELISA-One filter set was installed to read the fluorescence signal intensity.

The assay results were shown in Table 4 as follows.

TABLE 4 in vitro cell activity assay results

| Compound | Cell Activity |
|---|---|
| 1 | A |
| 2 | A |
| 3 | D |
| 4 | B |
| 5 | D |
| 7 | A |
| 8 | B |
| 9 | C |
| 10 | B |
| 11 | A |
| 12 | D |
| 14 | A |
| 15 | A |
| 16 | C |
| 20 | A |
| 21 | A |
| 22 | C |
| 23 | B |
| 25 | A |
| 27 | B |
| 28 | A |
| 29 | D |
| 30 | D |
| 32 | B |
| 33 | D |
| 34 | B |
| 35 | A |
| 36 | A |
| 37 | C |
| 42 | C |
| 43 | B |
| 62 | C |
| 63 | A |
| 65 | A |
| 66 | A |
| 68 | A |
| 69 | A |
| 70 | C |
| 72 | A |
| 75 | D |
| 76 | D |
| 77 | D |
| 78 | D |
| 79 | C |
| 81 | D |
| 82 | C |
| 85 | B |
| 88 | B |

TABLE 4-continued in vitro cell activity assay results

| Compound | Cell Activity |
|---|---|
| 89 | A |
| 90 | B |
| 91 | A |
| 94 | D |
| 95 | A |

Note:
A ≤50 nM;
50 nM < B ≤ 100 nM;
100 nM < C ≤ 250 nM; and
D >250 nM.

Conclusion: The compounds of the present invention have significant inhibitory effects on PI3K but weak inhibitory effects on mTOR.

In Vivo Pharmacodynamic Experiment:

The studies on whether the tested drugs had in vivo efficacy on human colon cancer CO-04-0032 animal model and gastric cancer ST-02-0013 animal model were conducted. Animal feeding, feed compositions, experimental observation, experimental indicators, and experimental termination and data analysis in the experiments were described as follows:

Animal feeding: Animals should be fed in experimental environment for 3-7 days before the experiment was started. Animals were cage-housed (5 per cage) in a SPF grade animal room with IVC (independent ventilation system). Cages, bedding and drinking water were all required to be sterilized before use, and the sterilization and disinfection records were shown in the annex. All laboratory personnels should wear protective clothing and latex gloves when operating in the animal room. Each cage information card should indicate the number, gender, strain, date of receipt, dosing regimen, experiment number, group, and experiment start date of the animal in the cage. Cages, feed and drinking water were replaced twice a week. Feeding environment and lighting conditions were as follows:

temperature: 20~26° C.
humidity: 40~70%
light cycle: 12 hours of light, 12 hours of dark Feed Compositions: the feed meet the requirements of food identification standards for experimental animals. The maximum pollutant content was under controllable range and the manufacturer was responsible for the routine check. The drinking water was autoclaved.

Animal grouping: Animals were weighed and tumor volumes were measured before dosing. The animals were randomly grouped based on their tumor volumes (randomized block design).

Observation: the experimental program and any modification thereto were carried out upon the approval of the Shanghai Wuxi AppTec Co., Ltd. Institutional Animal Care and Use Committee (IACUC). The use and welfare of the experimental animals were implemented according to the rules of the Association for Assessment and Accreditation of Laboratory Animal Care International (AAALAC). The health and mortality of the animals were monitored daily, and routine inspections included observation on the influence of tumor growth and drug therapy on the daily behavior of animals, such as activity, food and water intake, body weight changes (the weight was measured twice a week), appearance signs or other abnormal conditions. The number of animal deaths and side effects were recorded based on the number of animals in each group, and the relevant records were shown in the annex.

Experimental indexes: the experimental indexes were used for investigating whether tumor growth was inhibited or delayed, or whether the tumor was cured. Tumor diameter was measured twice a week by using a vernier caliper. Tumor volume was calculated as: $V=0.5 a \times b^2$, wherein a and b respectively represent the long and short diameter of the tumor. Tumor growth inhibition (TGI) of the compound was evaluated using T-C (days) and T/C (%). T-C (days) reflects tumor growth delay index, wherein T represents the average number of days for the tumor in administration group to reach a predetermined volume (e.g., 1,000 mm$^3$), and C represents the average number of days for the the tumor in control group to reach the same volume. T/C (%) reflects the tumor growth inhibition rate, wherein T and C respectively represent the tumor weight (tumor volume) in the administration group and control group on a given day.

The tumor growth inhibition rate was calculated as: TGI (%)=[1−(Ti−T0)/(Vi−V0)]×100, wherein Ti is the average tumor volume in a given administration group on a given day. T0 is the average tumor volume in the administration group immediately before dosing; Vi is the average tumor volume in the vehicle control group on a given day (the same day as Ti); and V0 is the average tumor volume in the vehicle control group immediately before dosing. After the experiment was finished, the tumor was weighed and the T/C ratio was calculated. T and C respectively represent the tumor weights in the administration group and the vehicle control group.

Experimental termination: the animal would be euthanized if its health condition continues to be worse, or the tumor volume exceeds 2,000 mm$^3$, or there is a serious illness or pain. The animal would be euthanized by a veterinarian if it exhibits any of the following conditions:

significant weight loss, greater than 20%;
cannot freely feed and drink water;
the average tumor volume in the control group was 2,000 mm$^3$, and the experiment was terminated.
the animal exhibits the following clinical manifestations and continues to be worse:
fur standing on end
arch back
ears, nose, eyes, or feet becoming pale
shortness of breath
convulsion
continuous diarrhea
dehydration
slow movement
vocalization Data analysis: comparsions among three or more groups were carried out using one-way ANOVA. If F values were significant different, multiple comparisons should be performed after ANOVA analysis. All data analysis was performed using SPSS 17.0, $p<0.05$ was considered as significant difference.

In Vivo Pharmacodynamics Studies on the Tested Drug in Human-Derived Colon Cancer CO-04-0032 Subcutaneous Xenograft Tumor Model Experimental Scheme:

Establishment of human-derived graft tumor model: human-derived colon cancer CO-04-0032 model was initially derived from tumor samples resected during clinical surgery. The samples were collected and used strictly in accordance with ethical laws and regulations of national, hospital and company, including patient's informed consent.

The model establishment procedure was strictly in accordance with the company's internal SOP. Passage nomenclature rules include: the nude mouse after being inoculated the tumor sample was assigned as generation P0; the continuing passage one was assigned as generation P1 and so on: a resuscitated sample was named as FP. The tumor tissue used in this experiment was generation FP4.

Animals: BALB/c nude mice, female, 6-8 weeks old, weight: 18-20 g; provided by Shanghai Sippr/BK Laboratory Animal Co., Ltd.

Tumor inoculation: CO-04-0032 tumor mass with a volume of about 30 mm³ was subcutaneously inoculated on the right back of each mouse. Grouping and administration were started when the average volume of the tumor reached about 100-200 mm³.

Pharmacodynamic assay results: see, FIGS. 1-1, 1-2a and 1-2b.

In Vivo Pharmacodynamics Study on the Tested Drugs in Human Gastric Cancer ST-02-0013 Subcutaneous Xenograft Mouse Model Experimental Scheme:

Establishment of human-derived graft tumor model: PDX model of ST-02-0013 was initially derived from clinical samples resected during surgery. The nude mouse after being implanted was assigned as generation P0: the next generation of P0 was assigned as generation P1, followed by generations of successive transplants in mice, and so on. The generation FP2 tumor was resuscitated to get generation FP3 tumor. The generation FP3 tumor was passed on to generation FP4 tumor, which was used in this study.

Animals: BALB/c nude mice, female, 6-8 weeks old, weight: 18-22 g; provided by Shanghai Ling Chang Biotechnology Co., Ltd.

Tumor inoculation: ST-02-0013 generation FP4 tumor tissue with a volume of about 30 mm³ was subcutaneously inoculated on the right back of each mouse. Grouping and administration were started when the average volume of the tumor reached about 150-200 mm³.

Figures 1, 2, 2A:
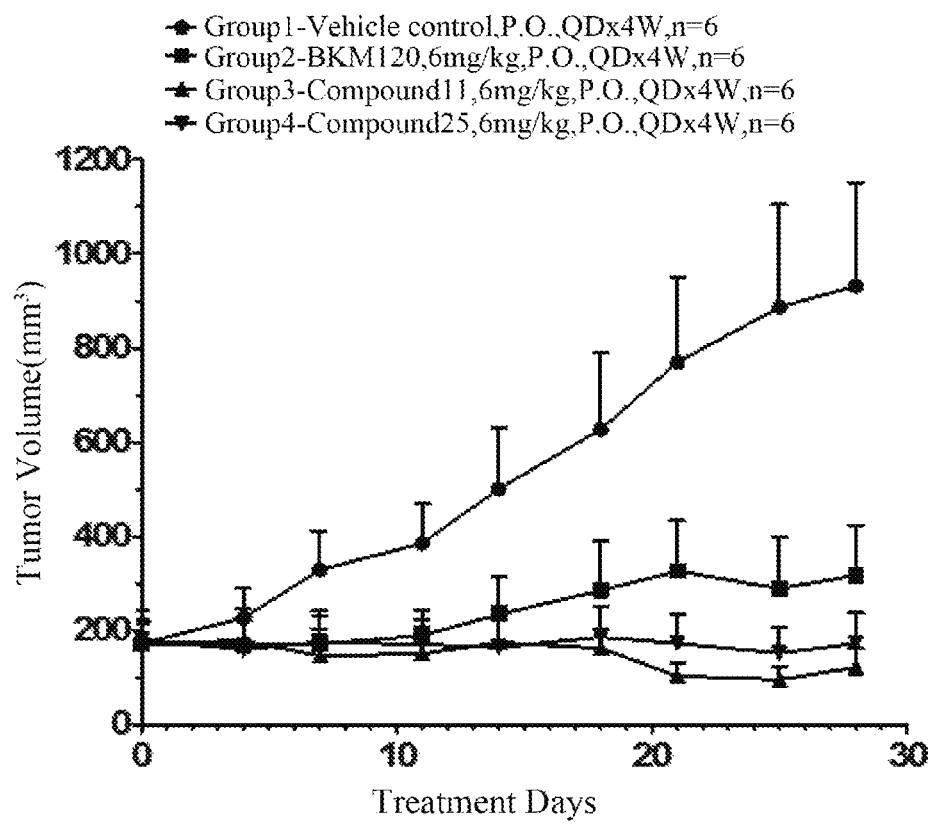
Figures 1, 2, 2B:
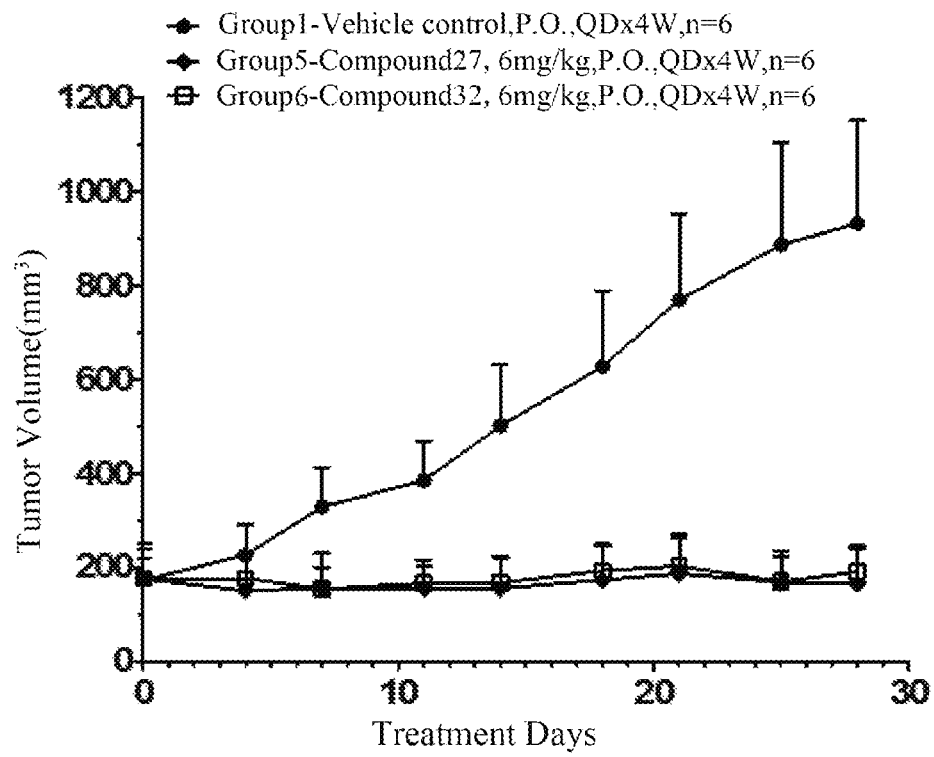
Figures 1, 2:
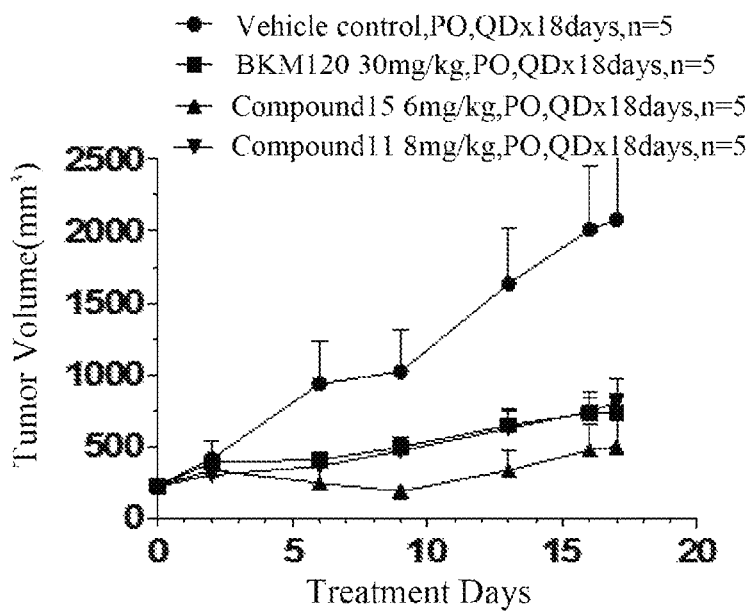
Figure 2:
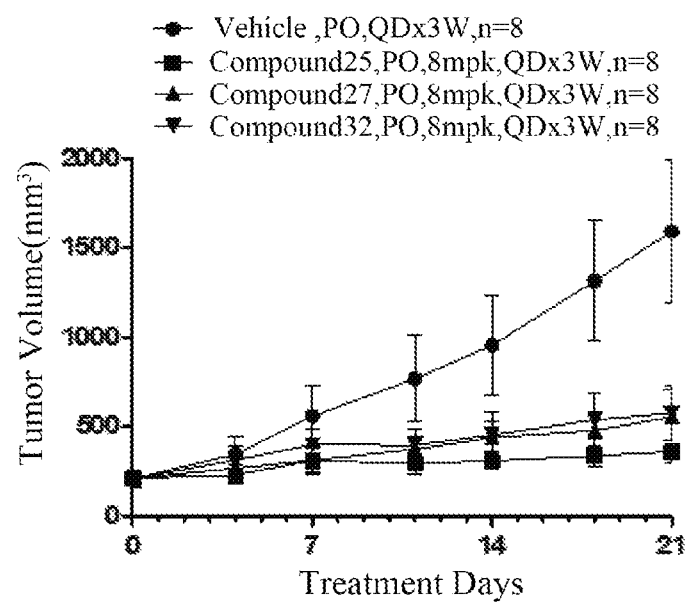

Pharmacodynamic assay results: see, FIGS. 2-1 and 2-2.

14. A compound having the following structure:
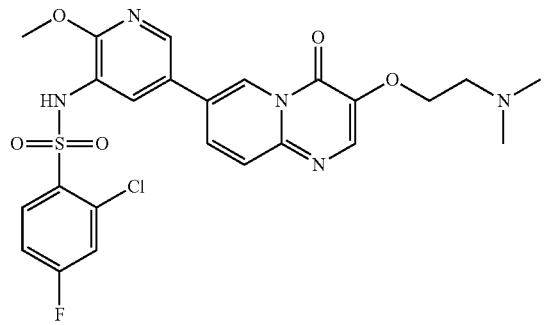 [SMILES: COc1ncc(-c2ccc3ncc(OCCN(C)C)c(=O)n3c2)cc1NS(=O)(=O)c1ccc(F)cc1Cl]
or a pharmaceutically acceptable salt thereof.
15. A compound of claim 4, wherein E is selected from the group consisting of
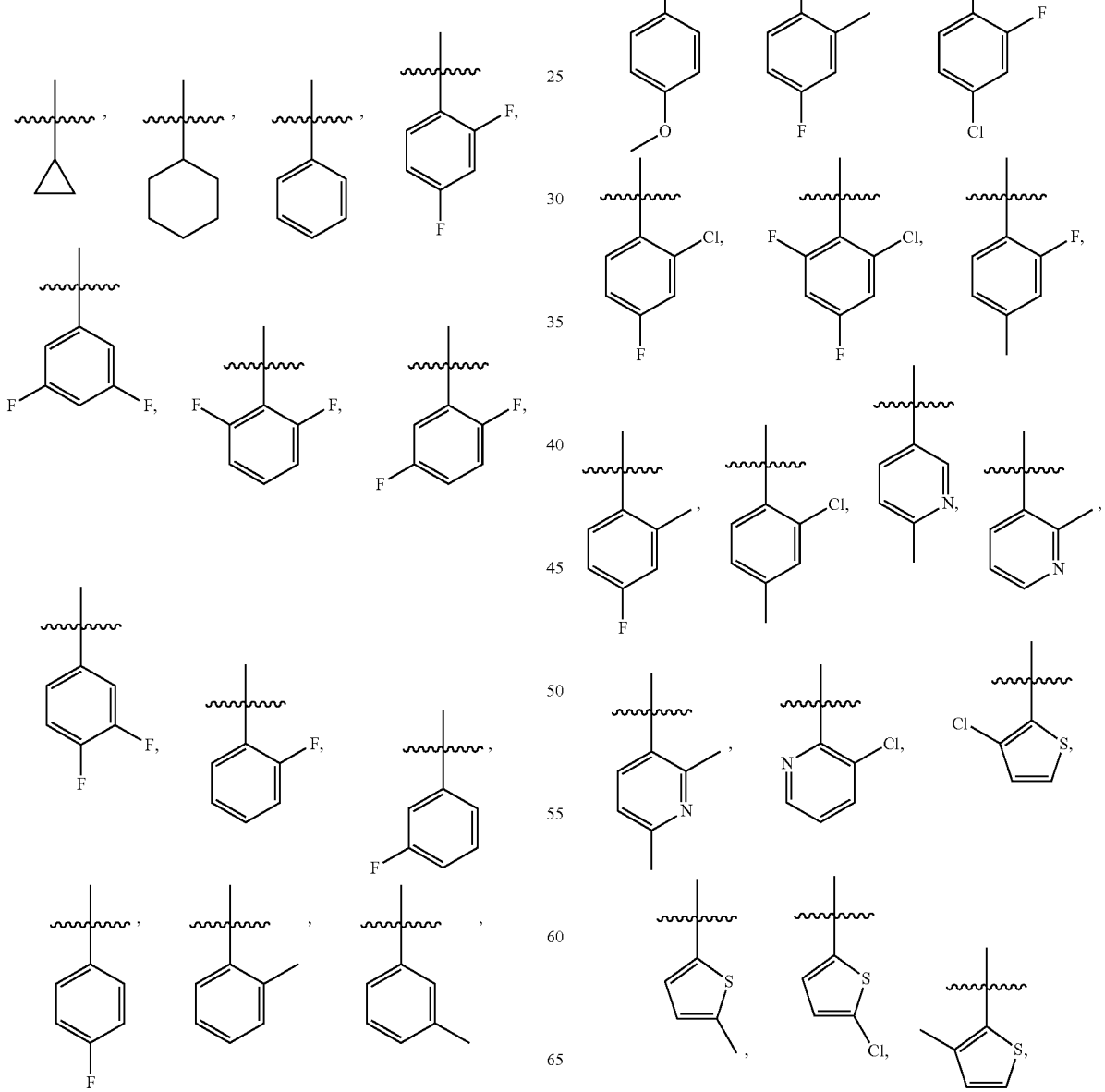

151
-continued
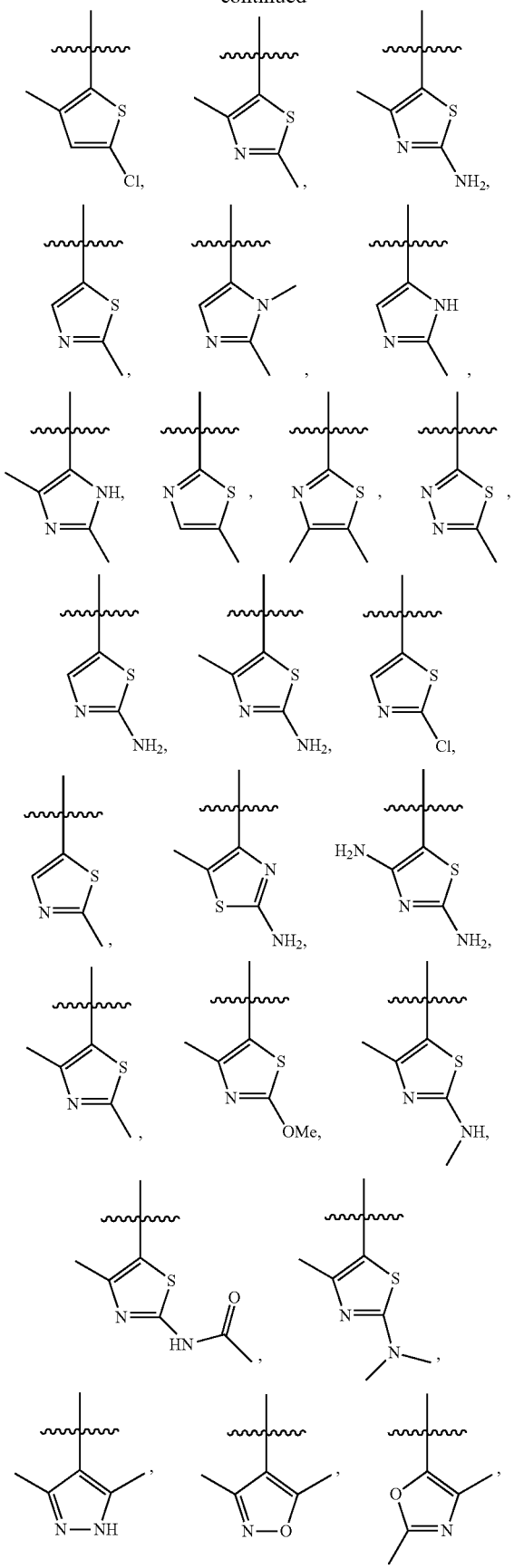
152
-continued
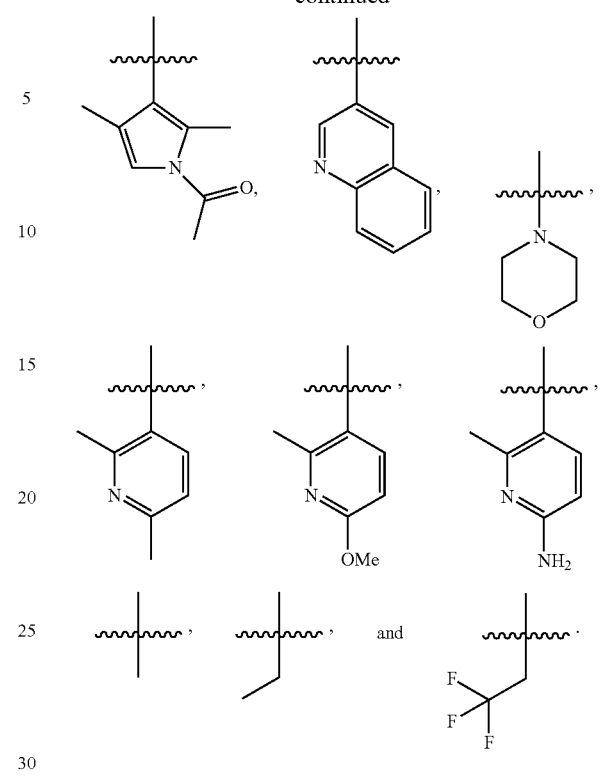
16. A compound of claim 8, wherein the ring formed between any two $R_1$, $R_{d1}$ and $R_{d2}$ in the same $D_2$, two $D_2$, $R_4$ and one $D_2$, or $R_4$ and $D_3$, is selected from the group consisting of
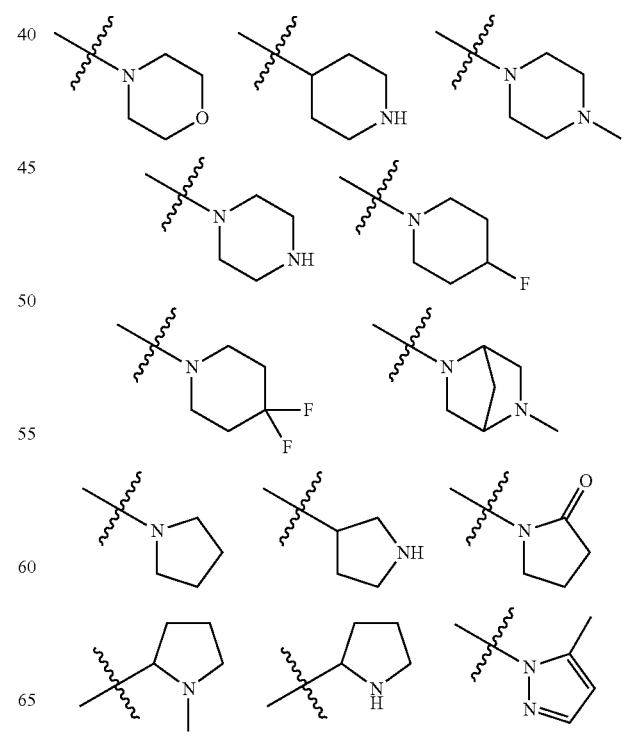

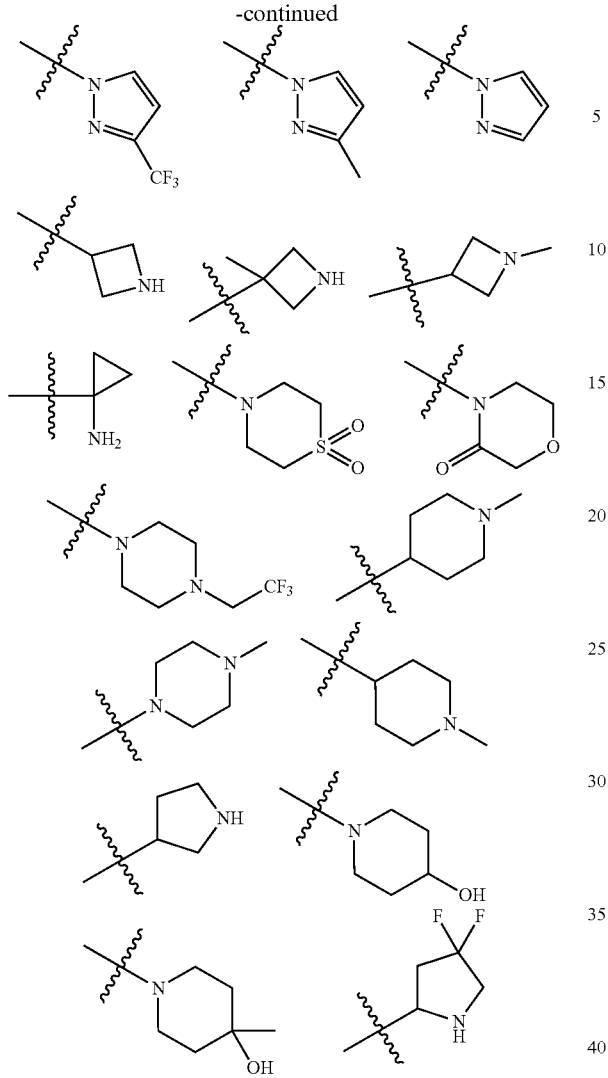
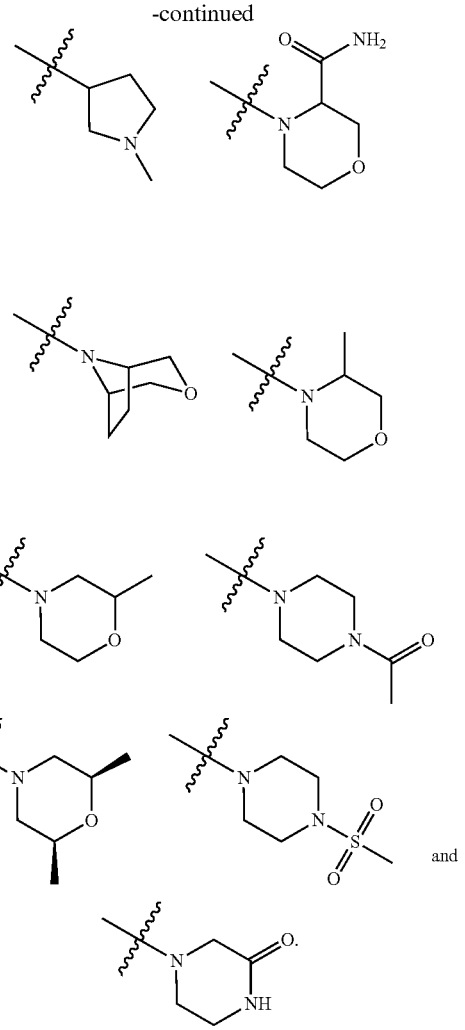

What is claimed is:

1. A compound represented by Formula (I) or a pharmaceutically acceptable salt thereof,

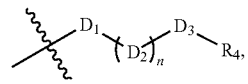

(I)

wherein,

E is selected from the group consisting of $C_{1-6}$ alkyl, and 3- to 10-membered cyclohydrocarbyl or heterocyclohydrocarbyl, wherein said $C_{1-6}$ alkyl and 3- to 10-membered cyclohydrocarbyl or heterocyclohydrocarbyl are optionally substituted with 1, 2 or 3 $R_3$;

one of L and Q is selected from the group consisting of $-C(R_{d1})(R_{d2})-$, $-C(=O)N(R_{d3})-$, $-N(R_{d4})-$, $-C(=NR_{d5})-$, $-S(=O)_2N(R_{d6})-$, $-S(=O)N(R_{d7})-$, $-O-$, $-S-$, $-C(=O)O-$, $-C(=O)-$, $-C(=S)-$, $-S(=O)-$, $-S(=O)_2-$ and $-N(R_{d8})C(=O)N(R_{d9})-$, and the other one is selected from the group consisting of a single bond and $-C(R_{d1})(R_{d2})-$;

A is selected from the group consisting of N and $C(R_t)$;

X, Y and Z are independently $C(R_t)$;

$m_1$ is independently 0, 1, 2 or 3;

one of $R_1$, $R_2$, and $R_3$ is

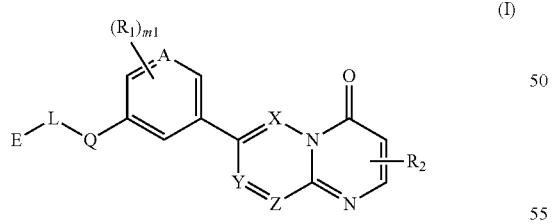

and the others are selected from the group consisting of H, F, Cl, Br, I, CN, OH, SH, $NH_2$, CHO, COOH, $C_{1-10}$ alkyl or heteroalkyl, 3- to 10-membered cyclohydrocarbyl or heterocyclohydrocarbyl, $C_{1-10}$ alkyl or heteroalkyl substituted with 3- to 10-membered cyclohydrocarbyl or heterocyclohydrocarbyl, 3- to 10-membered cyclohydrocarbyl-O— or heterocyclohydrocarbyl-O—, and 3- to 10-membered cyclohydrocarbyl-amino- or heterocyclohydrocarbyl-amino-, wherein said $C_{1-10}$ alkyl or heteroalkyl, 3- to 10-membered cyclohydrocarbyl or heterocyclohydrocarbyl, $C_{1-10}$ alkyl or heteroalkyl substituted with 3- to 10-membered cyclohydrocarbyl or heterocyclohydrocarbyl, 3- to 10-membered cyclohydrocarbyl-O— or heterocyclohydrocarbyl-O—, and 3- to 10-membered cyclohydrocarbyl-amino- or heterocyclohydrocarbyl-amino- are optionally substituted with $R_{01}$;

$D_1$ is selected from the group consisting of a single bond, $-C(R_{d1})(R_{d2})-$, $-C(=O)N(R_{d3})-$, $-N(R_{d4})-$, $-C(=NR_{d5})-$, $-S(=O)_2N(R_{d6})-$, $-S(=O)N(R_{d7})-$, $-O-$, $-S-$, $-C(=O)O-$, $-C(=O)-$, $-C(=S)-$, $-S(=O)-$, $-S(=O)_2-$ and $-N(R_{d8})C(=O)N(R_{d9})-$;

$D_2$ is $-C(R_{d1})(R_{d2})-$, $D_3$ is selected from the group consisting of $-N(R_{d4})-$, $-C(=O)N(R_{d4})-$, $-N(R_{d4})C(=O)-$, $-N(R_{d4})C(=O)O-$, $-N(R_{d4})OC(=O)-$, $-N(R_{d4})C(=O)N(R_{d4})-$, $-S(=O)-$, $-S(=O)_2-$, $-S(=O)_2N(R_{d6})-$ and $-S(=O)N(R_{d7})-$;

$R_4$ is selected from the group consisting of H, $C_{1-10}$ alkyl or heteroalkyl, 3- to 10-membered cyclohydrocarbyl or heterocyclohydrocarbyl, and $C_{1-10}$ alkyl or heteroalkyl substituted with 3- to 10-membered cyclohydrocarbyl or heterocyclohydrocarbyl, wherein said $C_{1-10}$ alkyl or heteroalkyl, 3- to 10-membered cyclohydrocarbyl or heterocyclohydrocarbyl, and $C_{1-10}$ alkyl or heteroalkyl substituted with 3- to 10-membered cyclohydrocarbyl or heterocyclohydrocarbyl are optionally substituted with $R_{01}$;

n is 1, 2, 3, 4, 5 or 6;

optionally, any two $R_1$, $R_{d1}$ and $R_{d2}$ in the same $D_2$, two $D_2$, $R_4$ and one $D_2$, or $R_4$ and $D_3$ are attached together to the same carbon atom or heteroatom to form one or two 3-, 4-, 5- or 6-membered carbocyclic ring or heterocyclic ring;

$R_t$, $R_{d1}$ and $R_{d2}$ are each independently selected from the group consisting of H, F, Cl, Br, I, CN, OH, SH, $NH_2$, CHO, COOH, $C(=O)NH_2$, $S(=O)NH_2$, $S(=O)_2NH_2$, $C_{1-10}$ alkyl or heteroalkyl, 3- to 10-membered cyclohydrocarbyl or heterocyclohydrocarbyl, and $C_{1-10}$ alkyl or heteroalkyl substituted with 3- to 10-membered cyclohydrocarbyl or heterocyclohydrocarbyl, wherein said $C_{1-10}$ alkyl or heteroalkyl, 3- to 10-membered cyclohydrocarbyl or heterocyclohydrocarbyl, and $C_{1-10}$ alkyl or heteroalkyl substituted with 3- to 10-membered cyclohydrocarbyl or heterocyclohydrocarbyl are optionally substituted with $R_{01}$;

$R_{01}$ is selected from the group consisting of F, Cl, Br, I, CN, OH, SH, $NH_2$, CHO, COOH, and $R_{02}$;

$R_{02}$ is selected from the group consisting of $C_{1-10}$ alkyl, $C_{1-10}$ alkylamino, N,N-di($C_{1-10}$ alkyl)amino, $C_{1-10}$ alkoxy, $C_{1-10}$ alkanoyl, $C_{1-10}$ alkoxycarbonyl, $C_{1-10}$ alkylsulfonyl, $C_{1-10}$ alkylsulfinyl, $C_{3-10}$ cycloalkyl, $C_{3-10}$ cycloalkylamino, $C_{3-10}$ heterocycloalkylamino, $C_{3-10}$ cycloalkoxy, $C_{3-10}$ cycloalkylacyl, $C_{3-10}$ cycloalkoxycarbonyl, $C_{3-10}$ cycloalkylsulfonyl, $C_{3-10}$ cycloalkylsulfinyl, 5- to 6-membered unsaturated heterocyclyl, and 6- to 12-membered aryl or heteroaryl;

the heteroatom or heteroatom group is each independently selected from the group consisting of —C(=O)N($R_{d3}$)—, —N($R_{d4}$)—, —C(=N$R_{d5}$)—, —S(=O)$_2$N($R_{d6}$)—, —S(=O)N($R_{d7}$)—, —O—, —S—, =O, =S, —C(=O)O—, —C(=O)—, —C(=S)—, —S(=O)—, —S(=O)$_2$— and —N($R_{d8}$)C(=O)N($R_{d9}$)—;

$R_{d3-d9}$ are each independently selected from the group consisting of H, OH, $NH_2$, and $R_{02}$;

$R_{02}$ is optionally substituted with $R_{001}$;

$R_{001}$ is selected from the group consisting of F, Cl, Br, I, CN, OH, N(CH$_3$)$_2$, NH(CH$_3$), $NH_2$, CHO, COOH, trifluoromethyl, aminomethyl, hydroxymethyl, methyl, methoxy, formyl, methoxycarbonyl, methyl sulfonyl, and methylsulfinyl; and in any of the foregoing cases, the number of $R_{01}$ or $R_{001}$ is each independently 0, 1, 2 or 3, and the number of the heteroatom or heteroatom group is each independently 1, 2 or 3.

2. The compound represented by Formula (I) or a pharmaceutically acceptable salt thereof according to claim 1, wherein, E is selected from the group consisting of $C_{1-6}$ alkyl and $C_{3-6}$ cycloalkyl, wherein said $C_{1-6}$ alkyl and $C_{3-6}$ cycloalkyl are substituted with $R_3$, and the number of $R_3$ is 0, 1, 2 or 3, or E is selected from the group consisting of

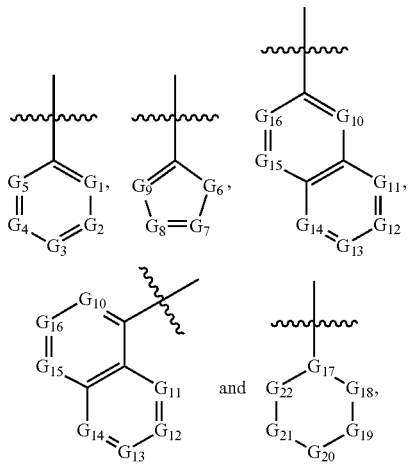

wherein, none or one or two or three of $G_{1-5}$ are N, and the others are $C(R_3)$;

$G_6$ is selected from the group consisting of —C($R_3$)($R_3$)—, —C(=O)N($R_{3a}$)—, —N($R_{3a}$)—, —C(=N$R_{3a}$)—, —S(=O)$_2$N($R_{3a}$)—, —S(=O)N($R_{3a}$)—, —O—, —S—, —C(=O)O—, —C(=O)—, —C(=S)—, —S(=O)—, —S(=O)$_2$— and —N($R_{3a}$)C(=O)N($R_{3a}$)—;

none or one or two of $G_{7-9}$ are N, and the others are $C(R_3)$;

none or one or two or three or four of $G_{10-16}$ are N, and the others are $C(R_3)$;

$G_{17}$ is selected from the group consisting of N and $C(R_3)$;

none or one or two or three of $G_{18-22}$ are selected from the group consisting of —C(=O)N($R_{3a}$)—, —N($R_{3a}$)—, —C(=N$R_{3a}$)—, —S(=O)$_2$N($R_{3a}$)—, —S(=O)N($R_{3a}$)—, —O—, —S—, —C(=O)O—, —C(=O)—, —C(=S)—, —S(=O)—, —S(=O)$_2$— and —N($R_{3a}$)C(=O)N($R_{3a}$)—, and the others are —C($R_3$)($R_3$)—;

$R_{3a}$ is selected from the group consisting of $C_{1-10}$ alkyl, $C_{1-10}$ alkylacyl, $C_{1-10}$ alkoxycarbonyl, $C_{1-10}$ alkylsulfonyl, $C_{1-10}$ alkylsulfinyl, $C_{3-10}$ cycloalkyl, $C_{3-10}$ cycloalkylacyl, $C_{3-10}$ cycloalkoxycarbonyl, $C_{3-10}$ cycloalkylsulfonyl, $C_{3-10}$ cycloalkylsulfinyl, 5- to 6-membered unsaturated heterocyclyl, and 6- to 10-membered aryl or heteroaryl; and all other variables are as defined in claim 1.

3. The compound represented by Formula (I) or a pharmaceutically acceptable salt thereof according to claim 2, wherein, E is selected from the group consisting of methyl, ethyl, propyl,

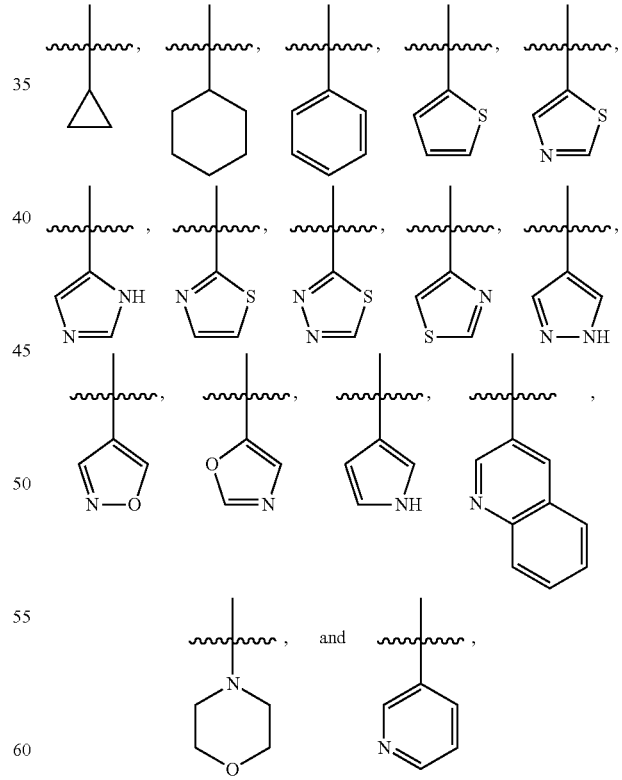

all of which are optionally substituted with 1, 2 or 3 $R_3$.

4. The compound represented by Formula (I) or a pharmaceutically acceptable salt thereof according to claim 3, wherein, E is selected from the group consisting of

125

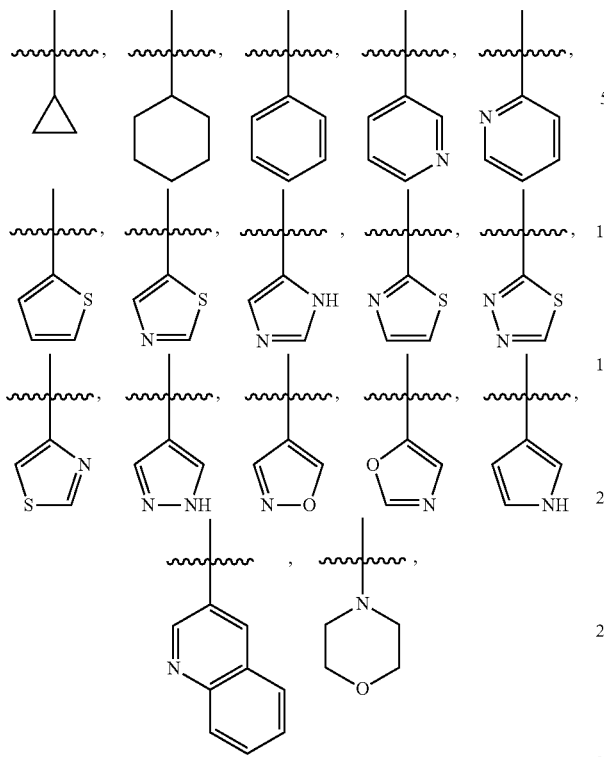

126

-continued

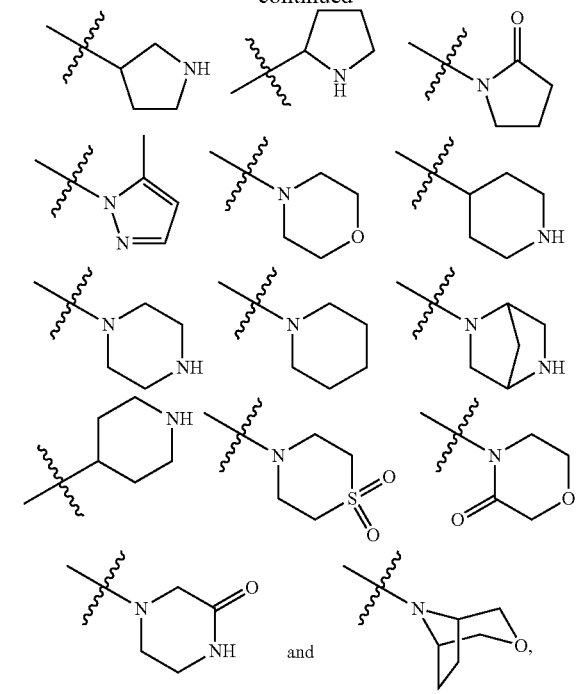

and C$_{1-3}$ alkyl, all of which are optionally substituted with 1, 2, or 3 halogens, OH, OC$_{1-3}$alkyl, CN, NH$_2$, NH(C$_{1-3}$alkyl), N(C$_{1-3}$alkyl)$_2$, C$_{1-3}$alkyl, trifluoromethyl, trifluoroethyl, C(=O)NH$_2$, C$_{1-3}$alkylC(=O), C$_{1-3}$alkylC(=O)NH, C$_{1-3}$alkylS(=O), C$_{1-3}$alkylS(=O)NH, C$_{1-3}$alkylS(=O)$_2$ or C$_{1-3}$alkylS(=O)$_2$NH.

5. The compound represented by Formula (I) or a pharmaceutically acceptable salt thereof according to claim 1, wherein, one of L and Q is selected from the group consisting of —S(=O)$_2$NH—, —S(=O)$_2$—, —NH—, and —NHC(=O)NH—, and the other one is selected from the group consisting of a single bond and —CH$_2$—.

6. The compound represented by Formula (I) or a pharmaceutically acceptable salt thereof according to claim 1, wherein, X, Y and Z are independently selected from the group consisting of CH, C(CH$_3$), C(CF$_3$), CCl, and CF.

7. The compound represented by Formula (I) or a pharmaceutically acceptable salt thereof according to claim 1, wherein, A and T are each independently selected from the group consisting of N, CH, C(CH$_3$), C(CF$_3$), CCl, and CF; alternatively, B is selected from the group consisting of NH, N(CH$_3$) and N(CF$_3$).

8. The compound represented by Formula (I) or a pharmaceutically acceptable salt thereof according to claim 1, wherein, the ring formed between any two R$_1$, R$_{d1}$ and R$_{d2}$ in the same D$_2$, two D$_2$, R$_4$ and one D$_2$, or R$_4$ and D$_3$, is selected from the group consisting of

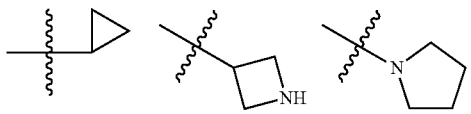

all of which are optionally substituted with 1, 2, or 3 halogens, OH, OC$_{1-3}$alkyl, CN, NH$_2$, NH(C$_{1-3}$alkyl), N(C$_{1-3}$alkyl)$_2$, C$_{1-3}$alkyl, trifluoromethyl, trifluoroethyl, C(=O)NH$_2$, C$_{1-3}$alkylC(=O), C$_{1-3}$alkylC(=O)NH, C$_{1-3}$alkylS(=O), C$_{1-3}$alkylS(=O)NH, C$_{1-3}$alkylS(=O)$_2$ or C$_{1-3}$alkylS(=O)$_2$NH.

9. The compound represented by Formula (I) or a pharmaceutically acceptable salt thereof according to claim 1, wherein, one of R$_1$, R$_2$, and R$_3$ is

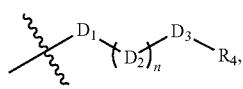

and the others are selected from the group consisting of H, F, Cl, Br, I, CN, OH, SH, NH$_2$, CHO, COOH, OR$_a$, N(R$_b$)(R$_c$), C$_{1-3}$ alkyl and cyclopropyl, wherein said C$_{1-3}$ alkyl and cyclopropyl are optionally substituted with R$_d$;
  D$_1$ is selected from the group consisting of a single bond, —C(R$_e$)(R$_e$)—, —C(=O)N(R$_a$)—, —N(R$_a$)—, —C(=NR$_a$)—, —S(=O)$_2$N(R$_a$)—, —S(=O)N(R$_a$)—, —O—, —S—, —C(=O)O—, —C(=O)—, —C(=S)—, —S(=O)—, —S(=O)$_2$— and —N(R$_a$)C(=O)N(R$_a$)—;
  D$_2$ is —C(R$_a$)(R$_a$)—;
  n is 1, 2, 3, 4, 5 or 6;
  R$_a$, R$_b$ and R$_c$ are each independently selected from the group consisting of H, C$_{1-6}$ alkyl and C$_{3-6}$ cycloalkyl, wherein said C$_{1-6}$ alkyl and C$_{3-6}$ cycloalkyl are optionally substituted with R$_d$;
  R$_e$ is selected from the group consisting of H, C$_{1-6}$ alkyl or alkoxy, and C$_{3-6}$ cycloalkyl or cycloalkoxy, wherein said C$_{1-6}$ alkyl or alkoxy and said C$_{3-6}$ cycloalkyl or cycloalkoxy are optionally substituted with R$_d$;
  R$_d$ is selected from the group consisting of F, Cl, Br, I, CN, OH, NH$_2$, CHO, COOH, CH$_3$, CF$_3$, CH$_3$O, and CH$_3$CH$_2$O, and the number of R$_d$ is 0, 1, 2 or 3; and optionally, any two $R_1$, $R_a$ and $R_a$ in the same $D_2$, two $D_2$, or $R_a$ and one $D_2$ are attached together to the same carbon atom or oxygen atom to form one or two 3-, 4-, 5- or 6-membered carbocyclic ring or oxacyclic ring, wherein the number of oxygen atoms is 1 or 2.

10. The compound represented by Formula (I) or a pharmaceutically acceptable salt thereof according to claim 9, wherein, the ring formed between any two $R_1$, $R_a$ and $R_a$ in the same $D_2$, two $D_2$, or $R_a$ and one $D_2$, is selected from the group consisting of cyclopropyl, cyclobutyl, cyclopentyl, cyclohexyl, oxetanyl, and 1,3-dioxolanyl.

11. The compound represented by Formula (I) or a pharmaceutically acceptable salt thereof according to claim 1, wherein, one of $R_1$, $R_2$, and $R_3$ is selected from the group consisting of

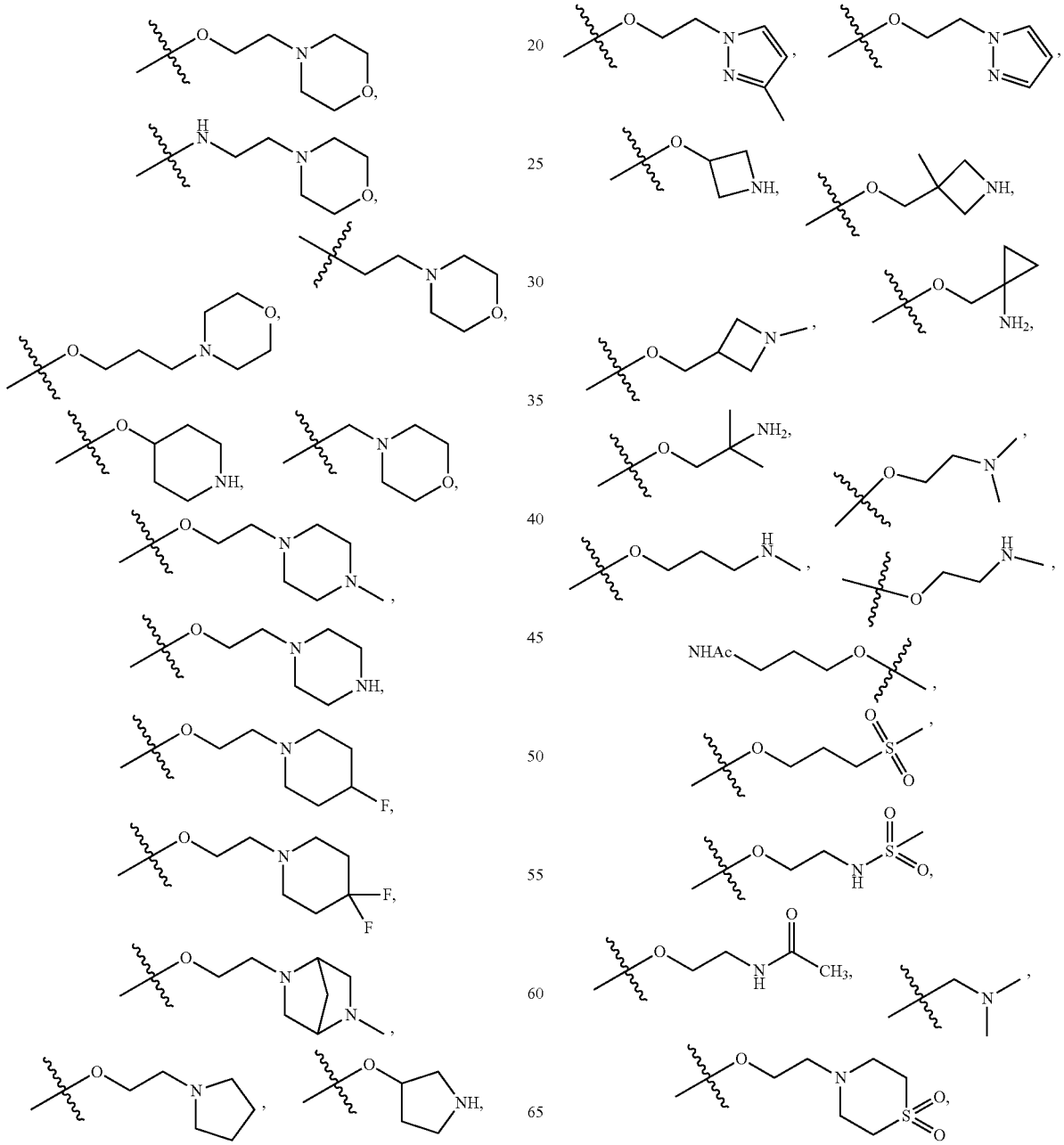

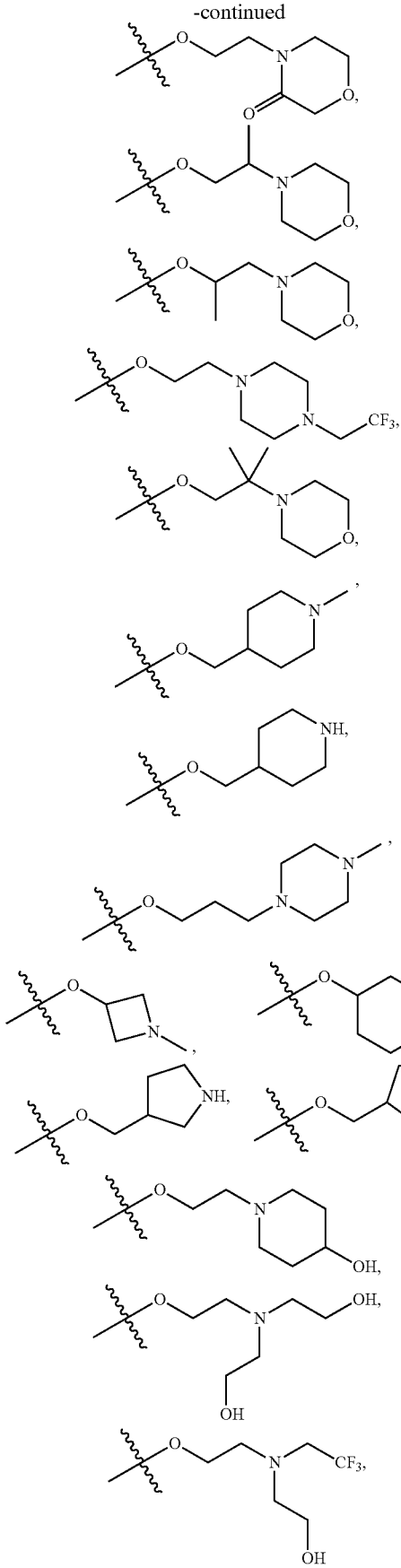
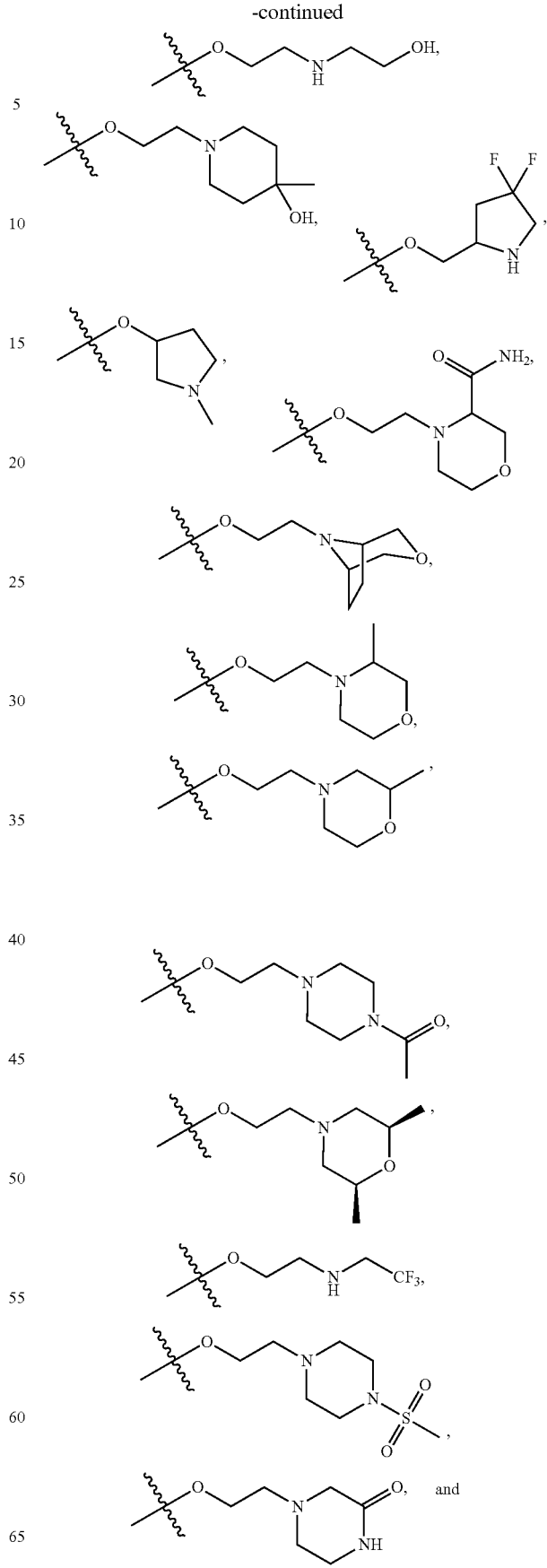

-continued

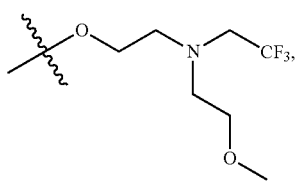

and the others are selected from the group consisting of H, F, Cl, Br, I, CN, OH, NH$_2$, methyl, ethyl, propyl, methoxy, ethoxy, propoxy, methylamino, dimethylamino, halomethyl, haloethyl, halopropyl, aminomethyl, aminoethyl, aminopropyl and cyclopropyl.

12. The compound represented by Formula (I) or a pharmaceutically acceptable salt thereof according to claim 1, the compound is selected from the group consisting of

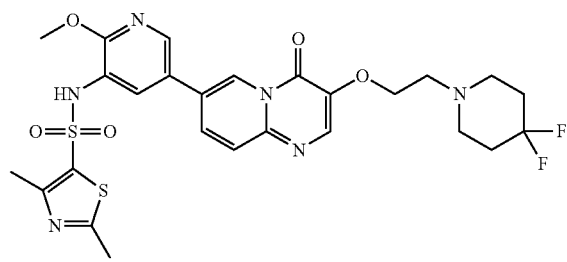

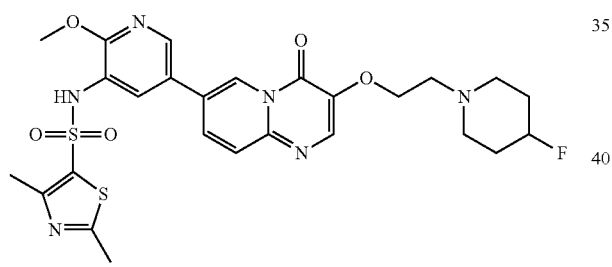

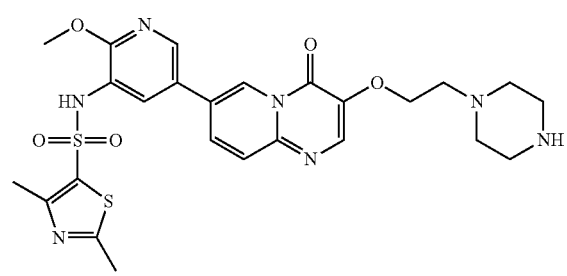

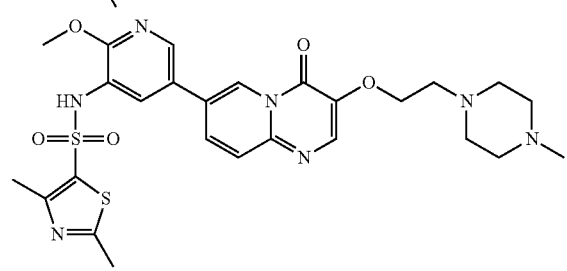

-continued

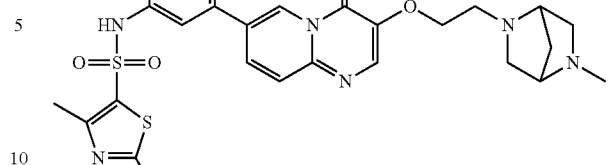

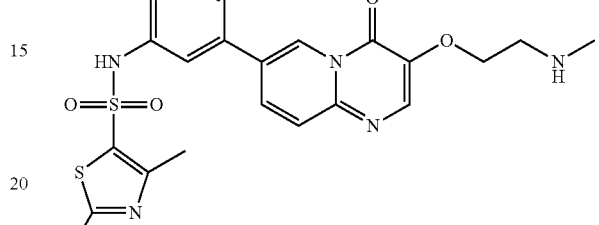

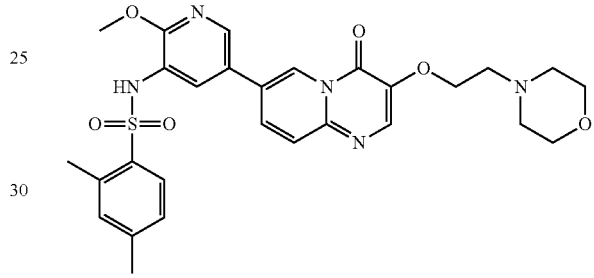

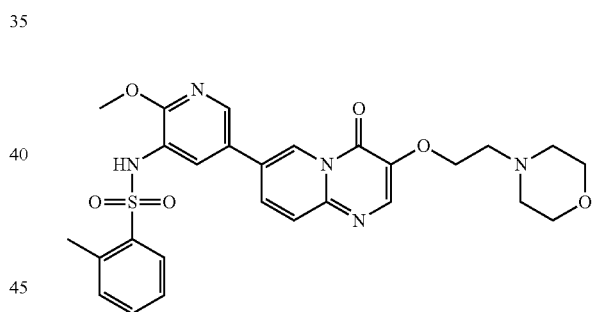

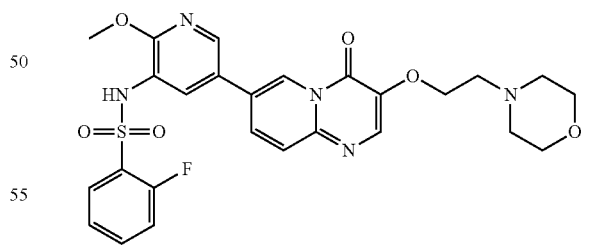

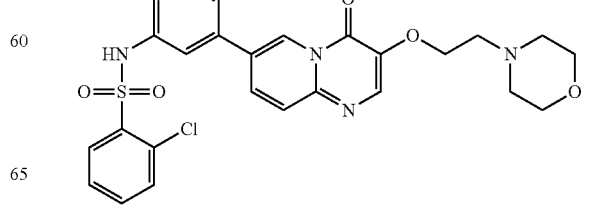

133
-continued
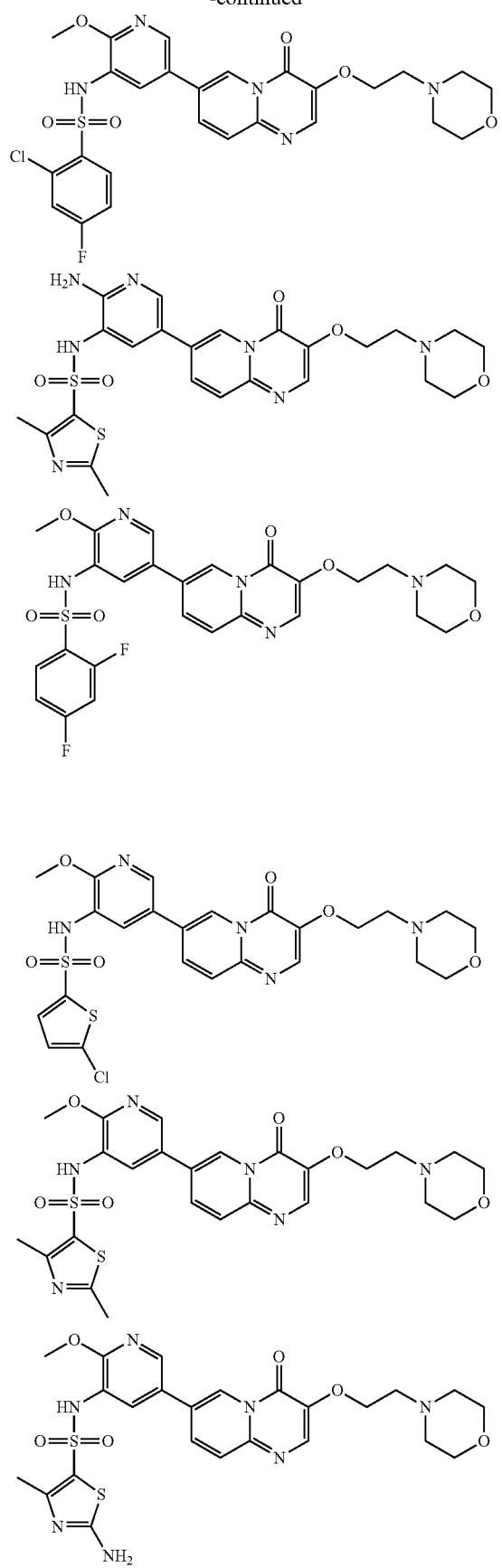
134
-continued
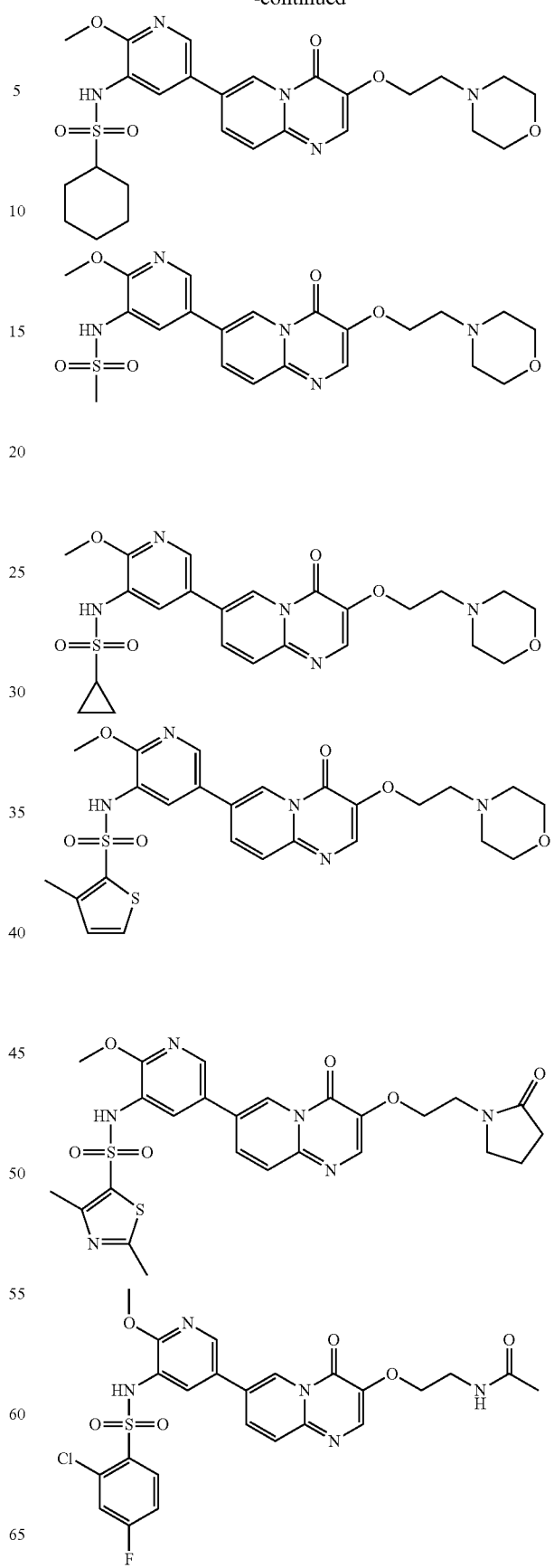

135
-continued
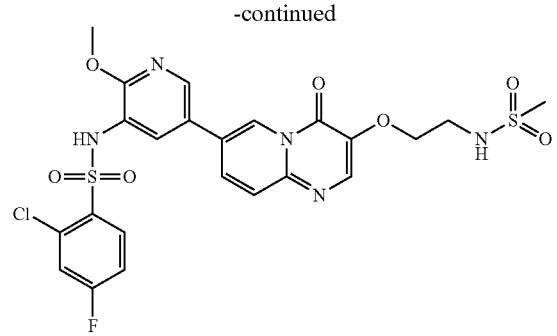
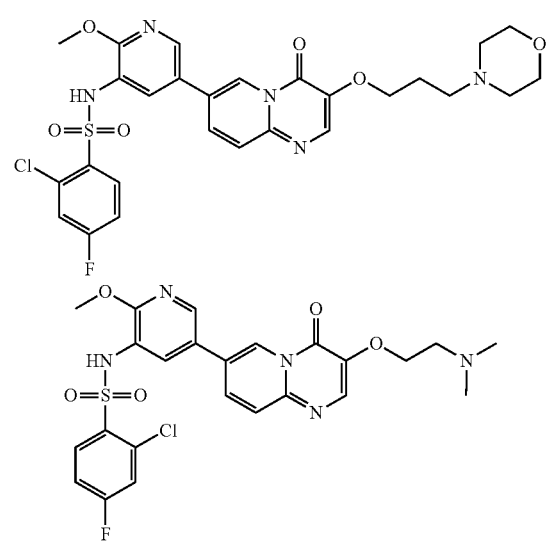
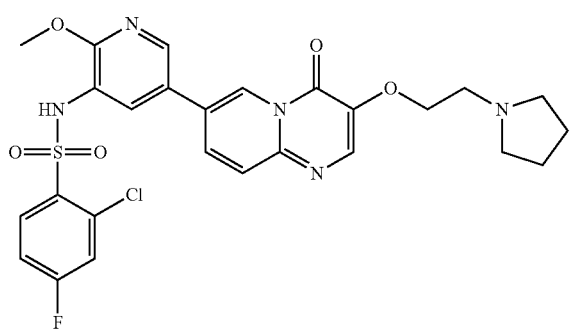
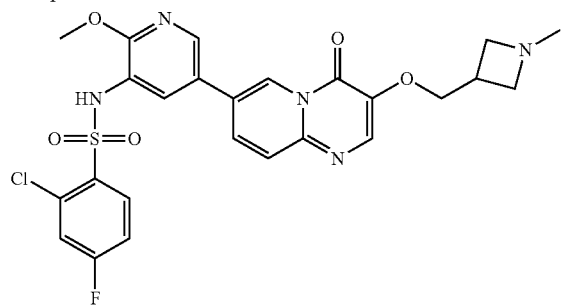
136
-continued
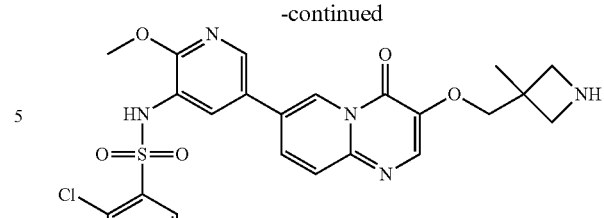
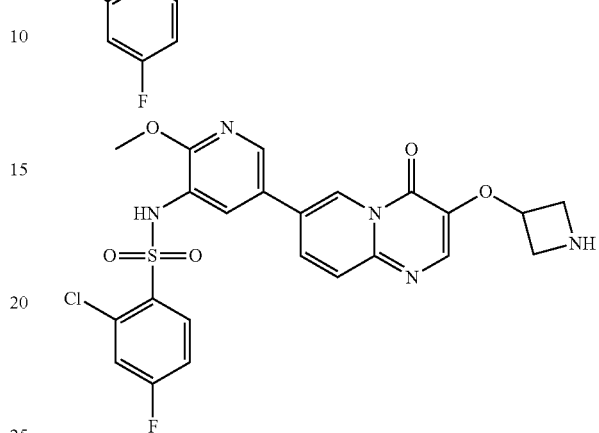
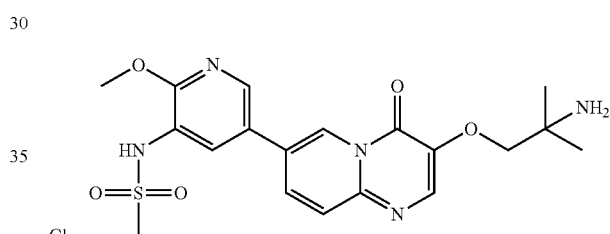
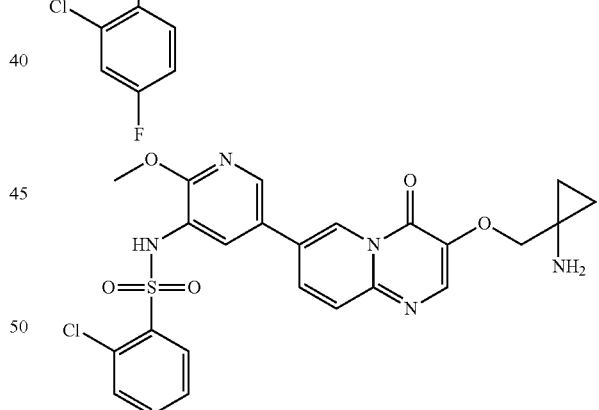
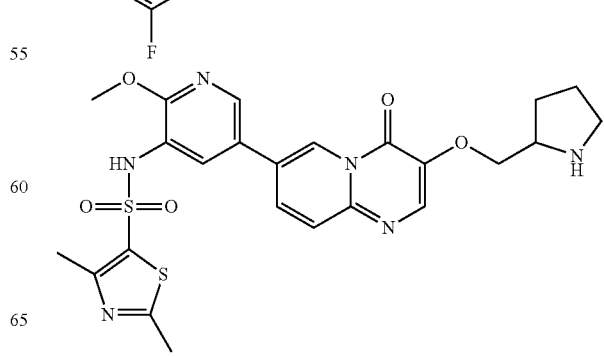

137
-continued
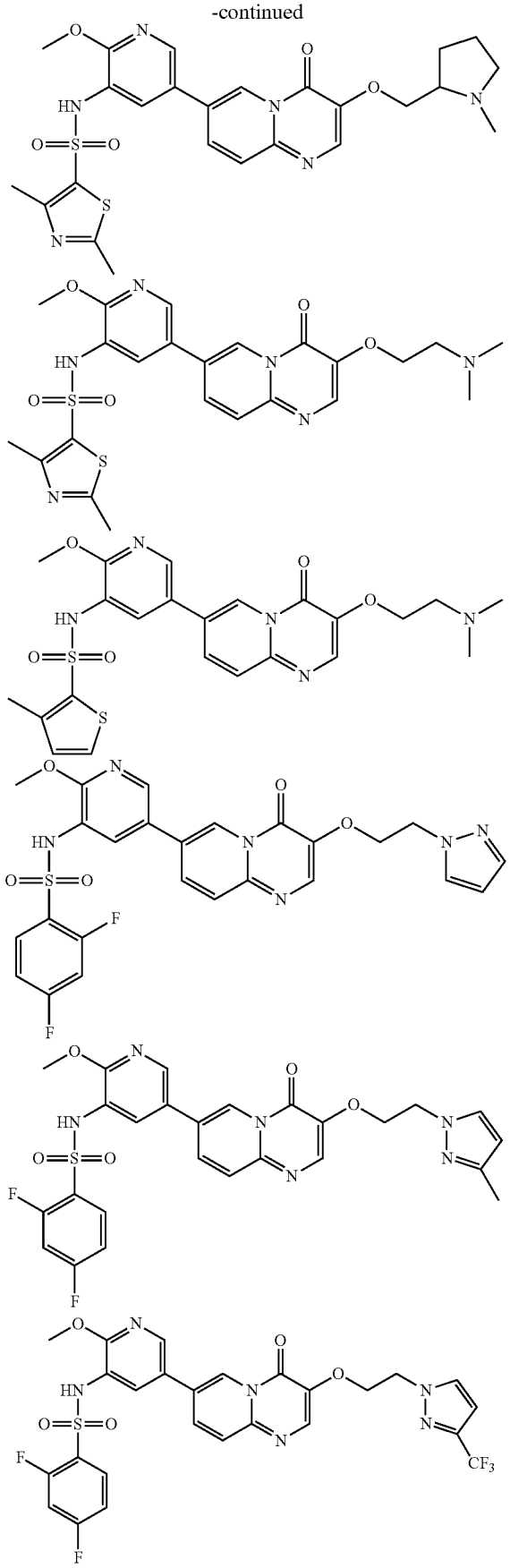
138
-continued
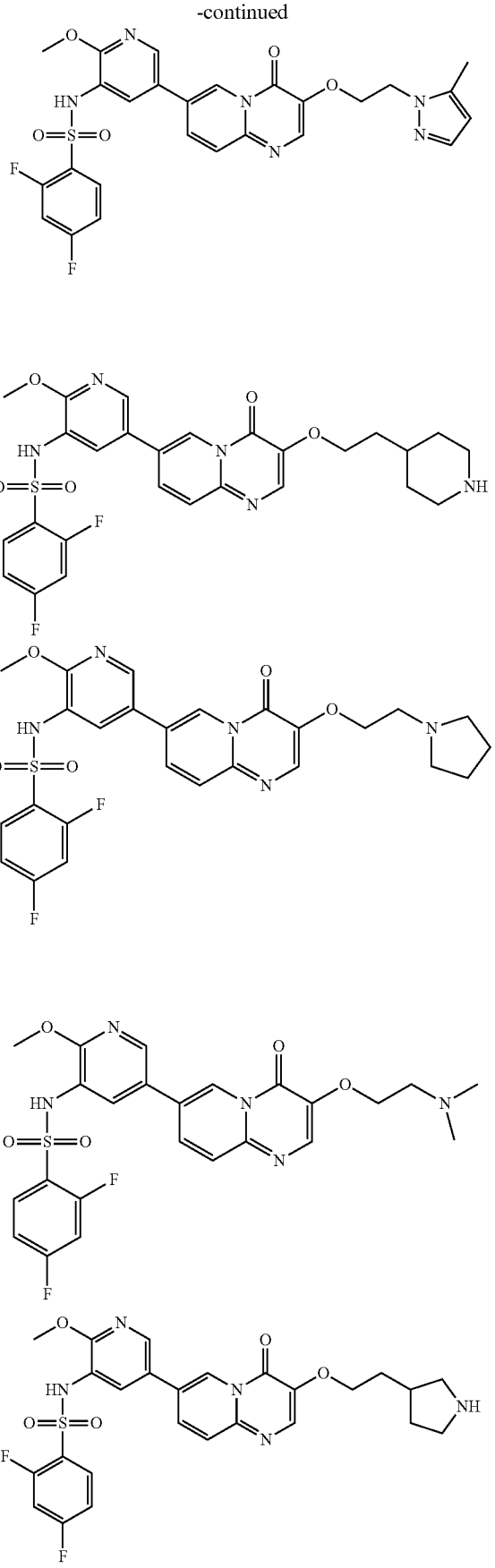

139
-continued
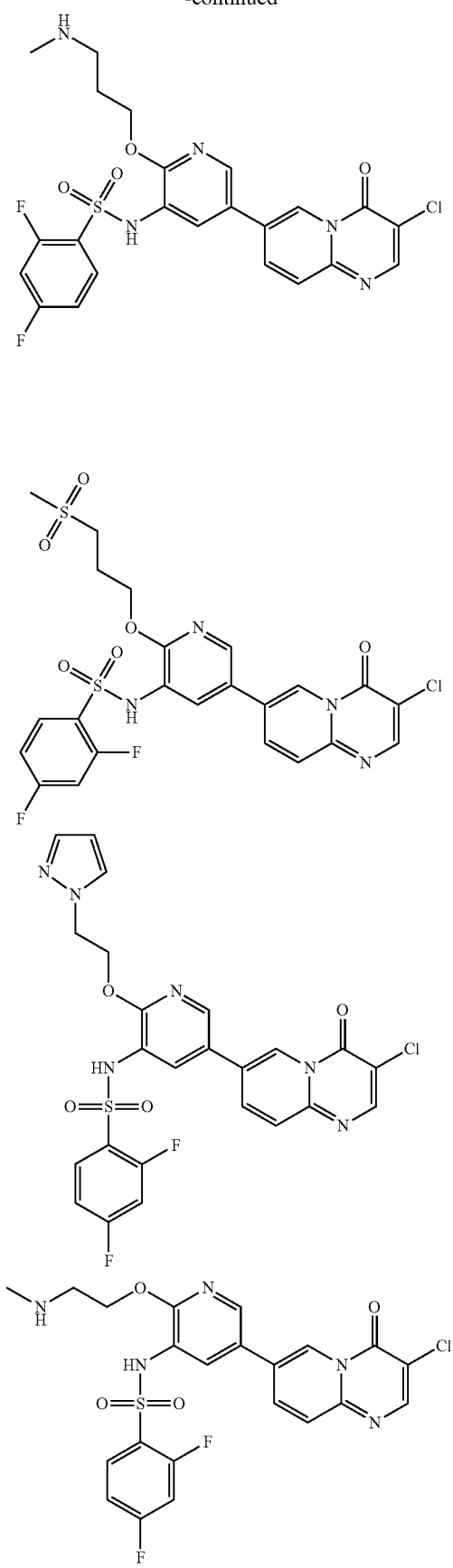
140
-continued
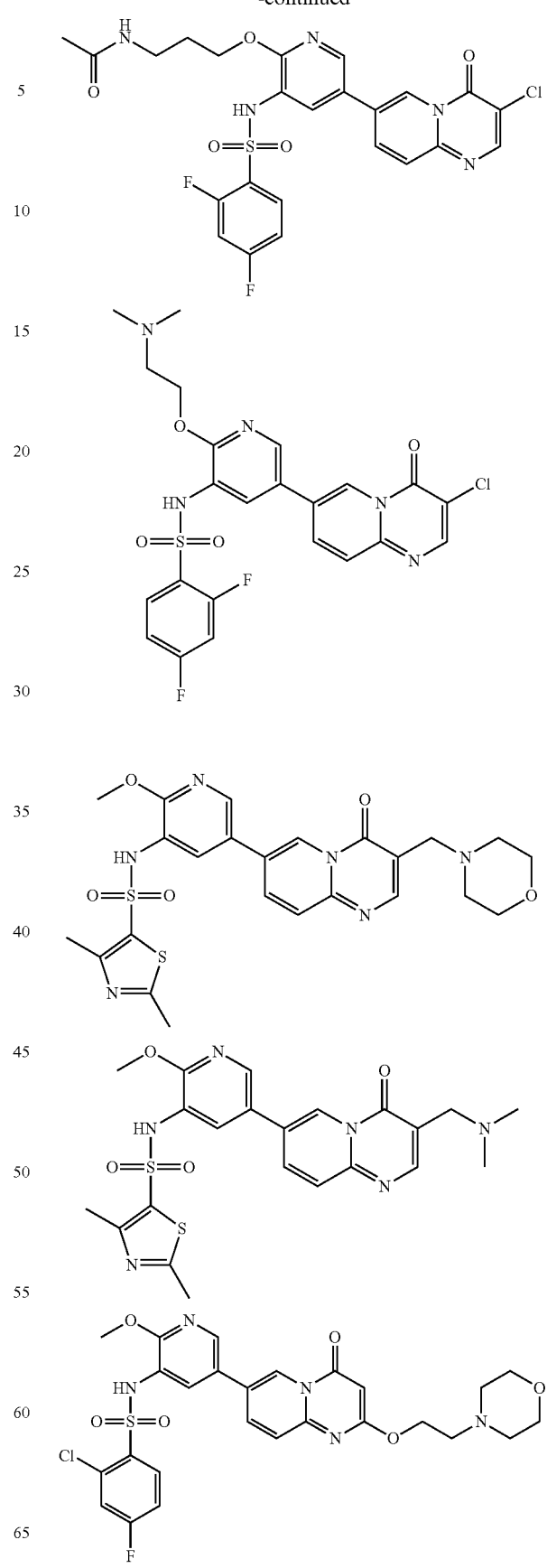

141
-continued
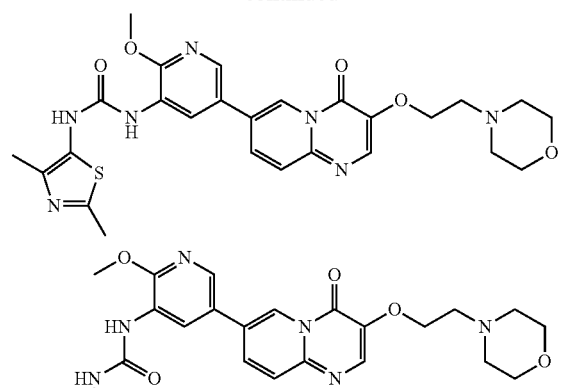
142
-continued
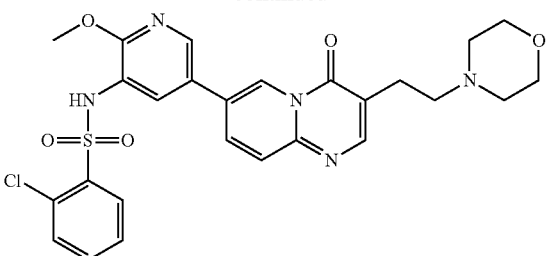
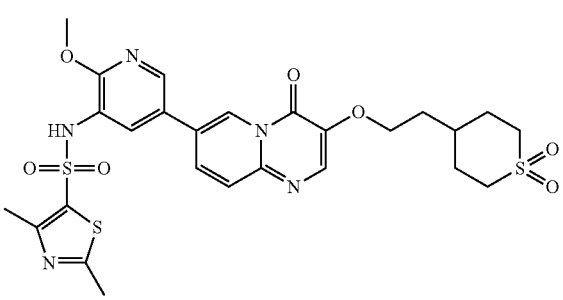
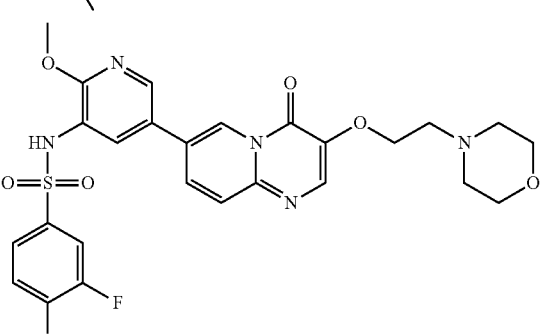
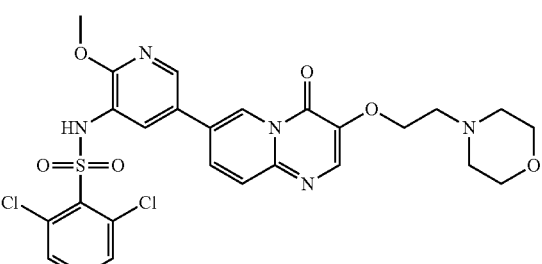
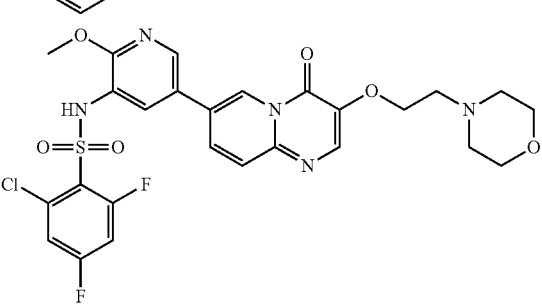

143
-continued
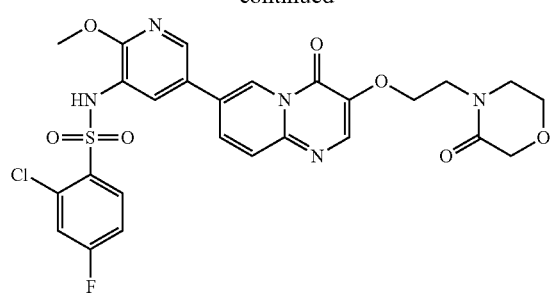
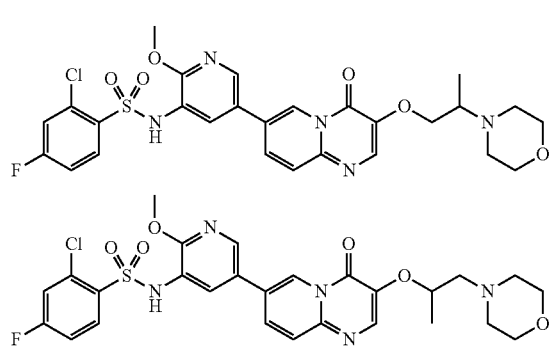
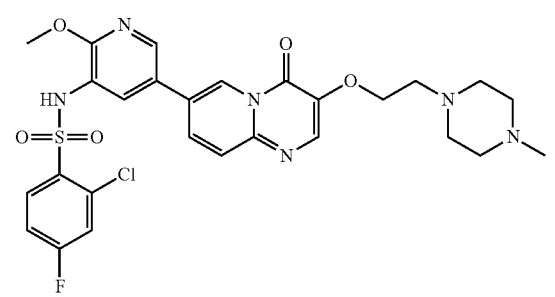
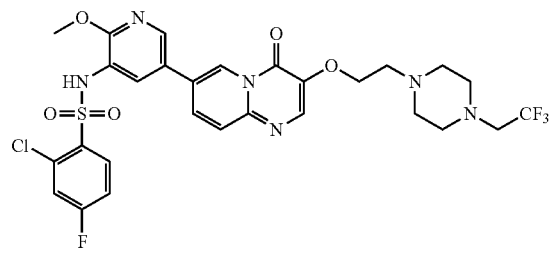
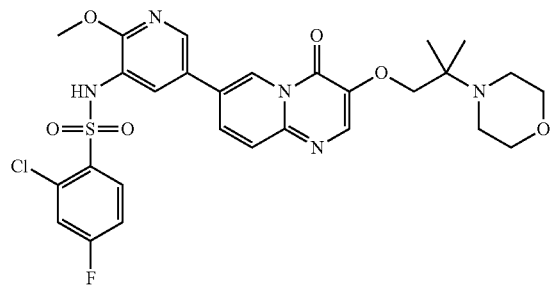
144
-continued
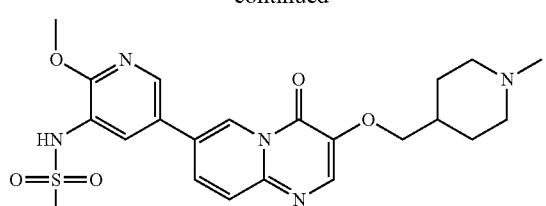
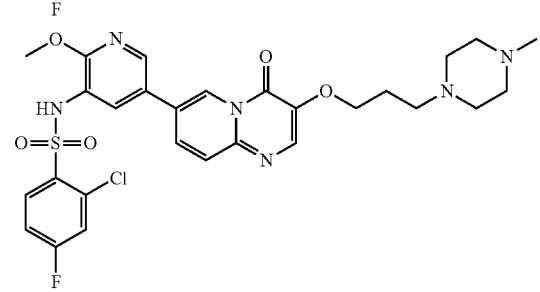
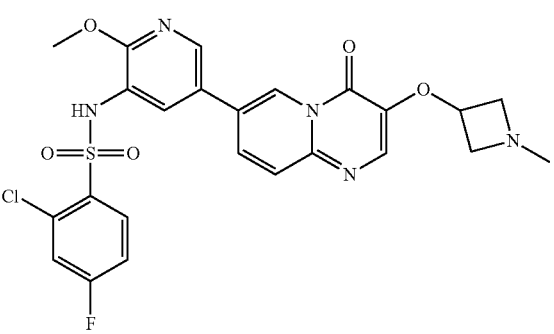
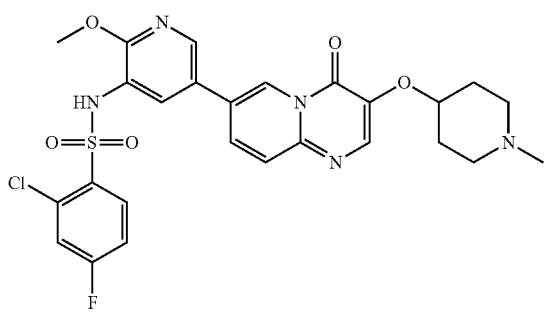
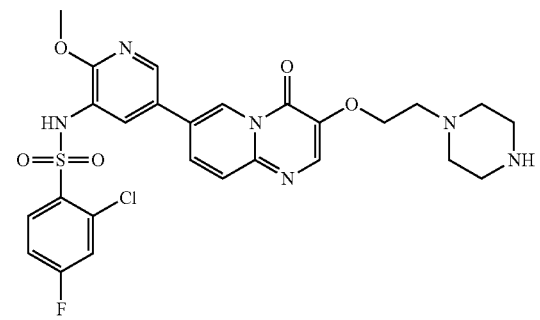

145
-continued
146
-continued
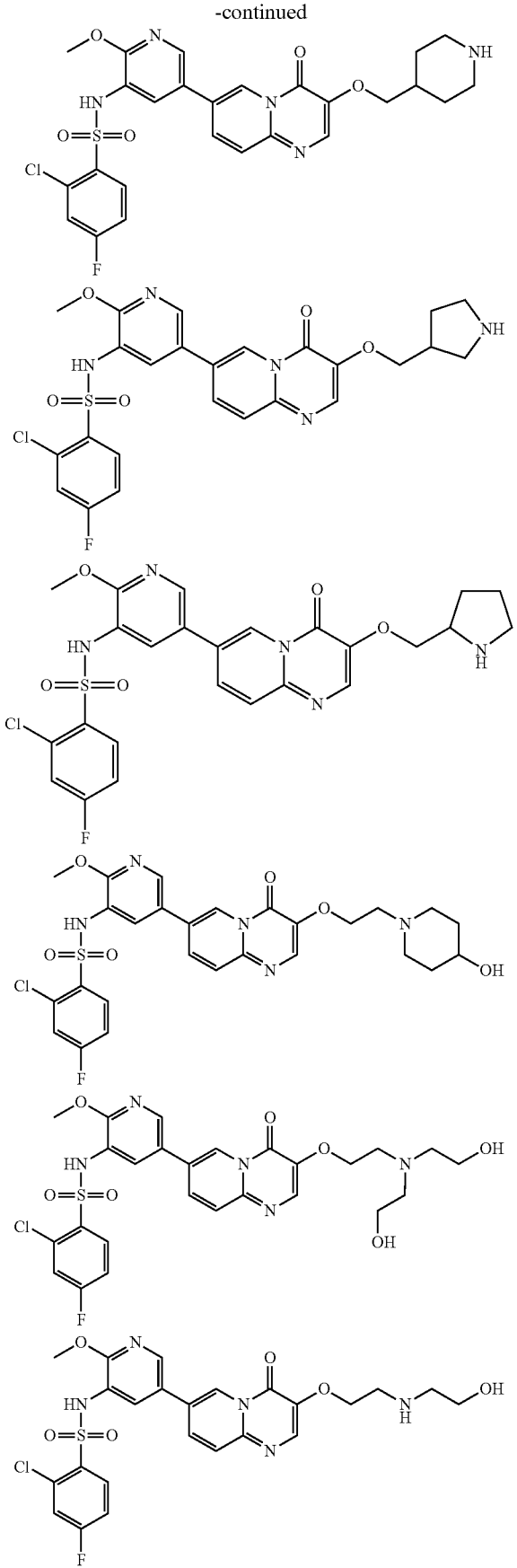
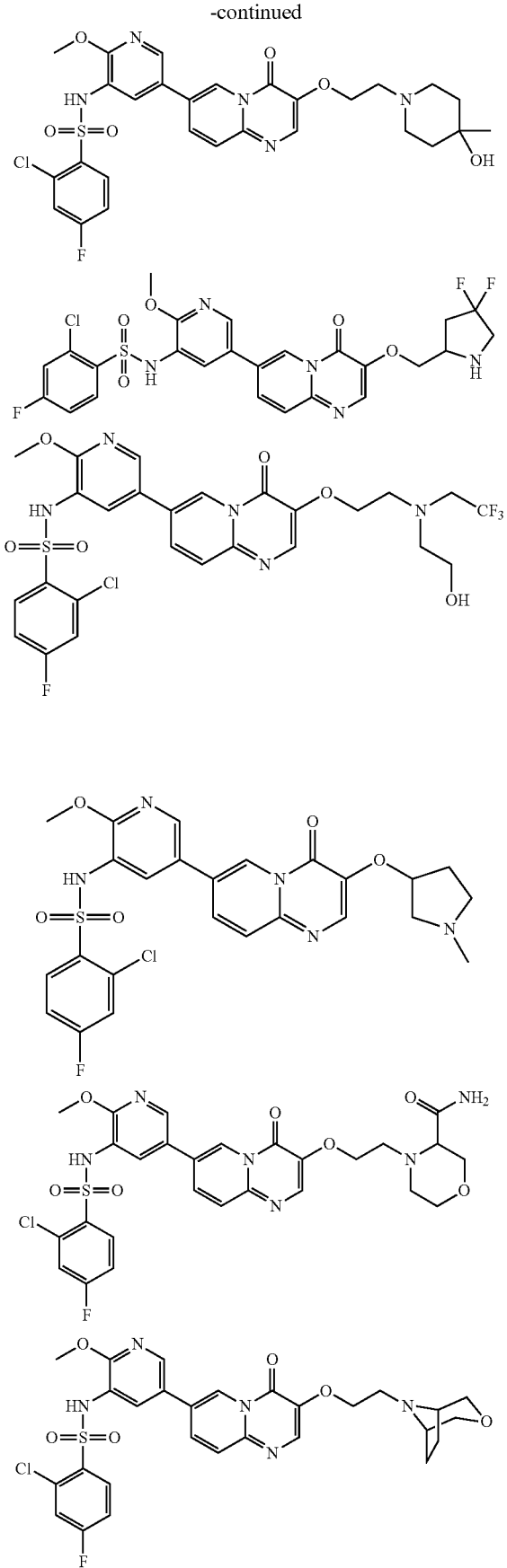

-continued
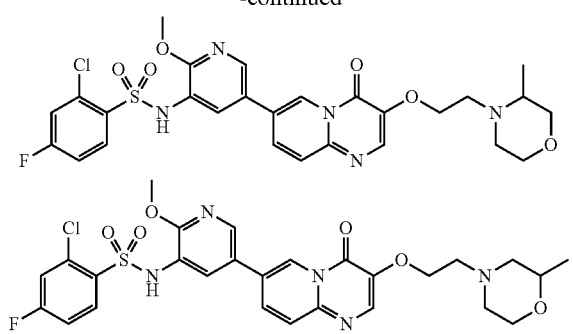
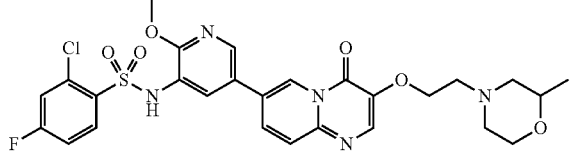
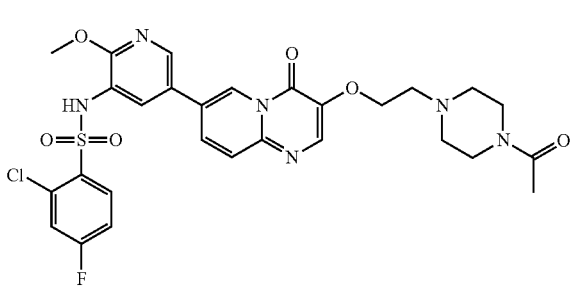
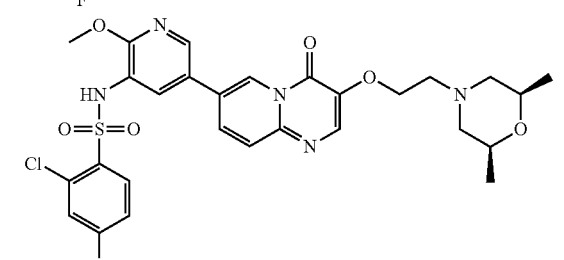
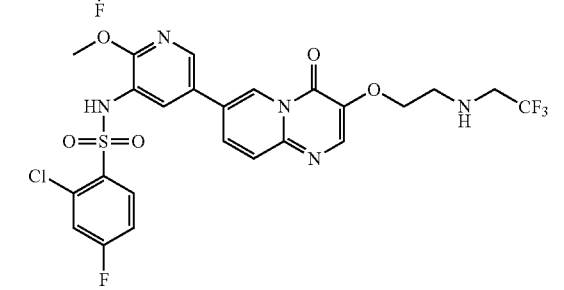
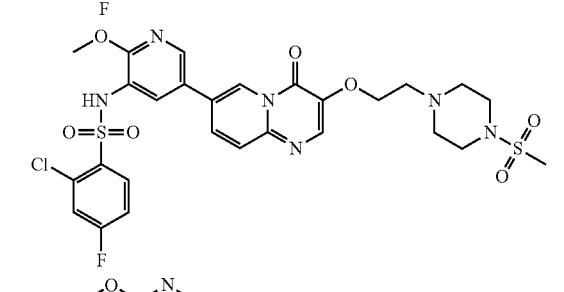
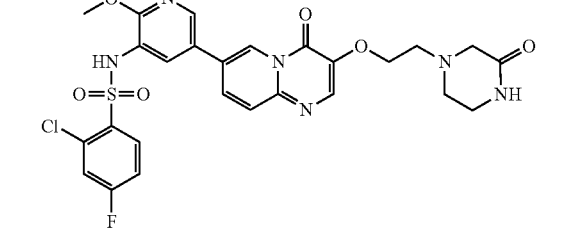
-continued
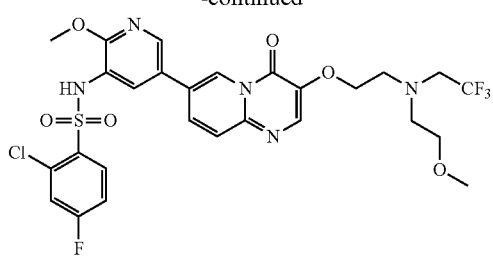
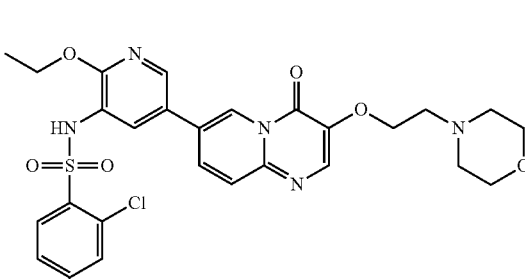
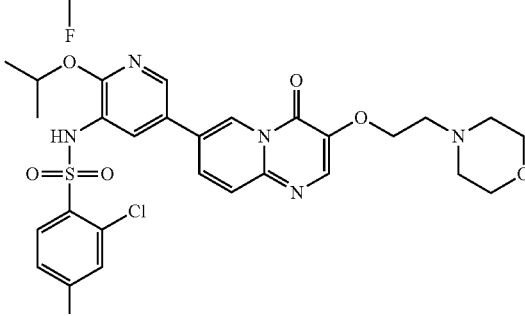
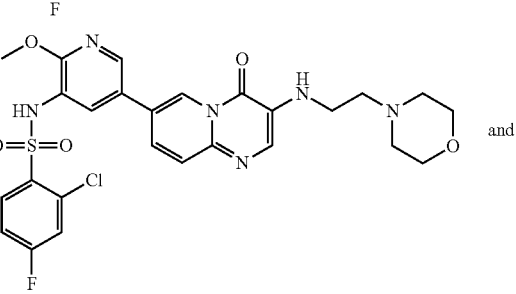
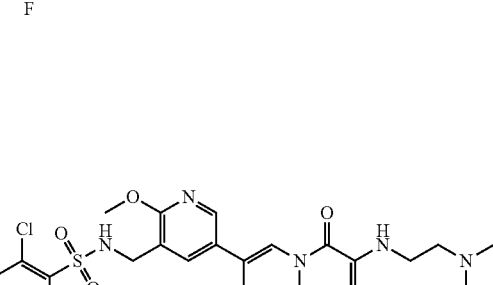 and
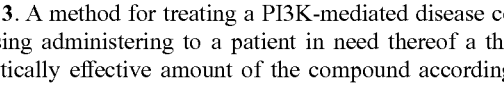
13. A method for treating a PI3K-mediated disease comprising administering to a patient in need thereof a therapeutically effective amount of the compound according to claim 1, or a pharmaceutically acceptable salt thereof, wherein the PI3K-mediated disease is colon cancer or gastric cancer.